United States Patent
Cauthen, III et al.

(10) Patent No.: US 9,675,347 B2
(45) Date of Patent: Jun. 13, 2017

(54) APPARATUS FOR THE TREATMENT OF TISSUE

(71) Applicant: KRT INVESTORS, INC., Trophy Club, TX (US)

(72) Inventors: Joseph C. Cauthen, III, Gainesville, FL (US); Matthew M. Burns, Orono, MN (US); Lawrence W. Wales, Maplewood, MN (US); Brian L. Dukart, Brooklyn Park, MN (US); Bradley J. Wessman, Wilmington, NC (US); Rodney L. Houfburg, Prior Lake, MN (US); Ishmael Bentley, Eagan, MN (US)

(73) Assignee: KRT INVESTORS, INC., Trophy Club, TX (US)

( * ) Notice: Subject to any disclaimer, the term of this patent is extended or adjusted under 35 U.S.C. 154(b) by 0 days.

(21) Appl. No.: 14/144,017

(22) Filed: Dec. 30, 2013

(65) Prior Publication Data
US 2014/0316439 A1 Oct. 23, 2014

Related U.S. Application Data

(63) Continuation of application No. 11/527,903, filed on Sep. 26, 2006, now Pat. No. 8,632,590, which is a (Continued)

(51) Int. Cl.
*A61F 2/44* (2006.01)
*A61B 17/068* (2006.01)
(Continued)

(52) U.S. Cl.
CPC ........ *A61B 17/068* (2013.01); *A61B 17/0401* (2013.01); *A61F 2/0063* (2013.01);
(Continued)

(58) Field of Classification Search
CPC .............................................. A61F 2002/4435
(Continued)

(56) References Cited

U.S. PATENT DOCUMENTS

| 1,995,970 A | 3/1935 | Dorough |
| 2,609,347 A | 9/1952 | Wilson |

(Continued)

FOREIGN PATENT DOCUMENTS

| DE | 43 23 959501 | 7/1994 |
| EP | 0 020 021 A2 | 12/1980 |

(Continued)

OTHER PUBLICATIONS

US 6,447,535, 09/2002, Jacobs et al. (withdrawn)
(Continued)

*Primary Examiner* — Matthew Lawson
(74) *Attorney, Agent, or Firm* — Faegre Baker Daniels LLP

(57) ABSTRACT

A system for treatment of tissue includes a fixation apparatus and a delivery tool releasably carrying the fixation apparatus. The fixation apparatus includes first and second anchors and an adjustable band connecting the anchors. The band includes a cinch line and a tether connected to one of the anchors. The delivery apparatus includes a body, a tubular shaft, a displacement rod within the tubular shaft, and an actuator.

20 Claims, 66 Drawing Sheets

Related U.S. Application Data continuation-in-part of application No. 11/120,750, filed on May 3, 2005, now Pat. No. 7,615,076, which is a continuation-in-part of application No. 10/352,981, filed on Jan. 29, 2003, now abandoned, and a continuation-in-part of application No. 10/327,106, filed on Dec. 24, 2002, now Pat. No. 7,004,970, said application No. 10/352,981 is a continuation-in-part of application No. 10/133,339, filed on Apr. 29, 2002, now Pat. No. 7,052,516, said application No. 10/327,106 is a continuation-in-part of application No. 10/133,339, which is a continuation-in-part of application No. 10/075,615, filed on Feb. 15, 2002, now abandoned, which is a continuation of application No. 09/947,078, filed on Sep. 5, 2001, now Pat. No. 6,592,625, which is a continuation of application No. 09/484,706, filed on Jan. 18, 2000, now abandoned.

(60) Provisional application No. 60/309,105, filed on Jul. 31, 2001, provisional application No. 60/160,710, filed on Oct. 20, 1999.

(51) Int. Cl.
| | |
|---|---|
| *A61B 17/04* | (2006.01) |
| *A61F 2/00* | (2006.01) |
| *A61F 2/46* | (2006.01) |
| *A61B 17/06* | (2006.01) |
| *A61B 17/064* | (2006.01) |
| *A61B 17/00* | (2006.01) |
| *A61F 2/30* | (2006.01) |
| *A61F 2/38* | (2006.01) |
| *A61F 2/28* | (2006.01) |

(52) U.S. Cl.
CPC ............ *A61F 2/442* (2013.01); *A61F 2/4611* (2013.01); *A61B 17/0642* (2013.01); *A61B 17/06166* (2013.01); *A61B 2017/00004* (2013.01); *A61B 2017/0404* (2013.01); *A61B 2017/0409* (2013.01); *A61B 2017/0412* (2013.01); *A61B 2017/0417* (2013.01); *A61B 2017/0427* (2013.01); *A61B 2017/0458* (2013.01); *A61B 2017/0462* (2013.01); *A61B 2017/0496* (2013.01); *A61B 2017/0647* (2013.01); *A61F 2/30907* (2013.01); *A61F 2/3872* (2013.01); *A61F 2002/0072* (2013.01); *A61F 2002/2817* (2013.01); *A61F 2002/305* (2013.01); *A61F 2002/3008* (2013.01); *A61F 2002/30062* (2013.01); *A61F 2002/30093* (2013.01); *A61F 2002/3097* (2013.01); *A61F 2002/30158* (2013.01); *A61F 2002/30299* (2013.01); *A61F 2002/30451* (2013.01); *A61F 2002/30461* (2013.01); *A61F 2002/30579* (2013.01); *A61F 2002/30777* (2013.01); *A61F 2002/30784* (2013.01); *A61F 2002/30841* (2013.01); *A61F 2002/30879* (2013.01); *A61F 2002/30892* (2013.01); *A61F 2002/4435* (2013.01); *A61F 2002/4627* (2013.01); *A61F 2210/0004* (2013.01); *A61F 2210/0019* (2013.01); *A61F 2220/0025* (2013.01); *A61F 2220/0058* (2013.01); *A61F 2220/0075* (2013.01); *A61F 2230/0026* (2013.01); *A61F 2230/0093* (2013.01); *A61F 2250/0098* (2013.01); *A61F 2310/00011* (2013.01)

(58) Field of Classification Search
USPC ........... 623/17.11–17.16; 606/79, 80, 83, 84, 606/86 R, 138–149, 151, 279
See application file for complete search history.

(56) References Cited

U.S. PATENT DOCUMENTS

| | | |
|---|---|---|
| 2,653,917 A | 9/1953 | Hammon |
| 2,659,935 A | 11/1953 | Hammon |
| 2,664,366 A | 12/1953 | Wilson |
| 2,664,367 A | 12/1953 | Wilson |
| 2,676,945 A | 4/1954 | Higgins |
| 2,683,136 A | 7/1954 | Higgins |
| 2,703,316 A | 3/1955 | Schneider |
| 2,758,987 A | 8/1956 | Salzberg |
| 2,846,407 A | 8/1958 | Wilson |
| 2,951,828 A | 9/1960 | Zeile |
| 3,531,561 A | 9/1970 | Trehu |
| 3,580,256 A | 5/1971 | Wilkinson |
| 3,796,497 A | 3/1974 | Mathisen et al. |
| 3,867,728 A | 2/1975 | Stubstad et al. |
| 3,874,388 A | 4/1975 | King et al. |
| 3,875,595 A | 4/1975 | Froning |
| 3,895,753 A | 7/1975 | Bone |
| 3,950,094 A | 4/1976 | Kano et al. |
| 3,990,619 A | 11/1976 | Russell |
| 4,006,747 A | 2/1977 | Kronenthal et al. |
| 4,007,743 A | 2/1977 | Blake |
| 4,013,078 A | 3/1977 | Feild |
| 4,059,115 A | 11/1977 | Jumashev |
| 4,070,117 A | 1/1978 | Johannsmeier et al. |
| 4,224,413 A | 9/1980 | Burbidge |
| 4,349,921 A | 9/1982 | Kuntz |
| 4,369,788 A | 1/1983 | Goald |
| 4,413,359 A | 11/1983 | Akiyama et al. |
| 4,502,161 A | 3/1985 | Wall |
| 4,512,338 A | 4/1985 | Balko et al. |
| 4,520,821 A | 6/1985 | Schmidt |
| 4,532,926 A | 8/1985 | O'Holla |
| 4,545,374 A | 10/1985 | Jacobson |
| 4,602,635 A | 7/1986 | Mulhollan et al. |
| 4,632,100 A | 12/1986 | Somers et al. |
| 4,663,358 A | 5/1987 | Hyon et al. |
| 4,669,473 A | 6/1987 | Richards et al. |
| 4,678,459 A | 7/1987 | Onik et al. |
| 4,736,746 A | 4/1988 | Anderson |
| 4,741,330 A | 5/1988 | Hayhurst |
| 4,743,260 A | 5/1988 | Burton |
| 4,744,364 A | 5/1988 | Kensey |
| 4,772,287 A | 9/1988 | Ray et al. |
| 4,781,190 A | 11/1988 | Lee |
| 4,790,303 A | 12/1988 | Steffee |
| 4,798,205 A | 1/1989 | Bonomo et al. |
| 4,834,757 A | 5/1989 | Brantigan |
| 4,837,285 A | 6/1989 | Berg et al. |
| 4,844,088 A | 7/1989 | Kambin |
| 4,852,568 A | 8/1989 | Kensey |
| 4,861,162 A | 8/1989 | Ina |
| 4,863,477 A | 9/1989 | Monson |
| 4,873,976 A | 10/1989 | Schreiber |
| 4,883,359 A | 11/1989 | Ina et al. |
| 4,884,572 A | 12/1989 | Bays et al. |
| 4,890,612 A | 1/1990 | Kensey |
| 4,895,148 A | 1/1990 | Bays et al. |
| 4,901,109 A | 2/1990 | Mitome et al. |
| 4,904,260 A | 2/1990 | Ray et al. |
| 4,904,261 A | 2/1990 | Dove et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,946,378 A | 8/1990 | Hirayama et al. |
| 4,955,908 A | 9/1990 | Frey et al. |
| 4,976,715 A | 12/1990 | Bays et al. |
| 5,002,576 A | 3/1991 | Fuhrmann et al. |
| 5,015,255 A | 5/1991 | Kuslich |

(56) References Cited

U.S. PATENT DOCUMENTS

| | | |
|---|---|---|
| 5,021,059 A | 6/1991 | Kensey et al. |
| 5,035,716 A | 7/1991 | Downey |
| 5,041,129 A | 8/1991 | Hayhurst et al. |
| 5,047,055 A | 9/1991 | Bao |
| 5,053,046 A | 10/1991 | Janese |
| 5,059,193 A | 10/1991 | Kuslich |
| 5,059,206 A | 10/1991 | Winters |
| 5,061,274 A | 10/1991 | Kensey |
| 5,062,344 A | 11/1991 | Gerker |
| 5,071,437 A | 12/1991 | Steffee |
| 5,085,661 A | 2/1992 | Moss |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,154 A | 6/1992 | Rhodes |
| 5,122,155 A | 6/1992 | Eberbach |
| 5,123,913 A | 6/1992 | Wilk et al. |
| 5,123,926 A | 6/1992 | Pisharodi |
| 5,129,912 A | 7/1992 | Noda et al. |
| 5,141,515 A | 8/1992 | Eberbach |
| 5,147,374 A | 9/1992 | Fernandez |
| 5,171,259 A | 12/1992 | Inoue |
| 5,171,278 A | 12/1992 | Pisharodi |
| 5,171,280 A | 12/1992 | Baumgartner |
| 5,171,281 A | 12/1992 | Parsons et al. |
| 5,176,682 A | 1/1993 | Chow |
| 5,176,691 A | 1/1993 | Pierce |
| 5,176,692 A | 1/1993 | Wilk et al. |
| 5,192,326 A | 3/1993 | Bao et al. |
| 5,195,541 A | 3/1993 | Obenchain |
| 5,203,787 A | 4/1993 | Noblitt et al. |
| 5,204,106 A | 4/1993 | Schepers et al. |
| 5,207,695 A | 5/1993 | Trout |
| 5,222,962 A | 6/1993 | Burkhart |
| 5,222,974 A | 6/1993 | Kensey et al. |
| 5,242,439 A | 9/1993 | Larsen et al. |
| 5,254,133 A | 10/1993 | Seid |
| 5,258,000 A | 11/1993 | Gianturco |
| 5,258,043 A | 11/1993 | Stone |
| 5,269,783 A | 12/1993 | Sander |
| 5,269,791 A | 12/1993 | Mayzels et al. |
| 5,269,809 A | 12/1993 | Hayhurst et al. |
| 5,282,827 A | 2/1994 | Kensey et al. |
| 5,282,863 A | 2/1994 | Burton |
| 5,304,194 A | 4/1994 | Chee et al. |
| 5,306,311 A | 4/1994 | Stone et al. |
| 5,312,435 A | 5/1994 | Nash et al. |
| 5,313,962 A | 5/1994 | Obenchain |
| 5,320,629 A | 6/1994 | Noda et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,344,442 A | 9/1994 | Deac |
| 5,350,399 A | 9/1994 | Erlebacher |
| 5,354,736 A | 10/1994 | Bhatnagar |
| 5,356,432 A | 10/1994 | Rutkow et al. |
| 5,366,460 A | 11/1994 | Eberbach |
| 5,368,602 A | 11/1994 | de la Torre |
| 5,369,486 A | 11/1994 | Matsumoto et al. |
| 5,370,660 A | 12/1994 | Weinstein et al. |
| 5,370,662 A | 12/1994 | Stone et al. |
| 5,370,697 A | 12/1994 | Baumgartner |
| 5,374,268 A | 12/1994 | Sander |
| 5,376,120 A | 12/1994 | Sarver et al. |
| 5,383,477 A | 1/1995 | DeMatteis |
| 5,383,905 A | 1/1995 | Golds et al. |
| 5,390,683 A | 2/1995 | Pisharodi |
| 5,391,182 A | 2/1995 | Chin |
| 5,397,326 A | 3/1995 | Mangum |
| 5,397,331 A | 3/1995 | Himpens et al. |
| 5,397,332 A | 3/1995 | Kammerer et al. |
| 5,397,991 A | 3/1995 | Rogers |
| 5,398,861 A | 3/1995 | Green |
| 5,405,352 A | 4/1995 | Weston |
| 5,405,359 A | 4/1995 | Pierce |
| 5,405,360 A | 4/1995 | Tovey |
| 5,407,763 A | 4/1995 | Pai |
| 5,411,520 A | 5/1995 | Nash |
| 5,411,523 A | 5/1995 | Goble |
| 5,417,691 A | 5/1995 | Hayhurst |
| 5,417,699 A | 5/1995 | Klein et al. |
| 5,425,772 A | 6/1995 | Brantigan |
| 5,425,773 A | 6/1995 | Boyd et al. |
| 5,429,598 A | 7/1995 | Waxman et al. |
| 5,437,631 A | 8/1995 | Janzen |
| 5,437,680 A | 8/1995 | Yoon |
| 5,439,464 A | 8/1995 | Shapiro |
| 5,441,502 A | 8/1995 | Bartlett |
| 5,456,720 A | 10/1995 | Schultz et al. |
| 5,464,407 A | 11/1995 | McGuire |
| 5,464,426 A | 11/1995 | Bonutti |
| 5,470,337 A | 11/1995 | Moss |
| 5,478,353 A | 12/1995 | Yoon |
| 5,489,307 A | 2/1996 | Kuslich et al. |
| 5,492,697 A | 2/1996 | Boyan et al. |
| 5,496,348 A | 3/1996 | Bonutti |
| 5,500,000 A | 3/1996 | Feagin et al. |
| 5,507,754 A | 4/1996 | Green et al. |
| 5,507,755 A | 4/1996 | Gresl et al. |
| 5,514,180 A | 5/1996 | Heggeness et al. |
| 5,520,696 A | 5/1996 | Wenstrom, Jr. |
| 5,520,700 A | 5/1996 | Beyar et al. |
| 5,527,342 A | 6/1996 | Pietrzak et al. |
| 5,527,343 A | 6/1996 | Bonutti |
| 5,531,678 A | 7/1996 | Tomba et al. |
| 5,531,759 A | 7/1996 | Kensey et al. |
| 5,534,012 A | 7/1996 | Bonutti |
| 5,534,028 A | 7/1996 | Bao et al. |
| 5,534,030 A | 7/1996 | Navarro et al. |
| 5,540,704 A | 7/1996 | Gordon et al. |
| 5,540,715 A | 7/1996 | Katsaros et al. |
| 5,543,921 A | 8/1996 | Uzawa et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,556,428 A | 9/1996 | Shah |
| 5,556,429 A | 9/1996 | Felt |
| 5,562,684 A | 10/1996 | Kammerer |
| 5,562,689 A | 10/1996 | Green et al. |
| 5,562,736 A | 10/1996 | Ray et al. |
| 5,562,738 A | 10/1996 | Boyd et al. |
| 5,569,242 A | 10/1996 | Lax et al. |
| 5,569,252 A | 10/1996 | Justin et al. |
| 5,569,303 A | 10/1996 | Johnson |
| 5,569,306 A | 10/1996 | Thal |
| 5,571,189 A | 11/1996 | Kuslich |
| 5,573,286 A | 11/1996 | Rogozinski |
| 5,573,548 A | 11/1996 | Nazre |
| 5,578,057 A | 11/1996 | Wenstrom, Jr. |
| 5,582,616 A | 12/1996 | Bolduc et al. |
| 5,584,862 A | 12/1996 | Bonutti |
| 5,591,177 A | 1/1997 | Lehrer |
| 5,591,223 A | 1/1997 | Lock et al. |
| 5,593,425 A | 1/1997 | Bonutti et al. |
| 5,599,279 A | 2/1997 | Slotman et al. |
| 5,601,557 A | 2/1997 | Hayhurst |
| 5,613,974 A | 3/1997 | Andreas et al. |
| 5,618,314 A | 4/1997 | Harwin |
| 5,620,012 A | 4/1997 | Benderev et al. |
| 5,624,463 A | 4/1997 | Stone et al. |
| 5,626,612 A | 5/1997 | Bartlett et al. |
| 5,626,613 A | 5/1997 | Schmieding |
| 5,626,614 A | 5/1997 | Hart |
| 5,634,931 A | 6/1997 | Kugel |
| 5,634,944 A | 6/1997 | Magram |
| 5,643,319 A | 7/1997 | Green et al. |
| 5,643,320 A | 7/1997 | Lower et al. |
| 5,645,084 A | 7/1997 | McKay |
| 5,645,597 A | 7/1997 | Krapiva |
| 5,649,945 A | 7/1997 | Ray et al. |
| 5,658,343 A | 8/1997 | Hauselmann et al. |

(56) References Cited

U.S. PATENT DOCUMENTS

| | | |
|---|---|---|
| 5,662,658 A | 9/1997 | Wenstrom, Jr. |
| 5,662,681 A | 9/1997 | Nash et al. |
| 5,662,683 A | 9/1997 | Kay |
| 5,669,935 A | 9/1997 | Rosenman et al. |
| 5,674,294 A | 10/1997 | Bainville et al. |
| 5,674,296 A | 10/1997 | Bryan et al. |
| 5,676,698 A | 10/1997 | Janzen et al. |
| 5,676,701 A | 10/1997 | Yuan et al. |
| 5,681,310 A | 10/1997 | Yuan et al. |
| 5,681,351 A | 10/1997 | Jamiolkowski et al. |
| 5,683,417 A | 11/1997 | Cooper |
| 5,683,418 A | 11/1997 | Luscombe et al. |
| 5,683,419 A | 11/1997 | Thal |
| 5,683,465 A | 11/1997 | Shinn et al. |
| 5,695,525 A | 12/1997 | Mulhauser et al. |
| 5,697,950 A | 12/1997 | Fucci et al. |
| 5,702,449 A | 12/1997 | McKay |
| 5,702,450 A | 12/1997 | Bisserie |
| 5,702,451 A | 12/1997 | Biedermann et al. |
| 5,702,454 A | 12/1997 | Baumgartner |
| 5,702,462 A | 12/1997 | Oberlander |
| 5,704,943 A | 1/1998 | Yoon et al. |
| 5,716,404 A | 2/1998 | Vacanti et al. |
| 5,716,408 A | 2/1998 | Eldridge et al. |
| 5,716,409 A | 2/1998 | Debbas |
| 5,716,413 A | 2/1998 | Walter et al. |
| 5,716,416 A | 2/1998 | Lin |
| 5,717,492 A | 2/1998 | Sentoku et al. |
| 5,718,717 A | 2/1998 | Bonutti |
| 5,725,552 A | 3/1998 | Kotula et al. |
| 5,725,577 A | 3/1998 | Saxon |
| 5,728,109 A | 3/1998 | Schulze et al. |
| 5,728,150 A | 3/1998 | McDonald et al. |
| 5,730,744 A | 3/1998 | Justin et al. |
| 5,733,307 A | 3/1998 | Dinsdale |
| 5,733,337 A | 3/1998 | Carr, Jr. et al. |
| 5,735,875 A | 4/1998 | Bonutti |
| 5,736,746 A | 4/1998 | Furutoh |
| 5,741,277 A | 4/1998 | Gordon et al. |
| 5,743,917 A | 4/1998 | Saxon |
| 5,746,755 A | 5/1998 | Wood et al. |
| 5,752,964 A | 5/1998 | Mericle |
| 5,755,797 A | 5/1998 | Baumgartner |
| 5,759,189 A | 6/1998 | Ferragamo et al. |
| 5,766,246 A | 6/1998 | Mulhauser et al. |
| 5,769,864 A | 6/1998 | Kugel |
| 5,769,893 A | 6/1998 | Shah |
| 5,772,661 A | 6/1998 | Michelson |
| 5,776,183 A | 7/1998 | Kanesaka et al. |
| 5,782,844 A | 7/1998 | Yoon et al. |
| 5,782,860 A | 7/1998 | Epstein et al. |
| 5,782,864 A | 7/1998 | Lizardi |
| 5,785,705 A | 7/1998 | Baker |
| 5,786,217 A | 7/1998 | Tubo et al. |
| 5,788,625 A | 8/1998 | Plouhar et al. |
| 5,792,152 A | 8/1998 | Klein et al. |
| 5,797,929 A | 8/1998 | Andreas et al. |
| 5,800,549 A | 9/1998 | Bao et al. |
| 5,800,550 A | 9/1998 | Sertich |
| 5,810,848 A | 9/1998 | Hayhurst |
| 5,810,851 A | 9/1998 | Yoon |
| 5,814,051 A | 9/1998 | Wenstrom, Jr. |
| 5,815,594 A | 9/1998 | Tanaka |
| 5,823,994 A | 10/1998 | Sharkey et al. |
| 5,824,008 A | 10/1998 | Bolduc et al. |
| 5,824,011 A | 10/1998 | Stone et al. |
| 5,824,082 A | 10/1998 | Brown |
| 5,824,093 A | 10/1998 | Ray et al. |
| 5,824,094 A | 10/1998 | Serhan et al. |
| 5,827,298 A | 10/1998 | Hart et al. |
| 5,827,325 A | 10/1998 | Landgrebe et al. |
| 5,827,328 A | 10/1998 | Buttermann |
| 5,836,315 A | 11/1998 | Benderev et al. |
| 5,842,477 A | 12/1998 | Naughton et al. |
| 5,843,084 A | 12/1998 | Hart et al. |
| 5,846,261 A | 12/1998 | Kotula et al. |
| 5,849,331 A | 12/1998 | Ducheyne et al. |
| 5,851,219 A | 12/1998 | Goble et al. |
| 5,853,422 A | 12/1998 | Huebsch et al. |
| 5,855,614 A | 1/1999 | Stevens et al. |
| 5,860,425 A | 1/1999 | Benderev et al. |
| 5,860,977 A | 1/1999 | Zucherman et al. |
| 5,861,004 A | 1/1999 | Kensey |
| 5,865,845 A | 2/1999 | Thalgott |
| 5,865,846 A | 2/1999 | Bryan et al. |
| 5,868,762 A | 2/1999 | Cragg et al. |
| 5,879,366 A | 3/1999 | Shaw et al. |
| 5,881,165 A | 3/1999 | Tanaka |
| 5,888,220 A | 3/1999 | Felt et al. |
| 5,888,222 A | 3/1999 | Coates |
| 5,888,226 A | 3/1999 | Rogozinski |
| 5,891,146 A | 4/1999 | Simon et al. |
| 5,893,592 A | 4/1999 | Schulze et al. |
| 5,893,889 A | 4/1999 | Harrington |
| 5,895,426 A | 4/1999 | Scarborough et al. |
| 5,899,920 A | 5/1999 | DeSatnick et al. |
| 5,904,703 A | 5/1999 | Gilson et al. |
| 5,916,225 A | 6/1999 | Kugel |
| 5,919,235 A | 7/1999 | Husson et al. |
| 5,922,026 A | 7/1999 | Chin |
| 5,922,028 A | 7/1999 | Plouhar et al. |
| 5,928,284 A | 7/1999 | Mehdizadeh |
| 5,935,147 A | 8/1999 | Kensey et al. |
| 5,940,528 A | 8/1999 | Tanaka et al. |
| 5,941,439 A | 8/1999 | Kammerer et al. |
| 5,944,738 A | 8/1999 | Amplatz et al. |
| 5,948,001 A | 9/1999 | Larsen |
| 5,948,002 A | 9/1999 | Bonutti |
| 5,954,716 A | 9/1999 | Sharkey et al. |
| 5,954,767 A | 9/1999 | Pajotin et al. |
| 5,957,939 A | 9/1999 | Heaven et al. |
| 5,961,538 A | 10/1999 | Pedlick et al. |
| 5,964,783 A | 10/1999 | Grafton et al. |
| 5,964,807 A | 10/1999 | Gan et al. |
| 5,972,000 A | 10/1999 | Beyar et al. |
| 5,972,007 A | 10/1999 | Sheffield et al. |
| 5,972,022 A | 10/1999 | Huxel |
| 5,976,174 A | 11/1999 | Ruiz |
| 5,976,186 A | 11/1999 | Bao et al. |
| 5,980,504 A | 11/1999 | Sharkey et al. |
| 5,980,558 A | 11/1999 | Wiley |
| 5,984,948 A | 11/1999 | Hasson |
| 5,995,198 A | 11/1999 | Mizutani |
| 6,001,130 A | 12/1999 | Bryan et al. |
| 6,007,567 A | 12/1999 | Bonutti |
| 6,007,570 A | 12/1999 | Sharkey et al. |
| 6,007,575 A | 12/1999 | Samuels |
| 6,010,525 A | 1/2000 | Bonutti et al. |
| 6,019,792 A | 2/2000 | Cauthen |
| 6,019,793 A | 2/2000 | Perren et al. |
| 6,024,096 A | 2/2000 | Buckberg |
| 6,024,754 A | 2/2000 | Engelson |
| 6,024,758 A | 2/2000 | Thal |
| 6,027,523 A | 2/2000 | Schmieding |
| 6,027,527 A | 2/2000 | Asano et al. |
| 6,036,699 A | 3/2000 | Andreas et al. |
| 6,039,761 A | 3/2000 | Li et al. |
| 6,039,762 A | 3/2000 | McKay |
| 6,045,561 A | 4/2000 | Marshall et al. |
| 6,045,573 A | 4/2000 | Wenstrom, Jr. et al. |
| 6,053,909 A | 4/2000 | Shadduck |
| 6,063,378 A | 5/2000 | Nohara et al. |
| 6,066,146 A | 5/2000 | Carroll et al. |
| 6,066,776 A | 5/2000 | Goodwin et al. |
| 6,073,051 A | 6/2000 | Sharkey et al. |
| 6,080,182 A | 6/2000 | Shaw et al. |
| 6,093,205 A | 7/2000 | McLeod et al. |
| 6,095,149 A | 8/2000 | Sharkey et al. |
| 6,099,514 A | 8/2000 | Sharkey et al. |
| 6,102,934 A | 8/2000 | Li |
| 6,106,545 A | 8/2000 | Egan |
| 6,112,853 A | 9/2000 | Beard |
| 6,113,609 A | 9/2000 | Adams |
| 6,113,623 A | 9/2000 | Sgro |

(56) References Cited

U.S. PATENT DOCUMENTS

| | | |
|---|---|---|
| 6,113,639 A | 9/2000 | Ray et al. |
| 6,117,162 A | 9/2000 | Schmieding et al. |
| 6,123,133 A | 9/2000 | Kim et al. |
| 6,123,715 A | 9/2000 | Amplatz |
| 6,126,682 A | 10/2000 | Sharkey et al. |
| 6,133,534 A | 10/2000 | Fukutomi et al. |
| 6,139,565 A | 10/2000 | Stone et al. |
| 6,140,452 A | 10/2000 | Felt et al. |
| 6,143,006 A | 11/2000 | Chan et al. |
| 6,143,017 A * | 11/2000 | Thal ............... 606/232 |
| 6,146,380 A | 11/2000 | Racz et al. |
| 6,146,406 A | 11/2000 | Shluzas et al. |
| 6,146,422 A | 11/2000 | Lawson |
| 6,152,144 A | 11/2000 | Lesh et al. |
| 6,162,203 A | 12/2000 | Haaga |
| 6,168,598 B1 | 1/2001 | Martello |
| 6,171,317 B1 | 1/2001 | Jackson et al. |
| 6,171,318 B1 | 1/2001 | Kugel et al. |
| 6,171,329 B1 | 1/2001 | Shaw et al. |
| 6,174,322 B1 | 1/2001 | Schneidt |
| 6,176,863 B1 | 1/2001 | Kugel et al. |
| 6,179,874 B1 | 1/2001 | Cauthen |
| 6,179,879 B1 | 1/2001 | Robinson et al. |
| 6,183,479 B1 | 2/2001 | Tormala et al. |
| 6,183,518 B1 | 2/2001 | Ross et al. |
| 6,187,048 B1 | 2/2001 | Milner et al. |
| 6,190,401 B1 | 2/2001 | Green et al. |
| 6,200,329 B1 | 3/2001 | Fung et al. |
| 6,203,554 B1 | 3/2001 | Roberts |
| 6,203,565 B1 | 3/2001 | Bonutti |
| 6,206,895 B1 | 3/2001 | Levinson |
| 6,206,921 B1 | 3/2001 | Guagliano et al. |
| 6,221,092 B1 | 4/2001 | Koike et al. |
| 6,221,109 B1 | 4/2001 | Geistlich et al. |
| 6,224,630 B1 | 5/2001 | Bao et al. |
| 6,231,561 B1 | 5/2001 | Frazier et al. |
| 6,231,615 B1 | 5/2001 | Preissman |
| 6,241,768 B1 | 6/2001 | Agarwal et al. |
| 6,245,080 B1 | 6/2001 | Levinson |
| 6,245,107 B1 | 6/2001 | Ferree |
| 6,248,106 B1 | 6/2001 | Ferree |
| 6,248,131 B1 | 6/2001 | Felt et al. |
| 6,258,094 B1 | 7/2001 | Nicholson et al. |
| 6,264,677 B1 | 7/2001 | Simon et al. |
| 6,267,772 B1 | 7/2001 | Mulhauser et al. |
| 6,280,453 B1 | 8/2001 | Kugel et al. |
| 6,287,324 B1 | 9/2001 | Yarnitsky et al. |
| 6,293,961 B2 | 9/2001 | Schwartz et al. |
| 6,296,659 B1 | 10/2001 | Foerster |
| 6,306,159 B1 | 10/2001 | Schwartz et al. |
| 6,306,177 B1 | 10/2001 | Felt et al. |
| 6,312,446 B1 | 11/2001 | Huebsch et al. |
| 6,312,448 B1 | 11/2001 | Bonutti |
| 6,319,263 B1 | 11/2001 | Levinson |
| 6,332,894 B1 | 12/2001 | Stalcup |
| 6,340,369 B1 | 1/2002 | Ferree |
| 6,342,064 B1 | 1/2002 | Koike et al. |
| 6,344,057 B1 | 2/2002 | Rabbe et al. |
| 6,344,058 B1 | 2/2002 | Ferree |
| 6,352,557 B1 | 3/2002 | Ferree |
| 6,355,052 B1 | 3/2002 | Neuss |
| 6,364,897 B1 | 4/2002 | Bonutti |
| 6,371,984 B1 | 4/2002 | Van Dyke et al. |
| 6,371,990 B1 | 4/2002 | Ferree |
| 6,391,060 B1 | 5/2002 | Ory et al. |
| 6,402,750 B1 | 6/2002 | Atkinson et al. |
| 6,402,784 B1 | 6/2002 | Wardlaw |
| 6,402,785 B1 | 6/2002 | Zdeblick et al. |
| 6,409,739 B1 | 6/2002 | Nobles et al. |
| 6,419,676 B1 | 7/2002 | Zucherman et al. |
| 6,419,702 B1 | 7/2002 | Ferree |
| 6,419,703 B1 | 7/2002 | Fallin et al. |
| 6,419,704 B1 | 7/2002 | Ferree |
| 6,419,706 B1 | 7/2002 | Graf |
| 6,423,065 B2 | 7/2002 | Ferree |
| 6,424,924 B1 | 7/2002 | Wagner et al. |
| 6,425,107 B1 | 7/2002 | Caldara et al. |
| 6,425,919 B1 | 7/2002 | Lambrecht |
| 6,425,924 B1 | 7/2002 | Rousseau |
| 6,428,562 B2 | 8/2002 | Bonutti |
| 6,428,576 B1 | 8/2002 | Haldimann |
| 6,432,107 B1 | 8/2002 | Ferree |
| 6,432,123 B2 | 8/2002 | Schwartz et al. |
| 6,436,098 B1 | 8/2002 | Michelson |
| 6,436,143 B1 | 8/2002 | Ross et al. |
| 6,443,988 B2 | 9/2002 | Felt et al. |
| 6,447,531 B1 | 9/2002 | Amplatz |
| 6,452,924 B1 | 9/2002 | Golden et al. |
| 6,454,804 B1 | 9/2002 | Ferree |
| 6,461,364 B1 | 10/2002 | Ginn et al. |
| 6,464,712 B1 | 10/2002 | Epstein |
| 6,482,235 B1 | 11/2002 | Lambrecht et al. |
| 6,488,691 B1 | 12/2002 | Carroll et al. |
| 6,491,724 B1 | 12/2002 | Ferree |
| 6,494,883 B1 | 12/2002 | Ferree |
| 6,500,132 B1 | 12/2002 | Li |
| 6,500,164 B1 | 12/2002 | Turner et al. |
| 6,500,184 B1 | 12/2002 | Chan et al. |
| 6,503,266 B1 | 1/2003 | Akerfeldt et al. |
| 6,506,204 B2 | 1/2003 | Mazzocchi |
| 6,508,828 B1 | 1/2003 | Akerfeldt et al. |
| 6,508,839 B1 | 1/2003 | Lambrecht et al. |
| 6,511,488 B1 | 1/2003 | Marshall et al. |
| 6,511,498 B1 | 1/2003 | Fumex |
| 6,511,958 B1 | 1/2003 | Atkinson et al. |
| 6,514,255 B1 | 2/2003 | Ferree |
| 6,514,514 B1 | 2/2003 | Atkinson et al. |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,530,933 B1 | 3/2003 | Yeung et al. |
| 6,533,799 B1 | 3/2003 | Bouchier |
| 6,533,817 B1 | 3/2003 | Norton et al. |
| 6,547,800 B2 | 4/2003 | Foerster et al. |
| 6,547,806 B1 | 4/2003 | Ding |
| 6,558,386 B1 | 5/2003 | Cragg |
| 6,558,390 B2 | 5/2003 | Cragg |
| 6,562,052 B2 | 5/2003 | Nobles et al. |
| 6,569,187 B1 | 5/2003 | Bonutti et al. |
| 6,569,442 B2 | 5/2003 | Gan et al. |
| 6,572,635 B1 | 6/2003 | Bonutti |
| 6,572,653 B1 | 6/2003 | Simonson |
| 6,575,979 B1 | 6/2003 | Cragg |
| 6,576,017 B2 | 6/2003 | Foley et al. |
| 6,579,291 B1 | 6/2003 | Keith et al. |
| 6,582,453 B1 | 6/2003 | Tran et al. |
| 6,592,608 B2 | 7/2003 | Fisher et al. |
| 6,592,609 B1 | 7/2003 | Bonutti |
| 6,592,625 B2 | 7/2003 | Cauthen |
| 6,596,012 B2 | 7/2003 | Akerfeldt et al. |
| 6,602,291 B1 | 8/2003 | Ray et al. |
| 6,605,096 B1 | 8/2003 | Ritchart |
| 6,607,541 B1 | 8/2003 | Gardiner et al. |
| 6,610,006 B1 | 8/2003 | Amid et al. |
| 6,610,071 B1 | 8/2003 | Cohn et al. |
| 6,610,079 B1 | 8/2003 | Li et al. |
| 6,610,091 B1 | 8/2003 | Reiley |
| 6,610,666 B1 | 8/2003 | Akerblom |
| 6,613,044 B2 | 9/2003 | Carl |
| 6,620,165 B2 | 9/2003 | Wellisz et al. |
| 6,620,185 B1 | 9/2003 | Harvie et al. |
| 6,620,196 B1 | 9/2003 | Trieu |
| 6,623,492 B1 | 9/2003 | Berube et al. |
| 6,623,506 B2 | 9/2003 | McGuckin, Jr. et al. |
| 6,623,508 B2 | 9/2003 | Shaw et al. |
| 6,626,899 B2 | 9/2003 | Houser et al. |
| 6,626,916 B1 | 9/2003 | Yeung et al. |
| 6,635,073 B2 | 10/2003 | Bonutti et al. |
| 6,645,227 B2 | 11/2003 | Fallin et al. |
| 6,645,247 B2 | 11/2003 | Ferree |
| 6,648,918 B2 | 11/2003 | Ferree |
| 6,648,919 B2 | 11/2003 | Ferree |
| 6,648,920 B2 | 11/2003 | Ferree |
| 6,652,561 B1 | 11/2003 | Tran |

(56) References Cited

U.S. PATENT DOCUMENTS

| | | |
|---|---|---|
| 6,652,585 B2 | 11/2003 | Lange |
| 6,656,182 B1 | 12/2003 | Hayhurst |
| 6,669,687 B1 | 12/2003 | Saadat |
| 6,669,707 B1 | 12/2003 | Swanstrom et al. |
| 6,669,729 B2 | 12/2003 | Chin |
| 6,673,088 B1 | 1/2004 | Vargas et al. |
| 6,676,665 B2 | 1/2004 | Foley et al. |
| 6,679,887 B2 | 1/2004 | Nicholson et al. |
| 6,679,914 B1 | 1/2004 | Gabbay |
| 6,684,886 B1 | 2/2004 | Alleyne |
| 6,685,695 B2 | 2/2004 | Ferree |
| 6,685,728 B2 | 2/2004 | Sinnott et al. |
| 6,689,125 B1 | 2/2004 | Keith et al. |
| 6,692,506 B1 | 2/2004 | Ory et al. |
| 6,695,858 B1 | 2/2004 | Dubrul et al. |
| 6,696,073 B2 | 2/2004 | Boyce |
| 6,699,263 B2 | 3/2004 | Cope |
| 6,706,068 B2 | 3/2004 | Ferree |
| 6,712,836 B1 | 3/2004 | Berg et al. |
| 6,712,837 B2 | 3/2004 | Åkerfeldt et al. |
| 6,712,853 B2 | 3/2004 | Kuslich |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,719,797 B1 | 4/2004 | Ferree |
| 6,723,058 B2 | 4/2004 | Li |
| 6,723,095 B2 | 4/2004 | Hammerslag |
| 6,723,097 B2 | 4/2004 | Fraser et al. |
| 6,723,107 B1 | 4/2004 | Skiba et al. |
| 6,723,133 B1 | 4/2004 | Pajotin |
| 6,723,335 B2 | 4/2004 | Moehlenbruck et al. |
| 6,726,696 B1 | 4/2004 | Houser |
| 6,726,721 B2 | 4/2004 | Stay et al. |
| 6,730,112 B2 | 5/2004 | Levinson |
| 6,733,531 B1 | 5/2004 | Trieu |
| 6,733,534 B2 | 5/2004 | Sherman |
| 6,736,815 B2 | 5/2004 | Ginn |
| 6,740,093 B2 | 5/2004 | Hochschuler et al. |
| 6,743,255 B2 | 6/2004 | Ferree |
| 6,752,831 B2 | 6/2004 | Sybert et al. |
| 6,758,863 B2 | 7/2004 | Estes |
| 6,761,720 B1 | 7/2004 | Senegas |
| 6,764,514 B1 | 7/2004 | Li et al. |
| 6,767,037 B2 | 7/2004 | Wenstrom |
| 6,770,076 B2 | 8/2004 | Foerster |
| 6,773,436 B2 | 8/2004 | Donnelly et al. |
| 6,773,699 B1 | 8/2004 | Soltz et al. |
| 6,780,198 B1 | 8/2004 | Gregoire et al. |
| 6,783,546 B2 | 8/2004 | Zuckerman et al. |
| 6,805,695 B2 | 10/2004 | Keith et al. |
| 6,805,697 B1 | 10/2004 | Helm et al. |
| 6,805,715 B2 | 10/2004 | Reuter et al. |
| 6,812,211 B2 | 11/2004 | Slivka et al. |
| 6,821,276 B2 | 11/2004 | Lambrecht et al. |
| 6,824,562 B2 | 11/2004 | Mathis et al. |
| 6,827,716 B2 | 12/2004 | Ryan et al. |
| 6,827,743 B2 | 12/2004 | Eisermann et al. |
| 6,830,570 B1 | 12/2004 | Frey et al. |
| 6,833,006 B2 | 12/2004 | Foley et al. |
| 6,835,205 B2 | 12/2004 | Atkinson et al. |
| 6,835,207 B2 | 12/2004 | Iacouto et al. |
| 6,835,208 B2 | 12/2004 | Marchosky |
| 6,841,150 B2 | 1/2005 | Halvorsen et al. |
| 6,843,799 B2 | 1/2005 | Bartlett |
| 6,852,128 B2 | 2/2005 | Lange |
| 6,860,895 B1 | 3/2005 | Akerfeldt et al. |
| 6,878,155 B2 | 4/2005 | Sharkey et al. |
| 6,878,167 B2 | 4/2005 | Ferree |
| 6,883,520 B2 | 4/2005 | Lambrecht et al. |
| 6,893,462 B2 | 5/2005 | Buskirk et al. |
| 6,896,675 B2 | 5/2005 | Leung et al. |
| 6,913,622 B2 | 7/2005 | Gjunter |
| 6,923,823 B1 | 8/2005 | Bartlett et al. |
| 6,932,833 B1 | 8/2005 | Sandoval et al. |
| 6,936,070 B1 | 8/2005 | Muhanna |
| 6,936,072 B2 | 8/2005 | Lambrecht et al. |
| 6,960,215 B2 | 11/2005 | Olson, Jr. et al. |
| 6,964,674 B1 | 11/2005 | Matsuura et al. |
| 6,966,910 B2 | 11/2005 | Ritland |
| 6,966,931 B2 | 11/2005 | Huang |
| 6,969,404 B2 | 11/2005 | Ferree |
| 6,972,027 B2 | 12/2005 | Fallin et al. |
| 6,974,479 B2 | 12/2005 | Trieu |
| 6,980,862 B2 | 12/2005 | Fredricks et al. |
| 6,984,247 B2 | 1/2006 | Cauthen |
| 6,997,956 B2 | 2/2006 | Cauthen |
| 7,001,431 B2 | 2/2006 | Bao et al. |
| 7,004,970 B2 | 2/2006 | Cauthen |
| 7,033,393 B2 | 4/2006 | Gainor et al. |
| 7,033,395 B2 | 4/2006 | Cauthen |
| 7,037,334 B1 | 5/2006 | Hlavka et al. |
| 7,052,516 B2 | 5/2006 | Cauthen, III et al. |
| 7,128,073 B1 | 10/2006 | Van der Burg |
| 7,153,312 B1 | 12/2006 | Torrie et al. |
| 7,160,314 B2 | 1/2007 | Sgro et al. |
| 7,189,235 B2 | 3/2007 | Cauthen |
| 7,217,279 B2 | 5/2007 | Reese |
| 7,223,289 B2 | 5/2007 | Trieu et al. |
| 7,309,337 B2 | 12/2007 | Colleran et al. |
| 7,318,840 B2 | 1/2008 | McKay |
| 7,320,701 B2 | 1/2008 | Haut et al. |
| 7,322,978 B2 | 1/2008 | West, Jr. |
| 7,329,272 B2 | 2/2008 | Burkhart et al. |
| 7,331,982 B1 | 2/2008 | Kaiser et al. |
| 7,371,253 B2 | 5/2008 | Leung et al. |
| 7,390,332 B2 | 6/2008 | Selvitelli et al. |
| 7,445,634 B2 | 11/2008 | Trieu |
| 7,615,076 B2 | 11/2009 | Cauthen, III et al. |
| 7,670,380 B2 | 3/2010 | Cauthen, III |
| 7,749,273 B2 | 7/2010 | Cauthen, III |
| 7,776,096 B2 | 8/2010 | Cauthen |
| 7,828,850 B2 | 11/2010 | Cauthen |
| 7,846,208 B2 | 12/2010 | Cauthen, III |
| 7,909,879 B2 | 3/2011 | Cauthen |
| 7,922,768 B2 | 4/2011 | Cauthen, III |
| 7,935,147 B2 | 5/2011 | Wales |
| 7,951,201 B2 | 5/2011 | Cauthen |
| 7,985,257 B2 | 7/2011 | Cauthen, III |
| 7,993,405 B2 | 8/2011 | Cauthen, III |
| 8,034,112 B2 | 10/2011 | Cauthen, III |
| 2001/0004710 A1 | 6/2001 | Felt et al. |
| 2001/0041916 A1 | 11/2001 | Bonutti |
| 2002/0019649 A1* | 2/2002 | Sikora et al. ............. 606/232 |
| 2002/0032483 A1 | 3/2002 | Nicholson et al. |
| 2002/0077701 A1 | 6/2002 | Kuslich |
| 2002/0082698 A1 | 6/2002 | Parenteau et al. |
| 2002/0111688 A1 | 8/2002 | Cauthen |
| 2002/0123750 A1 | 9/2002 | Eisermann et al. |
| 2002/0123807 A1 | 9/2002 | Cauthen, III |
| 2002/0147461 A1 | 10/2002 | Aldrich |
| 2002/0151979 A1 | 10/2002 | Lambrecht et al. |
| 2002/0173851 A1 | 11/2002 | McKay |
| 2003/0040796 A1 | 2/2003 | Ferree |
| 2003/0074075 A1 | 4/2003 | Thomas |
| 2003/0078579 A1 | 4/2003 | Ferree |
| 2003/0130669 A1* | 7/2003 | Damarati ............. 606/151 |
| 2003/0153976 A1 | 8/2003 | Cauthen, III et al. |
| 2003/0181193 A1 | 9/2003 | Wilhelmsson et al. |
| 2003/0181983 A1 | 9/2003 | Cauthen |
| 2003/0187445 A1 | 10/2003 | Keith et al. |
| 2003/0195514 A1 | 10/2003 | Trieu et al. |
| 2003/0195628 A1 | 10/2003 | Bao et al. |
| 2003/0220649 A1 | 11/2003 | Bao et al. |
| 2003/0220690 A1 | 11/2003 | Cauthen, III |
| 2003/0220693 A1 | 11/2003 | Cauthen, III |
| 2003/0220694 A1 | 11/2003 | Cauthen, III |
| 2004/0039392 A1 | 2/2004 | Trieu |
| 2004/0054414 A1 | 3/2004 | Trieu et al. |
| 2004/0092969 A1 | 5/2004 | Kumar |
| 2004/0097980 A1 | 5/2004 | Ferree |
| 2004/0138703 A1 | 7/2004 | Alleyne |
| 2004/0153074 A1* | 8/2004 | Bojarski et al. ............. 606/72 |
| 2004/0210310 A1 | 10/2004 | Trieu |
| 2004/0260300 A1 | 12/2004 | Gorensek et al. |

(56) References Cited

U.S. PATENT DOCUMENTS

| | | |
|---|---|---|
| 2004/0260397 A1 | 12/2004 | Lambrecht et al. |
| 2005/0004578 A1 | 1/2005 | Lambrecht et al. |
| 2005/0033363 A1 | 2/2005 | Bojarski et al. |
| 2005/0033440 A1 | 2/2005 | Lambrecht et al. |
| 2005/0038519 A1 | 2/2005 | Lambrecht et al. |
| 2005/0049592 A1 | 3/2005 | Keith et al. |
| 2005/0049704 A1 | 3/2005 | Jackson |
| 2005/0049708 A1 | 3/2005 | Atkinson et al. |
| 2005/0060038 A1 | 3/2005 | Lambrecht et al. |
| 2005/0149197 A1 | 7/2005 | Cauthen |
| 2005/0159762 A1* | 7/2005 | Nuutinen et al. ............ 606/148 |
| 2005/0187577 A1 | 8/2005 | Selvitelli et al. |
| 2005/0240269 A1 | 10/2005 | Lambrecht et al. |
| 2005/0256582 A1 | 11/2005 | Ferree |
| 2005/0283246 A1 | 12/2005 | Cauthen, III et al. |
| 2006/0060038 A1 | 3/2006 | Sammartin |
| 2006/0084994 A1 | 4/2006 | Atkinson et al. |
| 2006/0100711 A1 | 5/2006 | Cauthen |
| 2006/0129156 A1 | 6/2006 | Cauthen |
| 2006/0129245 A1 | 6/2006 | Cauthen |
| 2006/0142864 A1 | 6/2006 | Cauthen |
| 2006/0161258 A1 | 7/2006 | Cauthen |
| 2006/0167553 A1 | 7/2006 | Cauthen, III |
| 2006/0173545 A1 | 8/2006 | Cauthen, III et al. |
| 2006/0190085 A1 | 8/2006 | Cauthen |
| 2006/0195193 A1 | 8/2006 | Bloemer |
| 2006/0210310 A1 | 9/2006 | Takahashi et al. |
| 2006/0241773 A1 | 10/2006 | Cauthen |
| 2006/0247776 A1 | 11/2006 | Kim |
| 2006/0253152 A1 | 11/2006 | Evans et al. |
| 2006/0282167 A1 | 12/2006 | Lambrecht |
| 2006/0287731 A1 | 12/2006 | Cauthen, III et al. |
| 2007/0061012 A1 | 3/2007 | Cauthen, III |
| 2007/0061013 A1 | 3/2007 | Cauthen, III et al. |
| 2007/0067040 A1 | 3/2007 | Ferree |
| 2007/0073407 A1 | 3/2007 | Cauthen, III et al. |
| 2007/0088438 A1 | 4/2007 | Cauthen, III et al. |
| 2007/0100348 A1 | 5/2007 | Cauthen, III et al. |
| 2007/0100349 A1 | 5/2007 | O'Neil et al. |
| 2007/0100354 A1 | 5/2007 | Cauthen, III et al. |
| 2007/0156244 A1 | 7/2007 | Cauthen |
| 2007/0156245 A1 | 7/2007 | Cauthen, III et al. |
| 2007/0185497 A1 | 8/2007 | Cauthen et al. |
| 2007/0198021 A1 | 8/2007 | Wales |
| 2007/0225814 A1 | 9/2007 | Atkinson et al. |
| 2007/0225815 A1 | 9/2007 | Keith et al. |
| 2007/0225816 A1 | 9/2007 | Keith et al. |
| 2007/0233257 A1 | 10/2007 | Keith et al. |
| 2007/0239280 A1 | 10/2007 | Keith et al. |
| 2007/0288041 A1 | 12/2007 | Cauthen |
| 2008/0033561 A1 | 2/2008 | Cauthen |
| 2008/0140188 A1 | 6/2008 | Rahdert et al. |
| 2011/0257664 A1 | 10/2011 | Cauthen, III et al. |

FOREIGN PATENT DOCUMENTS

| | | |
|---|---|---|
| EP | 0 025 706 | 3/1981 |
| EP | 0 042 953 A2 | 1/1982 |
| EP | 0 049 978 | 4/1982 |
| EP | 0 061 037 | 9/1982 |
| EP | 0 062 832 | 10/1982 |
| EP | 0 076 406 | 4/1983 |
| EP | 0 110 316 A2 | 6/1984 |
| EP | 0 112 107 | 6/1984 |
| EP | 0 121 246 | 10/1984 |
| EP | 0 122 902 A2 | 10/1984 |
| EP | 0 126 570 A2 | 11/1984 |
| EP | 0 145 577 A2 | 6/1985 |
| EP | 0 193 784 A2 | 10/1986 |
| EP | 0 195 818 | 10/1986 |
| EP | 0 643 945 | 3/2002 |
| EP | 1 857 055 | 11/2007 |
| EP | 1 797 827 | 10/2012 |
| JP | 2-130908 | 5/1990 |
| JP | 63-32303 | 12/1994 |
| WO | WO 94/23671 | 10/1994 |
| WO | WO 95/22285 | 8/1995 |
| WO | WO 95/31946 | 11/1995 |
| WO | WO 95/31948 | 11/1995 |
| WO | WO 96/27339 | 9/1996 |
| WO | WO 97/20874 | 6/1997 |
| WO | WO 97/26847 | 7/1997 |
| WO | WO 98/01091 | 1/1998 |
| WO | WO 98/05274 | 2/1998 |
| WO | WO 98/22050 | 5/1998 |
| WO | WO 98/20939 | 9/1998 |
| WO | WO 99/00074 | 1/1999 |
| WO | WO 99/02108 | 1/1999 |
| WO | WO 99/04720 | 2/1999 |
| WO | WO 99/16381 | 8/1999 |
| WO | WO 99/61084 | 12/1999 |
| WO | WO 00/20021 | 4/2000 |
| WO | WO 00/25706 | 5/2000 |
| WO | WO 00/49978 | 5/2000 |
| WO | WO 00/42953 | 7/2000 |
| WO | WO 00/61037 | 10/2000 |
| WO | WO 00/62832 | 10/2000 |
| WO | WO 00/76409 | 12/2000 |
| WO | WO 01/10316 | 2/2001 |
| WO | WO 01/12107 | 2/2001 |
| WO | WO 01/21246 | 3/2001 |
| WO | WO 01/22902 | 4/2001 |
| WO | WO 01/26570 | 4/2001 |
| WO | WO 01/28464 | 4/2001 |
| WO | WO 01/45577 | 6/2001 |
| WO | WO 0139671 | 6/2001 |
| WO | WO 01/93784 | 12/2001 |
| WO | WO 01/95818 | 12/2001 |
| WO | WO 02/17825 | 3/2002 |
| WO | WO 2006/121474 | 11/2006 |

OTHER PUBLICATIONS

Ahlgren, B.D., MD., et al., "Anular Incision Technique on the Strength and Multidirectional Flexibility of the Healing Intervertebral Disc," *Spine* 19(8):948-954 (1994).

Cauthen, Joseph C., "Annulotomy Study, Preliminary Results: Updated Feb. 1999 for all procedures with at least one-year follow-up" (Table), Feb. 8, 1999.

Cauthen, Joseph C., MD., Microsurgical Annular Reconstruction (Annuloplasty) Following Lumbar Microdiscectomy: Preliminary Report of a New Technique, Abstract for Poster Presentation, AANSICNS Section on Disorders of the Spine and Peripheral Nerves Annual Meeting (1999).

Cauthen, Joseph, Draft Abstract entitled "Microsurgical Annular Reconstruction (Annuloplasty) Following Lumbar Microdiscactomy: Preliminary Report of a New Technique" from abstracts@neurosumery.org, Sep. 4, 1998.

International Search Report and Written Opinion issued in PCT/IB2007/004555, mailed Apr. 27, 2009, 19 pages.

International Search Report and Written Opinion issued in PCT/US2006/16292, mailed May 22, 2007.

International Search Report and Written Opinion issued in PCT/US2009/060425, mailed Feb. 15, 2010, 16 pages.

Lehmann, Thomas R., M.D., et al., "Refinements in Technique for Open Lumbar Discectomy," International Society for the Study of the Lumbar Spine (1997).

Mineiro, J., et al., "Dynamic Neutralization With Dynesys Review of 113 Cases with More than 1 Year Follow-Up," *Spineweek* 2004, Porto, Portugal May 30-Jun. 5, 2004, Abstract B19, p. 181.

Ordway, N.R., et al., "Failure Properties of a Hydrogel Nucleus in the Intervertebral Disc," North American Spine Society, pp. 168-169 (1997).

Osti, O.L., et al., Annular Tears and Disc Degeneration in the Lumbar Spine: *The Journal of Bone and Joint Surgery* 74-B(5):678-82 (1992).

Panjabi, Manohar, PhD., et al., "Intrinsic Disc Pressure as a Measure of Integrity of the Lumbar Spine", *Spine* 13(8):913-17 (1988).

Ray, Charles D., "Prosthetic Disc Nucleus Implants: Update", *North American Spine Society* 13th Annual Meeting. p. 252 (Oct. 1998).

(56) References Cited

OTHER PUBLICATIONS

Yasargil, M.G. "Microsurgical Operation of Herniated Lumbar Disc," Lumbar Disc Adult Hydrocephalus, p. 81 (1977).

* cited by examiner

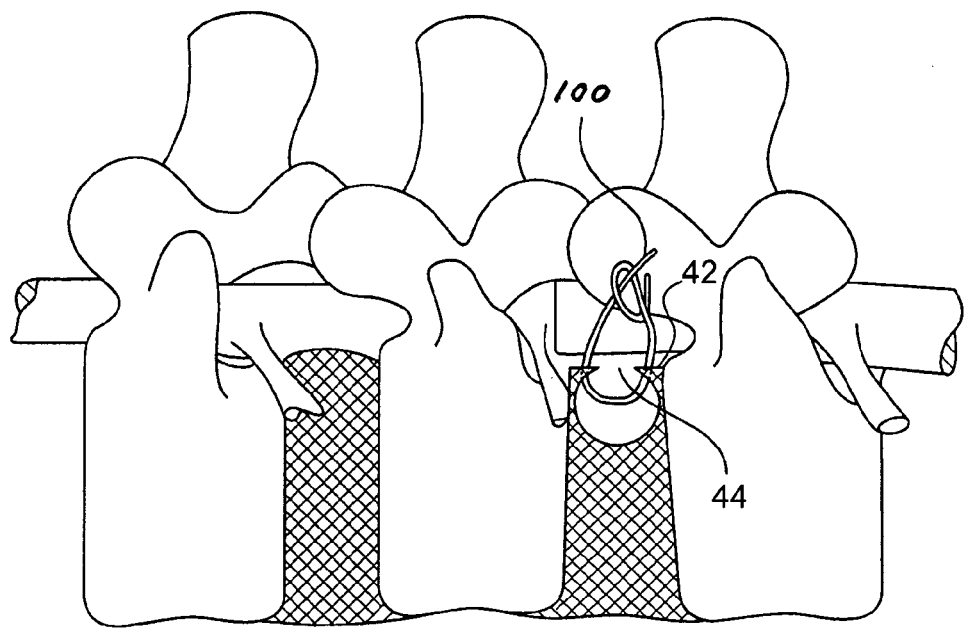
FIG. 1
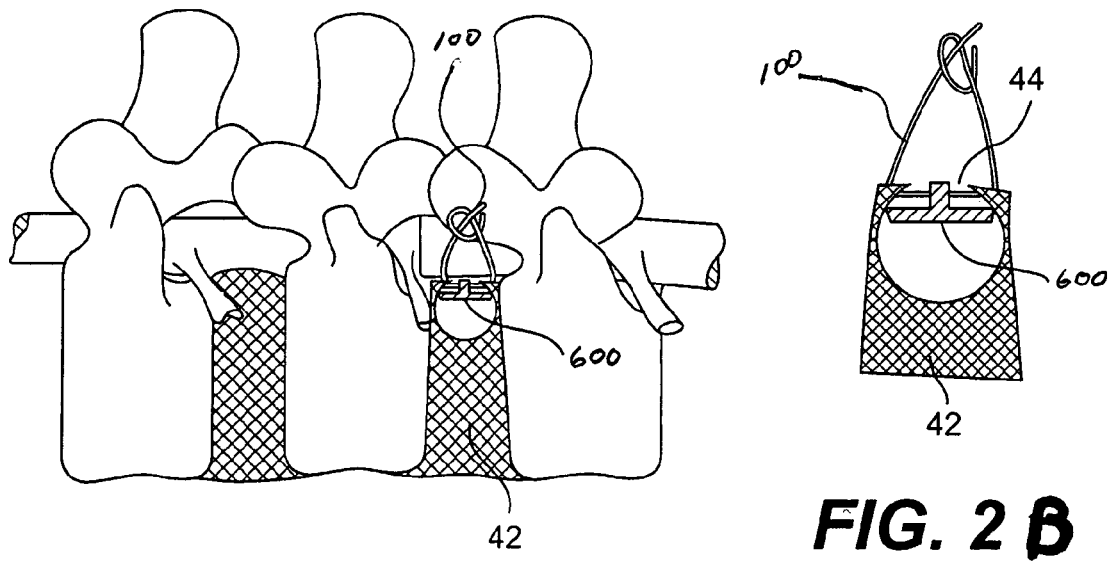
FIG. 2A
FIG. 2B

HERNIATED DISC

DISC, POST-DISCECTOMY

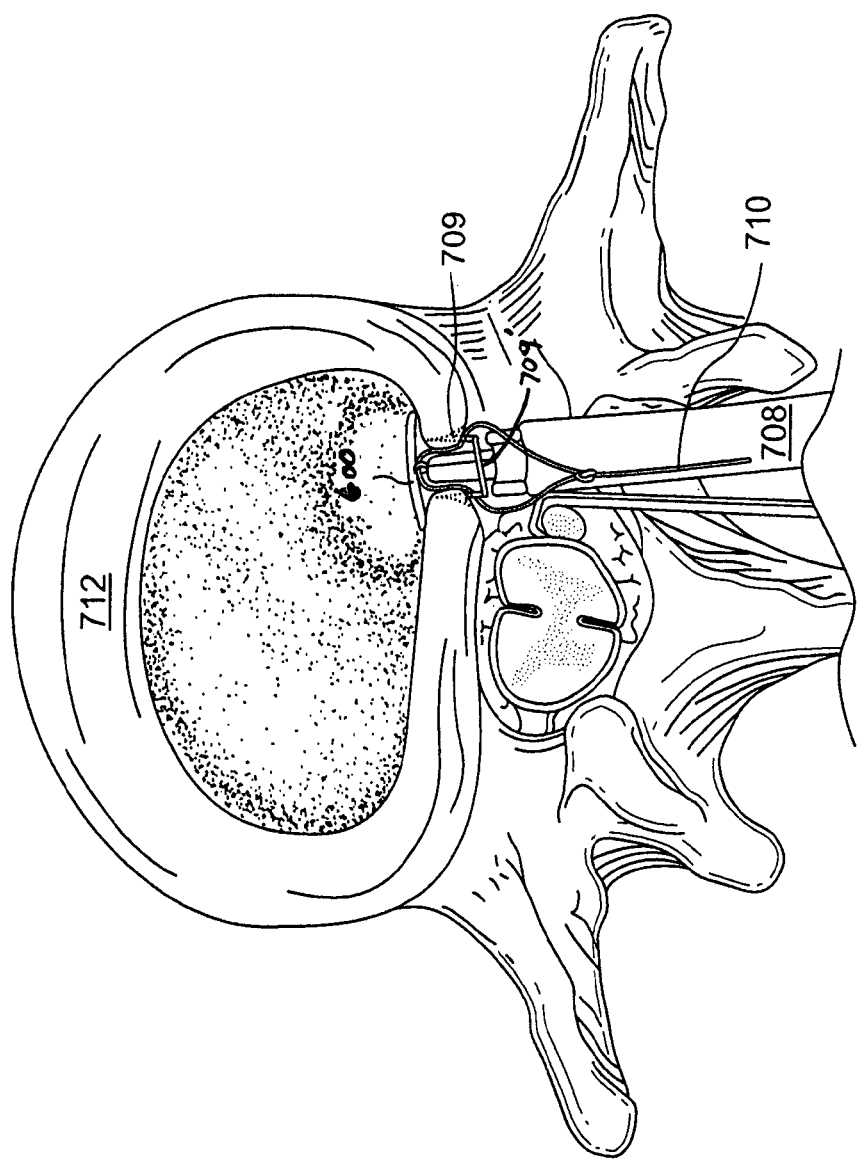

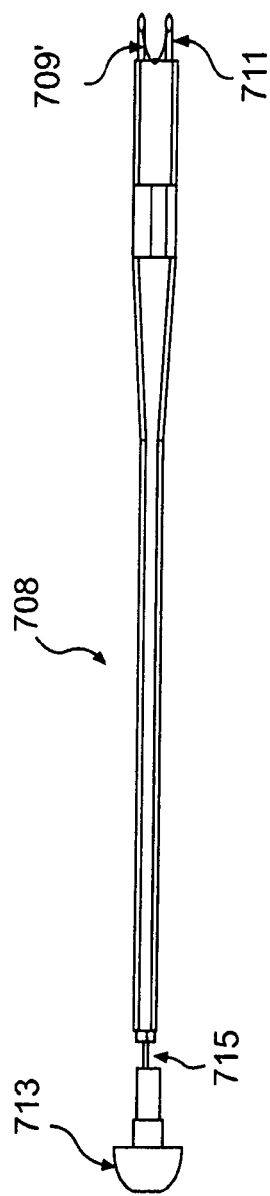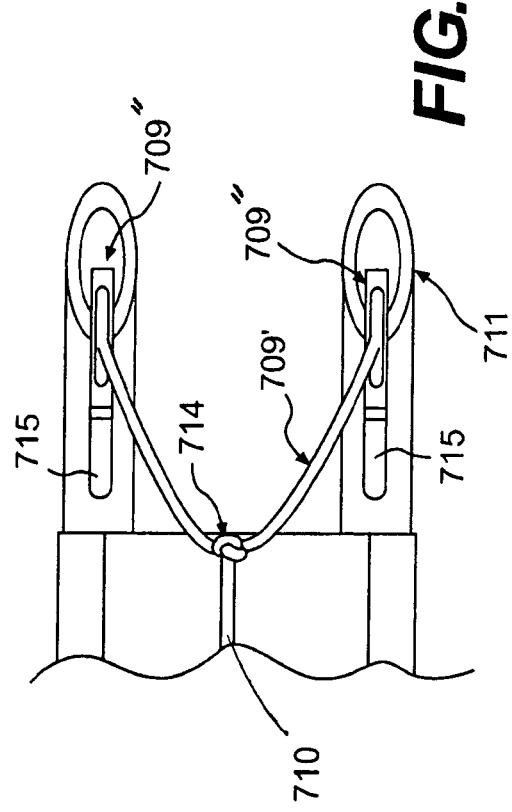
FIG. 10A
FIG. 10B

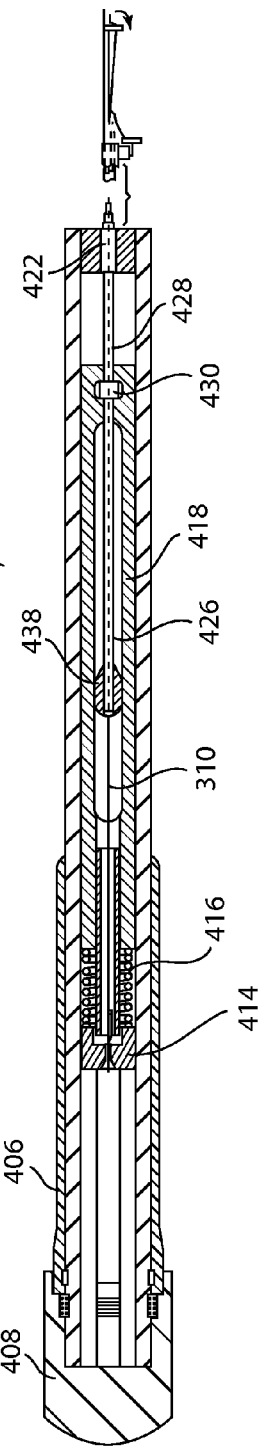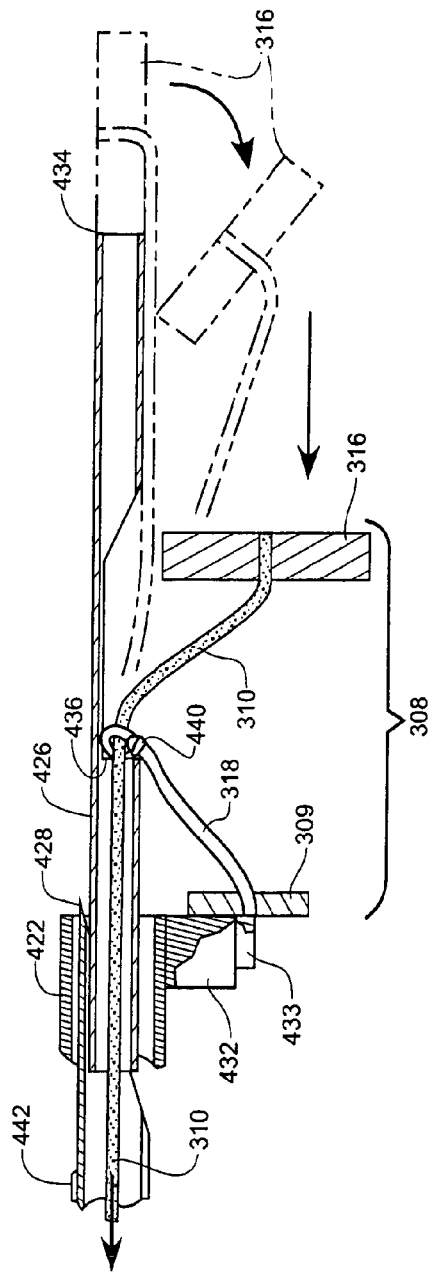

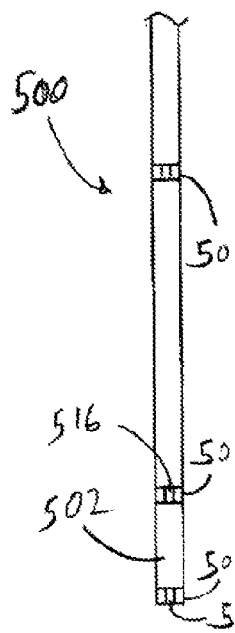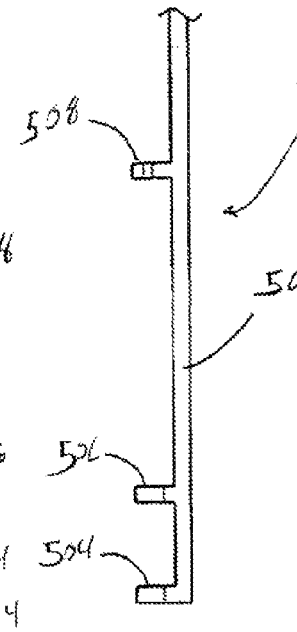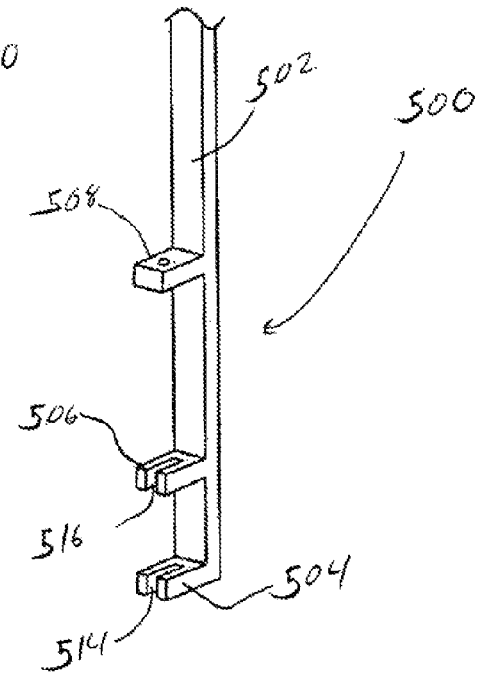
Fig. 34C  Fig. 34B  Fig. 34A
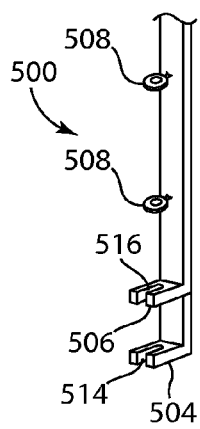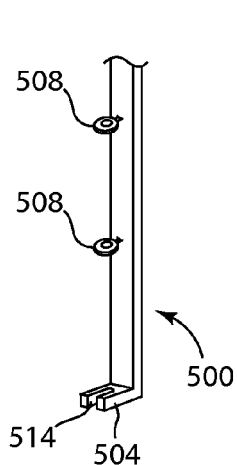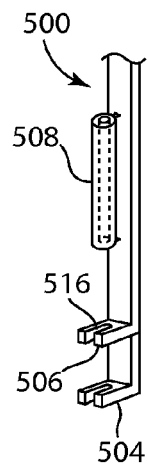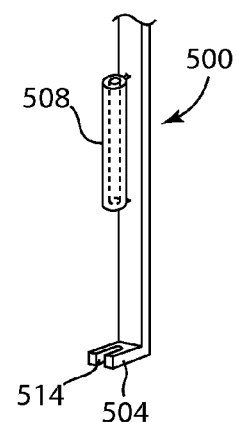
Fig. 36A  Fig. 36B  Fig. 35A  Fig. 35B

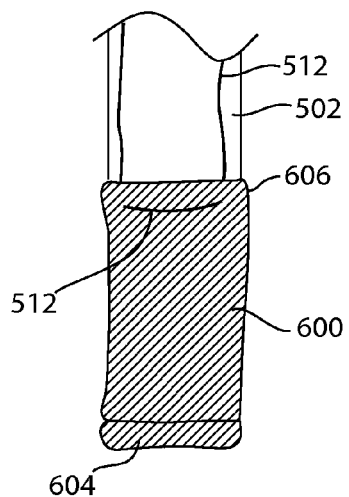
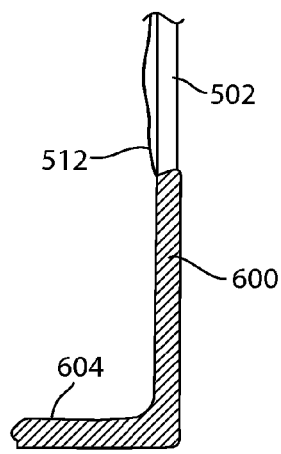
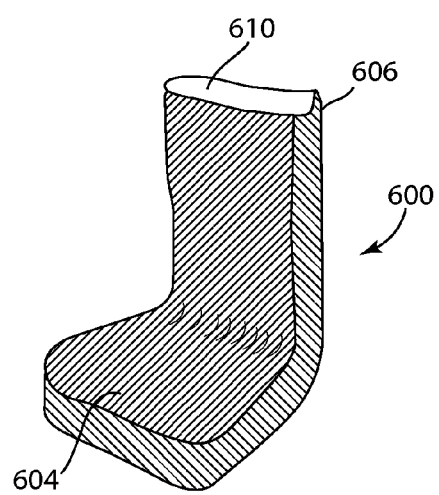
Fig. 40E  Fig. 40D  Fig. 40A
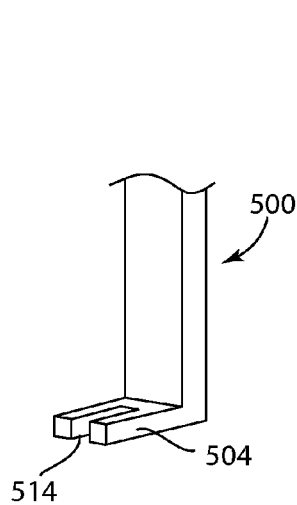
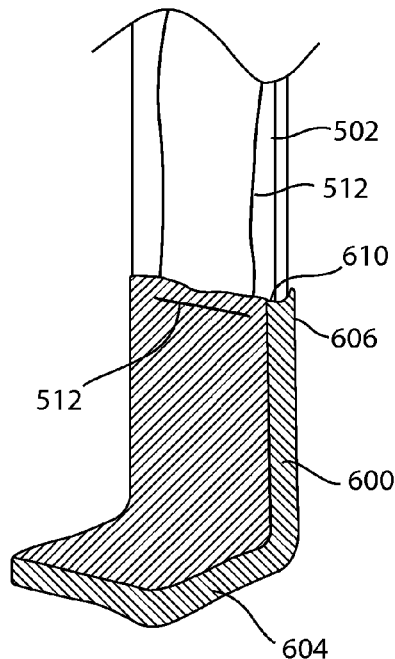
Fig. 40B
Fig. 40C

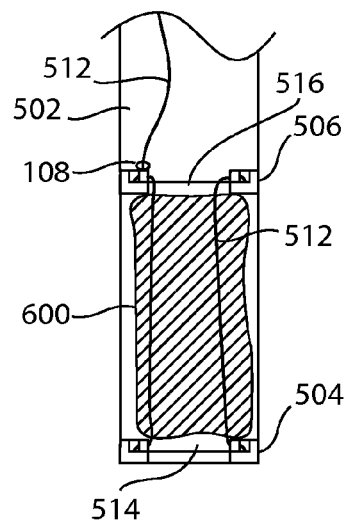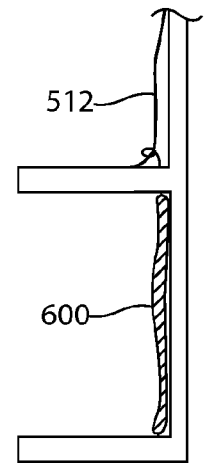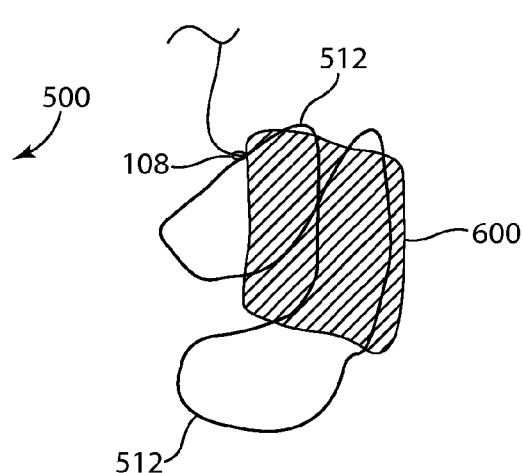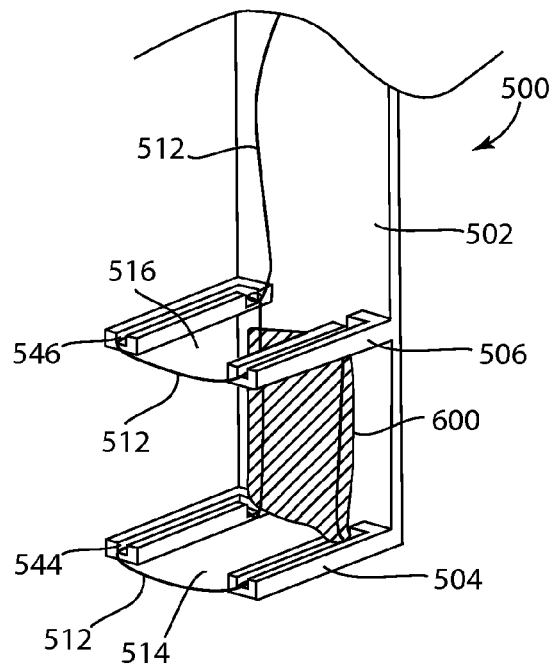

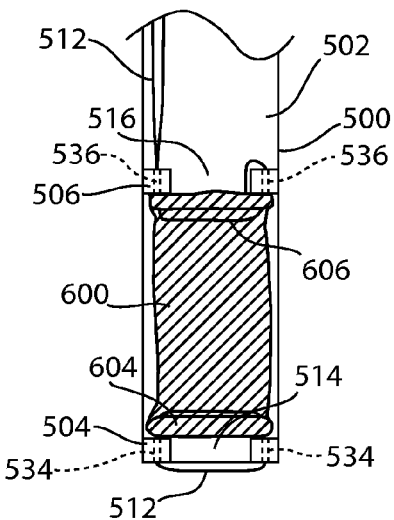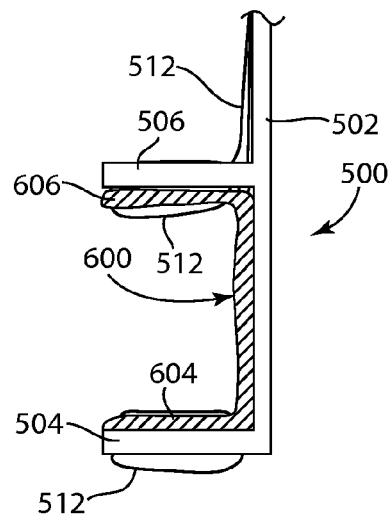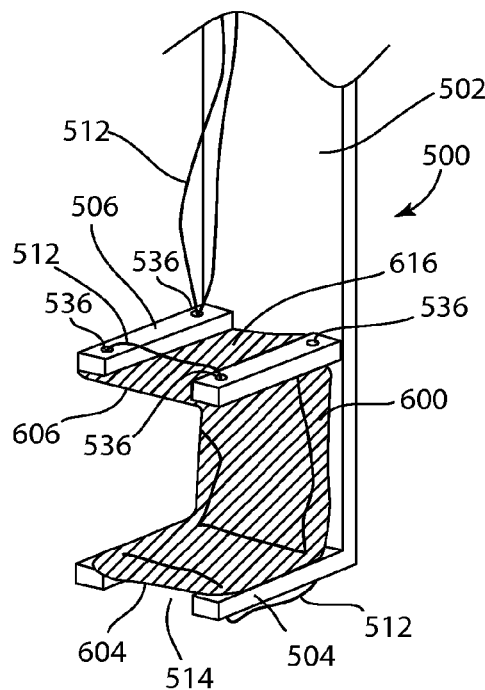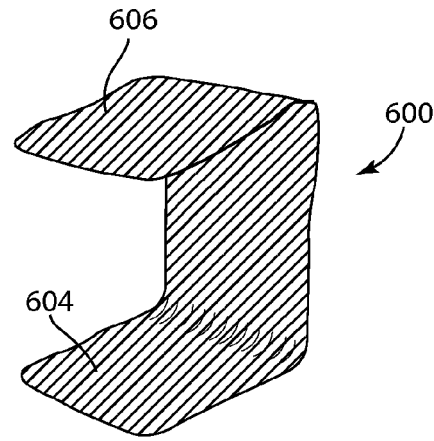
Fig. 42D
Fig. 42C
Fig. 42B
Fig. 42A

APPARATUS FOR THE TREATMENT OF TISSUE

CROSS-REFERENCE TO RELATED APPLICATION

The present application is a continuation of U.S. patent application Ser. No. 11/527,903, filed Sep. 26, 2006 which is a continuation in-part of U.S. patent application Ser. No. 11/120,750, filed May 3, 2005, now issued as U.S. Pat. No. 7,615,076 which is a continuation-in-part of U.S. patent application Ser. No. 10/352,981 filed Jan. 29, 2003, now abandoned and Ser. No. 10/327,106 filed Dec. 24, 2002, now issued as U.S. Pat. No. 7,004,970, each of which are continuations-in-part of U.S. patent application Ser. No. 10/133,339 filed Apr. 29, 2002, now issued as U.S. Pat. No. 7,052,516 and claims, through U.S. patent application Ser. No. 10/133,339, the benefit of U.S. Provisional Application Ser. No. 60/309,105 filed Jul. 31, 2001. U.S. Pat. No. 7,052,516 claims the benefit to and is a continuation-in part of U.S. patent application Ser. No. 10/075,615 filed Feb. 15, 2002, now abandoned which is a continuation of U.S. patent application Ser. No. 09/947,078 filed Sep. 5, 2001, now issued as U.S. Pat. No. 6,592,625 which is a continuation of U.S. patent application Ser. No. 09/484,706 filed Jan. 18, 2000, now abandoned which claims the benefit to U.S. Provisional Patent Application Ser. No. 60/160,710 filed Oct. 20, 1999. All of the preceding patents and patent applications are incorporated herein by reference in their entirety.

TECHNICAL FIELD

The present inventions relate to medical devices and, more particularly, to devices and methods for the closure, sealing, repair, reconstruction or otherwise treatment of an intervertebral disc.

BACKGROUND

The spinal column is formed from a number of bony vertebrae, which in their normal state are separated from each other by intervertebral discs. The intervertebral disc acts in the spine as a crucial stabilizer, and as a mechanism for force distribution between adjacent vertebral bodies. Without a competent disc, collapse of the intervertebral disc may occur, contributing to abnormal joint mechanics and premature development of degenerative and/or arthritic changes.

The normal intervertebral disc has an outer ligamentous ring called the annulus fibrosus surrounding the nucleus pulposus. The annulus fibrosus binds the adjacent vertebrae together and is constituted of collagen fibers that are attached to the vertebrae and cross each other so that half of the individual fibers will tighten as the vertebrae are rotated in either direction, thus resisting twisting or torsional motion. The nucleus pulposus is constituted of soft tissue, having about 85% water content, which moves about during bending from front to back and from side to side.

The aging process contributes to gradual changes in the intervertebral discs. The annulus fibrosus loses much of its flexibility and resilience, becoming more dense and solid in composition. The aging annulus fibrosus may also be marked by the appearance or propagation of cracks or fissures in the annular wall. Similarly, the nucleus desiccates, increasing viscosity and thus losing its fluidity. In combination, these features of the aged intervertebral discs result in less dynamic stress distribution because of the more viscousnucleus pulposus, and less ability to withstand localized stresses by the annulus fibrosus due to its desiccation, loss of flexibility and the presence of fissures. Fissures can also occur due to disease or other pathological conditions. Occasionally fissures may form rents through the annular wall. In these instances, the nucleus pulposus is urged outwardly from the disc space through a rent, often into the spinal column. Extruded nucleus pulposus can, and often does, mechanically press on the spinal cord or spinal nerve rootlet. This painful condition is clinically referred to as a ruptured or herniated disc.

In the event of the rupture of the annulus fibrosus, the subannular nucleus pulposus may migrate along the path of least resistance into the fissure forcing the fissure to open further. The increased size of the fissure can allow the migration of the nucleus pulposus through the wall of the disc. The migration of the nucleus pulposus may result in nerve compression and/or the introduction of inflammatory compounds into the space around the adjacent nerve roots. This compression and/or introduction of inflammatory compounds in the lumbar spine may adversely affect the nerves associated with the extremities, bladder, bowel and genitalia. The usual effect of nerve compression and/or inflammation in this region of the spine is intolerable back or neck pain, radiating into the extremities, with accompanying numbness, weakness, and in late stages, paralysis and muscle atrophy, and/or bladder and bowel incontinence. Additionally, injury, disease or other degenerative disorders may cause one or more of the intervertebral discs to shrink, collapse, deteriorate or become displaced, herniated, or otherwise damaged and compromised.

Surgical repairs or replacements of displaced or herniated discs are attempted approximately 390,000 times in the USA each year. Historically, there has been no known way to repair or reconstruct the annulus. Instead, surgical procedures to date are designed to relieve symptoms by removing unwanted disc fragments and relieving nerve compression. While results are currently acceptable, they are not optimal. Various authors report 3.1-21% recurrent disc herniation, representing a failure of the primary procedure and requiring re-operation for the same condition. An estimated 10% recurrence rate results in 39,000 re-operations in the United States each year.

Some have also suggested that the repair of a damaged intervertebral disc might include the augmentation of the nucleus pulposus, and various efforts at nucleus pulposus replacement have been reported. It is believed that nucleus replacement technologies may be enhanced through the use of complimentary annular repair. Furthermore, it is believed that various interbody technologies may be more readily sealed within the disc space through the repair of annular defects. Finally, annular repair may be utilized as a vehicle to deliver other reparative materials to the intervertebral disc space.

SUMMARY

An aperture or hole in the annulus may be a result of a surgical incision or dissection into the intervertebral disc annulus, or the consequence of a naturally occurring tear (rent). The effects of annular defect reconstruction is restoration of disc wall integrity, which may reduce the failure rate (3-21%) of a common surgical procedure (disc fragment removal or discectomy), or advantageously provide a barrier to intradiscal material migration.

Fixation apparatuses and related methods in accordance with the present inventions may resolve many of the needs and shortcomings discussed above and provide additional improvements and advantages as will be recognized by those skilled in the art upon review of the present disclosure. The inventions may comprise delivery tools for delivering fixation apparatus 100 and treatment devices 600, as well as kits comprising devices and tools. The present inventions provide fixation apparatuses 100 and patch-like devices 600 and related methods for repair, reapproximation, reinforcement, reconstruction or otherwise treatment of an intervertebral disc in cases of displaced, herniated, thinned, ruptured, or otherwise damaged or infirmed intervertebral discs. In accordance with the inventions, methods are disclosed for treating an intervertebral disc having an aperture, weakened or thin portion in the wall of the annulus fibrosus. Repair, reconstruction, sealing, occluding an aperture, weakened or thin portion in the wall of the annulus using apparatuses and methods in accordance with the present inventions may prevent or avoid migration of intradiscal material from the disc space.

Although much of the discussion is directed toward the repair of the intervertebral disc after a surgical procedure, such as discectomy (a surgical procedure performed to remove herniated fragments of the disc nucleus), it is contemplated that the devices of the present inventions may be used in other procedures that involve access (whether induced or naturally occurring) through the annulus of the intervertebral disc, or prophylactic application to the annulus. An example of another procedure that could require a repair technique involves the replacement of the nucleus (nucleus replacement) with an implantable nucleus material to replace the functioning of the natural nucleus when it is degenerated. In this case, the repair could maintain the replacement nucleus within the disc space.

Furthermore, it should be noted that surgeons differ in their techniques and methods in performing an intervention on a spinal disc, and the inventive descriptions and depictions of methods, devices and delivery tools to repair annular tissue could be employed with a variety of surgical techniques; such as, but not limited to: open surgical, microsurgical discectomy (using a magnifying scope or loupes), minimally invasive surgical (through, for example, a METRx™ system available from Medtronic, Inc.), and percutaneous access. Surgeons may also employ a variety of techniques for intra-operative assessment and/or visualization of the procedure, which may include: intra-operative probing, radiography (e.g., C-arm, flat plate), and endoscopy. It is contemplated that the inventive embodiments described are not limited by the various techniques that may be employed by the surgeon.

Treatment apparatuses, fixation apparatuses, and their delivery tools and related methods in accordance with the present inventions may also pull the tissues together that surround the aperture or defect, the inner surface, and the outer surface of the annulus to help close or otherwise repair the aperture, increase the integrity of the repair, and promote healing.

In addition, the surgical approach to the intervertebral disc throughout the Figures and descriptions depict a common approach, with related structures, to a lumbar discectomy; although, it is possible that surgeons may prefer alternative approaches to the intervertebral disc for various applications (for example, different intervertebral disclevels such as the cervical or thoracic region, or for nucleus augmentation), which may include, but are not limited to: posterior-lateral, anterior, anterior-lateral, transforaminal, extra-foraminal, extra-pedicular, axial (i.e., through the vertebral bodies), retroperitoneal, trans psoas (through the Psoas muscle), and contralateral. The approach to the intervertebral disc space should not be interpreted to limit the use of the inventions for the repair or reconstruction of a defect, aperture, weakened or thin portion of the annulus, as described herein.

BRIEF DESCRIPTION OF THE DRAWINGS

The accompanying drawings, which are incorporated in and constitute a part of this specification, illustrate illustrative embodiments of the invention and, together with the description, serve to explain the principles of the invention.

FIG. 1 illustrates an exemplary embodiment of a primary closure of an opening in the disc annulus in accordance with aspects of the present inventions.

FIGS. 2A-2B illustrate an exemplary embodiment of a primary closure with a stent in accordance with aspects of the present inventions.

FIGS. 5A-5G illustrate an exemplary embodiment of an introduced and expanded annulus stent/patch being fixated and the aperture reapproximated in accordance with aspects of the present inventions.

FIGS. 10A-10B illustrate exemplary embodiments of a fixation delivery apparatus and fixation apparatus in accordance with aspects of the present inventions.

FIG. 27 illustrates a detailed view of exemplary embodiments of an anchor band delivery tool in cross-section during the cutting of a suture tether and release of an anchor band in accordance with aspects of the present inventions.

FIG. 28 illustrates a detailed view of exemplary embodiments of the distal end of an anchor band delivery tool during release of the anchor band in accordance with aspects of the present inventions.

FIGS. 34A-34C illustrate exemplary embodiments of a patch-like delivery tool in accordance with aspects of the present inventions.

FIGS. 35A-35B illustrate exemplary embodiments of a treatment delivery tool in accordance with aspects of the present inventions.

FIGS. 36A-36B illustrate exemplary embodiments of a patch delivery tool in accordance with aspects of the present inventions.

FIGS. 40A-40E illustrate exemplary embodiments of a patch and a patch delivery tool in accordance with aspects of the present inventions.

FIGS. 41A-41D illustrate exemplary embodiments of a patch and a patch delivery tool in accordance with aspects of the present inventions.

FIGS. 42A-42D illustrate exemplary embodiments of a patch and a patch delivery tool in accordance with aspects of the present inventions.

Figure 3A:
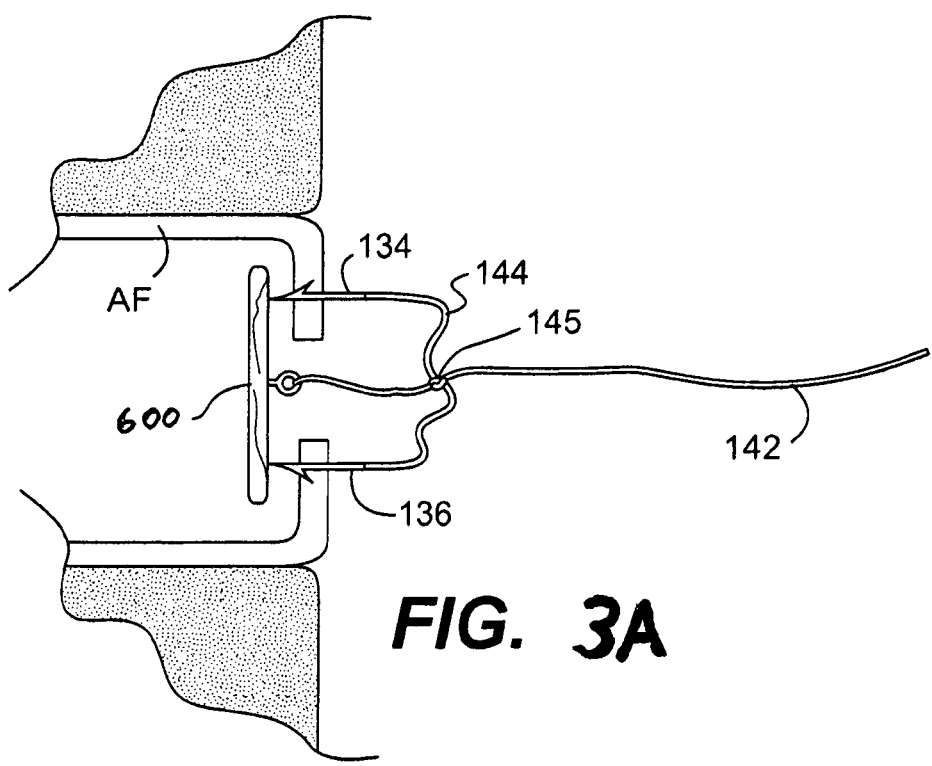
FIGS. 3A-3B illustrate an exemplary embodiment of an annulus stent employing secondary barbed fixation apparatus in accordance with aspects of the present inventions.

All Figures are illustrated for ease of explanation of the basic teachings of the present inventions only; the extensions of the Figures with respect to number, position, relationship and dimensions of the parts to form the preferred embodiment will be explained or will be understood within the skill of the art after the following description has been read and understood. Further, the exact dimensions and dimensional proportions to conform to specific force, weight, strength, and similar requirements will likewise be within the skill of the art after the following description has been read and understood.

Where used in various Figures of the drawings, the same numerals may designate the same or similar parts. Furthermore, when the terms "top," "bottom," "right," "left," "forward," "rear," "first," "second," "inside," "outside," and similar terms are used the terms should be understood to reference only the structure shown in the drawings and utilized only to facilitate describing the illustrated embodiments. Similarly, when the terms "proximal," "distal," and similar positional terms are used, the terms should be understood to reference the structures shown in the drawings as they will typically be utilized by a physician or other user who is treating or examining a patient with an apparatus in accordance with the present inventions.

DETAILED DESCRIPTION

All patents referred to or cited herein are incorporated by reference in their entirety to the extent they are not inconsistent with the explicit teachings of this specification, including; U.S. Pat. No. 5,108,438 (Stone), U.S. Pat. No. 5,258,043 (Stone), U.S. Pat. No. 4,904,260 (Ray et al.), U.S. Pat. No. 5,964,807 (Gan et al.), U.S. Pat. No. 5,849,331 (Ducheyne et al.), U.S. Pat. No. 5,122,154 (Rhodes), U.S. Pat. No. 5,204,106 (Schepers et al.), U.S. Pat. No. 5,888,220 (Felt et al.),U.S. Pat. No. 5,376,120 (Sarver et al.) and U.S. Pat. No. 5,976,186 (Bao et al.).

The figures generally illustrate fixation delivery apparatus 400, fixation apparatus 100, patches 600, and patch insertion tools 500 including aspects of the present inventions. The particular exemplary embodiments of the fixation delivery apparatus 400, fixation apparatus 100 and patches 600 as illustrated in the figures have been chosen for ease of explanation and understanding of various aspects of the present inventions. These illustrated embodiments are not meant to limit the scope of coverage but instead to assist in understanding the context of the language used in this specification and the appended claims. Accordingly, variations of fixation delivery apparatus 400, fixation apparatus 100, patch 600, and patch delivery apparatus 500 for use in annulus repair may differ from the illustrated embodiments and may be encompassed by the appended claims.

Reference will now be made in detail to selected illustrative embodiments of the inventions, with occasional reference to the accompanying drawings. When possible, although not intending to be limiting, many of the same reference numbers may be used throughout the drawings to refer to the same or similar elements.

In the surgical repair of an annulus 42 having an aperture 44, as shown in FIG. 1 and as described in related commonly-assigned U.S. Pat. No. 6,592,625 to Cauthen, a damaged annulus 42 is repaired by use of surgical fixation apparatus 100. One or more surgical sutures 100 are placed at about equal distances along the sides of a pathologic aperture 44 in the annulus 42. Reapproximation or closure of the aperture 44 is accomplished by tying the sutures 100 so that the sides of the aperture 44 are drawn together. The reapproximation or closure of the aperture 44 enhances the natural healing and subsequent reconstruction by the natural tissue (e.g., fibroblasts) crossing the now surgically narrowed gap in the annulus 42. Preferably, the surgical sutures 100 are biodegradable, but permanent non-biodegradable may be utilized. In all embodiments where biodegradable materials are indicated, suitable biodegradable materials may include, but are not limited to, biodegradable polyglycolic acid, swine submucosal intestine, collagen, silk or polylactic acid. Other suitable suturing (and band) materials include, e.g., polymeric materials such as polyethylene teraphthalate (PET), polyester (e.g., Dacron™), polypropylene, polyethylene, polycarbonate urethane and/or metallic material include, e.g., titanium, nickel titanium alloy, stainless steel, surgical steels or any combinations thereof.

Additionally, to repair a weakened or thinned wall of a disc annulus 42, a surgical incision or dissection can be made along the weakened or thinned region of the annulus 42 and one or more surgical sutures 100 can be placed at about equal distances laterally from the incision. Reapproximation or closure of the incision is accomplished by tying the sutures 100 so that the sides of the incision are drawn together. The reapproximation or closure of the incision/dissection enhances the natural healing and subsequent reconstruction by the natural tissue crossing the now surgically narrowed gap in the annulus 42. Preferably, the surgical sutures 100 are biodegradable, but permanent non-biodegradable materials may be utilized.

Where necessary or desirable, the method can be augmented by placing a patch 600 in and across the aperture 44. The patch 600 acts as a bridge in and across the aperture 44, providing a platform for traverse of fibroblasts or other normal cells of repair existing in and around the various layers of the disc annulus 42, prior to closure of the aperture 44. FIGS. 2A-B, for example, show a biocompatible device employed as an annulus stent 600, being placed in and across the aperture 44. The annulus stent 600 may act as a bridge in and/or across the aperture 44, providing a platform for a traverse of fibroblasts or other normal cells of repair existing in and around the various layers of the disc annulus 42, prior to closure of the aperture 44. In some embodiments the device, a stent or patch can act as a scaffold to assist in tissue growth that healingly scars the annulus.

In an illustrative embodiment, the annulus stent 600 is a solid unit, formed from one or more of the flexible resilient biocompatible or bioresorbable materials well know in the art. The selection of appropriate stent materials may be partially predicated on specific stent construction and the relative properties of the material such that, after fixed placement of the stent, the repair may act to enhance the healing process at the aperture by relatively stabilizing the tissue and reducing movement of the tissue surrounding the aperture.

For example, the annulus stent 600 may be made from:
A porous matrix or mesh of biocompatible and bioresorbable fibers acting as a scaffold to regenerate disc tissue and replace annulus fibrosus as disclosed in, for example, U.S. Pat. No. 5,108,438 (Stone) and U.S. Pat. No. 5,258,043 (Stone), a strong network of inert fibers intermingled with a bioresorbable (or bioabsorbable) material which attracts tissue ingrowth as disclosed in, for example, U.S. Pat. No. 4,904,260 (Ray et al.); a biodegradable substrate as disclosed in, for example, U.S. Pat. No. 5,964,807 (Gan et al.); or an expandable polytetrafluoroethylene (ePTFE), as used for conventional vascular grafts, such as those sold by W.L. Gore and Associates, Inc. under the trademarks GORETEX and PRECLUDE, or by Impra, Inc. under the trademark IMPRA.

Furthermore, the annulus stent 600, may contain hygroscopic material for a controlled limited expansion of the annulus stent 600 to fill the evacuated disc space cavity.

Additionally, the annulus stent 600 may comprise materials to facilitate regeneration of disc tissue, such as bioactive silica-based materials that assist in regeneration of disc tissue as disclosed in U.S. Pat. No. 5,849,331 (Ducheyne, et al.), or other tissue growth factors well known in the art.

It is anticipated that fibroblasts will engage, for example, fibers or fabric of the patch 600 forming a strong wall duplicating the currently existing condition of healing seen in the normal reparative process. Moreover, many of the materials disclosed and described above represent embodiments where the device actively promotes the healing process. It is also possible that the selection of alternative materials for the treatment devices or treatments may modulate the role in the healing process, and thus promote or prevent healing as may be required. It is also contemplated that these modulating factors could be applied to material substrates of the device as a coating, or similar covering, to evoke a different tissue response than the substrate without the coating.

Materials of the patch 600 could include a metallic material (e.g., NiTi alloy, Stainless steel, Titanium), or a polymeric material (e.g., polypropylene, polyethylene, polyurethane, polycarbonate urethane, Polyetheretherketone (PEEK), polyester, PET, poly olefin copolymer, polypropylene, polyethylene), or a biodegradable or bioresorbable material (e.g., collagen, cellulose, silk, polysaccharide, polyglycolic acid (PGA), a polylevolactic acid (PPLA), a polydioxanone (PDA) or for example a racemic polylactic acid (PDLLA), or a combination of these materials.

FIG. 3A shows an alternative fixation strategy where a pair of barbs 134 and 136 are plunged into the annulus fibrosus from the exterior of the annulus while the device 600 is retained in the sub-annular space by means of a tether 142. Although there are a wide variety of fixation devices that could be used in this particular example, a tether 142 may be knotted 145 with the band 144 holding the barbs 134 and 136 together to fix the device in the sub-annular space. The knot is shown in an uncinched position to clarify the relationship between the tether 142 and the bands 144. Using this approach, the device can be maintained in a subannular position by the barbed bands 134, 136 while the tether knot 145 is cinched, advantageously simultaneously reapproximating the annulus to close the aperture while drawing the device into sealing, bridging engagement with the subannular wall of the annulus fibrosus.

Figure 3B:
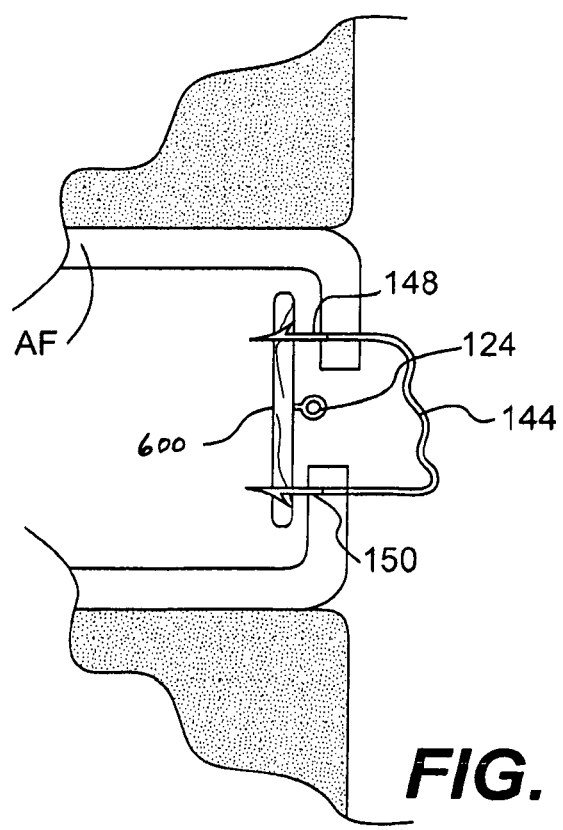

FIG. 3B shows an alternative fixation strategy where the barbs 148 and 150 are sufficiently long that they can pierce the body of the device 600 and extend all the way through the annulus fibrosus into the device 600. In this configuration, the band 144 connecting the barbs 148 and 150 may be tightened to gently restrain and position the device 600 in the sub-annular space, or tightened with greater force to reapproximate the aperture or rent.

It is understood that there can be a variety of device designs of patches, stents, meshes, barriers, scaffolds sealers, occluders or otherwise treatment devices 600 for repair of annular defects and they may, in at least some of the embodiments, be configured to accomplish the expansion of a device from a first configuration, to a second configuration to occupy at least a portion of the sub-annular space and reduce re-extrusion of the nucleus, or otherwise facilitate maintaining other intradiscal materials within the disc space. These devices can be constructed of single components or multiple components, with a variety of different materials, whether synthetic, naturally occurring, recombinant (genetically engineered) to achieve various objectives in the delivery, deployment and fixation of a device to repair or reconstruct the annulus. The following device concepts are further discussed for additional embodiments of a device and/or system for the repair of an intervertebral disc annulus. The following descriptions will illustratively depict and describe methods, devices, and tools to deliver a treatment to an intervertebral disc after a lumbar discectomy procedure; although, it is anticipated that these methods, devices, and tools may be similarly used in a variety of applications. As an example, the embodiments described herein may also advantageously maintain other materials within the disc space rather than natural disc tissue (nucleus, annulus, cartilage, etc.), such as implants and materials that may be used to replace and/or augment the nucleus pulposus or other parts of the disc's tissues. These procedures may be performed to treat, for example, degenerative disc disease. Whether these materials are intended to replace the natural functioning of the nucleus pulposus (i.e., implantable prosthetics or injectable, in-situ curable polymer protein, or the like) or provide a fusion between vertebral bodies (i.e., implantable bony or synthetic prosthetics with materials to facilitate fusion, such as growth factors like bone morphogenic proteins) one skilled in the art would realize that variations to the embodiments described herein may be employed to better address characteristic differences in the various materials and/or implants that could be placed within the disc space, and that these variations would be within the scope of the invention.

It is also important to note that the boundary in the intervertebral disc space between the annulus fibrosus and the nucleus pulposus as depicted herein may be demarked or otherwise highlighted; however, it is important to recognize that these tissues are not as precisely demarked in human tissues, and may be even less so as the patient ages or evinces degeneration of the intervertebral disc. This demarcation may be especially difficult to discern during an operative procedure, using for example; available surgical tools (i.e., probes), fluoroscopic guidance (x-ray), or visual (endoscope) guidance. However, in general, the layers of the annulus have more structural integrity (and strength) than the nucleus, and this integrity varies from the outer most layers of the annulus typically being of higher structural integrity than the inner most layers of the annulus.

Figure 4A:
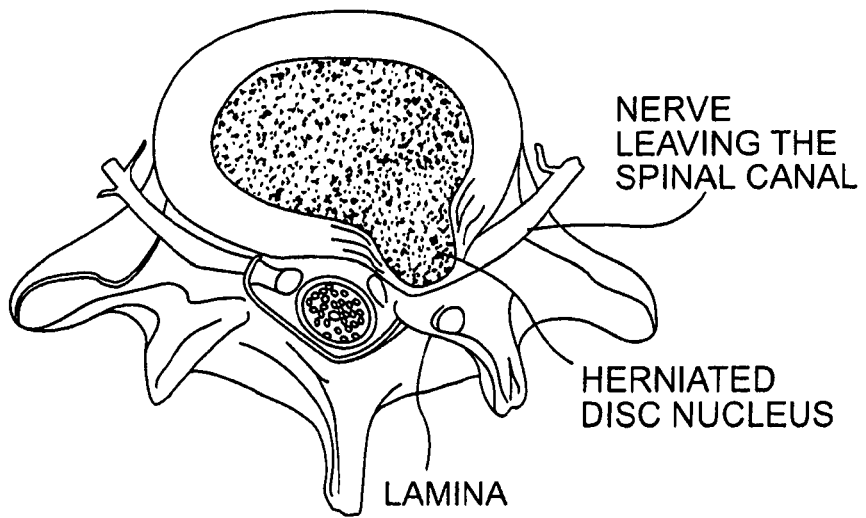
FIG. 4A illustrates an exemplary herniated disc in perspective view.
Figure 4B:
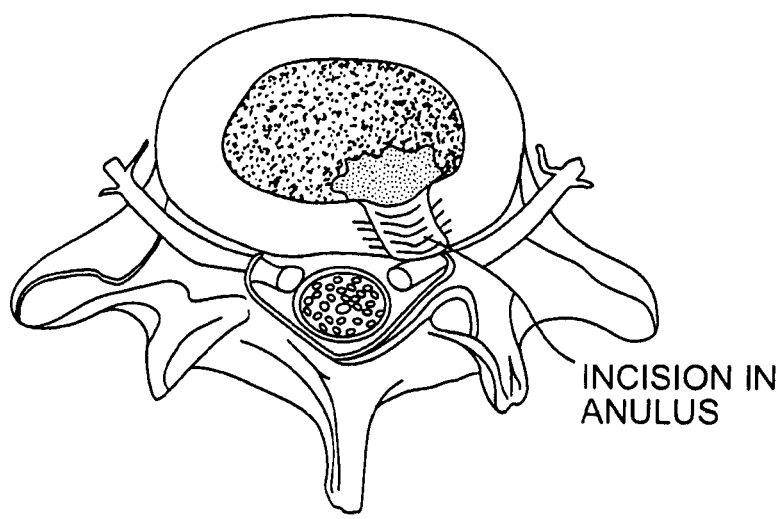
FIG. 4B illustrates the same disc after discectomy.

As depicted in FIG. 4A, a herniated disc occurs when disc nucleus material protrudes or emerges from the intervertebral disc. Herniated disc material can impinge on nerve tissue, causing pain. A discectomy attempts to relieve pressure on the nerve tissue through surgical removal of disc material, the result usually being an aperture and a defect in the disc annulus wall, and frequently a void in the disc space where disc nucleus fragment was removed, as shown in FIG. 4B. FIG. 4B typifies a disc after the discectomy procedure has been performed, as do most of the drawings and descriptions contained herein; although, one skilled in the art would understand that these inventions may be used to enable other disc repair procedures such as nucleus replacement, interbody fusion, and posterior/anterior dynamic stabilization. In addition, it should be understood that in order to perform a discectomy procedure, there are a variety of instruments and tools readily available to the surgeon during spine surgery, or other surgical procedures, to obtain the outcome as shown in FIG. 4, or other outcomes intended by the surgeon and the surgical procedure. These tools and instruments may be used to: incise, resect, dissect, remove, manipulate, elevate, retract, probe, cut, curette, measure or otherwise effect a surgical outcome. Tools and instruments that may be used to perform these functions may include: scalpels, Cobb elevators, Kerrison punch, various elevators (straight, angled, for example a Penfield), nerve probe hook, nerve retractor, curettes (angled, straight, ringed), rongeurs (straight or angulated, for example a Peapod), forceps, needle holders, nerve root retractors, scissors. This list is illustrative, but is not intended to be exhaustive or interpreted as limiting. It is anticipated that some of these tools and/or instruments could be used before, during, or after the use of the inventive methods, devices and tools described herein in order to access, probe (e.g., Penfield elevator), prepare (e.g., angled or ringed curette, rongeur, forceps), and/or generally assess (e.g., angled probe) a treatment site or facilitate the manipulation (e.g., forceps, needle holder), introduction (e.g., forceps, needle holder, angled probe), or deployment (e.g., forceps, needle holder, angled probe) of the treatment device and/or its components.

There are a variety of ways to affix a treatment device to a wall of the annulus as well as reparatively fix or mend an annular defect in addition to those discussed herein above. The following exemplary embodiments are introduced here to provide inventive illustrations of the types of techniques that can be employed to reduce the time and skill required to repair an annulus, versus suturing and tying a knot.

An illustrative example of affixing a device 600 to a wall of the annulus 712 is further illustrated by FIGS. 5A-5G. As discussed hereinabove, with reference to FIGS. 3A-3B, a patch 600 is placed with a delivery tool 704, through the inner lumen of a guidetube, into the disc space and then expanded. This step can also include a patch 600 folded and passed through a guide tube surrounded by and held by a delivery tool 704. Also shown is an anchor band or staple 709 and an anchor band delivery device 708. Within the guide tube, or within the delivery tool, there is a suture line or cinch line 710 that is attached to the center of the patch 600. This can be seen in FIG. 5A with the guide tube removed. The guide tube may be retracted after the patch 600 has been expanded and deployed. Next, as shown in FIGS. 5A-5G, an anchor band delivery tool 708 is used to deliver one or more "bands" 709 into and on the outer surface of the annulus. These are intended to be anchored into and/or through the wall of the annulus with barb shapes that do not allow for the barbs to be pulled back through the annulus. The tissue anchor bands or fixation apparatuses, resemble a construction of a "staple". The bands could actually be constructed by connecting two barbed elements with, for example, a suture between the two barbed elements.

Fixation apparatuses 100 comprising barbs and connection bands between barbs could be constructed of the same material or of different materials. For example, the barbed part 709" of the anchor band could be a biodegradable/bioabsorbable material (such as, for example, collagen, cellulose, polysaccharides, carbohydrates, polyglycolic acid, polylevolactic acid, polydioxanone, racemic polylactic acid) or could be constructed of a metallic or polymeric biocompatible material (e.g., titanium, NiTi alloy, stainless steel, platinum, gold, polyurethane, polycarbonate urethane, polyimide, polyamide, polypropylene, polyethylene, polypropylene, polyester, PET, PEEK). The anchors could also be constructed of a combination of these materials. In addition, the band 709' that connects these barbs could be constructed of materials that are similar to the barbs, or different materials. For example, the connection band could be a biodegradable/bioabsorbable suture, such as Vicryl, or a biocompatible material such as polypropylene, polyethylene, silk, stainless steel, PET. In addition, it is possible that these elements are constructed from multiple materials to accomplish the objective of anchoring into the annulus or other disc tissue in proximity of the annulus and providing for a fixation site to draw the tissues together.

Figure 5A:
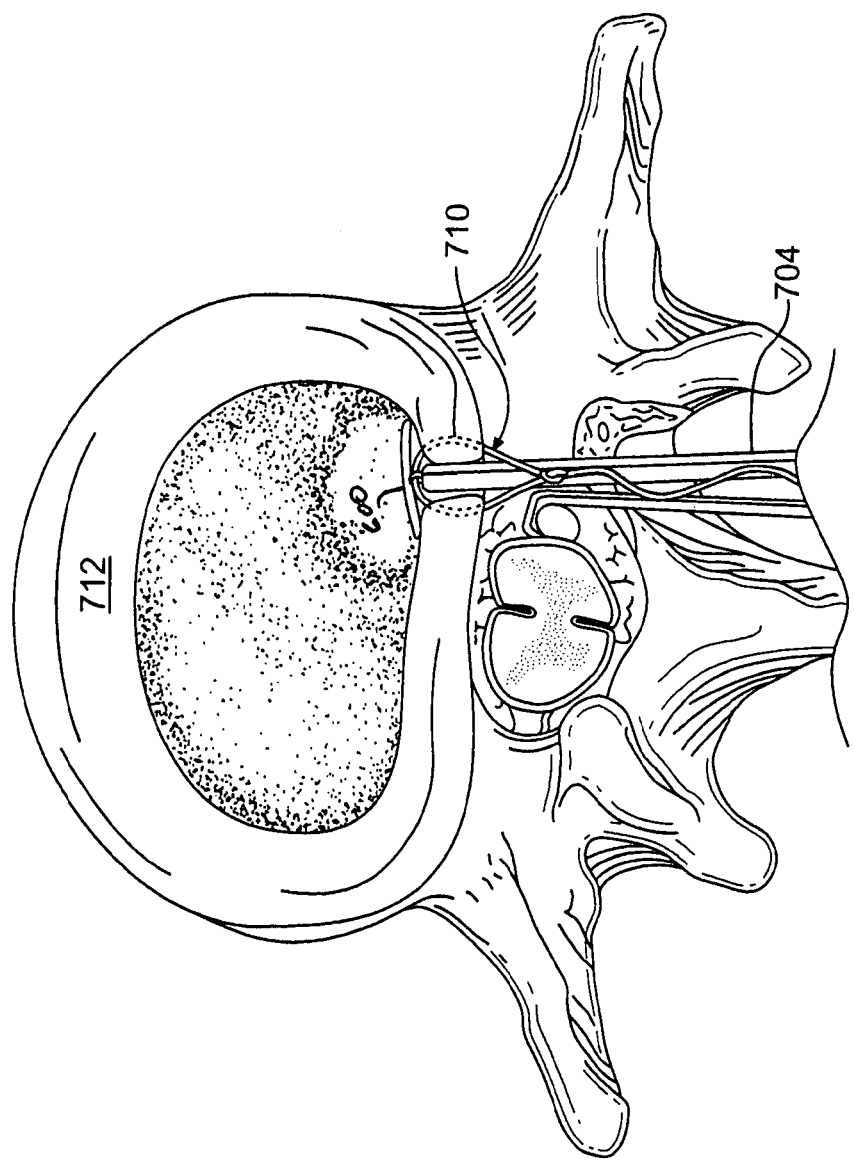
Figure 5D:
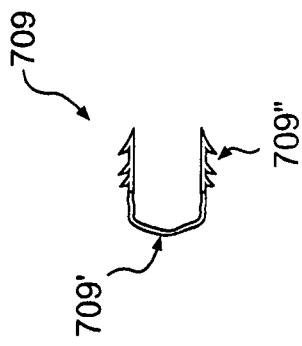
Figure 5C:
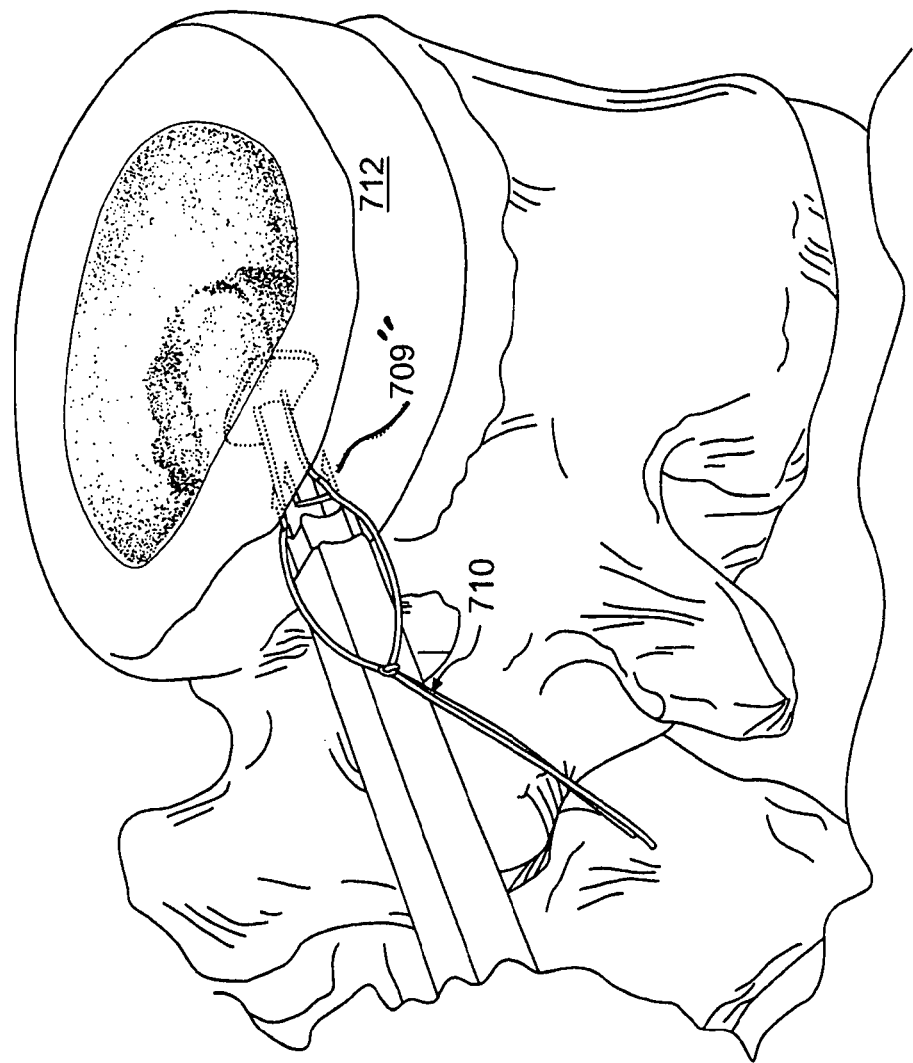
Figure 5E:
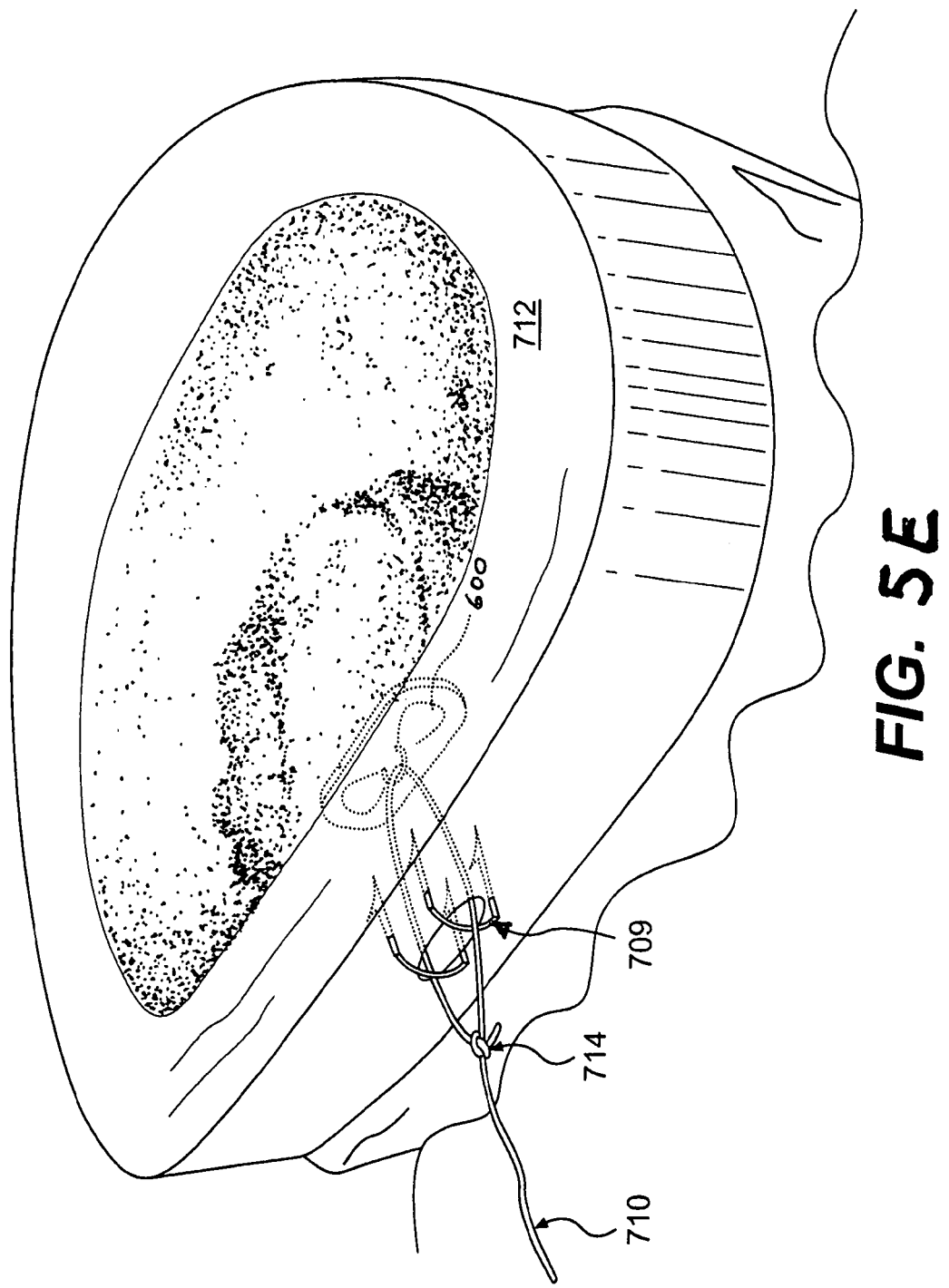
Figure 5F:
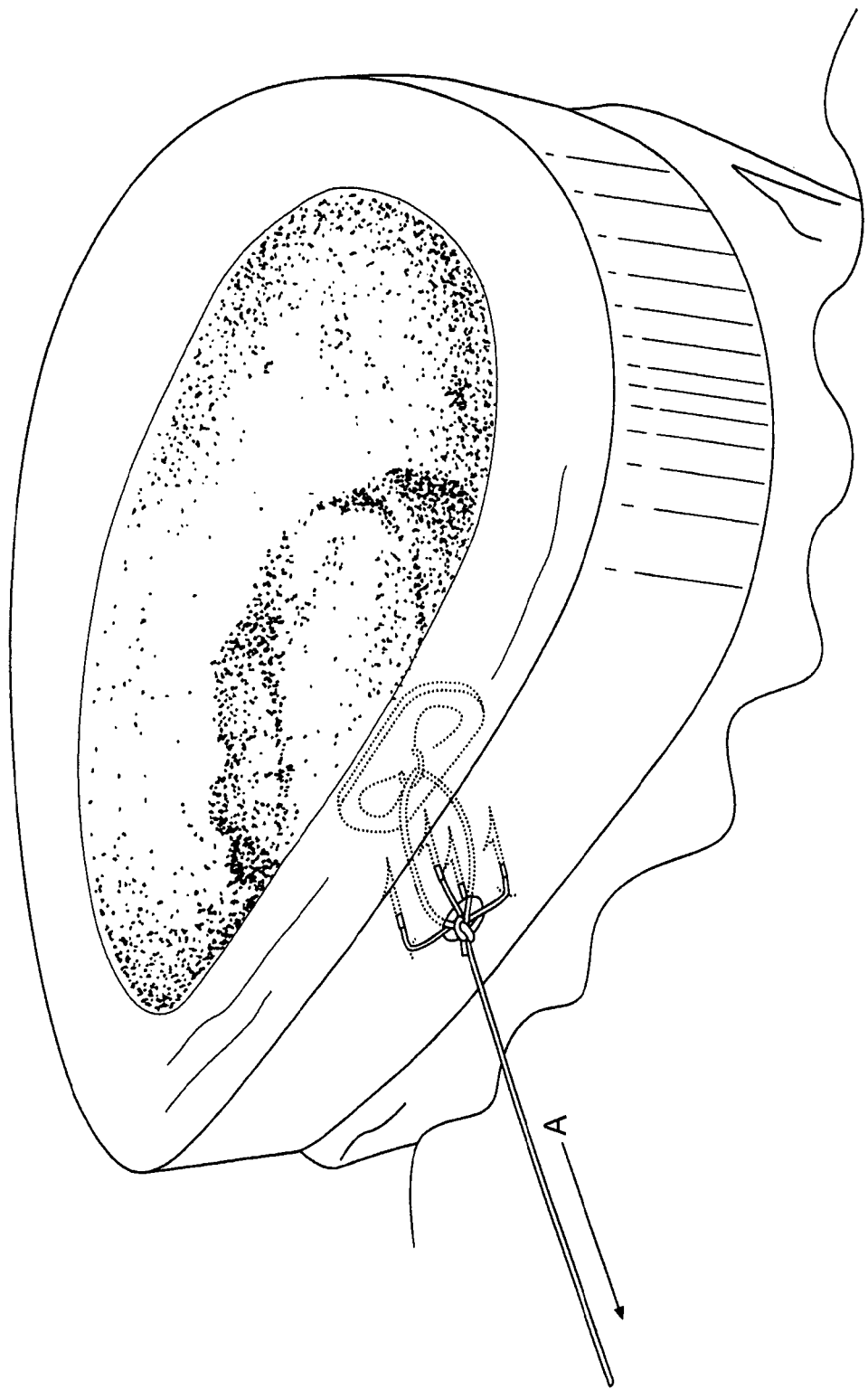
Figure 5G:
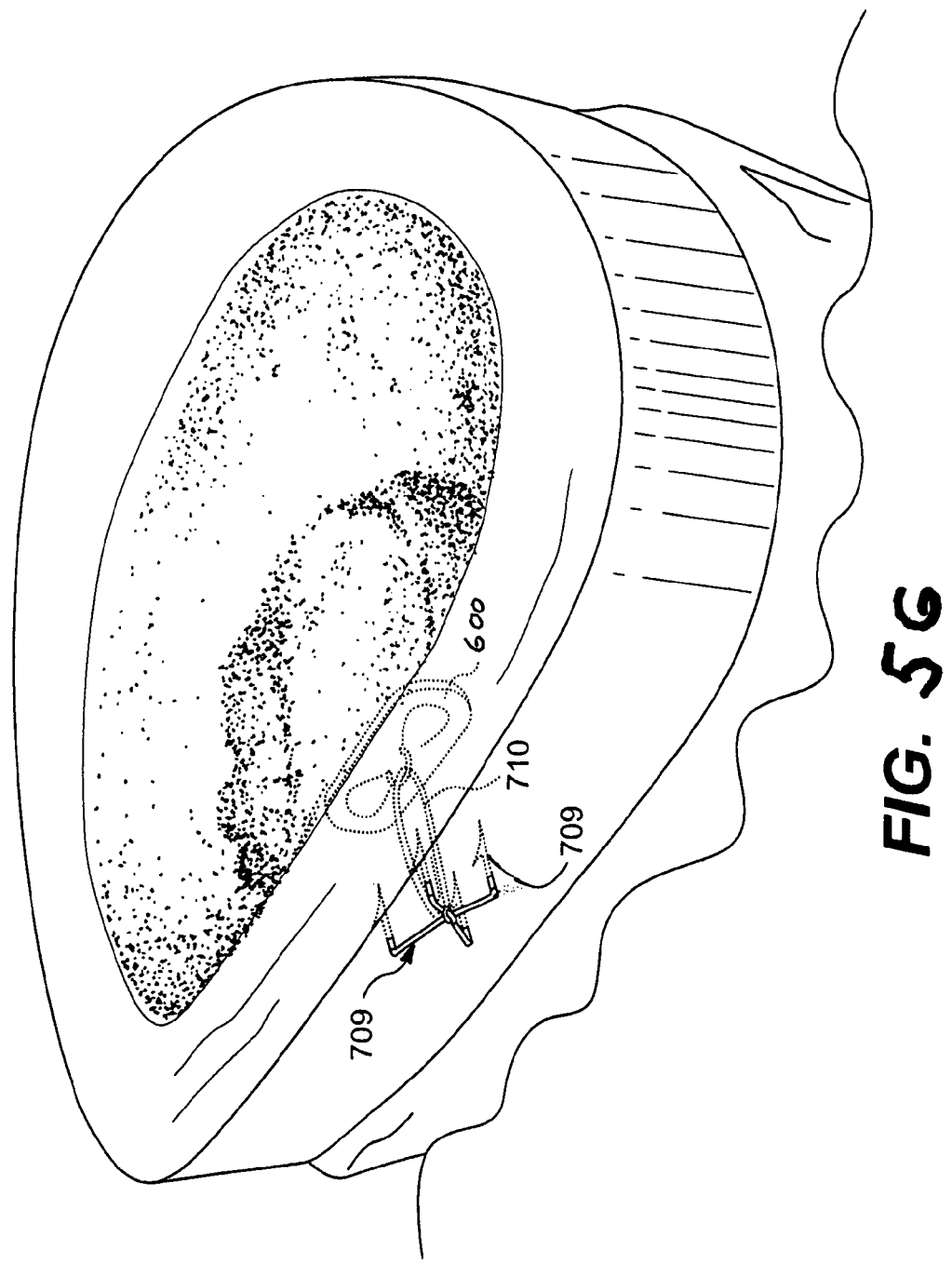

FIGS. 5A to 5G show the placement of a patch 600 with a patch delivery tool 704 and the placement of anchor bands 709 with delivery tool 708. The figures schematically show the placement of the tissue anchor bands 709 into the wall of the annulus 712 and the retraction of the anchor band delivery device 708 and the patch delivery tool 704. FIG. 5D depicts a representative anchor band 709, having a pair of stainless steel barbs 709" connected by a suture 709'. FIG. 5E shows the patch 600, anchor bands 709, and cinch line or suture 710 with the delivery tools removed, prior to drawing the patch and the tissues of the annulus together. In this embodiment there is a pre-fabricated slip knot 714 on the cinch line, although other locking elements or knots are possible. Suture loops can connect to the barbs directly, as in FIG. 5, or loop to surgical staples, or placed directly into the annulus. The presence of a pre-fabricated knot on the cinch line makes the process of repairing quicker since there is no need to tie a knot. It also facilitates drawing towards one another the tissues adjacent the aperture and the patch. The use of the cinch line and a pre-fabricated knot can be placed by, for example, an external tube such as a knot pusher. FIG. 5E is similar to FIG. 3 described hereinabove prior to "tying" the knot 714. FIG. 5F shows the drawing of the patch and the annular tissues together by pulling on the tether in the direction "A" indicated by the arrow. In this case, the knot pusher has been removed from the cinch line 710. The suture 710 is drawn proximally to draw the patch 600 into engagement with the inner wall of the annulus to seal the aperture from within, as well as it may draw the tissues of the annulus together so as to, at least partially, reapproximate the annular aperture. FIG. 5G show the cinch line suture 710 tied and drawing the annular tissues together, after the excess suture line has been cut. It is also apparent from this device, fixation and delivery system that the outer surfaces of the aperture may be drawn together for re-approximation.

The cinching of the tissue anchor bands and the patch also allows for taking-up the slack that allows for the accommodation of varying disc sizes. For example, the thickness of the annular wall surrounding the aperture can vary from 1 mm up to 10 mm. Therefore, if the tissue anchor bands have a set length, a design with a cinch line accommodates different dimensions of the thickness of the wall of the annulus by drawing the "slack" of the bands together within the aperture.

Although it has been described here as patch placement that involves two lateral anchor bands 709 with a suture to draw the patch, bands and tissues together, one or two or more bands could be used and two bands is only an example. Furthermore, the tissue anchor bands were placed with the barbs in a superior-inferior fashion. One skilled in the art would recognize that these could be placed at different locations surrounding the aperture, vertebral bodies or into the Sharpey's fibers Although the patch 600 depicted in the example above does not have barbs attached to the patch, it is also possible to have barbs attached to further promote the affixation of the patch to the wall of the annulus.

Finally, although the drawings depict an aperture that lends itself to re-approximating the tissues, it is conceivable that some apertures, whether natural or surgically made, may be relatively large and therefore might require the placement of additional material within the aperture to act as a scaffold for tissue ingrowth, between the patch on the inner wall of the annulus and the anchor bands located on the outer wall.

Figure 6:
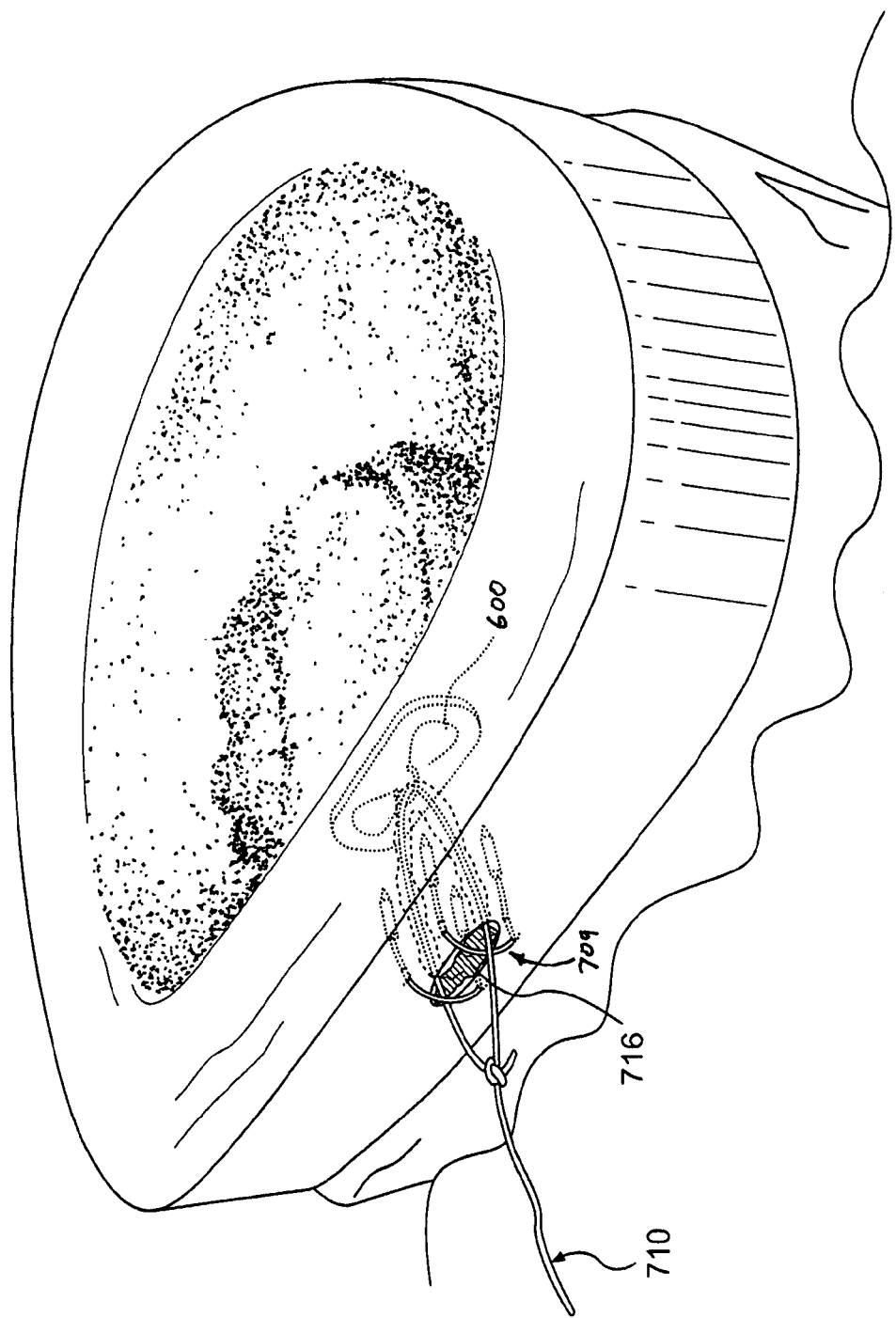
FIG. 6 illustrates an exemplary use of an embodiment of a filler material within the aperture during placement of a patch/stent tethered by a cinch line in accordance with aspects of the present inventions.

An example of material to fill the annular aperture might include autograft para-spinal fascial tissue, xenograft, allograft, or other natural collagenous materials. The filler material could also be of a biocompatible material such as a Dacron (polyester, or PET), polypropylene, polyethylene, silk, or other scaffolding-type material. FIG. 6 shows the illustrative filling of an aperture with implant material 716 prior to cinching the suture 710.

As an alternative embodiment of the present invention, the anchor bands 709 as described previously (anchor bands into annulus) could be sufficiently long enough to pass through the annulus and then through the patch. The barbs in this embodiment have an engaging involvement with the patch. This concept was previously discussed hereinabove in connection with FIG. 3.

As an alternative embodiment of the present invention, it is conceivable that some annular defects may be readily repaired without the use of a patch-like device and could advantageously be mended, partially or wholly, through tissue approximation. Exemplary of a reapproximation without a patch-like device could be performed with the repair apparatus of FIG. 5G wherein cinch line 710 is employed to draw together bands 709 without patch 600 present. It is also possible, given alternative presentations of annular defects, that a re-approximation could also be performed with the repair of FIG. 6 wherein cinch-line 710 is employed to draw together bands 709 with filler material 716 and without patch 600 present. In this alternative embodiment, fill material 716 may be directed affixed, or otherwise secured, to cinch-line 716 and/or one or more bands 709 so as to retain filler material 716 in proximity of the annular defect.

Although the bands shown in FIGS. 5A to 5G take the form of a "barb", they could as easily take a form of a simple T-barb, or a C-type element wherein the object is to have irrevocable engagement with the patch device 600 or tissue after the penetration through the patch or tissue. A T-type attachment, when aligned longitudinally with the suture, passes through the patch. The T-section may then rotate so as to prevent the suture anchor from being pulled back through the patch. In another embodiment a "C" retainer made of a superelastic material may be attached to the end of the suture band. The C-retainer is loaded into a needle wherein it is held straight. The needle is used to pass the C-retainer and suture through the patch and deploy the retainer in a second configuration in the shape of a "C". In general those skilled in the art can realize alternative anchoring forms for patch device affixation or reparative treatment that may take a variety of configurations including barbs, t-anchors, staples, anchors, c-retainers, open helical screws, screens, darts, tines, etc.

It is also foreseen within the scope of the invention that there may be patch-like designs 600 which will accommodate the placement and securement of the anchor to the fabric that covers the frame of the patch. For example, a frame for a patch that is made out of metal such as Nitinol can provide for "windows". The device, covered with a mesh fabric, for example silicone or Dacron, might allow for the anchoring barbs to be passed through the "windows" in the frame of the patch. In this case, the barb may be secured to the patch in the fabric covering the frame.

Alternatively, the patch could be secured by passing barbs that engage the lattice of the patch frame. These embodiments of the invention illustrate designs in which the barbs engage with the vertical, horizontal or criss-crossed structures/members of the frame. In this case, the barbs would pass through the mesh or lattice of the frame and they would be unable to pass back out of the frame structure.

Although this discussion refers to "anchor bands" that are shown to be two anchors connected by a suture, it is also contemplated that single barbs with sutures could be placed and the sutures' ends, at the outer surface of the annulus, could be tied after placement through the patch. It is also possible that these "single anchors" could be retained by a suture "pledget" on the outer wall of the annulus to better hold the outer surface, or could include a suture (or band) locking device.

One objective in the designs discussed hereinabove is to provide a way to "pull up the slack" in a system to adjust the length of sutures or anchor bands. According to another embodiment of the inventions, a "Lasso Cinch Knot" was developed as a means to draw the tissue anchor bands together with a suture cinch line that is incorporated into the patch design.

Figure 7A:
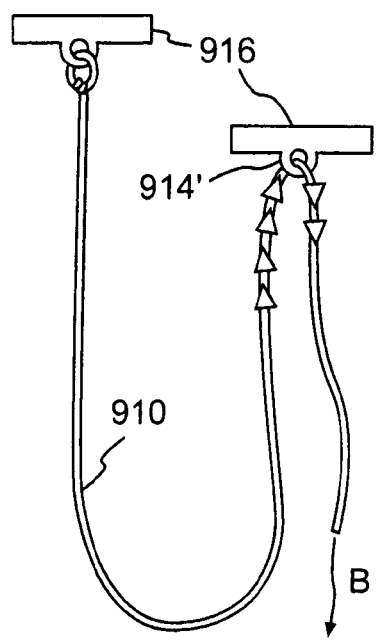
FIGS. 7A-7C illustrate exemplary embodiments of fixation apparatuses in accordance with aspects of the present inventions having fixation tissue anchors.
Figure 7B:
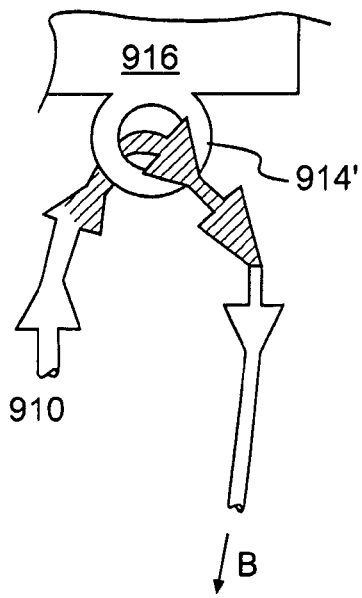
Figure 7C:
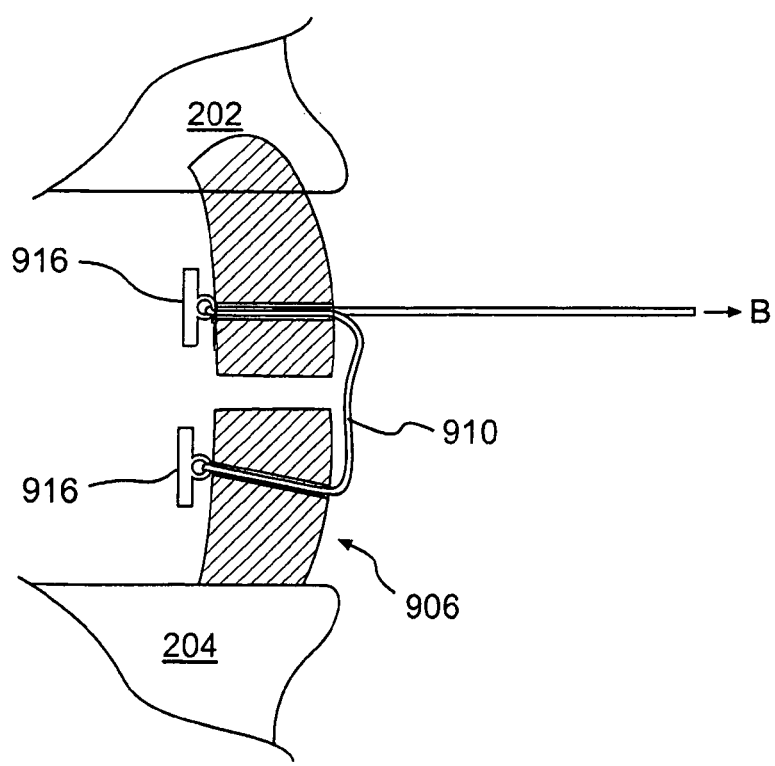

Alternative exemplary locking mechanisms are shown in FIGS. 7A to 7C, although in this case the engagement of the locking element 914' takes part on the anchor 916. Pulling tether 910 in the direction of arrow B will tighten and lockingly hold in tension to aid in securement and tissue approximation. The adjustable length of band between the two anchors allows slack to be taken up between the anchors 916. Two T-type anchors are illustratively shown in this example, but multiple tissue anchors of differing configurations could be used. The locking features can be included on the band, as depicted here, and allow for substantially one-way locking engagement with the anchor members. This adjustability advantageously promotes for the accommodation of varying thickness of the annulus from patient to patient and pathological presentation. The suture/band slack in this embodiment may be taken up to partially or wholly close the defect in the annulus and/or to shorten the band between anchors for a secondary cinching of multiple tensioned suture bands as described herein.

Figure 8A:
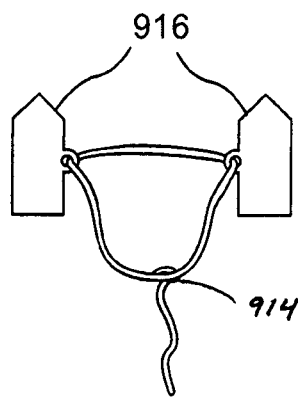
FIGS. 8A-8C illustrate additional exemplary embodiments of fixation apparatuses in accordance with aspects of the present inventions having fixation anchors.
Figure 8B:
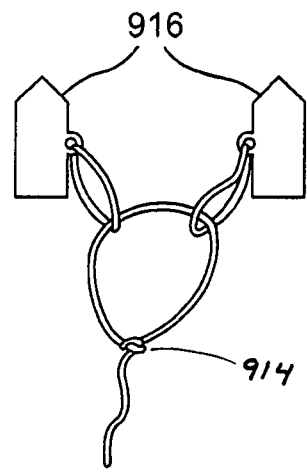
Figure 8C:
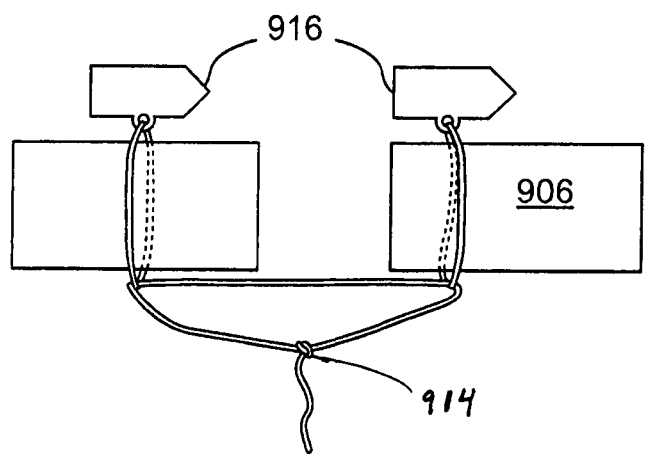

FIGS. 8A to 8C show alternative embodiments for tightening "anchoring barbs" with different configurations of bands and cinch lines. In one example, each independent barb has a looped, elongate, flexible element, such as a suture, attached to it. Through each of these loops is passed a cinch line, which comprises a knot. After placement of the barbs within and/or through the annulus, and possibly through the patch, the cinch line draws the loops of the barbs together. The advantage of this embodiment is that it allows for the independent placement of multiple barbs and the ability to draw all of them together.

Although cinch lines have been described as using a knot to "lock" the length of the suture, other mechanisms could also lock the length, for example, those shown in FIG. 7. The locking of the suture length is accomplished through a mechanical element located on the barb which engages with three dimensional elements attached to the suture line which mechanically press fit through the engagement element on the barb, thus locking the length of the suture line into place.

Although the embodiments of FIG. 7 and FIG. 8 depict the use of a single locking mechanism (e.g., knot on cinch line), it is conceivable that various designs could use more than one locking element to achieve the re-approximation and drawing towards one another tissue adjacent an annular aperture or defect.

Similarly, an alternative embodiment to cause tension within the device and draw the tissues together after placement of the anchor bands might include an elastic band or band with a spring which one end can be attached to the anchor bands and the other end attached to the patch. Alternatively, the anchor bands might, in and of themselves may be made of an elastic band between the barbs, or may contain a spring element between the barbs. Again, it is contemplated that the elastic or resilient element could be made from a wide variety of metals, polymeric, or biodegradable/bioabsorbable material.

As previously mentioned, the present invention also encompasses delivery devices or tools. The delivery devices of the present invention are configured to deliver at least one, or a portion thereof, reparative device within, through, onto, proximate or into, the annulus or other surface or tissue surrounding the intervertebral disc. The delivery tools (or devices) will typically comprise devices or shafts having proximal and distal ends. As referred to herein, the proximal portion of a device or tool or component will generally refer to the portion of the device/tool/component that is located furthest away from the patient (and closest to the surgeon); whereas, the distal portion will generally refer to the portion that is within (in use), or closest to the patient (and therefore furthest away from the surgeon). Although some of the device descriptions may refer to some fixation element embodiments as being "fixation" or "anchor/anchor band/barb", this is done for clarity reasons and should not be misconstrued to suggest that the device is not capable of also performing a treatment and/or a repair.

In addition, the following descriptions of delivery devices/tools are generally intended to be single-use and disposable; however, it is clear that these tools could as easily be constructed to be partially, or wholly, re-usable and re-sterilizable.

Figure 11A:
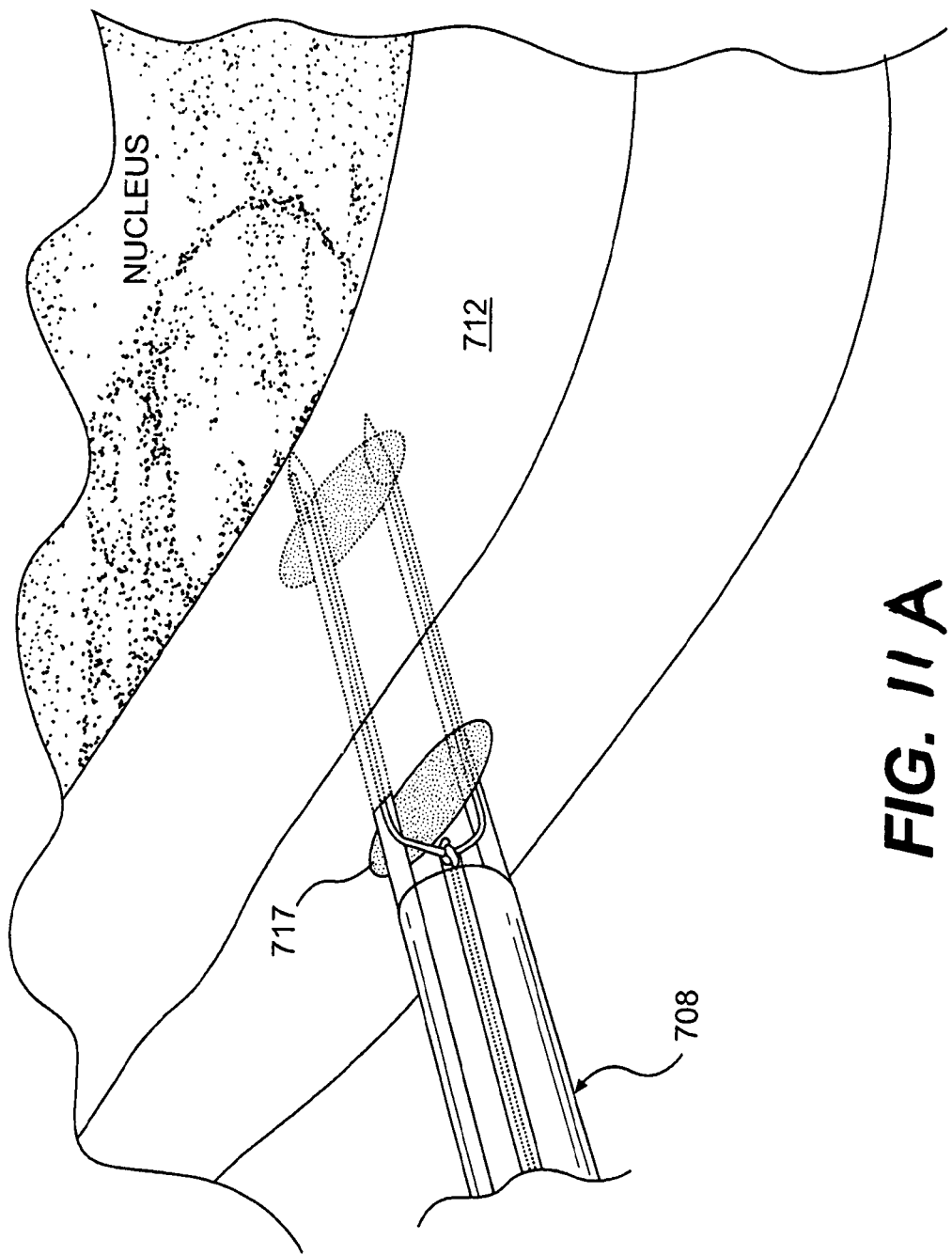
FIGS. 11A-11D illustrate exemplary embodiments of a fixation delivery apparatus configured to simultaneously deliver two tissue anchors of a fixation apparatus and the use of multiple fixation apparatuses together in repair of an intervertebral disc in accordance with aspects of the present inventions.
Figure 11B:
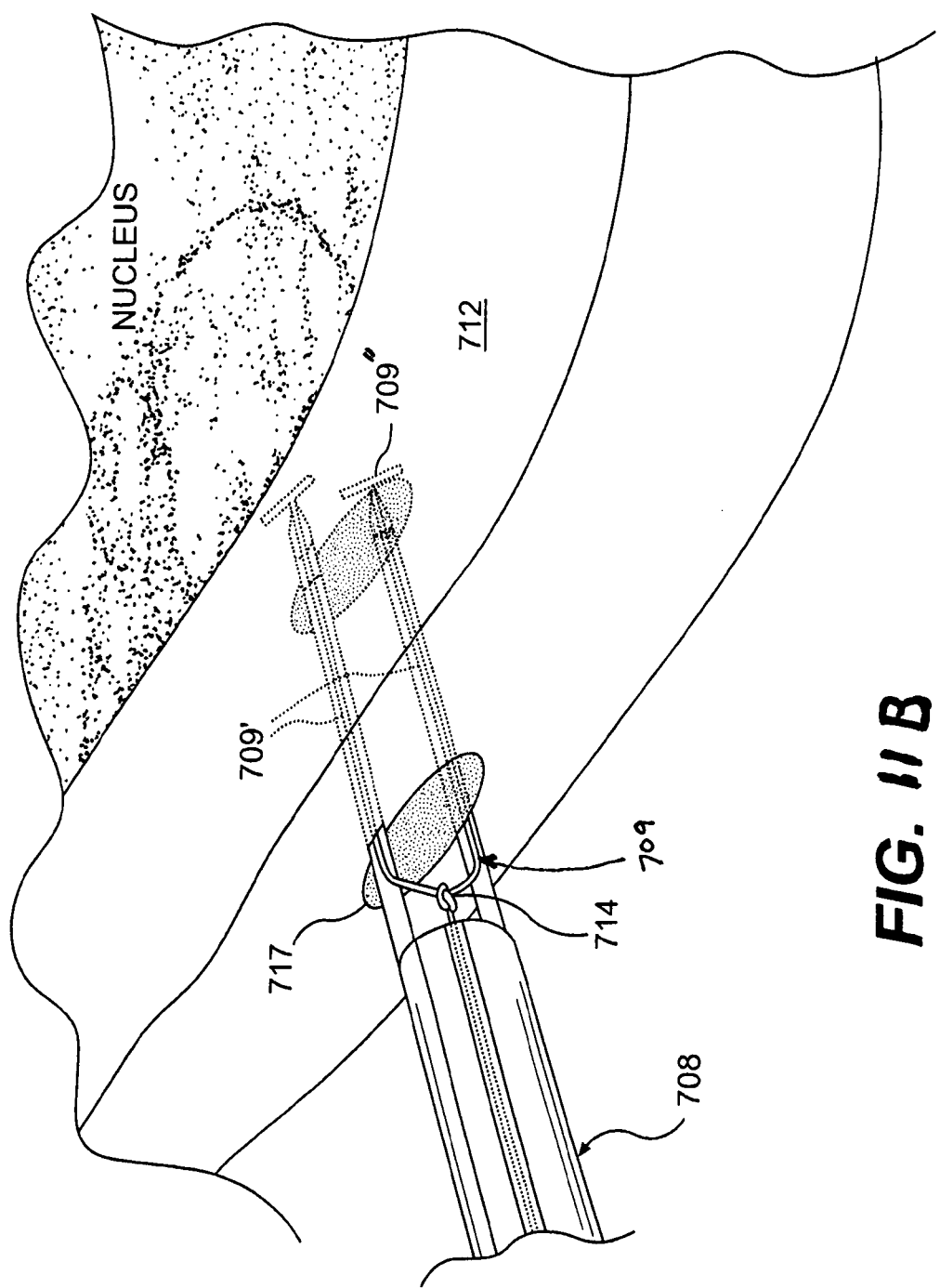
Figure 11C:
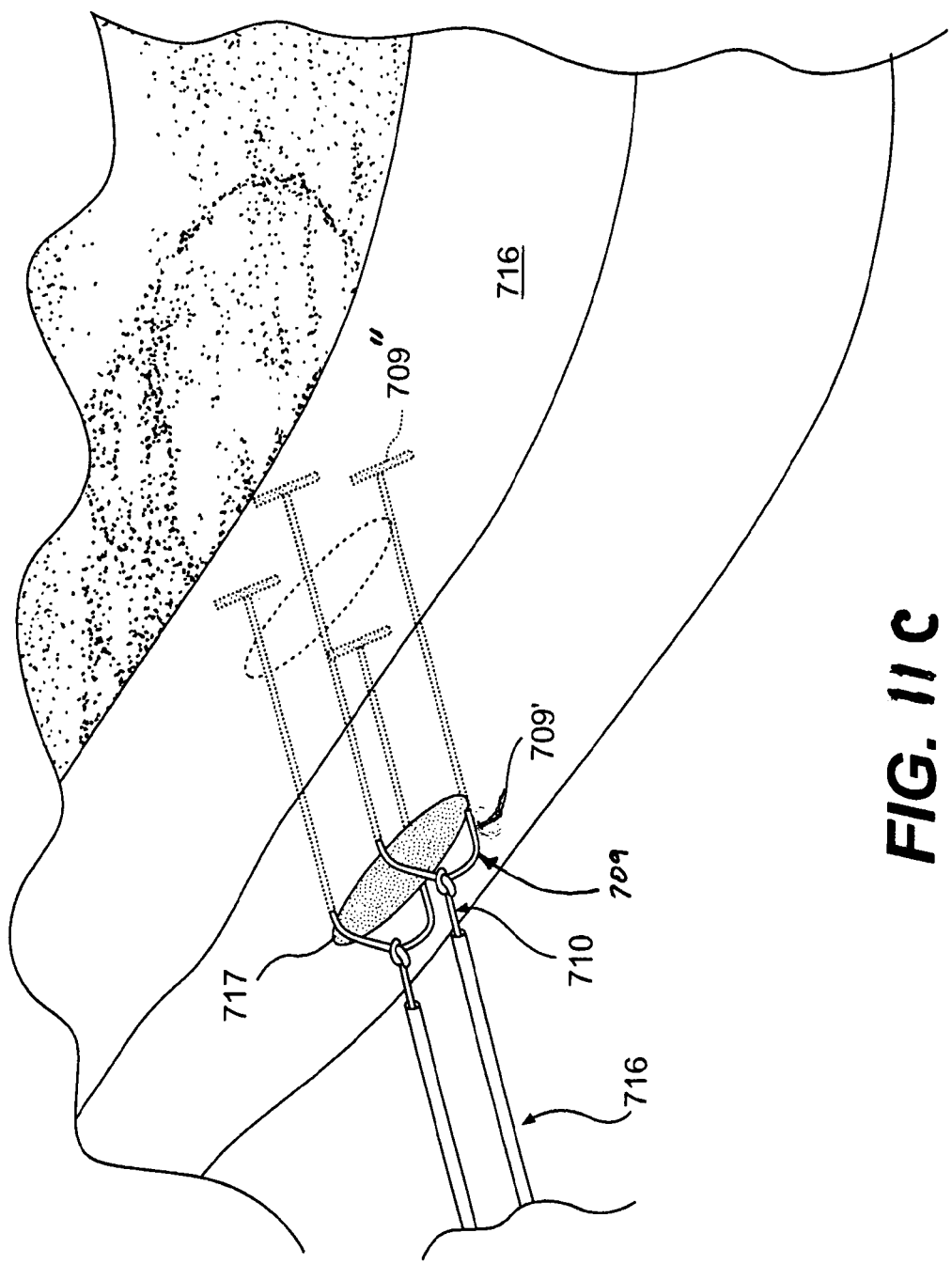
Figure 11D:
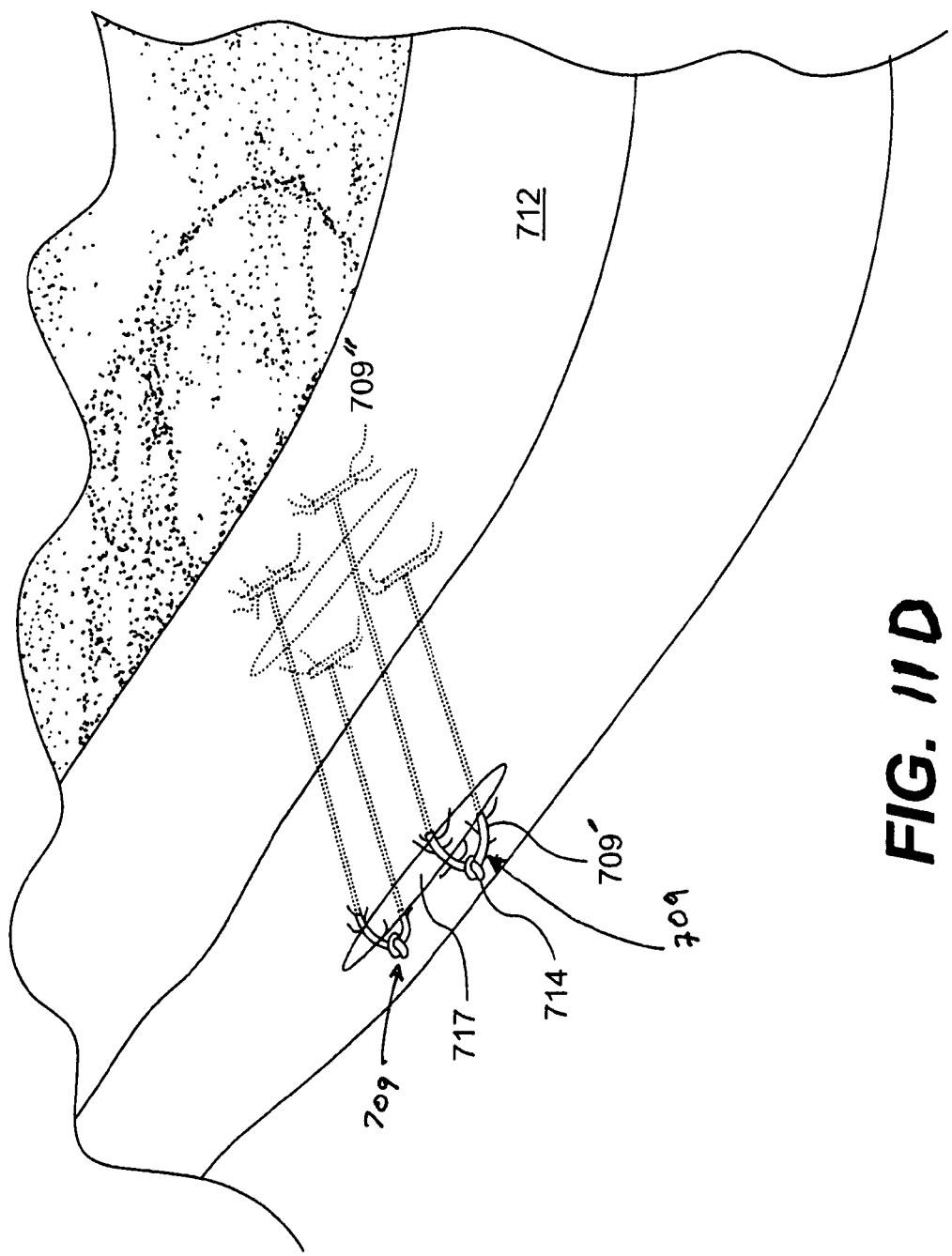
Figure 12:
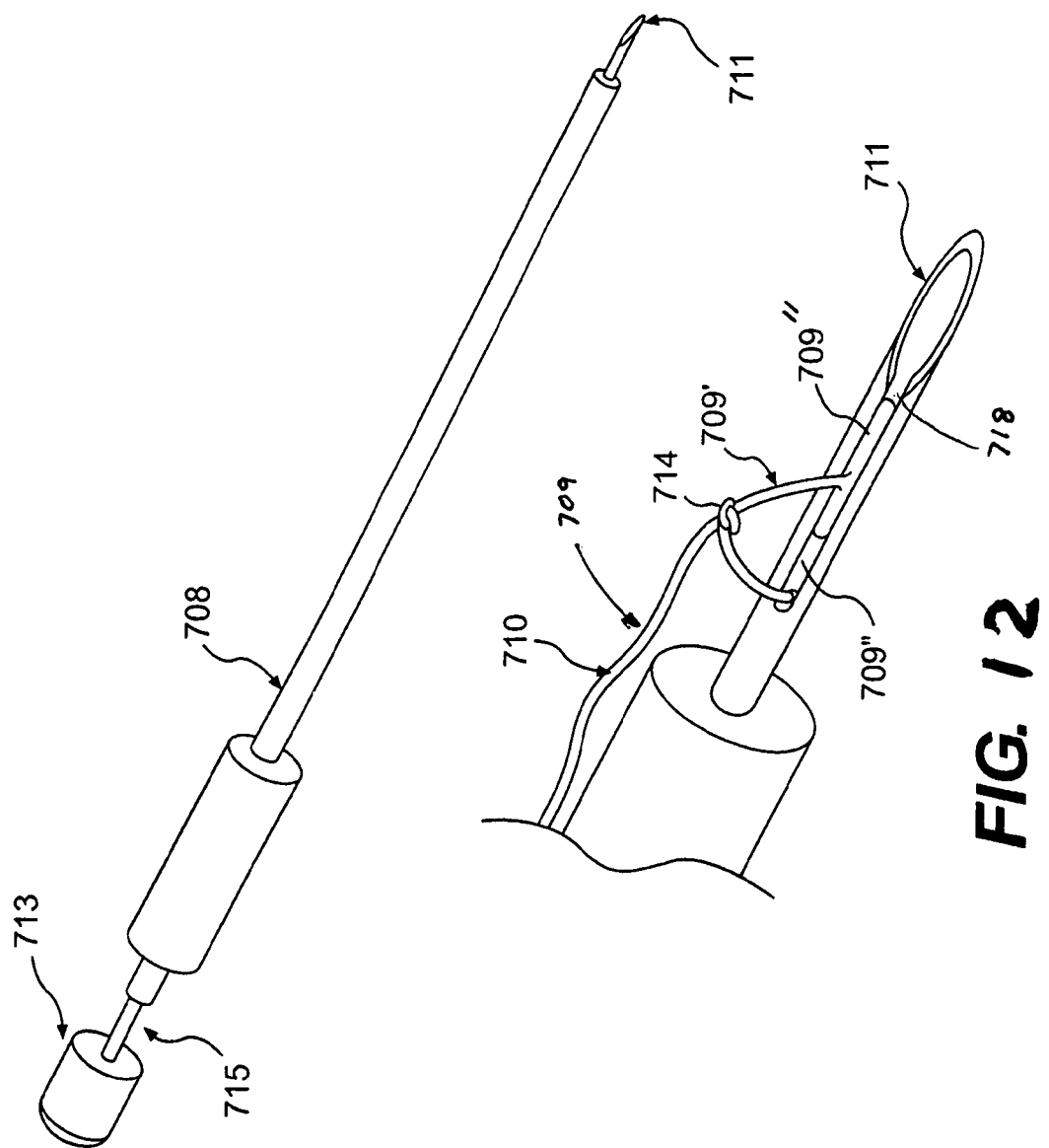
FIG. 12 illustrates exemplary embodiments of a fixation apparatus and fixation delivery apparatus in accordance with aspects of the present inventions.

Illustrative delivery devices as depicted in FIGS. 10-12 may be configured to accommodate and deploy at least one anchor device, such as a barb or T-anchor with one or more associated bands. Advantageously, the distal end of the delivery device will comprise a hollow needle or cannula 711, having a circular, elliptical, triangular, hexagonal or other inner cross-sectional area, suitable to accommodate the cross-sectional shape of the fixation device within. The distal point of the cannula 711 is advantageously sharpened, as a needle, to accommodate insertion into tissue. The cannula 711 is advantageously cut obliquely as shown in FIG. 12 to form a sharp leading surface or point for ease of insertion. The cannula 711 may contain a cut or groove 718 along its side to accommodate one or more anchors 709" with bands 709' as shown (or barbs, not shown), e.g., in FIG. 10B or 12. In one embodiment, the at least one fixation device (including band and barb or T-anchor), or portion thereof, is disposed within the cannula 711 as shown in FIGS. 10*a*, 10*b*, and/or 12. Alternatively, the T-anchor assembly 709 (or barb, not shown), or other fixation device may be hollow and disposed in a manner surrounding, and mounted on the device of the delivery device.

The delivery device 708 may also advantageously contain within it an ejection rod 715. The proximal end of the ejection rod 715 may contain an end portion 713 to function as a stopper, e.g., having a diameter larger than the remaining portion of the rod, such as is shown in FIG. 10A or 12. The diameter of the remaining portion of the ejection rod 715 may be small enough for insertion within the shaft of the device 708. Upon insertion of the cannula 711 into the location of choice, the ejection rod is pushed to deliver the fixation device. The delivery device is then removed.

Advantageously, the ejection rod 715 and delivery device may be configured to deliver multiple fixation devices, sequentially or simultaneously. Thus, if multiple fixation devices are contained within the device, the ejection rod 715 and delivery device may be configured such that the rod 715 be pushed a first distance, sufficient to deliver a first anchor of a fixation device. The delivery device is then removed from the first insertion point and inserted into a second insertion point, where the ejection rod is then pushed a second distance for delivery of a second anchor of a fixation device, and so-on as desired. For simultaneous delivery of multiple fixation devices, multiple delivery devices may be arranged in parallel (or substantially parallel). The distance between (or among) the delivery devices may be fixed or adjustable, as desired.

The distance the ejection rod 715 is pushed to define a first, second, and subsequent distances may be regulated by feel. Alternatively, the distance can be regulated by the architecture of the device. For example, the shaft and ejection rod may be fitted with a notch-and-groove configuration, respectively. In such configuration, the notch in the outer surface of the ejection rod may be aligned with a groove in the inner surface of the device. The length of the groove defines a first distance. The ejection rod 715 would be then turned or rotated within the device, aligning the notch within the device to a second groove defining a second distance, and so-on. In an alternative embodiment, the ejection rod and tissue anchor portion of the fixation device (e.g., barb or T-anchor) may surround the shaft of the device, as a sleeve surrounds an arm. In such a configuration, the delivery tool would comprise a solid shaft and the ejection rod and fixation device would be at least partially hollow and disposed over the distal portion of the delivery device. Pushing the ejection rod in a proximal to distal direction would deploy the tissue anchor portion of the fixation device.

FIGS. 10A and 10B describe one embodiment of an anchor band delivery device 708 and fixation means. FIG. 10A shows a general drawing of a delivery device. FIG. 10B further depicts the distal end of the delivery device. As illustrated, anchor band delivery device 708 contains two pointed needles or cannulae 711. Each cannula 711 contains an anchoring T-type anchor 709" (or barb) positioned within the distal end of the cannula 711. A band 709' links the two tissue anchors 709" (or barbs) together and a cinch knot 714 secures the anchors (or barbs). Cinch line 710 is pulled to decrease the length of the band 709' that attaches the anchors 709".

Referring to FIG. 11A, anchor band delivery device 708 is inserted into the annulus 712 sufficiently to engage the layers of the annulus 712, and preferably located at the inner wall of the annulus 712. The anchors 709" may be ejected from the delivery device by pressing the ejection rod 715 in a fashion to expel the T-anchors 709" (or barbs, not shown) from the device. For example, pressing on the proximal end of ejection rod 715, as shown in FIG. 10A, drives the ejection rod 715 in a distal direction, thus expelling the anchor from the device. FIG. 11B shows the anchors 709" (or barbs) after being ejected. FIG. 11C shows a knot pusher 716, that can be attached to the delivery tool 708, or used separately, that can be used to tighten the knot 714 once the fixation device is secured into the annular tissue. FIG. 11C shows the placement of two anchor bands or fixation devices 709 (anchors and bands), after they have been delivered to the annulus and before the bands 709 have been tightened. The knot pushers 716 of both devices are still in contact with the knots and the delivery needles have been pulled back, away from the annulus. FIG. 11D shows the final placement of the two anchor bands or fixation apparatuses 709 after drawing together the tissues surrounding the aperture 717, the inner wall of the annulus 712, and/or the outer wall of the annulus; and, after tightening the knot and cutting excess suture material located on each anchor band. Although this FIG. 11 shows the passage of two bands 709 superior and inferior to the aperture and along the defect, these bands could as easily be placed in a multitude of locations to effect desired or equivalent outcomes, including and not to be limited to, a cruciate configuration.

In addition, as previously described, one could use barbs having a multitude of configurations. One could also configure delivery devices to deliver one (as in FIG. 12), two (as in FIG. 10A), or more barbs simultaneously, and according to predetermined or variable distances or patterns. The delivery devices may also be configured to eject one, two, or more barbs sequentially. Further, the barbs could be delivered by a delivery device that does not require a cannula to cover the barb. In such a configuration, the barb may be disposed on the tip or outside of the delivery device's shaft, and removed therefrom upon injection into the desired location of the annulus or other tissue. Bands and knots may be pre-tied to accommodate each configuration, as previously discussed.

For example, although FIGS. 10 and 11A-B depict a device that places a fixation apparatus (e.g., two anchors 709" banded together) with one delivery device, one could accomplish an equivalent or other desired result with a single device that delivers multiple bands at the same time, or conversely multiple delivery devices that deliver portions of the fixation apparatus.

FIG. 12 shows an alternative delivery device that delivers two or more anchors (or barbs) from a single cannula 711. In this embodiment, a first single tissue anchor 709" may be ejected from the cannula 711 by pushing the ejection rod 715 a first distance sufficient to eject the first tissue anchor 709", but insufficient to eject the second. Then the delivery device is removed from the first site and passed into another annular location. The second anchor (or barb) 709" connected to the first anchor or barb by band 709', is ejected out of the cannula 711 by pushing the ejection rod 715 an additional distance sufficient to eject the second anchor 709"(or barb) into a second fixation point in the annulus.

Although much of this description has described placement of anchors into the annulus (or soft tissue) of the disc, one could perform tissue anchoring into other tissues surrounding the annular defect, including the bone, Sharpey fibers or surrounding ligaments. It is also contemplated that, given the delivery device construction, a bone drill or similar device may be necessary to facilitate the placement of the delivery device through bony or similar tissue.

The band 709' connecting the thus implanted anchors may advantageously contain a moveable knot 714 between the anchors. Suitable knots include, but are not limited to, the Roeder knot and its functional equivalents, and are advantageously, but not necessarily, pre-tied. After insertion of both anchors 709", the band 709' is advantageously tightened by hand or by pushing on the knot with a knot-pusher or similar device. Although not shown in FIG. 12, the knot pusher may be integral to the delivery device. After drawing together the tissues surrounding an annular defect the excess suture line can be cut. It is also possible to use a cutting device integral to the delivery device to cut the band after cinching. Although the device shown in FIG. 12 depicts two tissue anchors being delivered from a single device, multiple tissue anchors or barbs could be delivered from the same or a similar type of device. Additionally, a delivered configuration of fixation means may result from the use of a single device to deliver multiple tissue anchors sequentially.

The shaft of the device may be of any convenient length, typically from, e.g., 1 inch to 10 inches. Materials of which to make the delivery device include, but are not limited to: metals, such as stainless steel, nickel, titanium alloy, and titanium; plastics, such as PTFE, polypropylene, PEEK, polyethylene, and polyurethane, acrylic, polycarbonate, engineering plastics; and/or composites.

Advantageously, the shaft of the device may have a cross-sectional shape suitable to accommodate an ejection rod and at least one fixation element, or portion thereof. In one embodiment, at least a portion of the shaft of the device may be hollow, having a circular, elliptical, triangular, trapezoidal or other suitable cross-sectional area sufficient to accommodate an ejection member.

The delivery device may also contain a handle or raised surface configured to accommodate the shape of surgeon's hands or fingers for easier handling. Such raised or configured portion may be made of the same or different material as the tube or shaft. Suitable materials known in the art include, among others, polymers, such as acrylic polymers, polyurethane, polycarbonate, engineering plastics; and metals, such as stainless steel and titanium.

Many of the inventive embodiments disclosed herein relate to the use of a patch stent, barrier, scaffold, membrane, mesh or similar reparative treatment device for annular repair and/or reconstruction. In some clinical instances, the method of the invention may be accomplished without the use of a patch-like device, however. For example, a patch may be unnecessary to repair small apertures or apertures of certain shapes, or certain weakened or thin portion(s) of an annulus. Therefore, inventions herein also encompasses methods for repairing or reconstructing annular tissue that do not necessarily necessitate the use of a patch, has exemplified in FIG. 11. Accordingly, an additional embodiment of the invention also provides fixation devices that may be used to reapproximate, repair, reconstruct, reinforce, support, hold, retain or otherwise treat annular tissue. Such fixation devices and their delivery apparatuses, as described herein, may contain an anchor portion and a band portion. The tissue anchor portion serves to fix the fixation device in tissue proximate the disc. The band portion, attached to the tissue anchor portion, serves to reparatively draw together annular tissue when tightened and secured. At least one fixation device may be placed into, or through, the wall of an annulus surrounding an aperture, weakened, delaminated, or thin portion of the annulus. The device is then drawn in tension to pull together, wholly or partially, the surrounding annular tissue.

The band and the barbs may be separate elements or comprise one continuous element. Bands and barbs may be made of the same or different materials.

The bands, or elongate members, may be string-like, made from suture or similar material, or of any construction or dimension that is amenable to the delivery and engagement of the fixation device. For example, the band may have a width greater than, in some embodiments far greater than, its thickness. The suture material may in some embodiments have a width:height ratio of 1.25:1. In some embodiments, bands may be constructed, wholly or partially, of a mesh tube. Moreover, different segments along the length of the band may have different dimensions and constructions. For example, the band may be constructed of thin material, such as nickel titanium alloy or stainless steel wire, close to the anchor barbs, while the middle portion that spans the aperture may comprise a much wider band made of optionally softer material, or materials conducive to tissue ingrowth and/or tissue regeneration.

Figure 9:
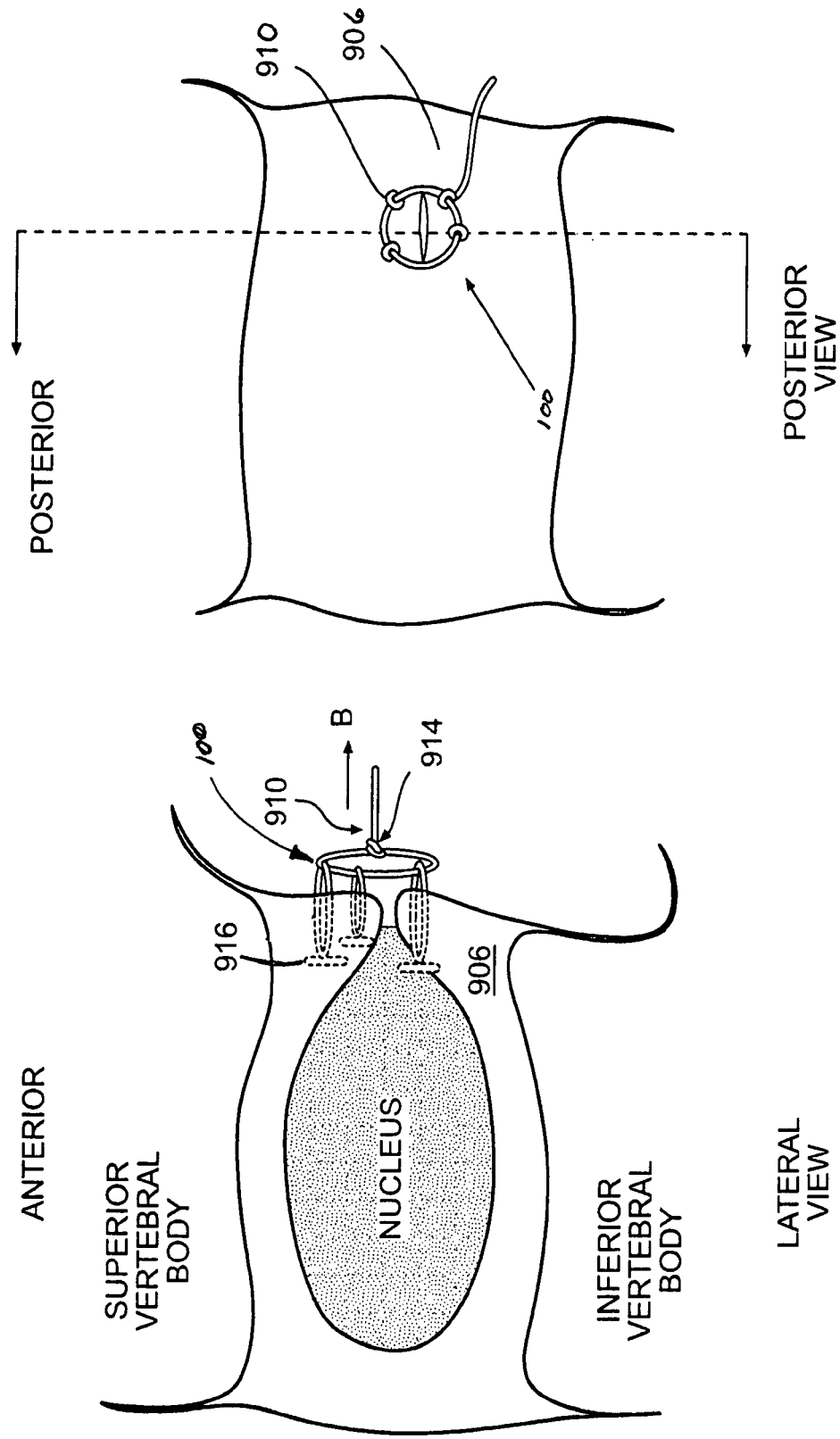
FIG. 9 illustrates exemplary embodiments of a fixation apparatus in accordance with aspects of the present inventions in a delivered configuration that may result from the use of a single, or multiple, devices to deliver multiple barbs, tissue anchor, or T-anchors sequentially or simultaneously.

FIGS. 7, 8, and 9 show examples of embodiments of the invention for repair or reconstruction of the annulus that could be utilized without the additional use of a patch-like device. For instance, in FIGS. 7A-7C, in lieu of (or optionally in addition to) a patch, two anchors are shown having passed into annular tissue 906. By drawing on band 910, the annular tissue 906 may be drawn together in tension, and may also reapproximate the tissue surrounding the annular aperture. FIG. 7C shows a single tissue anchor band being placed along an incision or tear in the annulus.

The fixation devices 100 of the invention could be delivered as a pair of barbs attached by a single band, or each barb could be delivered individually. Alternatively, multiple barbs (anchors) may be pre-attached to a single or multiple bands for ease and speed of delivery. For example, FIG. 9 exemplifies a fixation device that has multiple anchors 916 (or barbs, not shown) connected together in a configuration similar to FIGS. 8B and 8C, with each anchor 916 being delivered individually into, or through the nucleus or annulus. The anchors, if present, may be shown as in FIG. 9. By drawing on the cinch line, the tissues surrounding the aperture and/or the inner wall of the annulus and/or the outer wall of the annulus may be drawn together. Although a knot 914 is shown to affix the suture lines together, other means to lock, fasten clip, retain, or otherwise secure the sutures together may also be used.

FIGS. 13-19 depict an illustrative method for the deployment of a treatment device into the intervertebral disc 200. As described previously, there are a variety of applications, approaches, techniques, tools, and methods for accessing and performing spinal disc surgery which may be dependent on physician preferences and could be arbitrary. Therefore, the following description and depiction of the method should be considered illustrative and not limiting. In the illustrative scenario which is used in the following descriptions, and the disc 200, which is comprised of the annulus fibrosus 202 and the nucleus pulposus 204, is shown in a transverse cross-section in FIGS. 13-16 and a sagittal cross-section in FIGS. 17 and 19. The disc 200, as described above, is disposed anatomically between caudal and cephalad vertebral bodies. The disc 200 may be accessed for treatment via a surgical incision 208 made in the paramedian region lateral of the spinal canal 210. A microdiscectomy procedure may precede the placement of a treatment device in order to remove disc fragments and may result in a subannular cavity. The cavity, however, may be preexisting or may be created for the purpose of performing an adjunctive surgical procedure, such as a nuclear augmentation. A resulting aperture 214 in the annulus may provide a path for the mesh or treatment device delivery tool 500 to place treatment device 600. The treatment device 600 can take the form as described in commonly-assigned co-pending U.S. patent application Ser. No. 11/120,750, filed on May 3, 2005 and Ser. No. 10/352,981, filed on Jan. 29, 2003 which are incorporated herein by reference, or any other appropriate form. Likewise, the anchor band delivery device 400 can take the form as described in the embodiments above, or as additionally described below with reference to FIGS. 20-29, or as described in commonly-assigned co-pending U.S. patent application Ser. No. 11/120,750 filed on May 3, 2005 and U.S. patent application Ser. No. 10/327,106, filed on Dec. 24, 2002 now issued U.S. Pat. No. 7,004,970 and incorporated herein by reference or any other appropriate form.

Figure 13:
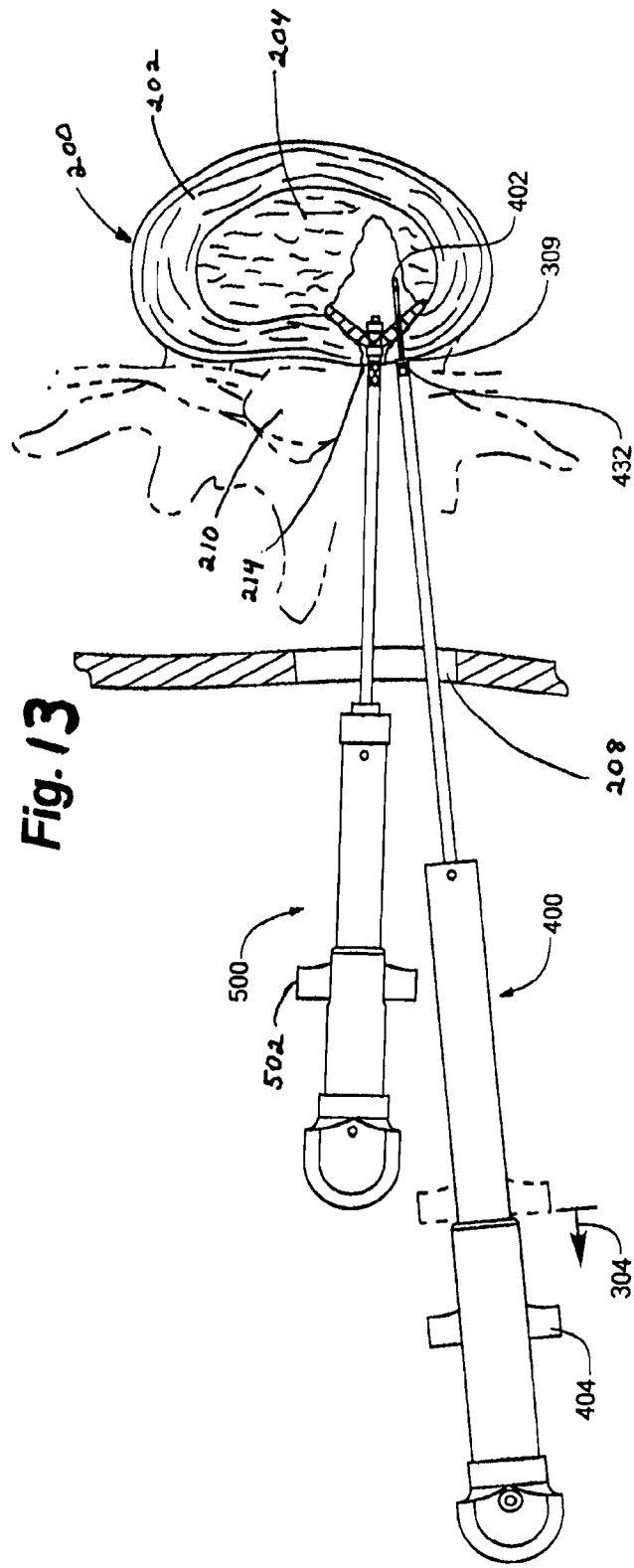
FIG. 13 illustrates exemplary embodiments of a transverse view of the placement of a fixation element through a treatment device and the annular wall in accordance with aspects of the present inventions.

A patch delivery device 500 is introduced through surgical incision 208 to traverse aperture 214 and position treatment device 600 in subannular cavity 212. The, treatment device 600 is in a first configuration sized to permit its passage to the subannular cavity 212. FIG. 13 shows a transverse view of mesh device 600 mounted on the distal portion of delivery tool 500, introduced to the cavity and deployed.

Figure 17:
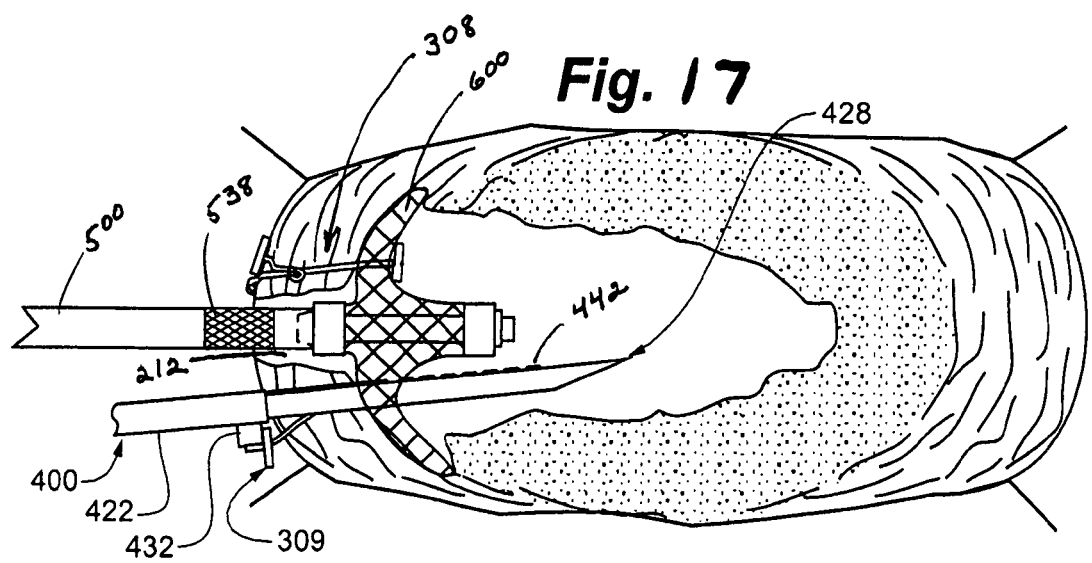
FIG. 17 illustrates exemplary embodiments of a sagittal view of the placement of a fixation element delivery tool through a treatment device and the annular wall in accordance with aspects of the present inventions.
Figure 18:
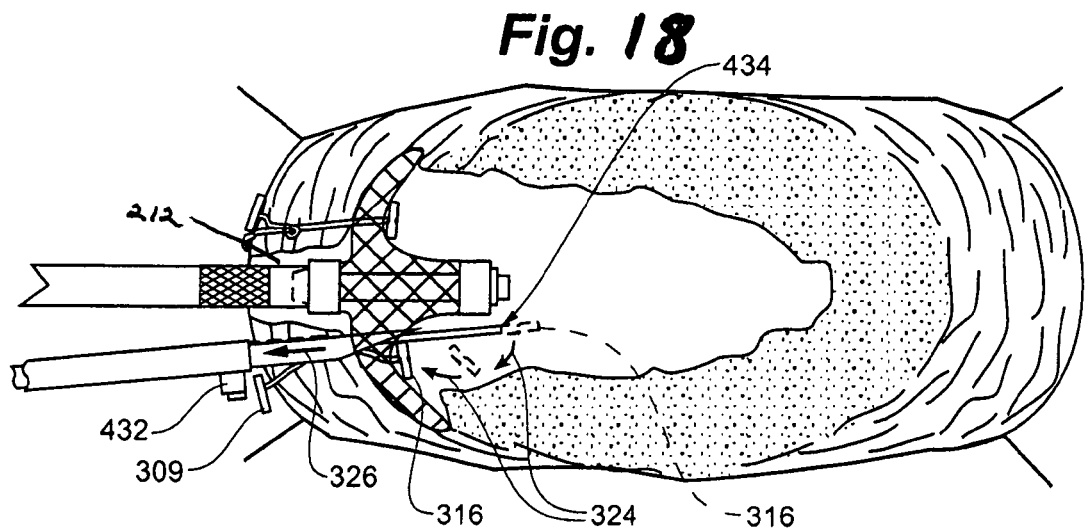
FIG. 18 illustrates exemplary embodiments of a sagittal view of the placement of an additional fixation element through a treatment device and the annular wall in accordance with aspects of the present inventions.

The treatment device delivery tool 500 can be manipulated by, for example, pulling a finger grip 502 to deploy treatment device 600. This deployment may involve a longitudinal shortening of the treatment device resulting in a lateral expansion of the treatment device 600. The pulling of the finger grip 502 may be preceded by the release of a safety lock preventing deployment of the treatment device until intended by the surgeon. Also shown in FIG. 17 is a marking 538 on the delivery tool 500 that may visually assist the surgeon in assessing the degree to which the device has been placed in subannular space.

Once the finger grip 502 reaches its intended limit, and the concomitant full intended deployment of treatment device 600, the deployed device 600 may then be pulled to internally engage and at least partially conform to the cavity 212. Naturally, the full travel of the finger grip 502 can be determined by the design of the delivery device, or informed by the judgment of the surgeon through visualization, tactile realization, or the like. Once the intended limit has been achieved and the device fully deployed, the delivery device 500 can lock finger pull 502 in place so as to maintain the treatment device 600 in the deployed configuration. It may also be advantageous for the delivery tool 500 to have a perceptible (i.e., audible, tactile, visual) indication that the treatment device has been fully deployed. The mesh/patch delivery tool 500 may be of the type described hereinabove, or as additionally described in other figures and/or sections of this disclosure.

As exemplified in FIGS. 13-19, a fixation element or anchor band delivery device 400 may then be introduced through surgical incision 208, where the distal end 402 is passed through the annulus fibrosus 202 adjacent to the aperture 214, and subsequently through treatment device 600. Fixation element delivery tool 400 may have features to provide tactile feedback once the delivery tool has been introduced into tissue to an acceptable extent, for example a feature like tissue-stop 432. As illustrated, delivery device 400 is passed distally until stop 432 and/or pledget member 309 of the fixation apparatus 308 come in contact with the outer surface of the annulus. Alternatively, and without tissue stop 432 use, pledget member 309 could be of construction to similarly resist, or otherwise visually or tactilely indicate ceasing the passage of delivery device 400 through annular tissue. FIG. 17 shows a detail, sagittal view of a distal end of a fixation element delivery tool 400 introduced into disc tissue and through treatment patch 600. As shown in FIG. 17, one fixation apparatus 308 has been deployed and fixated. FIG. 17 also depicts an exemplary treatment device detection feature 442 on the outer surface of needle cannula 428, as more clearly illustrated in FIG. 21. The patch detection feature 442 on the distal end of needle cannula 428 may advantageously provide perceptible feedback (tactile and/or audible) to the surgeon that the tissue anchor band delivery tool has accessed and penetrated the patch and it is therefore acceptable to deliver the band. Feature 442 is discussed in more detail below. In operation as illustrated in FIG. 13, the delivery device 400 can be manipulated similarly to the treatment device delivery tool. For example, moving finger grip 404 in the direction of arrow 304 will withdraw a portion (for example, the slotted needle cannula 428) of distal end 402 of the delivery device 400 and deploy a fixation element 308, as more described below, in the cavity 212 to secure the treatment device 600. The pulling of the finger grip 404 may be preceded by the release of a safety lock 406 preventing deployment of the fixation element until intended by the surgeon. The fixation element delivery tool 400 may be of the type described hereinabove, or as additionally described in FIGS. 20-29 below, or in other areas of this disclosure.

Figure 21:
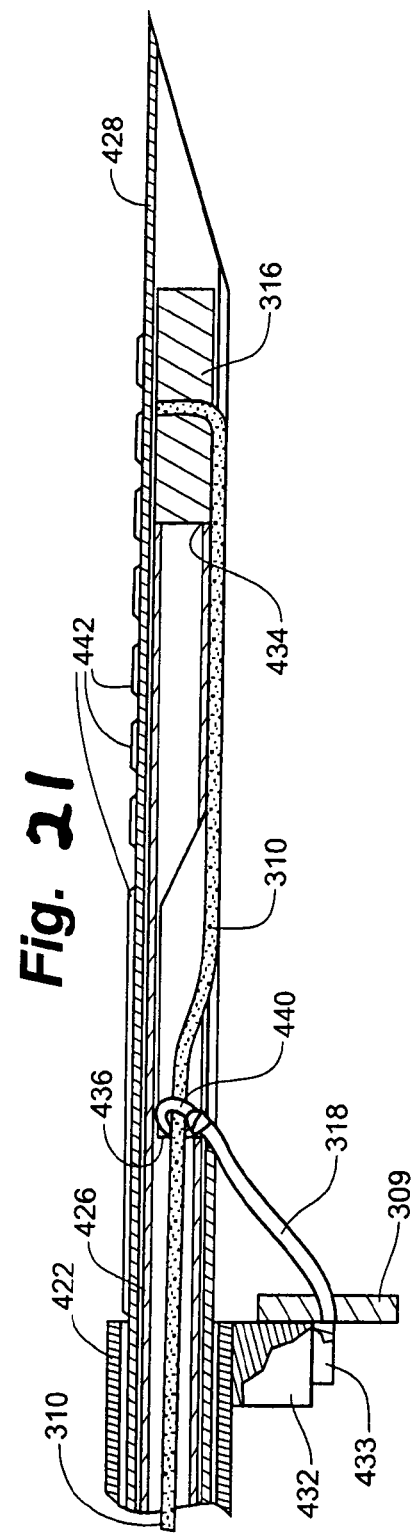
FIG. 21 illustrates a detailed view of the distal end of an exemplary embodiment of an anchor band (fixation element) delivery tool in cross-section in accordance with aspects of the present inventions.

FIG. 13 depicts the deployment of a fixation element 308 into disc tissue. The fixation device may be as described above, for instance comprising T-anchors, sutures, tethers, knots, pledgets or barbs. As illustrated here, the fixation element 308 is a T-anchor with suture bodies, knot, and pledget as more fully described below. During the pulling of finger grip 404 and retraction of slotted needle cannula 428, a knot pusher end 436 of inner cannula 426 is shown, for example in FIG. 21, holding a proximal portion of the fixation device's 308 slip knot 440, while T-anchor 316 is drawn in tension proximally by tether or suture line 310, to adjust the length of the fixation element 308 to provide the proper tension to securely hold the treatment device 600 in situ. A proximal end of the fixation element, such as a pledget 309, is held or urged into engagement with a bearing surface on the exterior of the annulus. The proximal end of the fixation device can also include a T-anchor or knot or similar tissue locking element. FIG. 21 is a cross-sectional view of the distal end of delivery tool 400 as it may be introduced in disc tissue. FIG. 28 shows the distal end of the delivery tool 400 after retraction of the slotted cannula 428 (as shown by arrow 326 of FIG. 18), and tensioning and drawing T-anchor 316 proximally to a potential final state. The proximal drawing of T-anchor 316 is also illustrated in a detail, sagittal view in FIG. 18, with arrows 324 illustrating motion of the T-anchor. The construction of the locking element 316 is exemplary and is not intended to be limiting of alternative constructions of 316, such as one or more pledgets, knots, barbs or other forms to affect the same function of anchoring in tissue.

Figure 14:
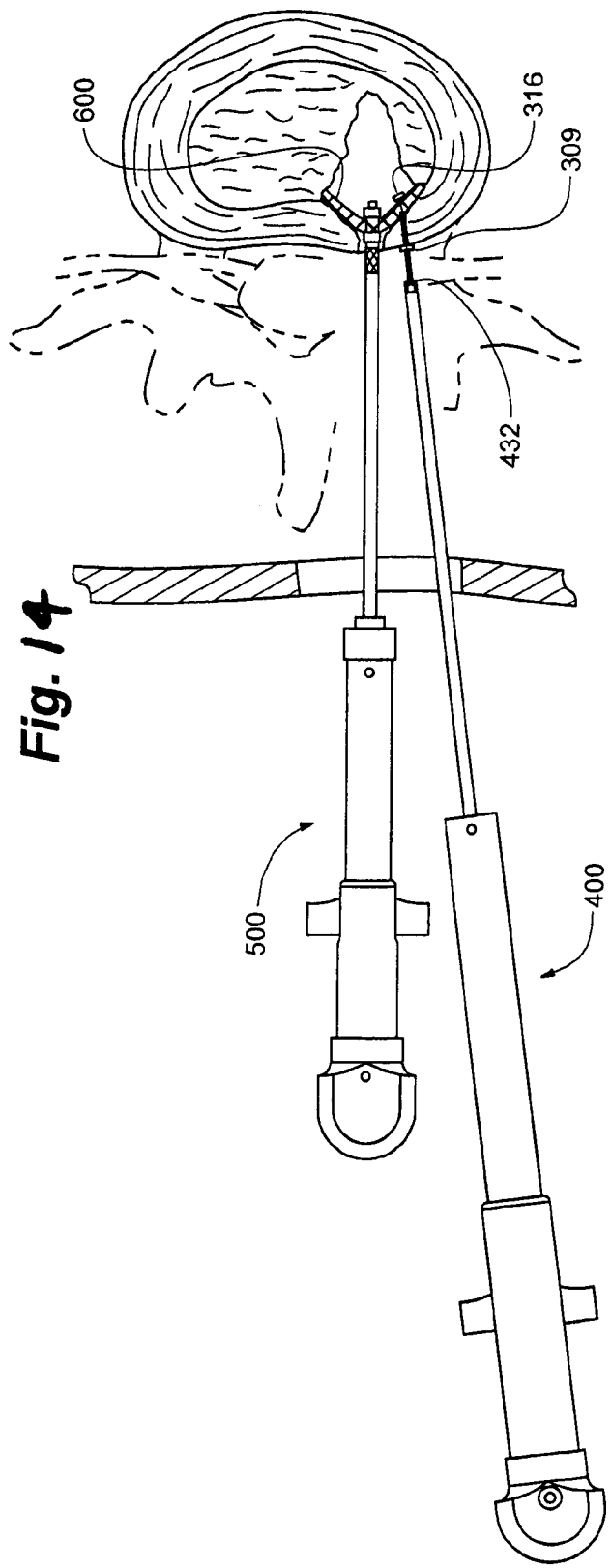
FIG. 14 illustrates exemplary embodiments of a transverse view of a fixation element delivery device after affixing a fixation element delivered in FIG. 13 and partial removal of the fixation element delivery device in accordance with aspects of the present inventions.
Figure 15:
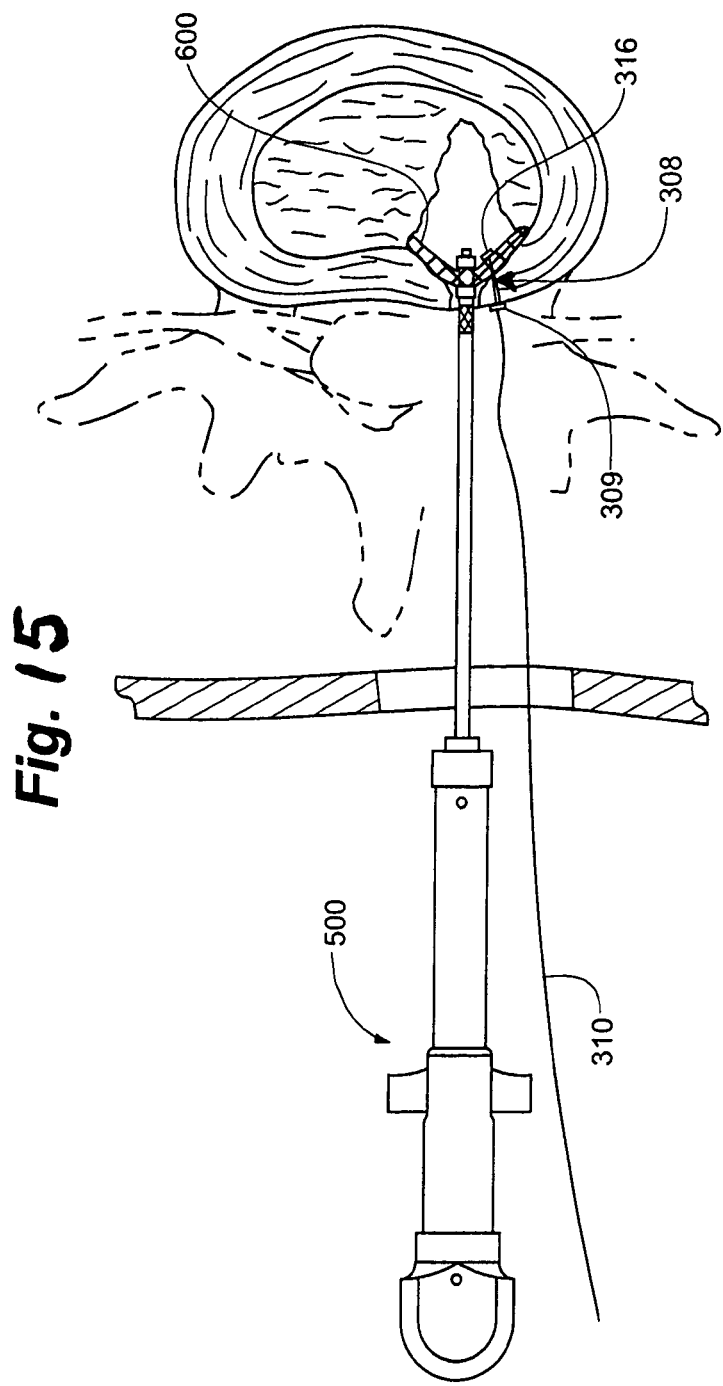
FIG. 15 illustrates exemplary embodiments of a transverse view of the fixation element after removal of the fixation element delivery tool in accordance with aspects of the present inventions.
Figure 16:
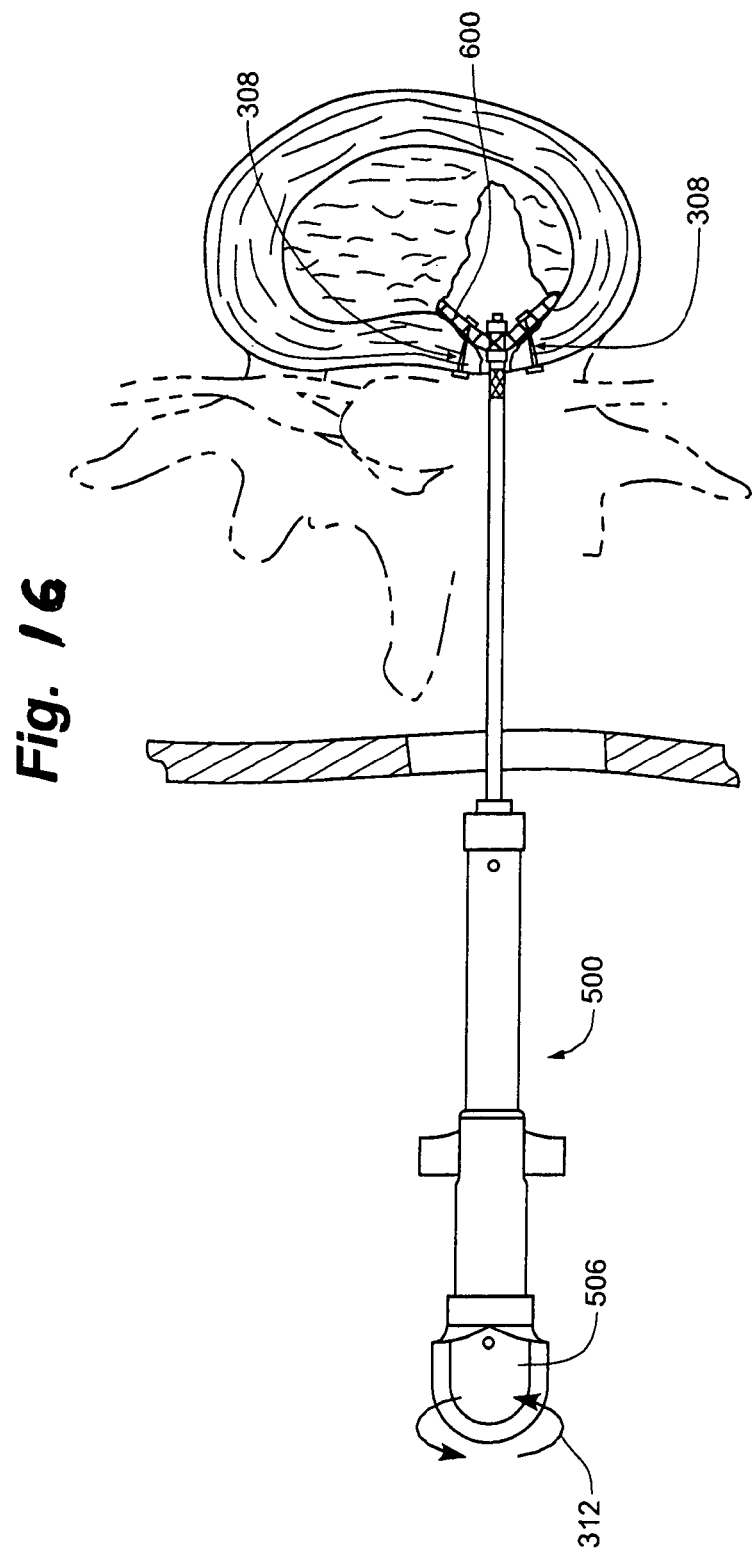
FIG. 16 illustrates exemplary embodiments of a transverse view of an additional fixation element locked in place on the opposite side of the treatment device in accordance with aspects of the present inventions.
Figure 19:
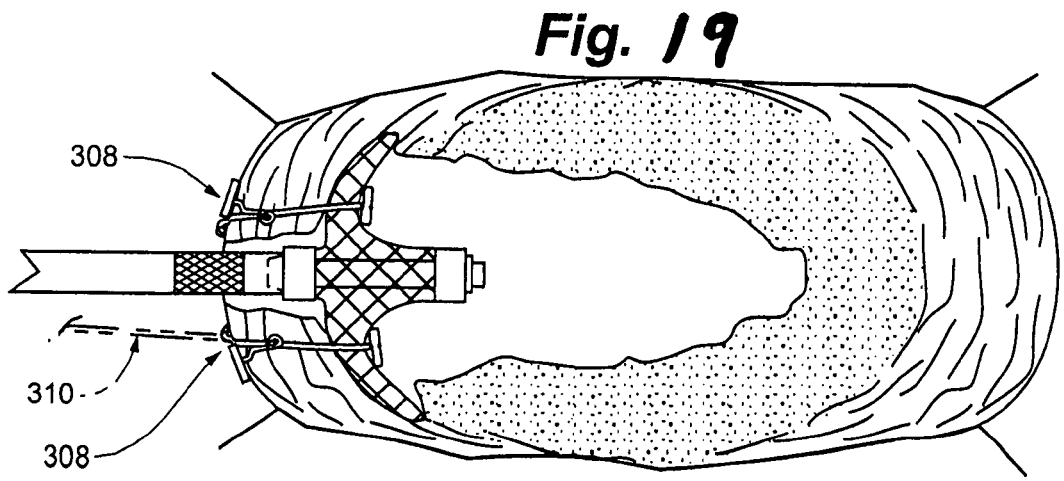
FIG. 19 illustrates a saggital view of an-exemplary embodiments after the removal of the fixation element delivery tool in accordance with aspects of the present inventions.

FIG. 14 shows the partial withdrawal of the fixation element delivery device once the fixation element has been deployed. In the illustrations shown, the final step during the pulling of finger grip 404 proximally results in the release of the fixation element in situ. The release may be accompanied by visual or tactile or auditory confirmation, such as a click. Once released, the fixation element delivery tool can be completely withdrawn as shown in FIG. 15, leaving the suture body 310 of a fixation element extending through the surgical incision 208. The proximal portion of suture body 310 may be cut to a suitable length with readily available surgical tools such as a scalpel or surgical scissors and removed from the surgical site. The fixation element 308 is fixedly engaged with the disc tissue and the patch 600. FIG. 16 depicts the treatment device 600 after placement of two fixation devices 308, as does FIG. 19 shown in a detail, sagittal view. Of course, any number of fixation devices appropriate to secure the treatment device 600 can be used. It is also anticipated that device 600 may be of a construction and design, as described herein, that does not necessitate anchor bands to effect securement of device 600 within the disc space and therefore, illustrations using fixation elements are to be exemplary, and not limiting. Once secured, the treatment device 600 is released from the mesh delivery tool 500. This may be accomplished in a two or more step process. For example, the release mechanism may be enabled by rotating knob 506 in the direction of arrows 312. An indicator may then be activated to notify the surgeon that the treatment device has been released from the delivery tool 500. Accompanying the deployment of indicator may be the uncoupling of the treatment device 600. The delivery tool 500 can then be withdrawn leaving treatment device 600 in situ.

FIGS. 20-29 depict illustrative embodiments of a fixation element delivery tool (or FEDT) as discussed above, which may be referred to alternatively as an anchor band delivery tool (or ABDT) or a fixation apparatus delivery apparatus. The fixation element 308 is depicted as loaded in the distal end 402 of the ABDT, which will be discussed in greater detail with reference to FIG. 21. The ABDT 400 is comprised of a main body member 410 which may be fixedly attached distally to outer cannula 422, and also to inner cannula 426 at inner cannula anchor 438. Distally, inner cannula 426, as better illustrated in detail in FIG. 21, may comprise a knot pusher 436 (or other means to effect securement of suture tethers 310 and 318 with locking element 440) and T-anchor stand-off 434. Proximally, main body 410 has disposed safety member 406 with an outside diameter telescopically and rotatably received in the inner diameter of a knob 408. Knob 408 and main body member 410, may be rigidly attached to one another. Slidably disposed within the lumen of the main body member 410 is suture retention block 414, depicted with elongate member body 310 threaded through its center hole. A spring 316 may also be slidably disposed within the lumen of the main body member and can abut either suture retention block 414 or slider member 418. Slider member 418 can be integral with finger grip 404 (shown in FIG. 13). Attached to the proximal end of slider member 418 is a suture cutting blade assembly 420. The blade assembly, as will be discussed in greater detail below, serves to sever the suture body 310 after deployment of the fixation elements as described herein. A slot in the slider member 418 allows the slider member 418 to slide past the cannula 426 and, as described previously, 426 may be stationary with respect to main body 410. A slotted needle cannula 428, slidably disposed in the lumen of the outer cannula 422, is secured to the distal end of slider member 418 by needle cannula anchor 430, such that the translation of the slider member 418 within main body member 410 concomitantly translates the slotted hypotube 428 within the outer cannula 422.

FIG. 21 is a detailed view of the distal end 402 of the ABDT 400. As described above, the slotted hypotube 428 is slidably received in the outer cannula 422. A tether, consisting of a suture line 318 and a pledget body 309 is located in proximity to an optional tissue stop 432 on the outer cannula 422. It is also possible for pledget 309 to be held by an optional outer cannula pledget holder 433 until release of the anchor band. The suture line 318 is slidably knotted to suture body 310. The distal end of suture body 310 is attached to T-anchor 316, which is held by T-anchor stand off 434. As described above, T-anchor stand-off 434 and knot pusher 436 may be components of inner cannula 426. In the initial configuration, needle hypotube 428 extends distally of outer cannula 422 and allows the point of slotted hypotube 428 to extend distally of the T-anchor holder 434.

Figure 20:
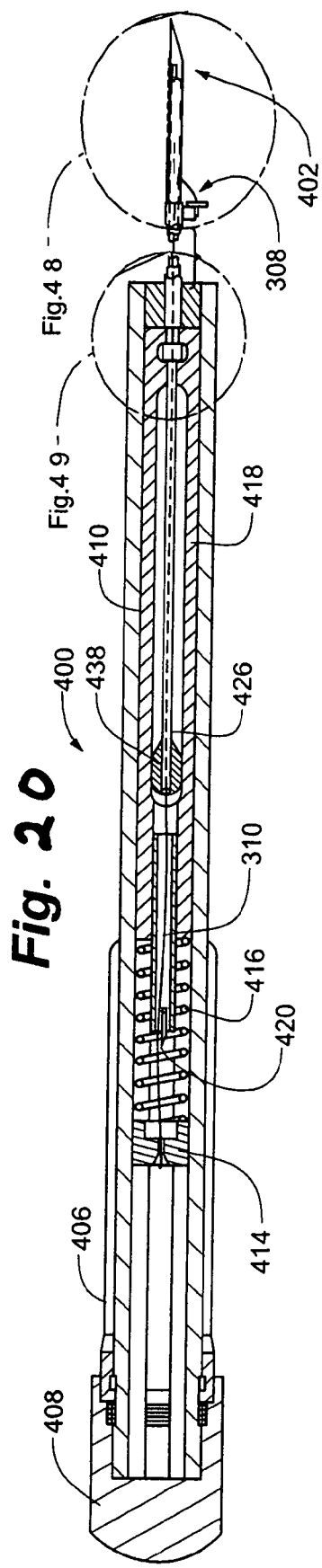
FIG. 20 illustrates a view of an exemplary embodiment of a fixation delivery apparatus pre-deployment in cross-section in accordance with aspects of the present inventions.

FIGS. 20 and 21 depict the ABDT in its initial delivery configuration. The ABDT is locked in this configuration by the distal end of safety 406 engaging the finger grip 404 (not shown) as depicted in FIGS. 13 and 14. Rotation of handle member 406, as shown by arrow 306 in FIG. 23, may allow the finger grip 404 to engage a slot on safety 406, and permit the surgeon to pull finger grip 404 proximally toward the proximal knob 408. Doing so results in the translation of the slider member 418 proximally, and concomitantly, the proximal translation of the slotted needle cannula 426 (as a result of slotted needle cannula anchor 430) in the direction of arrow 326 (illustrated in FIG. 18). The result, as discussed above, is the unsheathing by the needle 428 of T-anchor 316 held by T-anchor holder 434. The translation of the slide body 418 proximally also urges the spring 416 and suture retention block 414 proximally. The suture retention block 414 is attached to suture body 310, and therefore tension is leveraged onto the suture body 310 to hold it taught and, when appropriate, draw T-anchor 316 from within the delivery tool to a position proximally.

Figure 22:
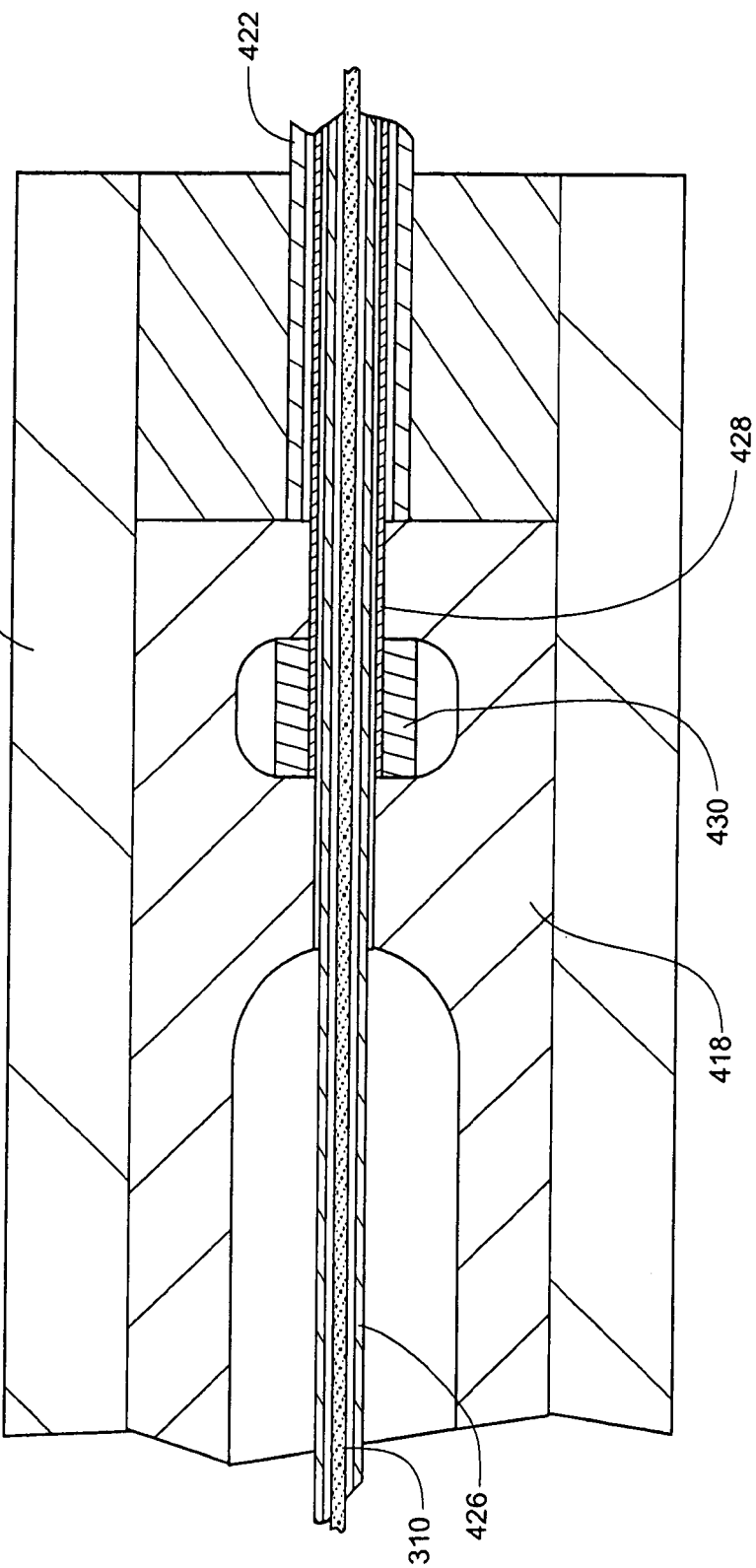
FIG. 22 illustrates a detailed view of exemplary embodiments of a slide body and cannula anchor of an exemplary fixation element delivery tool in cross-section in accordance with aspects of the present inventions.
Figure 23:
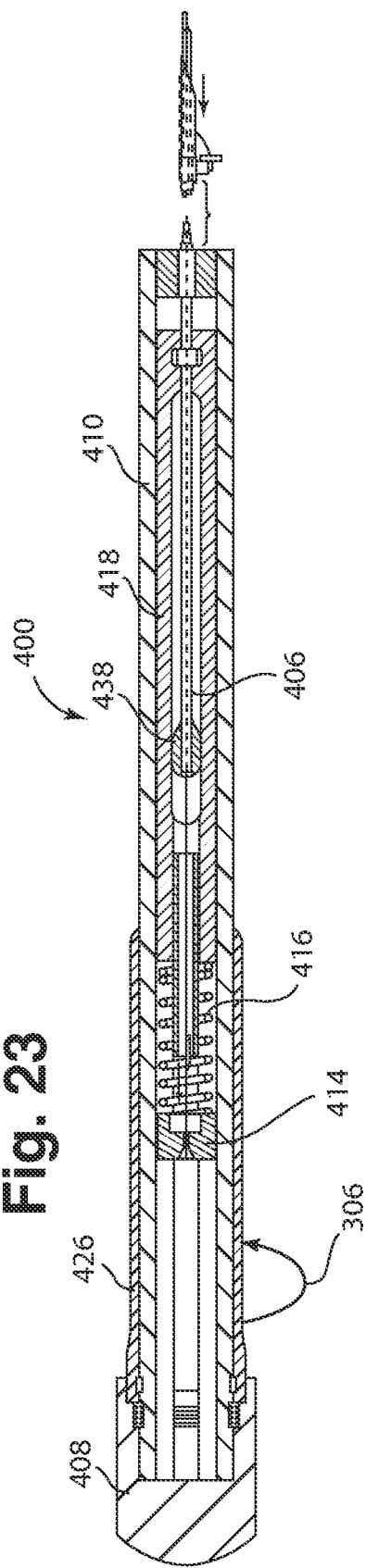
FIG. 23 illustrates a detailed view of exemplary embodiments of an anchor band delivery tool in cross-section during a deployment cycle in accordance with aspects of the present inventions.
Figure 24:
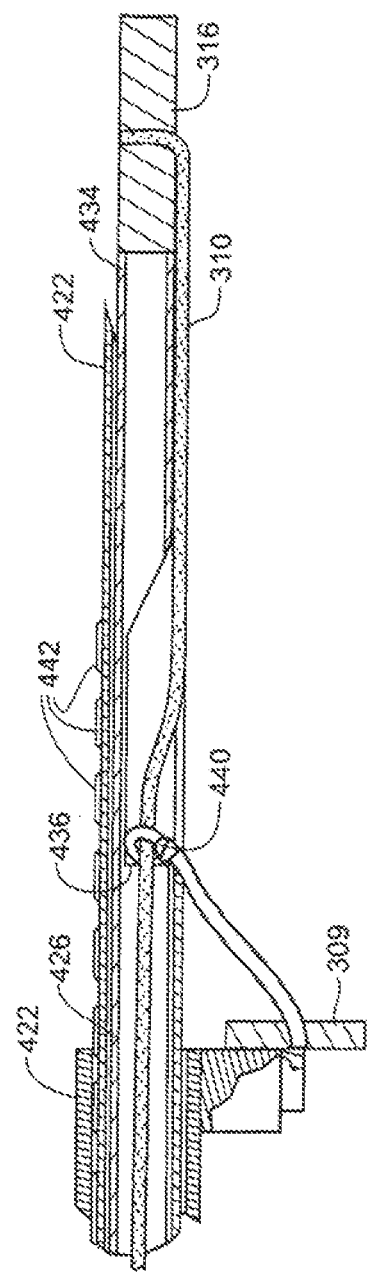
FIG. 24 illustrates a detailed view of exemplary embodiments of the distal end of an anchor band delivery tool depicted in FIG. 23.
Figure 25:
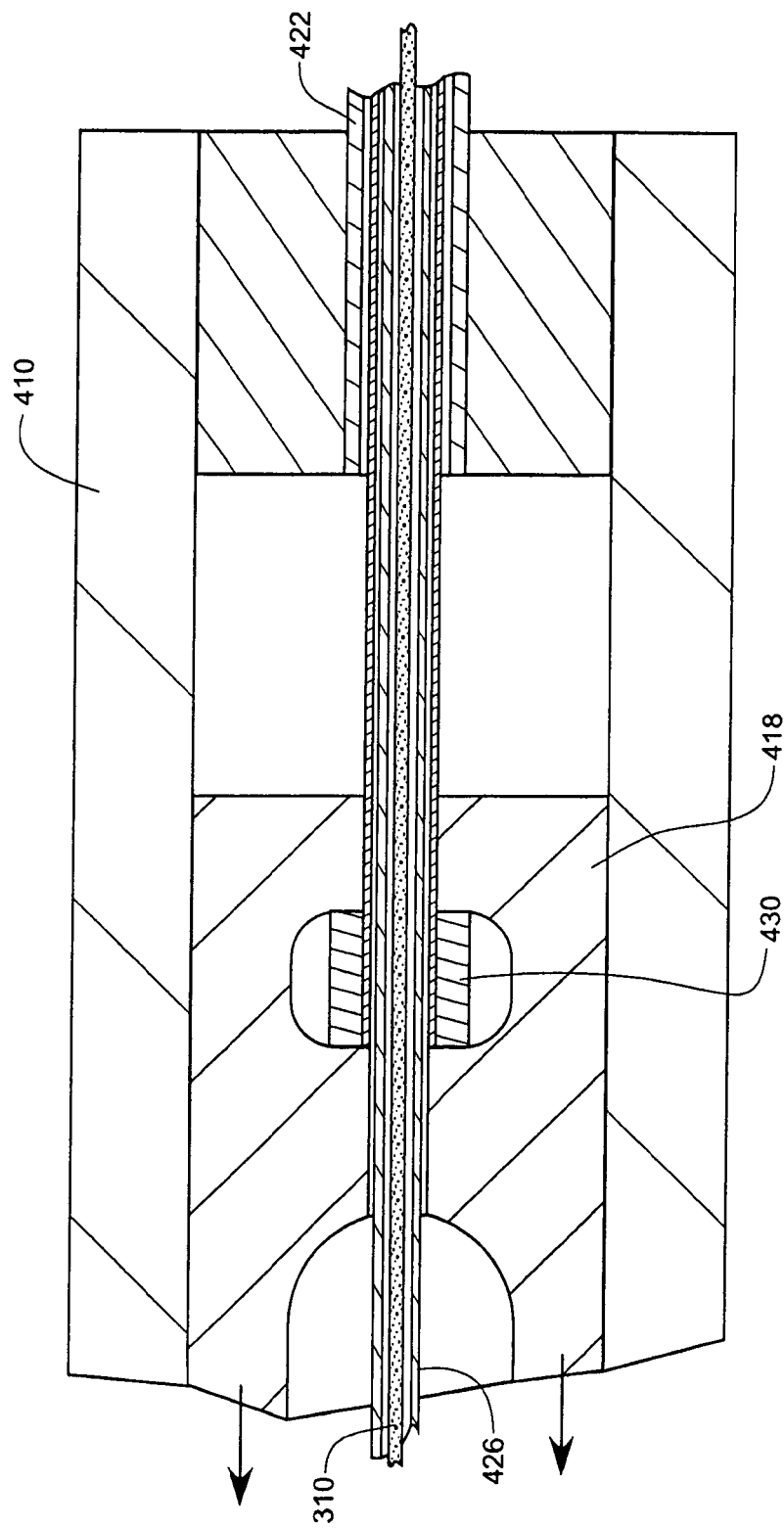
FIG. 25 illustrates a detailed view of exemplary embodiments of a slide body and cannula anchor of an exemplary fixation element delivery tool in cross-section during a deployment cycle in accordance with aspects of the present inventions.
Figure 26:
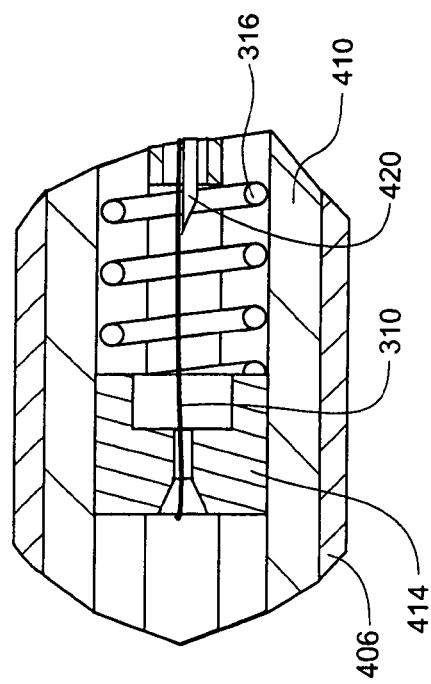
FIG. 26 illustrates a detailed view of exemplary embodiments of a suture retention block and blade assembly of an anchor band delivery tool.

FIGS. 23 and 24 illustrate the partial deployment of anchor band assembly from ABDT, wherein slotted needle cannula 428 has been partially retracted to expose Tanchor 316. FIG. 22 is a detail, cross-sectional view of the distal end of the handle of ABDT 400, illustratively showing the inter-relationships of delivery tool components in the initial configuration and FIG. 25 is a similar detail, cross-sectional view showing the inter-relationships after at least a partial deployment of device 400. FIG. 26 is a detail of the suture retention body 414, suture body 310, spring 316 and cutting assembly blade 420, during partial deployment of delivery tool 400, as discussed above.

Figure 29:
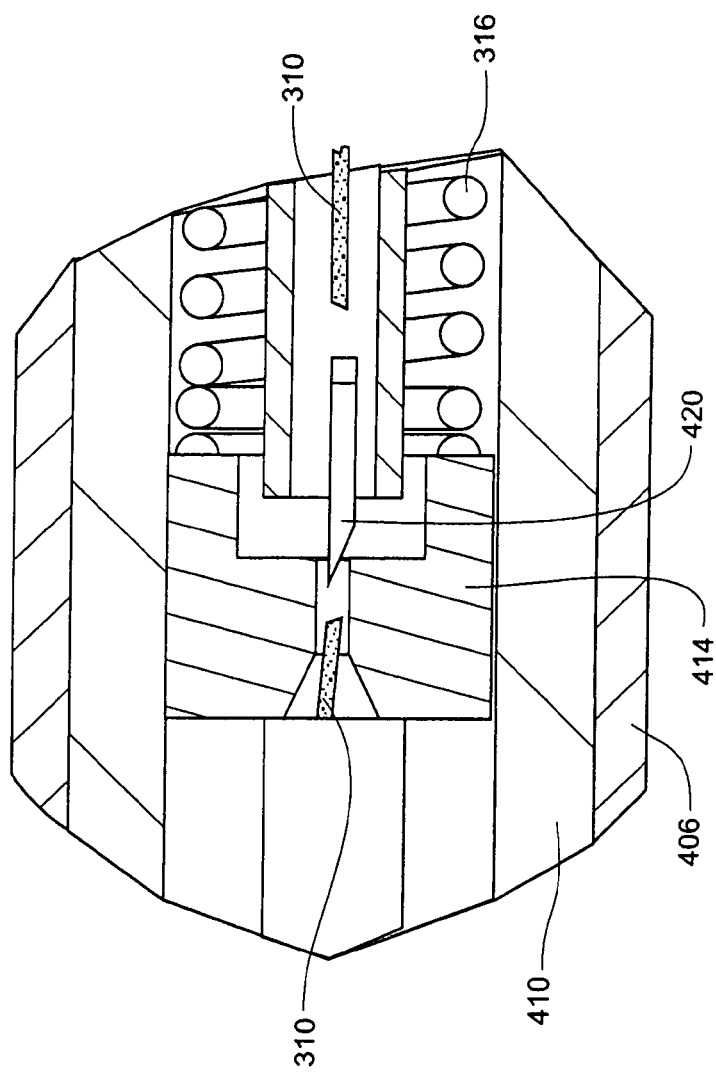
FIG. 29 illustrates a detailed view of exemplary embodiments of a suture retention block and blade assembly of an anchor band delivery tool during the cutting of the tether in accordance with aspects of the present inventions.

As depicted in FIG. 27 and detail drawings of FIGS. 28 and 29, as slider body 418 continues to slide proximally, in addition to continuing to draw T-anchor as shown in FIG. 28 with arrows, the tether retention block 414 reaches the limit of its proximal translation (discussed further below), and the slider member engages and compresses spring 316. As the spring is compressed, the blade assembly 420, which is aligned with the hole of suture retention body 414 through which suture body 310 passes, comes into engagement with the suture body 310. FIG. 29 is a detail view of the blade 420 severing the elongate member 310. Up to the limit of travel of the suture block 414 and the severing of tether 310, the suture body 310 continues to apply tension to the T-anchor, as shown in greater detail in FIG. 28. With knot pusher holding knot 440, pledget 309, and suture 318 in apposition, and in distally exerted fashion, to the tensioning of suture body 310, fixation apparatus assembly 308 is advantageously cinched into a fixing and/or compressive relationship between ends 309 and 316, as well as any structures (e.g., nucleus, annulus, treatment device) between elements 309 and 316. After severing suture body 310, suture body 310 is still attached to the anchor band, but has at this point been severed proximally. The suture body 310 will therefore be unthreaded from the interior of the ABDT as the ABDT is withdrawn. As discussed above the suture line 310 may be further cut to length with readily available surgical scissors. Alternatively, a severing mechanism similar to those described herein within the distal portion of tool 400 may be employed to avoid an additional step of trimming the end of body 310.

FIG. 26 is a detail of the suture retention body 414, suture body 310, spring 316 and cutting assembly blade 420, during partial deployment of delivery tool 400, as discussed above.

Additionally inventive of the anchor band device (and its delivery and deployment tools) is the unique inter-relationship of the slide body, spring, and the tension delivered to the T-anchor and tissue during deployment. For example, T-anchor assembly can be designed to pass through softer, or otherwise more pliable tissues (e.g., nucleus pulposus, softer annular layers) while resisting, under the same tension, passage through tougher tissues and/or substrates (e.g., outer annular layers, treatment device construct). In further illustrative description, tension delivered to the member line 310 can be limited by the interface between the slide body member 318 and the suture retention block 414, through spring 316 such that tension is exerted on T-anchor body 316 which may sufficiently allow movement of T-anchor 316 through softer tissue, but alternatively requires a greater force to pull T-anchor body through other materials or substrates such as the treatment device 600 or outer layers of the annulus 202. Spring 316 can be designed to sufficiently draw tissues and/or the patch together, while not overloading suture line 310 when the fixation has been effected. Spring 316 may also be advantageously designed to allow blade assembly 420, upon reaching an appropriate loading to effect the delivery, to sever the suture line 310. As illustrative example, but not intended to be limiting, T-anchor body and suture line may be constructed to require approximately 5 pounds of force to draw the T-anchor assembly through nuclear tissue, but substantially greater load to draw T-anchor through annular tissue and/or patch device. Spring may be designed to exert approximately five (5) pounds, sufficiently pulling tissue anchor through nuclear tissue, and in proximity to treatment device, as intended. Once sufficient load has been applied to move T-anchor to engage patch, the loading on the suture line is not allowed to substantially increase. Advantageously, additional loading would cause the final compression of spring between suture retention block and blade assembly to sever suture line. Preferably, the severing and the design of the tether elements are such that the ultimate strength of the filament line 310 is greater than the load required to draw an anchor through soft tissue, or the like, and less than the load inflicted to cause the severing by blade assembly. The description herein is intended to be illustrative and not limiting, in that other device and delivery tools could be derived to employ the inventive embodiments.

Figure 31A:
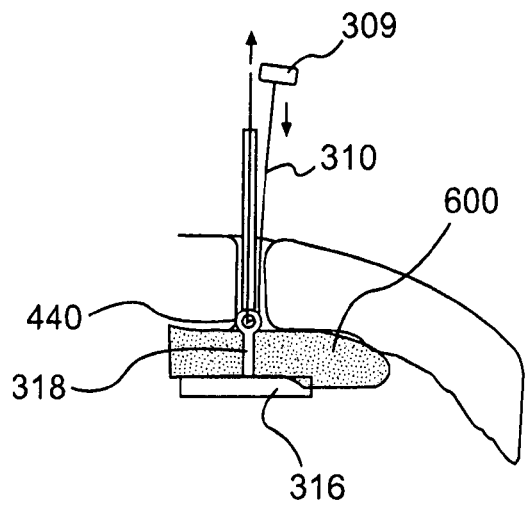
FIGS. 31A-31B illustrate alternative illustrative mechanisms of drawing together locking elements/anchors in accordance with aspects of the present inventions.
Figure 31B:
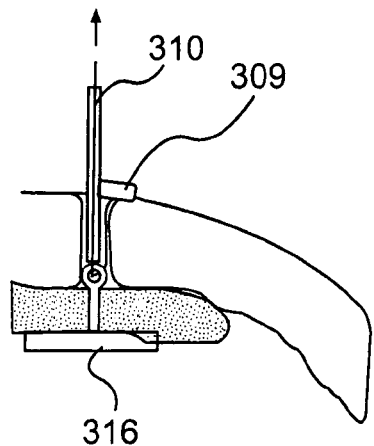
Figure 32A:
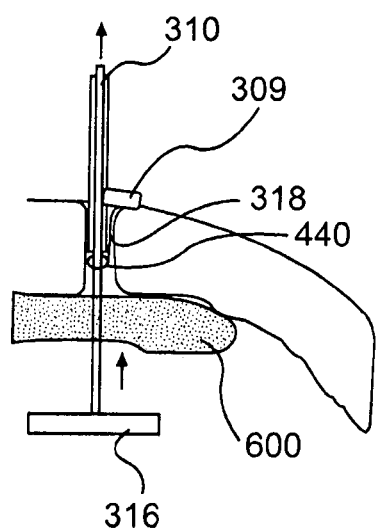
FIGS. 32A-32B illustrate alternative illustrative attachment mechanisms where a pledget element that-initially resides on outer annular surface.
Figure 32B:
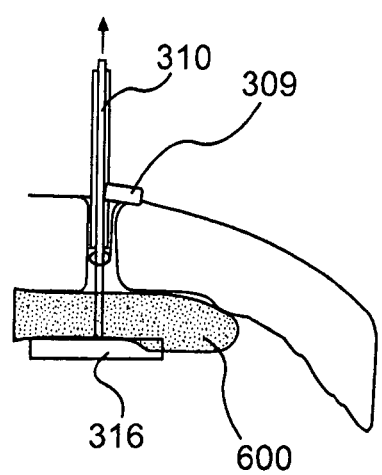

With regards to introduction, delivery, deployment and/or fixation of fixation element 308 as described previously and in particular, with regards to FIGS. 20-29, for example, anchor band assembly 308 and its associated delivery tool 400 may be described as effecting a fixation as shown in FIGS. 32A and 32B. FIG. 32A shows a pledget element 309 that, initially, may be placed on outer annular surface. As depicted, tether 318 is attached to pledget 309, and pledget and tether are secured to suture line 310 via a slip knot 440, for example. During deployment, T-anchor is drawn toward, and engaged with, treatment device 600 as illustrated in FIG. 32B. There may be alternative methods and mechanisms of drawing together locking elements/tissue anchors 309 and 316, as exemplified in FIG. 31. FIGS. 31A and 31B illustrate a T-anchor member 316 that may be positioned, initially, in proximity of patch 600. As depicted, tether 318 is attached to T-anchor, and T-anchor and tether are secured to suture line 310 via a slip knot 440, for example. During deployment, pledget 309 may be drawn to, and engage with, the surface of outer annulus tissue, as illustrated in FIG. 31B. The description of methods of drawing members together and effecting a fixation of a fixation element with its fixation element delivery tools are intended to be illustrative, and not limiting in the scope of the invention.

Figure 30A:
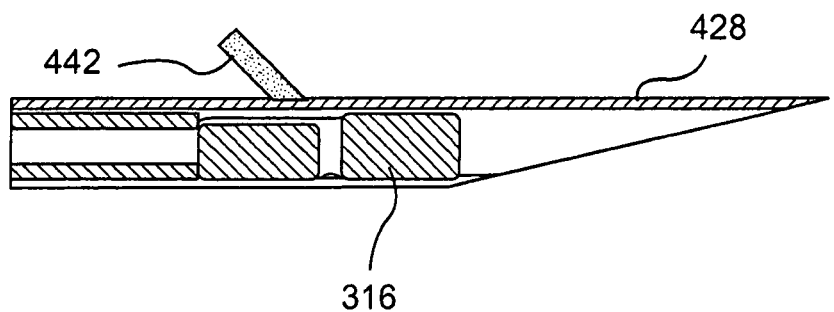
FIGS. 30A-30C illustrate a detailed view of exemplary embodiments of an anchor band or anchor band delivery tool for providing perceptible feedback in accordance with aspects of the present inventions.
Figure 30B:
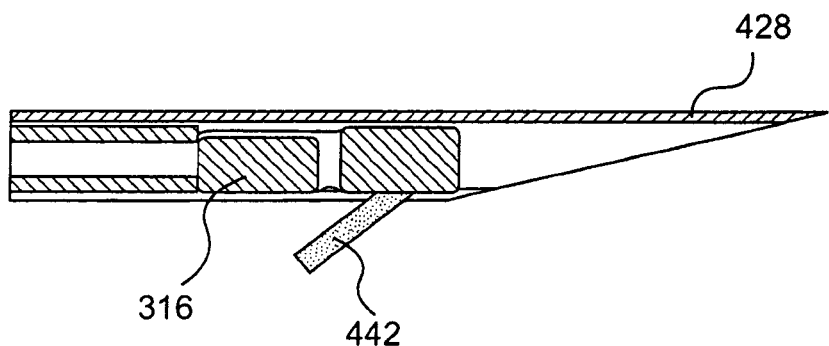
Figure 30C:
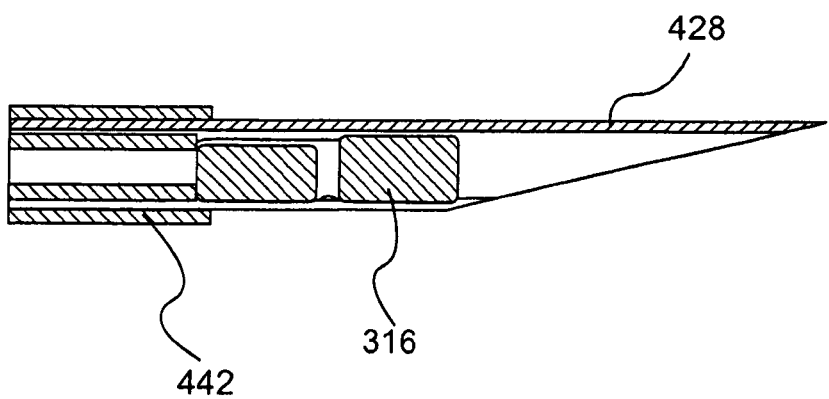

Since the surgeon's visualization during discectomy procedures is typically limited to the epi-annular space and the aperture at the outside surface of the annulus, any tactile, visual or audible signals to assist, or otherwise enhance, the surgeon's ability to reliably deliver and deploy treatment devices and/or anchor bands may be advantageous. The tissue anchor band delivery tool 400, may have a patch detection feature 442 on the distal end of slotted needle cannula 428 which may provide perceptible feedback (tactile and/or audible) to the surgeon that the fixation apparatus delivery tool has accessed and penetrated the patch and it is therefore acceptable to deliver the band. As shown, detection feature 442 is composed of multiple bands or ribs along the outer surface of needle 428. The movement of the ribs of 442 against the patch structure (e.g., the filaments of treatment device 600) may produce a clicking sound and feel, and the interface of the components of the devices and tools may be optimally designed to enhance such feedback features. One, or multiple, ribs or tabs may be utilized to achieve the perceptible features. The feed back may be perceived on or with the patch and/or patch delivery tool or through the anchor band and/or anchor band delivery tool, or both. FIGS. 30A-30C illustratively show additional means that may be attached to the anchor band or anchor band delivery tool which might also provide perceptible feedback. These depictions are meant to be illustrative and not limiting in scope of the invention. FIG. 30A shows a tab 442 attached to needle cannula 428 which may be laser cut from the distal end of needle 428. Detection tab 442 may be designed to readily pass through soft tissue and the patch 600 without causing significant disruption, but may be capable due to its design construction to produce tactile and/or audible sensation as it engages the patch lattice or structure. Lateral extent of tab 442 of FIG. 30A may advantageously deflect, or otherwise deform or bend toward the distal end of needle cannula upon removal of the delivery tool so as not to be restricted by the lattice or structure of treatment device 600 upon its removal. Alternatively, detection tab 442 of FIG. 30B is affixed to, or integral with, T-anchor 316. Similarly, detection tab 442 may be designed to readily pass through soft tissue and treatment device 600 without causing significant disruption, but may be capable of producing tactile and/or audible sensation as it engages the patch lattice or structure. In this embodiment, tab 442 advantageously remains with T-anchor 316 after removal of delivery tool 400. Moreover, it is possible to have a detection feature 442 as depicted in FIG. 30C, wherein the feature is wholly, or partially, coaxial disposed on the delivery tool and feature 442 may be of a construction that does not readily pass through patch 600, but it is capable of passing through soft tissue of the disc and produce a tactile and/or audible sensation as it engages the patch lattice or structure. Although some of the embodiments illustrate a single tab or rib, it is possible to use more than a single element. Detection features described herein may be of a variety of shapes and affixed to the devices or delivery tools (for example, welding ribs onto the surface of the delivery tool, affixing a flexible filament member to the T-anchor) or be incorporated as an integral component thereof (for example, laser cutting or stamping tabs out of a portion of needle 428, injection molding tabs as part of T-anchor 316). Exemplary materials that could be used to construct the various detection features include, but are not limited to: biocompatible polymeric materials (polyester, polypropylene, polyethylene, polyimides and derivatives thereof (e.g., polyetherimide), polyamide and derivatives thereof (e.g., polyphthalamide), polyketones and derivatives thereof (e.g., PEEK, PAEK, PEKK), PET, polycarbonate, acrylic, polyurethane, polycarbonate urethane, acetates and derivatives thereof (e.g., acetal copolymer), polysulfones and derivatives thereof (e.g., polyphenylsulfone), or biocompatible metallic materials (stainless steel, nickel titanium, titanium, cobalt chromium, platinum and its alloys, gold and its alloys).

As generally illustrated in the following FIGS. 33A to 46F, alternative embodiments of present inventions include various additional fixation delivery apparatus described previously as, for example, 400 will now be further described by 400 in FIGS. 32A-46F and associated methods. Fixation delivery apparatus in accordance with the present inventions may permit the placement of a fixation apparatus described previously as for example, 308 and 100 will now be further described by 100 in FIGS. 32A-46F and within an intervertebral disc of a patient. Typically, the fixation delivery apparatus may be configured to deliver one or more anchors described previously as, for example, 916, 709, 316, 309 and now will be further described by 102 in FIGS. 33A-46F of a fixation apparatus 100 into and/or through an intervertebral disc, which may include the annulus fibrosus, the nucleus pulposus, vertebral bodies and surrounding connective tissues. The fixation delivery apparatus 100 may be configured to deliver multiple anchors 102, for example, a first anchor 112 to a first location on an intervertebral disc and a second anchor 122 to a second location on the intervertebral disc. The anchors 102 are typically interconnected by one or more elongate members described previously as, for example, 144, 142, 710, 709, 910, 310, 318 and now will be further described by 104 in FIGS. 33A-46F, such as bands, sutures, wires, and cables for example, which may be cinched, tightened, reduced, or otherwise shortened so as to reduce the length of the connection between at least a first anchor 112 and a second anchor 122. Two or more elongate members 104 may include retention devices and/or knots 108 described previously as, for example, 145, 714, 914, 440 to interconnect the members and to permit the cinching of the elongate members 104. The cinching of the elongate members 104 may reconstruct, retain, stabilize, re-approximate and/or draw together tissues surrounding a defect, tear, cut or delamination in the tissues of an intervertebral disc of a patient.

As generally illustrated throughout the FIGS. 33A-46A, fixation delivery apparatus 400 generally includes a delivery apparatus body 12, one or more shafts 14, actuators 16, and displacement rods 18. The delivery apparatus body 12 is typically secured to one or more shafts 14 to allow a surgeon to position the distal end of the shaft 14 within an intervertebral disc of a patient. Each shaft 14 may define a lumen 24 and/or slot 34 which may removably receive at least a portion of at least one anchor 102 and or connecting band or loop 110, 104. A displacement rod 18 may be positioned through at least a portion of the lumen 24 and/or slot 34. A displacement rod 18 may be axially slidable along at least a portion of the lumen 24 and/or slot 34 of a shaft 14. A displacement rod 18 may communicate with anchor 102 and/or fixation apparatus 100 to displace an anchor 102 from the lumen 24 and/or slot 34 of a shaft 14. An actuator 16 may be movable by a user relative to a delivery apparatus body 12. The actuator 16 may be in communication with a displacement rod 18 to confer movement of the displacement rod 18 within the lumen 24 and/or slot 34 of a shaft 14 such that at least one anchor 102 may be expelled from the lumen 24 and/or slot 34 of the shaft 14 while the distal portion of the shaft 14 is positioned proximate and/or within an intervertebral disc of a patient and the delivery apparatus body 12 and actuator 16 maybe positioned at least partially external to the patient to allow actuation by a surgeon.

In one aspect, a fixation delivery apparatus 400 may include a single shaft 14. The shaft 14 may define a lumen 24 and/or slot 34 to serially receive two or more anchors 102. The tissue anchors 102 may be sequentially dispensed from the distal end of the shaft 14 at one or more locations within an intervertebral disc. In this embodiment, the distally positioned anchor 102 may be particularly referred to as the first anchor 112 and the proximally positioned anchor 102 may be particularly referred to as the second anchor 122. The anchors 102 are displaced from the lumen 24 and/or slot 34 of the shaft 14 by a displacement rod 18. A displacement rod 18 may communicate with an actuator 16 so that a user may advance a displacement rod 18 within the lumen 24 and/or slot 34 to dispense anchors 102 from the lumen 24 and/or slot 34 of the shaft 14. The first anchor 112 may be sized to be frictionally held within the lumen 24 and/or slot 34, may be retained in the lumen 24 and/or slot 34 by one or more detents formed within the lumen 24 and/or slot 34, may be retained in the lumen 24 and/or slot 34 by an elongated member 104 or other interconnecting members between anchors 102 and/or tethers 124, or may be otherwise temporarily secured to the lumen 24 and/or slot 34 of shaft 14. The second anchor 122 may be similarly secured to shaft 14 in a manner similar to a first anchor 112 or, alternatively, may be tethered by a tether 28 to retain a second anchor 112 secured to lumen 24 and/or slot 34 during and/or after displacement of the first anchor 112 into the intervertebral disc of a patient. In one aspect, the tether 28 may be secured to the displacement rod 18 or the actuator 16. Before, or upon, or after placement of the second anchor 122, the tether 28 may be severed, broken, cut or otherwise released from an actuator 16, displacement rod 18, and/or the delivery apparatus body 12 or shaft 14 to permit the release of the second anchor 122 from the structure to which the tether 28 is secured. In this exemplary embodiment, the first anchor 112 can be displaced from the shaft 14 by movement of the displacement rod 18 a first distance sufficient to displace the first anchor 112. This first distance may be insufficient to displace the second anchor 122. Then, the shaft 14 of the fixation delivery apparatus 400 may be moved from the first location where the first anchor 112 was dispensed and repositioned at a second location on or in the intervertebral disc to dispense the second anchor 122. The second anchor 122 may be connected to the first anchor 112 by one or more loops 110 and/or elongate members 104.

In another aspect, a fixation delivery apparatus 400 may include two or more shafts 14. In an exemplary embodiment, wherein there are two shafts, (similar to, for example, FIG. 10), one shaft 14 may be particularly referred to as the first shaft and the other shaft 14 may be particularly referred to as the second shaft. The first shaft and the second shaft may be adjacent one another and could be parallel to one another over at least a portion of their length. Each shaft 14 may define a lumen 24 and/or slot 34 to receive one or more anchors 102. In various configurations, the anchors 102 may be simultaneously or sequentially dispensed at one or more locations within an intervertebral disc from the distal end of the respective shaft 14 in which the anchors 102 are positioned. In this embodiment, the anchor 102 positioned in the first shaft may be particularly referred to as the first anchor 112 and the anchor 102 positioned in the second shaft may be particularly referred to as the second anchor 122. In this embodiment, a first anchor 112 can be displaced from the first shaft by movement of a first displacement rod 118 a distance sufficient to displace the first anchor 112 from the lumen 24 and/or slot 34 of the first shaft. A second anchor 122 may be displaced from the second shaft by movement of a second displacement rod a distance sufficient to displace the second anchor 122 from the lumen 24 and/or slot 34 of the second shaft. The first displacement rod 118 and second displacement rod may communicate with one or more actuators 16 to simultaneously or sequentially dispense the first anchor 112 and the second anchor 122 from the respective lumen 24 and/or slot 34 in which they are secured. The second anchor 122 is typically connected to the first anchor 112 by one or more loops 110 and/or elongate members 104. The first anchor 112 and the second anchor 122 may be sized to be frictionally held within the respective lumen 24 and/or slot 34 of first shaft and second shaft, may be retained in the respective lumen 24 and/or slot 34 by one or more detent within the lumen 24 and/or slot 34 or may be otherwise temporarily secured within the lumen 24 and/or slot 34 as described previously.

The delivery apparatus body 12 may be generally configured to provide a user with a structure to manipulate the distal portion of the shaft 14 within a patient. The delivery apparatus body 12 may have an elongated form and define a longitudinal aspect. In one aspect the proximal portion of the shaft 14 may be secured to a distal portion of the delivery apparatus body 12. When the shaft 14 is secured to the delivery apparatus body 12, the longitudinal axis of the shaft 12 may be coaxial with the longitudinal axis of the delivery apparatus body 12. In one aspect, the delivery apparatus body 12 may include a handle 40 integral with the body, or secured to the delivery apparatus body 12. When secured to the delivery apparatus body 12, the handle 40 may be secured to the outer surface of the delivery apparatus body 12. The handle 12 is typically positioned to facilitate the manipulation of the fixation delivery apparatus 400 by a surgeon and may be particularly configured to assist the surgeon in the positioning and/or dispensing of a fixation apparatus 100 within a patient. In another aspect, the delivery apparatus body 12 may include a raised textured surface for increased friction between a user's hands and the fixation delivery apparatus 400. The delivery apparatus body 12 may further cooperate with the actuator 16 to control the movement of the displacement rod 18 within a lumen 24 and/or slot 34 of shaft 14. In another aspect, the delivery apparatus body 12 may define a body cavity 22 to movably receive the actuator 16. The delivery apparatus body 12 may also comprise a tether access portal 30 as a primary or secondary structure to access and/or sever the tether 28 to facilitate the release of the fixation apparatus 100.

The delivery apparatus body 12 may be formed from a metal, polymeric material or other material that will be recognized by those skilled in the art upon review of the present disclosure. Some exemplary suitable materials recognized by those skilled in the art, include among others, polymers, such as acrylic polymers polyurethane, polycarbonate, engineered plastics; and metals, such as stainless steel and titanium.

The shaft 14 may be an elongate member that could be secured to and distally extend from the delivery apparatus body 12. Although the various embodiments described and illustrated herein typically define a delivery device 400 configuration that extends along a longitudinal axis, it is contemplated that the shaft and/or device components could extend along different projections so as to provide better visualization of the distal portions of the instruments within the surgical site. For example, it is possible that the handle and/or the proximal portion of shaft 14 define a longitudinal axis that is at a different angle than, for example, the distal portion of shaft 14. With this configuration, the handle, in use, may extend from the surgical site at a lateral position from the access incision and provide better visualization of the distal portion of shaft 14 within the surgical site. The shaft 14 may define a lumen 24 and/or slot 34 in at least a distal portion of the shaft 14. The lumen 24 and/or slot 34 may be configured to releasably secure one or more anchors 102, or portions thereof. The lumen 24 and/or slot 34 may be particularly sized and shaped to receive anchors 102 and the associated connecting loops 110 and/or elongate members 104, or portions thereof. The slots 34 may permit various components of the anchors 102 and/or elongate members 104 (including components of anchors 102, loops 110 or elongated members 104 such as retention devices and/or knots 108 or retention members, for example) to extend from the shaft 14 at a distal portion of the shaft 14. In one aspect, the lumen 24 and/or slot 34 may extend from the proximal end to the distal end of the shaft 14. In this configuration, the lumen 24 and/or slot 34 may communicate with the body cavity 22 of the delivery apparatus body 12 at a proximal portion of the shaft 14. In one aspect, the lumen 24 and/or slot 34 may be configured to slidably receive a filament 28. The lumen 24 and/or slot 34 may extend distally to about the distal portion of shaft 14 and may extend to the distal tip of the shaft 14. The lumen 24 and/or slot 34 of the shaft 14 may have a circular, elliptical, hexagonal, pentagonal square, diamond, rectangular, triangular, or other cross sectional shape and may be configured to releasably receive at least a portion of an anchor 102. In one aspect, the cross sectional shape of the lumen 24 and/or slot 34 may correspond to the cross-sectional shape of the anchor 102. In one aspect, the lumen 24 and/or slot 34 of shaft 14 may have a cross-sectional shape suitable to accommodate a displacement rod 18 and at least one anchor 102, or portion thereof. The lumen 24 and/or slot 34 may have the same or a varying configuration along their length.

The distal tip of the shaft 14 may be generally configured to permit the shaft 14 to penetrate the surface of an intervertebral disc using a force exerted by a surgeon on the delivery apparatus. In one aspect, the distal tip of the shaft 14 may include a sharpened tip. In another aspect, the distal tip of the shaft 14 may be chamfered to provide a point which may be sharpened to accommodate insertion through at least a portion of the annulus fibrosus of an intervertebral disc. In one embodiment, the distal tip of the shaft 14 may be cut obliquely to form a sharp leading surface or point for ease of insertion. In one embodiment, the tip may be serrated in order to accommodate delivery of the apparatus into and/or through boney tissue, such as the vertebral bodies.

A sheath 43 may be provided over at least a portion of the length of the shaft 14. The sheath 43 may function to reinforce the shaft 14. In alternative embodiments, the sheath 43 may provide a change in diameter longitudinally along the shaft 14 such that the penetration of the annulus fibrosus may be inhibited as the leading edge of the sheath 43 contacts the annulus. In another aspect, the shaft may include a tissue stop 54 positioned relative to the distal end of the shaft 14 to inhibit the penetration of the annulus fibrosus. Typically, the tissue stop 54 may inhibit the penetration of the annulus fibrosus by providing a region of the shaft 14 with increased surface area. The tissue stop 54 may be typically sized and shaped to efficiently inhibit the penetration of the shaft 14 through the annulus fibrosus while being relatively atraumatic to the tissues which it may contact.

The distal portion of the shaft 14 may include a tactile indicator similar, as an example, to 442 of FIG. 21 to indicate that the distal tip of the shaft 14 has penetrated the intervertebral disc and/or a patch 600 in the case where a reparative fixation apparatus 100 is used in conjunction with a reparative patch 600. The tactile indicator 442 may be integrally formed from the material of the shaft 14 or may be secured to the shaft 14 to provide a tactile indication of proper penetration. Typically, the tactile indicator 442 is provided on an outer surface of the shaft 14, although it is possible for indicator to be provided on other components of the delivery apparatus, such as the sheath 43 and/or the fixations apparatus, such as the anchors 102, as previously described in FIG. 30. The tactile indicator 442 may comprise a series of ribs on the outer surface of the shaft 14 or may comprise an external arm configured to "click" to an extended position when the shaft 14 enters an area of increased diameter or a region of softer material within a patient.

The shaft 14 is typically from about 1 inch to 10 inches long. However, the length of the shaft 14 may vary considerably depending upon the configuration of the fixation apparatus 100 and the fixation delivery apparatus 400, and may vary particularly depending upon the configuration of the delivery apparatus body 12 to which the shaft 14 may be secured, as well as the technique used to access the intervertebral disc space. The shaft 14 may be made from a wide range of materials having the desired performance characteristics depending, at least in part, on the overall configuration of the fixation delivery apparatus 400 and may include: metals, such as stainless steel, nickel-titanium alloy, and titanium; plastics, such as PTFE, polypropylene, PEEK, polyethylene, and polyurethane, acrylic, polycarbonate, engineering plastics; and/or composites.

The displacement rod 18 may confer a motive force to anchors 102 to displace one or more of the anchors 102 from the lumen 24 and/or slot 34 of the shaft 14. In some embodiments, the displacement rod may also function to withdraw one or more anchors 102 into the lumen 24 and/or slot 34. A portion of the displacement rod 18 may communicate with anchors 102 which may be least partially positioned within the lumen 24 and/or slot 34 of shaft 14. In one aspect, the displacement rod 18 extends through at least a portion of lumen 24 and/or slot 34. The displacement rod 18 may be slidably received within the lumen 24 and/or slot 34. In one aspect, the displacement rod 18 may be of a size and cross-sectional shape to correspond with the size and/or internal shape of the lumen 24 and/or slot 34 in which at least a portion of the displacement rod 18 may be received. Although the characteristic of the displacement rod 18 may be typically of a unitary structure, a displacement rod 18 in accordance with the present invention may include multiple components which act in conjunction with one another to displace the anchors 102 from the shaft 14.

In one embodiment, the displacement rod 18 may define a displacement rod lumen 26. In one aspect, the displacement rod lumen 26 may extend from a proximal portion to a distal portion of the displacement rod 18. The displacement rod lumen 26 may communicate with the body cavity 22 of the delivery apparatus body 12 at a proximal portion of the displacement rod 18. In one aspect, the displacement rod lumen 26 may be configured to receive a tether line, suture, wire, filament or otherwise elongate member. Tether 28 can be formed of multiple materials and/or components to perform its function. In addition, a tether passage 38 may be defined in the wall along the proximal portion of the displacement rod 18. The tether passage 38 may permit a portion of tether 28 to exit a displacement rod lumen 26 at a proximal location or a location distal to the proximal end of the displacement rod lumen 26. The proximal portion of the displacement rod 18 may communicate with actuator 16 to actuate or regulate the movement of the displacement rod 18. In one embodiment, a proximal portion of the displacement rod 18 may be secured to actuator 16. The distal portion of the displacement rod 18 may typically communicate with at least one anchor 102. In one aspect, the distal end of the displacement rod 18 may communicate with the proximal end of anchor 102 to confer a motive force to the anchor 102.

In one exemplary embodiment, the displacement rod 18 can be advanced distally a first distance, sufficient to dispense a first anchor 112. The shaft 14 of the fixation delivery apparatus 400 may be then removed from the first insertion point in the intervertebral disc and inserted into the intervertebral disc at a second insertion point, where the displacement rod 18 may then be advanced distally a second distance to dispense a second anchor 122, and so-on as may be desired for more than two anchors 102. Alternatively, for simultaneous delivery of multiple anchors 102, multiple shafts 14, each including a displacement rod 18, may be provided on the fixation delivery apparatus 400 and may be arranged adjacent to, parallel or substantially parallel along a portion of their lengths. In such configurations, the distance between the shafts 14 may be fixed or inter-operatively adjustable, as desired. When adjustable, the fixation delivery apparatus 400 may include a mechanism, such as a ratchet or displacement mechanism (not shown), or otherwise, as will be recognized by those skilled in the art upon review of the present disclosure, to adjust the distances between the distal portions of the shafts 14. The multiple shaft embodiment may also be additionally configured for sequential displacement of anchors 102.

An actuator 16 may communicate with one or more displacement rods 18 or components thereof to assist a user in advancing the displacement rods 18 along the respective shafts 14. The actuator 16 may be configured as an enlarged body residing at the proximal portion of displacement rod 18 which may be integral with, or secured to the displacement rod 18 to assist a user in advancing displacement rod 18. In this aspect, the distance the displacement rod 18 is pushed to define a first, second, and subsequent distances may be regulated by feel. Alternatively, the distance can be regulated by the architecture of the device. In this aspect, the actuator 16 may cooperate with the delivery apparatus body 12 to control the advancing and/or retracting of the displacement rod 18 within shaft 14, for example as shown in FIG. 33.

Exemplary cooperation of actuator 16 and body 12 as shown in FIG. 33, the actuator 16 and delivery apparatus body 12 may cooperate by having a guide 32, such as a pin or projection for example, on one component that is slidably received in a groove 36 or similar guide receiving apparatus of the other component. In one such configuration, the guide 32 may be formed in, or positioned in the body and/or the body cavity 22 of the delivery apparatus and a groove 36 may be defined by the outer surface of the actuator 16. The groove 36 may extend longitudinally along and circumferentially (or laterally depending upon the actuator's shape) around the actuator 16. The actuator 16 may be slidably positioned in the body cavity 22 of the delivery apparatus body 12 such that the guide 32 is received within the groove 36. The guide 32 extending from the body cavity 22 may be aligned within a groove 36 in the actuator 16 defined on the surface of actuator 16 such that the guide 32 is slidably received within the groove 36 and tracks the groove 36 as the actuator 16 is moved within the body cavity 22. Thus, when the displacement rod 18 is mechanically secured to actuator 16, wherein the movement of the actuator 16 corresponds one to one with the movement of the displacement rod 18, the movement of the displacement rod 18 will correspond to the configuration of the groove 36 on the actuator 16.

Fixation apparatus 100 as described herein may be various constructs utilized as primary reparative treatment of the soft tissues of the spine wherein re-approximation, reinforcement, stabilization, retention, reconstruction, and/or fixation as it would be otherwise achieved may be necessary for prophylactic or therapeutic repair of a defect, aperture, weakened, thinned or infirmed portion of the disc including the annulus fibrosus. In addition, fixation apparatus 100 described herein may be utilized in combination with other treatment constructs 600 such as patches, membranes, scaffolds, barriers, stents (used interchangeably) wherein fixation devices may additionally enable a treatment device 600 to be affixed to the soft tissue, including the annulus fibrosus, of the spine.

Fixation apparatus 100 may contain two or more anchors 102 and one or more elongate members 104 or may contain one or more anchors 102, one or more pledgets 309 and one or more elongate members 104. Furthermore, it is understood that multiple fixation apparatuses 100 may be used together to perform a repair or other procedure. Anchors 102 may generally be configured to maintain a position within an intervertebral disc as forces are applied to the elongate members 104. The one or more elongate members 104 may typically be connected to a first anchor 112 and a second anchor 122, or an anchor 102 and a pledget 309 and may be configured to apply a force between the first anchor 112 and the second anchor 122 or the anchor 102 and the pledget 309, while allowing the components to be drawn toward one another. One of the elongate members 104 may be elongated and may function as a cinch line 124 that is accessible to a surgeon after implantation of the anchors 102 of the fixation apparatus 100. In operation, the elongate members 104 secured between the anchors 102 may allow drawing together disc tissue, such as the annulus, between the anchors 102 when tightened. Accordingly, the fixation apparatus 100 can be placed in tension applying a force to pull together, wholly or partially, the surrounding tissue of the intervertebral disc. The forces may be applied to reapproximate, reinforce, retain, reconstruct or otherwise fix a tear, defect, incision, rent and/or delamination in the intervertebral disc of a patient.

Anchors 102 are generally configured to substantially maintain a desired position within and/or on an intervertebral disc as tension is applied to a band 104 or multiple elongate members 104 securing two or more anchors 102 together. The anchors 102 are typically configured to permit their positioning within and/or on an intervertebral disc using a fixation delivery apparatus 400 and, once positioned and secured, to resist movement within the intervertebral disc. The anchors 102 may be configured as barbed anchors, T-anchors, coiled anchors, darts, conical, elliptical or other configurations as will be recognized by those skilled in the art upon review of the present disclosure. In an exemplary embodiment a barbed anchor 102 may include an elongated body having at least one barb extending laterally from its longitudinal axis. One end of the elongated body may be particularly configured to penetrate the tissues of an intervertebral disc when the anchor 102 is directed through tissue in a direction along its longitudinal axis. In an exemplary embodiment, an anchor 102 may be connected to an elongated body, band 104, filament, filament loop or eyelet 110 secured at, near or proximate its midpoint such that, after insertion in a longitudinal orientation, the anchor 102 tends to assume a position perpendicular to a line of force exerted by the loops 110 and/or band 104. Loops or eyelets 110 may be a rigid structure or may be a flexible structure defining a loop through which a band 104 may be positioned. In one aspect, the eyelets 110 are integral with or secured to the anchor 102 and are a rigid structure. In another aspect, the eyelets 110 are secured to the anchors 102 and are a flexible structure such as a wire, filament, line, tether or suture, for example. In an exemplary embodiment of a coiled anchor, a anchor 102 may include an elongated body in the form of a coil that is formed from flexible and resilient material such that it may be insertable from a lumen 24 and/or slot 34 in a shaft 14 in a substantially straightened or collapsed position and once dispensed from the shaft may resume its original shape. In an alternative exemplary embodiment of a coiled anchor, an anchor 102 may include an open-wound, helically configured rigid element that may be attachably connected to the distal end of the shaft 14. Rotation of the shaft 14 or displacement rod 18 may, for example, advantageously "screw" the coiled anchor into tissue of an intervertebral disc.

The anchors 102 may be elongated in shape. The anchors 102 may be integral with or secured to elongate members 104. The elongate members 104 can be secured to the anchors 102 through loops or eyelets 110 which may be integral with or attached to the anchors 102, can be secured to the anchor 102 through band passages extending into or through the anchors 102. In one aspect, a band passage may extend through the anchor 102 perpendicular to or substantially perpendicular to the longitudinal axis of the anchor 102. In other aspect, the band passage may extend through the anchor 102 at other angles relative to the longitudinal axis of the anchor 102. Typically, the anchors 102 will be configured to permit at least partial placement within a lumen 24 and/or slot 34 of the shaft 14 of a fixation delivery apparatus 400. Alternatively, anchor 102 may have a defined cavity or passage to permit anchor 102 to be positioned at least partially over the distal tip of shaft 14 of a fixation delivery apparatus 400. In this alternative embodiment, anchor 102 may have a surface configured to pierce the soft tissue of the intervertebral disc and allow delivery of the anchor 102.

The anchors 102 are typically formed from a substantially biocompatible material of a metallic or polymeric biocompatible material such as, for example, titanium, NiTi alloy, stainless steel, platinum, gold, polyurethane, polycarbonate urethane, polyimide, polyamide, polypropylene, polyethylene, polypropylene, polyester, PET, or PEEK, or could be constructed from a biodegradable/bioabsorbable material such as, for example, collagen, silk, cellulose, polysaccharides, carbohydrates, polyglycolic acid, polylevolactic acid, polydioxanone, or racemic polylactic acid. In addition, the anchors 102 can be constructed of a combination of these materials.

One or more elongate members 104 may interconnect anchors 102 and/or pledgets 309 of fixation apparatus 100. At a first end or region, the elongate members 104 may secured to one or more anchors 102. The elongate members 104 may be tied to the anchors 102, may be mechanically secured to the anchors, may be integral with the anchors 102 or may be otherwise secured to the anchors as will be recognized by those skilled in the art upon review of the present disclosure. In one aspect, one or more anchors 102 may be slidably secured to the elongate members 104 or may be slidably received over the elongate members 104. Typically, one or more elongate members 104 may be tied to one another with one or more retention devices and/or knots 108 that may permit the cinching (or shortening) of the length of elongate members 104 separating two or more of the anchors 102. The retention devices and/or knots 108 in the band are typically movable along one of the elongate members 104 but may be movable along two or more elongate members 104. The retention devices and/or knots 108 are typically positioned between the anchors 102. One suitable family of retention devices and/or knots 108 include, but are not limited to, the Roeder knot 108 and its functional equivalents. These knots may be pre-tied during the assembly of a fixation apparatus 100. Alternatively, a mechanical element slidably received over a first band 104 and secured to the end of another band 104 which is lockable in a desired position over the first band 104 may also be used. In another aspect, two or more anchors 102 may include loops or eyelets 110 which may be comprised of looped elongate members 104 through which a band 104 in the form of a cinchable loop or "lasso" may be passed. The cinching of the elongate members 104, or a loop in a band 104, allows for taking-up slack and drawing towards one another intervertebral disc tissues so as to reapproximate, retain, reinforce or otherwise repair tissues surrounding a disc tear, incision, defect, rent, infirmation or delamination.

As noted previously, the elongate members 104 may be formed from a variety of materials. In one aspect, the elongate members 104 may be formed from sutures or suture materials commonly used by surgeons. The elongate members 104 may be configured to have sufficient strength to re-approximate or draw together tissue surrounding tear, rent, incision, defect or delamination in the annulus fibrosus of a patient. In one aspect, the elongate members 104 may be substantially inelastic to, among other things, permit a surgeon to sufficiently retain or draw the tissue of the intervertebral disc together by cinching the elongate members 104. In another aspect, the elongate members 104 may be formed from an elastic material and configured to be in a stretched position upon implantation in a patient to apply a closing force to a defect in an annulus fibrosus of a patient. The elasticity of the elongate members 104 may also be selected to substantially correspond to that of the intervertebral disc of the patient. The elongate members 104 may be string-like filaments having a construction and dimension, as disclosed herein and as will be understood by those skilled in the art upon review of the present disclosure, that are amenable to the delivery to and repair of the intervertebral disc, as well as engagement with the fixation apparatus 100. For example, an elongate member 104 may have a width greater than, in some embodiments far greater than, its thickness. When the elongate member 104 is formed from a suture or similar filamentous material, the elongate member 104 may, in some embodiments, have a width/height ratio of 1.25:1. In some embodiments, elongate members 104 may be constructed, wholly or partially, of a mesh tube. Moreover, different segments along the length of the band may have different dimensions and constructions. For example, the elongate member 104 may be constructed of thin material, such as nickel titanium alloy or stainless steel wire, close to the anchor, while the middle portion that may span the aperture may comprise a much wider band made of optionally softer material and/or a material that has a surface texture or porosity conducive to fibrotic ingrowth and repair or may be otherwise configured as disclosed elsewhere in the present disclosure and/or as will be understood by those skilled in the art upon review of the present disclosure.

A patch-like device 600 in the form of a patch, membrane, scaffold, barrier, stent, sealing device, reinforcement, plug, occlusion device, or otherwise, may be provided for repair, reconstruction, reinforcement, re-approximation, or otherwise treatment of apertures, weakened, thinned or otherwise infirmed tissue such as tears, rents, defects, delaminations and/or incisions within an intervertebral disc. In one embodiment, an apparatus 600 may used in combination with other reparative apparatuses, such as fixation apparatus 100, for the re-approximating, reinforcing, or otherwise repairing tissues. Particularly, it is conceivable that some natural and surgically made defects may be relatively large and accordingly, reapproximation of tissues surrounding an aperture is not actually or practically possible without the introduction of additional material. A device 600 in accordance with the present inventions may provide the material for positioning in and around a defect to bridge some, all or a portion of the defect to facilitate a medically appropriate stabilization of the tissues. The patch 600 may function to reinforce the portion of an intervertebral disc through which a fixation apparatus 100 is implanted. And, patch 600 may be used to bridge tissues of a defect and may also act as a scaffold for tissue ingrowth.

The patch 600 may be configured as a membrane, webbing, mesh, scaffolding, barrier or otherwise as will be recognized by those skilled in the art upon review of the present disclosure. The patch 600 may be of a rigid construction, may be flaccid, or may of an intermediate rigidity. The patch may also have configurations that include multiple rigidities associated with different portions of the patch as may be necessary to address alternative defect pathologies and/or delivery and deployment considerations. The patch 600 may be of a solid material, webbing or otherwise, or may comprise one or more mounting cavities 610 within the patch. In one aspect, the mounting cavities or receptacles 610 may cooperate with a patch insertion tool 500 to assist in the placement of the patch 600. In one aspect, the patch 600 defines a single patch mounting cavity 610 extending along its length and, accordingly, may be configured as a sleeve or a sock. In alternative embodiments, the patch 600 may define a plurality of mounting cavities 610 which are configured to receive one or more projections, brackets, arms or otherwise mounting or retaining elements 504 or 506 of the patch insertion tool 500.

Patches 600 can be formed from a variety of materials or combinations of materials known to those skilled in the art. These materials are typically biocompatible. The patch 600 may be configured from natural or synthetic materials including, but not limited to, various polymers, metals and biological tissues, for example. In one aspect, the patch 600 may be formed from autograft para-spinal fascial tissue, xenograft, allograft, or other natural or processed collagenous materials. The material could also be polymeric such as a Dacron (polyester, or PET), polypropylene, polyethylene, polymethylmethacrylate, silicone, PTFE, ePTFE, Surlyn, or PEBAX material, for example. In some exemplary embodiments, the patch 600 could comprise biocompatible metal, such as NiTi alloy, chromium cobalt alloy, titanium, stainless steel or the like. Webbing materials could also be woven or non-woven, or braided. Patches may also be partially or wholly constructed from biodegradeable or bioabsorbable materials. It is also possible for the patches to be constructed, partially or wholly, from previously herein described materials, as well as to comprise of one or more of these materials, as may be generally understood by those skilled in the art. Patches may also comprise bioactive materials and may also be for mechanical, biochemical and medicinal purposes. The patch 600 may also be drug eluting, as known in the medical implant arts. Furthermore, in one exemplary embodiment, the material of the patch 600 may contain a structure sufficient to readily permit the passage of the distal portion of a shaft 14 of a fixation delivery apparatus 400 with little or no resistance while providing resistance to the dislodging of an anchor 102 dispensed within or through patch 600.

Patch delivery tools 500 in accordance with the present inventions are generally configured to position one or more patches 600 at positions in proximity, adjacent or within an intervertebral disk 200 of a patient. Typically, patch delivery tools 500 are configured to releasably secure devices 600 on or about the distal portions of delivery tools 500 such that, after a surgeon has secured at least a portion of the patch 600 to the intervertebral disk 200 of a patient, the patch 600 may be released from the patch delivery tool 500 and the patch delivery tool 500 may be removed from the patient.

A patch insertion tool 500 may be provided in accordance with aspects of the present inventions. The patch insertion tool 500 may include an elongated body 502. The proximal end of the elongated body 502 may generally be configured to be manipulated by a surgeon. The distal end of the elongated body 502 may generally be configured to releasably hold patch 600 for positioning in, on, about, and/or across a defect, tear, rent, delamination or incision in an intervertebral disc. Although the various embodiments described and illustrated herein typically define a patch delivery device 500 configuration that extends along a longitudinal axis, it is contemplated that the shaft and/or device components could extend along different projections so as to provide better visualization of the distal portions of the instruments within the surgical site. For example, it is possible that the handle and/or the proximal portion of elongate body 502 defines a longitudinal axis that is at a different angle than, for example, the distal portion of elongate body 502. With this configuration, the proximal portion, in use, may extend from the surgical site at a lateral position from the access incision 208 and provide better visualization of the distal portion of body 502 within the surgical site.

The patch insertion tool 500 may further include one or more guides 508 between the proximal and distal end to receive at least a portion of shaft 14 or any other components of fixation delivery apparatus 400 and/or a patch retention line 512. One or more patch retaining arms 504 and/or 506 may extend generally laterally from a longitudinal axis of the patch insertion tool. The patch retaining arms 504 and/or 506 may be generally configured to retain a patch and typically may define gap 514 and/or 516, respectively. For example, gap 514 may be generally configured to permit the passage of a shaft 14, or other component, of a fixation delivery apparatus 400 through the gap 514. Gap 514 may be positioned on the patch retaining arm 504 and aligned with guide 508 to aid in the proper positioning of a fixation apparatus 100 and its delivery tool 400. In operation, the shaft 14 of fixation delivery apparatus 400 may extend through the patch 600 at the location secured over the gap 514 of the patch retaining arm 504. The location of the gap 514 selected such that the fixation apparatus 100 adequately secures the patch 600 to the intervertebral disc when it is delivered and deployed. Two or more patch retaining arms 504 may be positioned along or about the elongated body 502 of the patch delivery tool 500. Various embodiments of patch delivery tool 500 configurations and their respective parts, including body 502, guides 508, arms 504, 506 and gaps 514, 516 are illustratively shown in FIGS. 34A to 36A. In an alternative embodiment, the patch retaining arms, for example 504 and 506, may be fixed or adjustable and/or movable relative to the elongated body 502. In one aspect, the longitudinal spacing between two or more patch retaining arms 504, 506 may be adjustable to allow the patch retaining arms to accommodate various sized patches 600 and/or various anatomical features of the intervertebral disc 200 being treated. One such adjustable embodiment is illustratively shown in FIG. 37. Moreover, it is possible that the length of arms 504, 506 that emanate from body 502 may be adjustable (not shown) and may allow the lateral projection of arms 504, 506 from body 502 to be increased and/or decreased before or during the delivery and deployment of patch 600 so as to accommodate various anatomical features of the intervertebral disc to be repaired. These adjustments may be advantageously made through a mechanism (not shown) residing within or adjacent body 502 that adjustably allows the release of arms from body 502 wherein the release may be controlled or actuated by the surgeon, as required, by an actuator (not shown) residing on the proximal portion of delivery apparatus 500.

Patch retaining arms 504, 506 may also define one or more patch retaining line passages 534, 536 or patch retaining line grooves 544, 546 to secure patch 600 onto and/or over one or more of the patch retaining arms 504, 506.

FIGS. 33A to 33D illustrate exemplary embodiments of a fixation delivery apparatus 400 in accordance with aspects of the present inventions. As particularly illustrated in FIGS. 33A to 33D, the fixation delivery apparatus 400 may include a delivery apparatus body 12, shaft 14, actuator 16, and a displacement rod 18. The illustrated fixation delivery apparatus 400 may be configured to accommodate and sequentially deploy two or more anchors 102 of one or more fixation apparatuses 100. The illustrated fixation delivery apparatus may include a mechanism for regulating the advancing of displacement rod 18 for release of the two or more anchors 102 of a fixation apparatus 100 from the shaft 14. The embodiments of the fixation delivery apparatus 400 illustrated in FIGS. 33A to 33D are for exemplary purposes only. Any description of these particular figures not written in the permissive form is merely to explain the nature and relationship of the particular components of the illustrated embodiments and is in no way intended to limit the disclosure to the particularly illustrated components.

The delivery apparatus body 12 may include a body cavity 22 within at least a portion of the delivery apparatus body 12. The delivery apparatus body 12 may be elongated and include a handle 40 at the proximal portion of the delivery apparatus body 12. The shaft 14 may be secured to the distal portion of the delivery apparatus body 12. A guide, pin, or projection 32 may extend into the body cavity 22 and may be received by slot or groove 36 of actuator 16.

The shaft 14 extends from delivery apparatus body 12 and may include a sheath 43. The shaft 14 may comprise a lumen 24 which may extend from the proximal portion to the distal portion of shaft 14. The lumen 24 is illustrated with a circular cross-sectional shape that may be suitable to accommodate the circular cross-sectional shape of the illustrated anchors 102 and to slidably receive displacement rod 18, although, alternative cross-sectional configurations could be employed to accomplish the same function. The lumen 24 of the shaft 14 may be in communication with body cavity 22 of the delivery apparatus body 12 and may permit the at least one displacement rod 18 and/or its components to be slidably received within shaft 14. As illustrated, the distal tip of the shaft 14 may be cut obliquely to form a sharp leading surface or point for ease of insertion into an intervertebral disc. The shaft 14 may include a slot 34 along its side to accommodate portions of fixation apparatus 100, such as elongate members 104, 110 and anchors 102, and knots 108 that may not reside completely within lumen 24.

The actuator 16 and/or the displacement rod 18 may be movably received within a portion of body cavity 22. As illustrated, the actuator 16 may function as a handle to interface with a user and extends proximally from the proximal end of the delivery apparatus body 12. A distal portion of the actuator 16 may be secured to a proximal portion of displacement rod 18. The displacement rod 18 is particularly shown as secured to the distal portion of the actuator 16. The actuator 16 may configured to advance displacement rod 18 in a 1 to 1 ratio. A displacement spring 20 may be positioned within the body cavity 22 between the distal portion of body cavity 22 and the distal portion of actuator 16, in the example shown. The displacement spring 20 may bias the illustrated actuator 16 and displacement rod 18 in a proximal direction. A groove 36 on actuator 16 may be configured to cooperate with the projection 32 of the delivery apparatus body 12. Those skilled in the art would realize this is an exemplary configuration and, for example, groove 36 could as easily be located on the apparatus body 12 and the pin 32 could reside on the actuator 18.

The displacement rod 18 may generally be configured to apply a motive force to dispense t-anchors 102 from the distal end of the lumen 24 and/or slot 34. The displacement rod, as shown, is an elongated structure having a substantially circular cross-sectional shape and may comprise a displacement rod lumen 26 extending along at least a portion of the length of the displacement rod 18. At least a distal portion of the displacement rod 18 may be slidably received within the lumen 24 of the shaft 14. The movement of the displacement rod 18 within lumen 24 may be modulated by actuator 16. As particularly illustrated, the actuator 16 is configured to advance the displacement rod 18 in a 1 to 1 ratio. A tether passage 38 may be defined in a proximal portion of the displacement rod 18. The tether passage 38 may permit a portion of tether 28 to extend from the displacement rod lumen 26 to be positioned within body cavity 22 of the delivery apparatus body 12. Although tether 28 here is used as a general term, those skilled in the art would recognize that tether 28 could be a wire, string, suture band or other elongate member to satisfy the same purpose.

The tether 28 may be provided to secure an anchor 102 prior to deployment. The proximal portion of tether 28 may be secured to the actuator 16, displacement rod 18, and/or delivery apparatus body 12. As illustrated, the tether 28 is secured to a portion of the actuator 16. More particularly, the distal portion of the actuator 16 defines a flange 88 about which tether 28 is looped around the flange 88 to secure the proximal end of the tether to the actuator 16. Advantageously, the distal end of the actuator 16 may have a tether severing cavity 48 which includes a lip 68. In addition, a tether severing element 58 may be provided in the distal portion of the body cavity 22. The tether severing element 58 may include a cutting edge 78. The tether severing cavity 48 and the tether severing element 58 may cooperate to sever the tether 28 and thus allow anchor 102 to be released from lumen 24 and/or slot 34. As illustrated, the tether 28 is cut by positioning the actuator 16 distally with the passage 38 and the lip 68 of tether severing cavity 48 overlapping the longitudinal axis of the cutting edge 78 of the tether severing element 58 to press the tether 28 against the cutting edge 78. Alternatively, if an automated cutting feature is not used, a tether access portal 30 may be provided through the delivery apparatus body to permit access to the tether 28 with other cutting devices such as scissors or scalpels for example.

A sheath 43 may be secured about the outer surface of shaft 14. The sheath 43 may extend from the delivery apparatus body 12 to a location proximal to the distal end of shaft 14. A tissue stop 54 may be secured to the distal portion of shaft 14. As illustrated, the tissue stop 54 may also be particularly secured on sheath 43. The shaft 14 may further define a slot 34. Slot 34 may be configured to slidably receive components of fixation apparatus 100 as the components slide along the longitudinal axis of the shaft 14. As illustrated in FIG. 33B, eyelets 110 comprised of looped elongate members 104 or filaments extend from the slot 34 and loops 110 are interconnected by an adjustable elongate member 104, such as a cinch line 124 as shown.

Figure 33A:
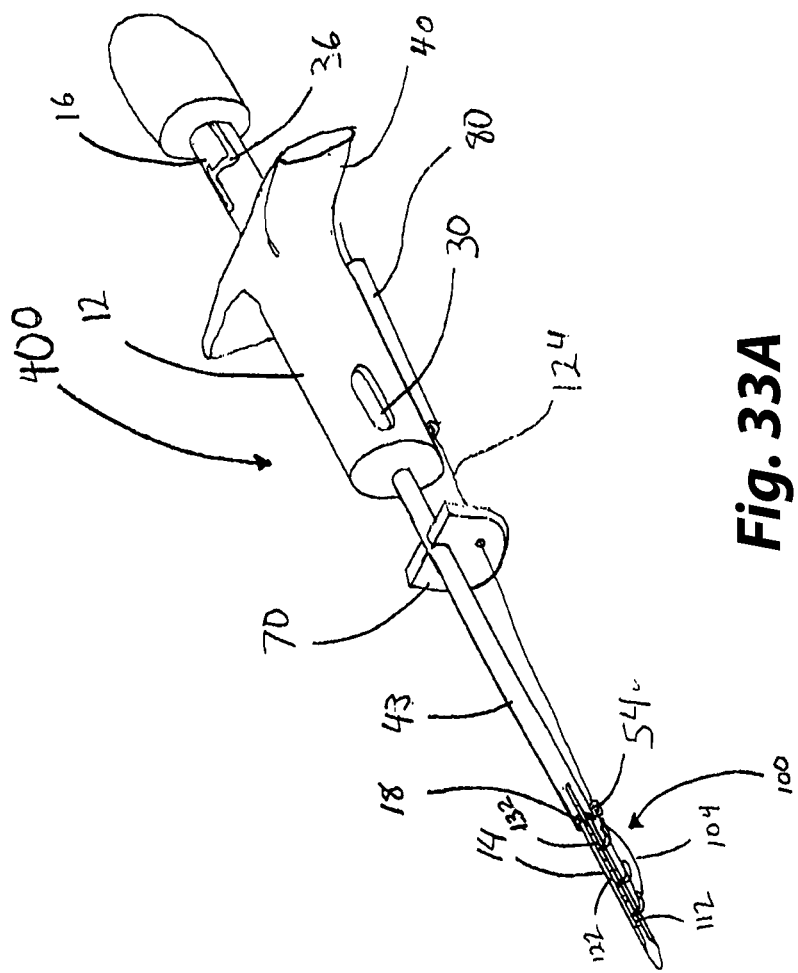
FIGS. 33A-33D illustrate a fixation delivery apparatus and fixation apparatus in accordance with aspects of the present inventions.
Figure 33B:
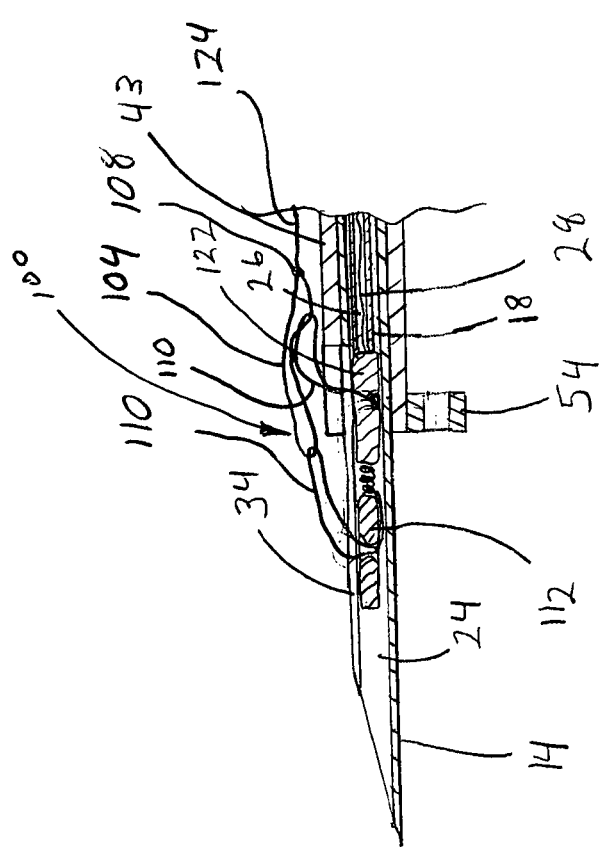

The illustrated fixation apparatus 100 include three anchors 102 in FIG. 33A and two anchors 102 in FIG. 33B. The anchors 102 are sequentially at least partially positioned in a lumen 24 of shaft 14. As illustrated, the anchors 102 are configured as T-anchors, although those skilled in the art would recognize other anchor configurations are possible to achieve the same effect. Each anchor 102 defines a transverse passage which receives a portion of a connecting member 104. As illustrated, elongate connecting member 104 comprises a filament loop or eyelet 110. As illustrated, filament loops or eyelets 110 are flexible lines formed into loops which are secured within the transverse passages of the anchors by enlarged knotted portions. Also, shown, the filament loops 110 extend through the slot 34 from first anchor 112, the second anchor 122, and, when present, the third anchor 132 and are interconnected by an additional elongate band 104 formed into a loop which passes through the passages defined by each of the eyelets 110. The band 104 connecting the implanted anchors 102 with their eyelets 110 includes a moveable knot 108 which permits foreshortening of band 104. With foreshortening of band 104, a trailing end of cinch line 124 may become longer as slack is removed from the loop of band 104. A portion of band 104 may have sufficient length to extend outside the patient and form a cinch line 124 which is accessible by a surgeon after implantation. A pull or tab 70 may be secured to the cinch line 124 to more easily facilitate the locating and/or manipulating of the cinch line 124. The pull 70 may be removably securable to the shaft 14, as illustrated, or the delivery apparatus body 12. Pull tab 70 may also be advantageously coupled (not shown) to body 12, displacement rod 18, and/or actuator 16 so as to limit to ability to slideably dispense anchors 102 until and/or when the surgeon desires; at which time, removal of pull tab 70 may allow dispensing of one or more anchors 102. In addition, a cinch line holder 80 may be provided on the delivery apparatus body 12, pull tab 70, shaft 14, or a combination of components of apparatus 400 so as to allow for line management during the delivery and deployment of fixation apparatus 100. Holder 80 may include features that resistively allow controlled dispensing of line 124 during anchor deployment to assist in the management of the cinch line 124 during a surgical procedure. Resistance on line 124 could be accomplished by the selective sizing of holder 80 with respect to line 124. Alternatively, knotted elements (not shown) along line 124 could be received within holder 80 that comprises mechanical interlocking components (not shown) so as to resistively impede and provide controlled dispensing of line 124. These are intended to be illustrative examples of causing resistance and control of line 124 and should not be interpreted as being limiting as those skilled in the art would recognize a variety of ways to accomplish a similar effect.

Figure 33C:
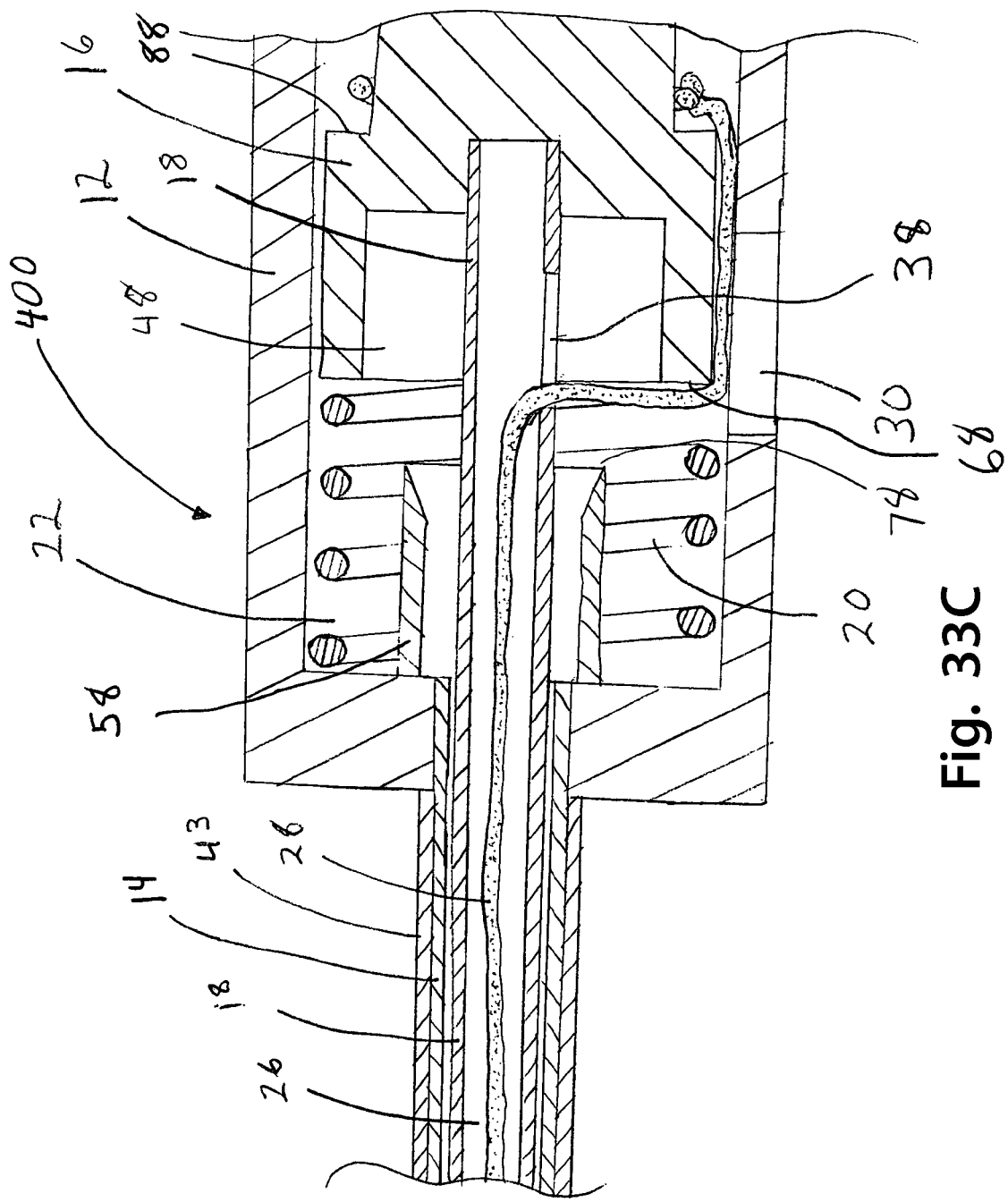
Figure 33D:
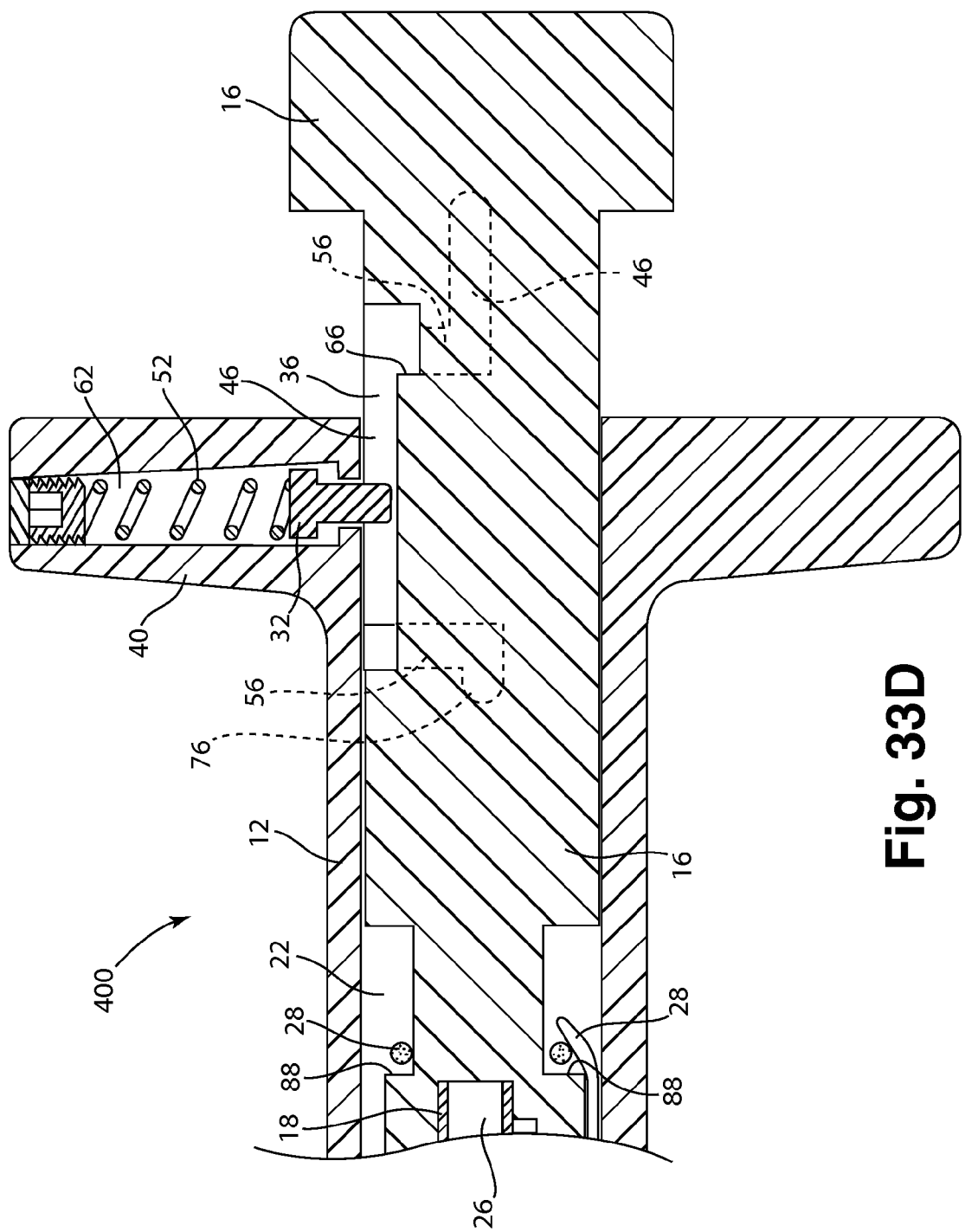

As illustrated in FIG. 33D, a mechanism for regulating movement of displacement rod 18 may generally include a guide 32 extending into body cavity 22 and a groove 36 defined on the surface of the actuator 16. The guide 32 on the delivery apparatus body 12 cooperates with the groove 36 on the actuator 16 and may regulate at least the axial movement of the displacement rod 18.

The guide, pin or projection 32 may be slidably received in groove 36 of the actuator 16. The guide 32 may be secured to or within the body cavity 22 of the delivery apparatus body 12. As illustrated, in FIG. 33D, guide 32 is positioned within a guide cavity 62 and includes a guide spring 52 biasing the guide 32 outward into the body cavity 22. The illustrated guide 32 includes a flange which abuts a cavity flange on a portion of the guide cavity 62 to prevent the guide 32 from being displaced from the guide cavity 62. Note that guide 32, spring 52, body 12 and their cooperative relationship with groove 36 may also advantageously allow for tactile and/or auditory feedback to the surgeon during delivery of anchors as guide 32 passes along groove 36. In alternative embodiments, the guide 32 could be otherwise rigidly or movably secured within the body cavity 22 without departing from the scope of this aspect of the present inventions.

As illustrated in FIG. 33D, the groove 36 may extend along the outer surface of the actuator 16. The groove 36 may include longitudinally extending portions 46 and radial extending portions 56. The longitudinally extending portions 46 may allow for longitudinal advancing the actuator 16 and associated displacement rod 18. The radially extending portions may function to stop the longitudinal advancing of the actuator 16 and associated displacement rod 18. The groove 36 may also include a step 66 wherein the depth of the groove 36 increases. When the guide 32 is biased within the groove 36 for example, the step 66 could prevent, for example, further proximal withdrawal of the actuator 16 and/or the displacement rod 18 from the body cavity 22 beyond the point where the guide 32 contacts the step 66.

In operation, the guide 32 may be initially positioned within a safety lock position 76 where the displacement rod 18 may be in a most proximal position with respect to shaft 14 and wherein the actuator 16 may be biased in a proximal position with respect to shaft 14 and/or by the displacement spring 20, as seen in FIG. 33C. The tip of the shaft 14 of the fixation delivery apparatus 400 may be positioned adjacent to a first location for insertion of the first anchor 112. The tip of the shaft 14 is inserted at the first location and the shaft 14 is advanced into the intervertebral disc. In the illustrated embodiment, the motive force is typically applied to the delivery apparatus body 12 by the surgeon. The shaft 14 may be advanced until the distal aspect of the tissue stop 54 contacts an outer surface of the intervertebral disc or the tip of the shaft 14 has otherwise been determined to be at the desired location within the intervertebral disc. The surgeon may note that the shaft 14 has been properly advanced by the resistance to further movement resulting from the stop 54 or sheath 43 contacting the outer surface of the intervertebral disc. Once properly positioned, the displacement rod 18 may be advanced relative to the delivery apparatus body 12 by the surgeon to displace the first anchor 112 from the tip of the shaft 14 into the intervertebral disc. To do this, the surgeon may distally displace the actuator 16 relative to the body cavity 22 to release the guide 32 from the safety lock position 76. The actuator may then be rotated approximately 90 degrees sliding the guide 32 through a first radially extending portion 56 of the groove 36. The surgeon may then advance the actuator 16 distally within the cavity 22 which may slide the guide 32 through the first longitudinal extending portion 46 of groove 36. This movement of the actuator may displace the first anchor 112 from the lumen 24 and/or slot 34 of shaft 14 by distally advancing the displacement rod 18 a first distance. The first distance is selected to be sufficient to displace the first anchor 112, but to be insufficient to eject the second anchor 122. As the guide 32 reaches the proximal portion of the first longitudinal extending portion 46 of groove 36, the guide 32 may pass over step 66 and extend further into groove 36 due to forces exerted on the guide 32 by guide spring 52. As seen in FIG. 33D, the first longitudinal extending portion 46 of groove 36 may extend proximally beyond the second radially extending portion 56 of groove 36 to assure proper displacement of the first anchor 112 from shaft 14. A surgeon would have to apply sufficient force to the actuator 16 to slide the guide 32 to the most proximal portion of the first longitudinal extending portion 46 of groove 36. Once the surgeon removes the distally extending force on the actuator, the actuator is forced in a proximal direction by the displacement spring 20 until guide 32 contacts the step 66 preventing further proximal movement of the actuator 16 relative to delivery apparatus body 12. This proximal motion of the actuator 16 may function to draw the tethered second anchor 122 proximally in lumen 24 and/or slot 34 of shaft 14 dispensing the first anchor 112 from lumen 24. After the first anchor 112 has been positioned at the first location within the intervertebral disc, the shaft 14 of the fixation delivery apparatus 400 may be withdrawn from the first location. The first anchor 112 is left secured within the intervertebral disc.

The second anchor 122 and fixation delivery apparatus 400 may remain secured to the first anchor 112 connecting bands 104 such as 104, 110 and/or trailing cinch line 124 of elongate bands, as shown in FIG. 33B. A loop in elongate member 104 may be configured to be at least long enough to extend from a first anchor location to a second anchor location prior to cinching band 104. The tip of shaft 14 of the fixation delivery apparatus 400 may be then repositioned adjacent to a second location on the intervertebral disc for insertion of the second anchor 122. The tip of the shaft 14 is inserted at the second location and the shaft 14 is again advanced into the intervertebral disc. The shaft 14 may again be advanced until the distal aspect of the tissue stop 54 or sheath 43 contacts an outer surface of the intervertebral disc or the tip of the shaft 14 has otherwise been determined to be at the desired location within the intervertebral disc. Once properly positioned, the displacement rod 18 may be advanced relative to the delivery apparatus body 12 by the surgeon to displace the second anchor 122 from the tip of the shaft 14 into the intervertebral disc. To do this, the surgeon may rotate the actuator approximately 90 degrees by sliding the guide 32 through a second radially extending portion 56 of the groove 36. The surgeon may then advance the actuator 16 distally within cavity 22 which may slide the guide 32 through the second longitudinal extending portion 46 of groove 36. The movement of the actuator may displace the second anchor 122 from the distal portion of shaft 14 by distally advancing the displacement rod 18 a second distance. The second distance being selected to be sufficient to displace the second anchor 122 from the lumen 24 and/or slot 34 of the shaft 14 into the intervertebral disc. The surgeon then removes the shaft 14 from the intervertebral disc leaving the second anchor 122 at the second anchor location within the intervertebral disc.

After insertion of at least the first anchor 112 and the second anchor 122, the loop of elongate member 104 is shortened by hand or by pushing on, for example, a slip knot 108 with a knot-pusher or similar device to apply a force to the knot to slide the knot along the band 104 and reduce the size of the loop which tends to draw towards one another the anchors 102 and adjacent tissues surrounding an annular defect. Typically, the tightening is managed using a cinch line 124 that can be manipulated by the surgeon. Once tightened, the excess cinch line 124 can be cut.

It is contemplated that one or more fixation apparatuses 100 (and their respective delivery apparatuses 400) as illustratively described and shown in FIGS. 33A to 33D could be used to effect annular repairs as further illustrated in, for example, FIGS. 44A to 44E, but without the use of patch-like device 600 (and its respective delivery tool 500), as is currently depicted in FIGS. 44A to 44E. It is possible that some annular defects may be readily repaired without the use of a patch-like device 600 and could advantageously be mended or otherwise repaired, partially or wholly, through tissue approximation. Exemplary of a re-approximation without a patch-like device could be performed with one or more repair apparatuses 100 comprising anchors 102, loops 110, bands 104, retainers 108 and tethers 124, for example. And it could be delivered via delivery device 400 as described previously and as is partially illustrated as shaft 14 in FIGS. 44B and 44C. In this alternative embodiment, tissues surrounding an annular defect may be advantageously drawn towards one another to effect a repair, as previously described with respect to, for example, FIGS. 7 to 12. One, two or more fixation apparatuses 100 may be used to accomplish the repair. These apparatuses may be positioned along an annular aperture or may be conveniently placed in a non-lineal fashion, such as a cruciate across the annular rent. It is also possible, given alternative presentations of annular defects, that a re-approximation could also be performed that is similar to that of FIG. 6 wherein fixation apparatuses 100 may be used in conjunction with a filler material 716 and without patch 600 present. In this alternative embodiment, fill material 716 may be directly affixed, or otherwise secured, to portions of one or more fixation devices 100 so as to retain filler material 716 in proximity of the annular defect.

Furthermore, it is conceivable that, in order to repair an intervertebral disc annulus that is damaged, degenerated or otherwise infirmed with defects of a circumferential and/or delaminated physiology, one might employ one or more fixation devices 100 so as to draw together or otherwise radially stabilize or retain tissues in a reparative fashion. In this alternative embodiment (which may be additional or further described in co-pending application Ser. No. 11/120, 750) there may not be an annular aperture readily apparent in the intervertebral disc, but rather the degenerative pathology may be recognized as high intensity zones under radiological examination, such as for example MRI and CT scans. It is also possible, given this type of repair, that the anchors 102 of apparatus 100 may be placed at spatially far greater distances apart (prior to foreshortening band 104) than may be needed for repair of annular apertures. For example, it is conceivable to repair some large posterior protrusions and/or delaminations of an annulus that anchors 102 could be deployed as far apart as the total posterior, or more, of the annulus so as to reparatively restore or otherwise stabilize the incompetent annular tissue.

Alternative embodiments wherein one or more patches 600 (and their delivery tools 500) and one or more fixation apparatuses 100 (and their delivery tools 400) may be used cooperatively, in a reparative fashion, are further described in FIGS. 43 to 46.

FIGS. 34A to 42D illustrate some exemplary embodiments of patch delivery tools 500 in accordance with aspects of the present inventions. The patch delivery tools 500 in accordance with aspects of the present inventions are generally configured to deliver, deploy or otherwise position a patch 600 in proximity adjacent or otherwise partially or wholly within an intervertebral disk 200 of a patient. More particularly, a treatment delivery apparatus 500 in accordance with aspects of the present inventions may be generally configured to position a patch 600 in, on, through, about, and/or across a defect tear, rent, incision or delamination of an intervertebral disc. Typically, patch delivery tools 500 are configured to releasably secure patch 600 on a distal portion of delivery tool 500 such that after a surgeon has secured at least a portion of the patch 600 to the intervertebral disk 200 of a patient, the patch 600 may be released from the patch delivery tool 500 and the patch delivery tool 500 may be removed from the patient.

The illustrated patch insertion tools 500 of FIGS. 34 to 46 generally include an elongated body 502 and at least a distal patch retaining arm 504. A proximal end of the elongated body 502 may include a handle or may otherwise be configured to allow a surgeon to manipulate the patch insertion tool 500 during a surgical procedure on an intervertebral disc of a patient. The distal patch retaining arm 504 may extend from the longitudinal axis of the elongated body 502 and is generally configured to releasably secure or otherwise retain at least one patch 600 for implantation into a patient. The patch delivery tool 500 may also include a proximal patch retaining arm 506. The proximal patch retaining arm 506 may also extend from the longitudinal axis of the elongated body 502 and may be generally configured to releasably secure or otherwise retain a patch 600 for implantation into a patient. In one aspect, the distal patch retaining arm 504 and the proximal patch retaining arm 506 may be generally parallel to one another along a portion of their extension.

As particularly illustrated in FIGS. 34A to 36B, the distal scaffold retaining arm 504 and, when present, the proximal scaffold retaining arm 506 may be generally configured to be received within one or more scaffold mounting cavities 610 of scaffold 600 to secure the scaffold 600 over the distal scaffold retaining arm 504 and the proximal scaffold retaining arm 506. A guide 508 may be positioned proximally to the distal scaffold retaining arm 504. The guide 508 may be configured to guide shaft 14, or other portion of a fixation delivery apparatus 400, to scaffold 600 for introduction of a fixation apparatus 100. Guide 508 may also be configured to accommodate a scaffold retention line 512 so as to retain the scaffold 600 to at least the distal patch retaining arms 504. Guide 508 may also be configured to perform both functions.

Figure 37:
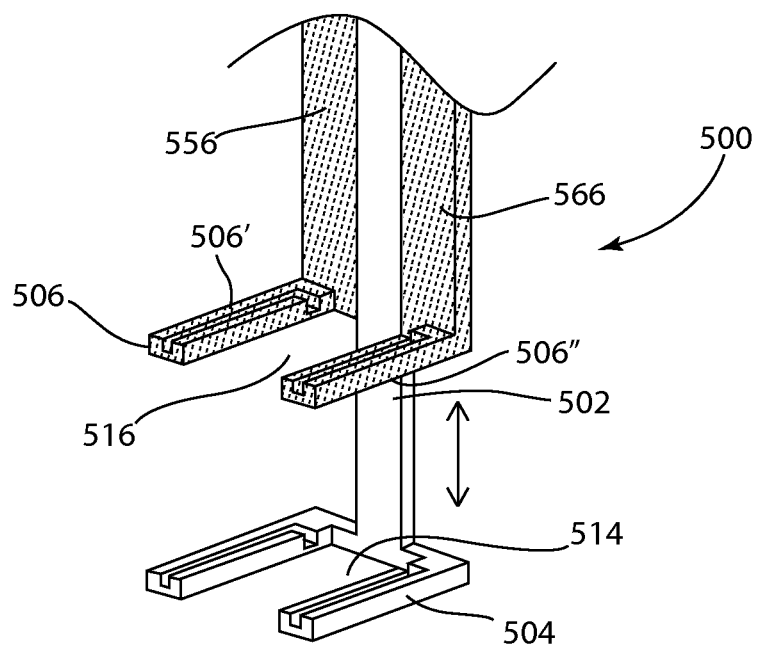
FIG. 37 illustrate exemplary embodiments of a device delivery tool in accordance with aspects of the present inventions.

The distal patch retaining arm 504 illustrated in FIGS. 34A to 36B and, when present, proximal patch retaining arm 506 may extend laterally from a longitudinal axis of a portion of elongated body 502 to which the distal patch retaining arm 504 and the proximal patch retaining arm 506 may emanate. The distal patch retaining arm 504 and the proximal patch retaining arm 506 may be configured to independently, or cooperatively secure a patch 600 in a manner which permits the anchoring of a patch on and/or in an intervertebral disc. The distal patch retaining arm 504 and proximal patch retaining arm 506 may be sized and shaped to be positioned on, in or about an intervertebral disc after being guided through an incision 208 in a patient. The distal patch retaining arm 504 and proximal patch retaining arm 506 are spaced apart along the longitudinal axis of the elongated body 502. The distal patch retaining arm 504 and proximal patch retaining arm 506 may be fixed or movable relative to the elongated body 502 as illustrated in FIG. 37. As illustrated the distal patch retaining arm 504 and proximal patch retaining arm 506 may extend outwardly within a plane that may be substantially perpendicular to the longitudinal axis of the elongated body 502, for exemplary purposes. The distal patch retaining arm 504 and the proximal patch retaining arm 506 may define a distal patch retaining arm gap 514 and a proximal patch retaining arm gap 516, respectively. As illustrated, the distal patch retaining arm 504 may generally be configured to suspend a portion of a patch 600 across the distal patch retaining arm gap 514 to permit a shaft 14 of a fixation delivery apparatus 400 to penetrate the portion of patch 600 suspended over the patch retaining arm gap 514. Similarly, the proximal patch retaining arm 506 may generally be configured to suspend another portion of patch 600 across a portion of the proximal patch retaining arm gap 516 to permit shaft 14, or other component of a fixation delivery apparatus 400, to penetrate a portion of the patch 600 suspended across patch retaining arm gap 516. In one embodiment, the distal patch retaining arm gap 514 of arm 504 may be aligned with the proximal patch retaining arm gap 516 of arm 506 along an axis which may be substantially parallel to the longitudinal axis of the elongated body 502. Such an alignment may permit a shaft 14, or other component of a fixation delivery apparatus 400, to be directed through the portions of the patch 600 suspended between both the patch retaining arm gaps 516 and 514, while following an axis of insertion substantially parallel to the longitudinal axis of the elongated body 502.

An alternative embodiment particularly illustrated in FIG. 37 is a patch insertion tool 500 with a distal patch retaining arm 504 and a proximal patch retaining arm 506 which are adjustably spaced along the longitudinal axis of the elongated body 502. A range of mechanisms for adjusting the spacing of the distal patch retaining arm 504 and a proximal patch retaining arm 506 will be recognized by those skilled in the art upon review of the present disclosure. For exemplary purposes, the exemplary mechanism includes the distal patch retaining arm 504 secured in a position relative to the elongated body 502. As illustrated, the exemplary proximal patch retaining arm 506 is configured as two separate components, a first proximal arm portion 506' and a second proximal arm portion 506". The first proximal arm portion 506' may be secured to a first proximal arm mount 556. The second proximal arm portion 506" may be secured to a second proximal arm mount 566. Both the first proximal arm mount 556 and the second proximal arm mount 566 may be movably attached to elongated body 502. In one aspect, the first proximal arm mount 556 and the second proximal arm mount 566 may be independently slidably secured to the elongated body 502. In operation, the distance between the distal patch retaining arm 504 and the proximal patch retaining arm 506 may be increased as the first proximal arm mount 556 and the second proximal arm mount 566 are moved proximally along the longitudinal axis of the elongated body 502. The distance between the distal patch retaining arm 504 and the proximal patch retaining arm 506 may be decreased as the first proximal arm mount 556 and the second proximal arm mount 566 are moved distally along the longitudinal axis of the elongated body 502 (see arrow in FIG. 37). The movement of the first proximal arm mount 556 and the second proximal arm mount 566 may be independent or dependent upon the movement of the other depending upon the configuration of the mechanism used as will be recognized by those skilled in the art upon review of the present disclosure.

Although treatment delivery tool 500 and retaining arms 504, 506 are generally depicted with rectangular configurations, it is clear that alternative configurations (e.g., circular, elliptical, tubular, curvilinear) could be employed to accomplish similar effects. Furthermore, it is also clear that delivery tool 500 components may be constructed of multiple materials and/or components to accomplish the same objectives. In addition, guide 508 of apparatus 500 may have alternative forms such as eyelets, holes and tubes illustrated in FIG. 34-36. Guides 508 may also have cut-outs or other similar features (not shown) that allow for passing fixation delivery apparatus 400 laterally through the side of the guide structure 508 rather than being limited to passing the apparatus 400 solely along the longitudinal axis of patch delivery tool 500.

Although the modality of arms 504 and 506 has been represented with one alternative embodiment incorporating groves on 504 and 506 to retain patch to delivery tool 500, alternative patch securement facilities as discussed herein could also be employed.

Figure 38C:
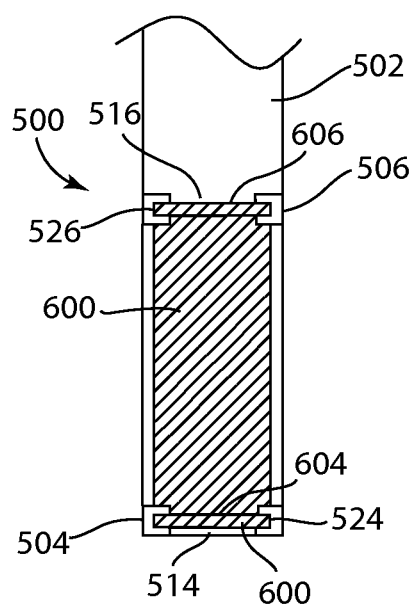
FIGS. 38A-38C illustrate exemplary embodiments of a patch and a patch delivery tool in accordance with aspects of the present inventions.
Figure 38B:
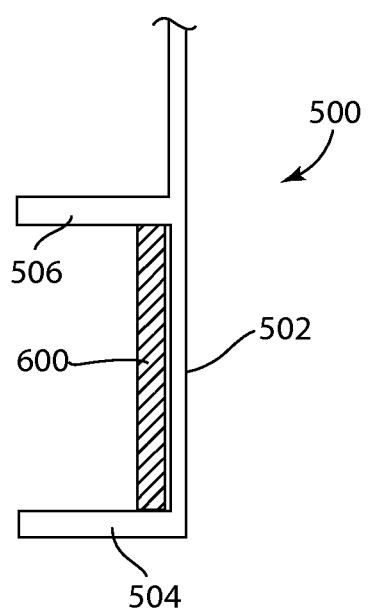
Figure 38A:
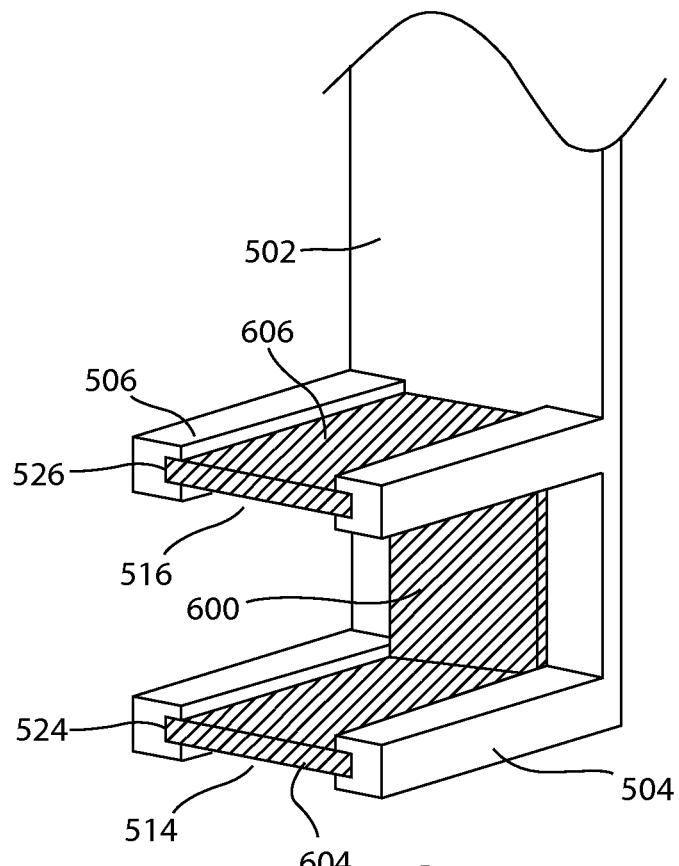

Alternative embodiments of a patch delivery tool 500 as illustrated in FIGS. 38A to 38C, may include a patch 600 secured by a distal retaining arm 504 and a proximal retaining arm 506. The patch 600 may be secured within retaining grooves 524 and 526 of the distal patch retaining arm 504 and proximal patch retaining arm 506, respectfully. The retaining grooves 524 and 526 may be positioned on opposing sides of patch retaining arm gaps 514 and 516. The patch retaining grooves 524 and 526 may be generally configured to receive and releasably secure a portion of patch 600. The portion of the patch 600 may be compressionally, adhesively, mechanically (such as with detents, for example), or otherwise held within the patch retaining grooves 524 and, when present, the proximal peripheral patch retaining grooves 526, as will be recognized by those skilled in the art upon review of the present disclosure. The distal patch retaining grooves 524 are illustrated as securing a distal portion 604 of patch 600. The distal portion 604 of the patch 600 may be secured across a portion of the arm gap 514 of the distal retaining arm 504. The proximal patch retaining grooves 526 are also illustrated as securing a proximal portion of patch 600. The proximal portion 606 of patch 600 also may be secured across a portion arm gap 516 of the proximal retaining arm 506. The distal and proximal portions of patch 600 may typically be secured such that a portion of distal patch portion 604 and/or proximal patch portion 606 of patch 600 may be anchored by a fixation apparatus 100 (or 308 as discussed previously) as delivered and deployed by fixation delivery apparatus 400.

Figure 39E:
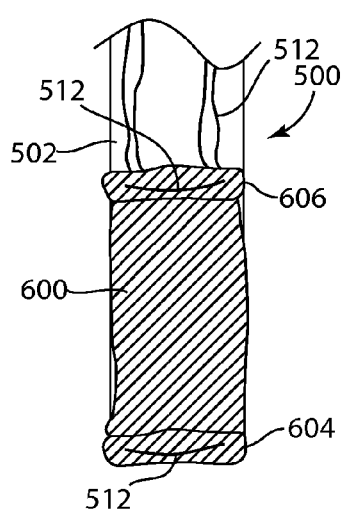
FIGS. 39A-39E illustrate exemplary embodiments of a treatment device and a treatment delivery tool in accordance with aspects of the present inventions.
Figure 39D:
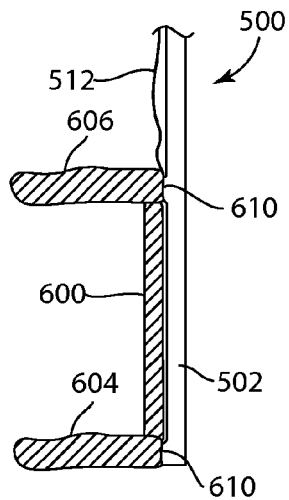
Figure 39A:
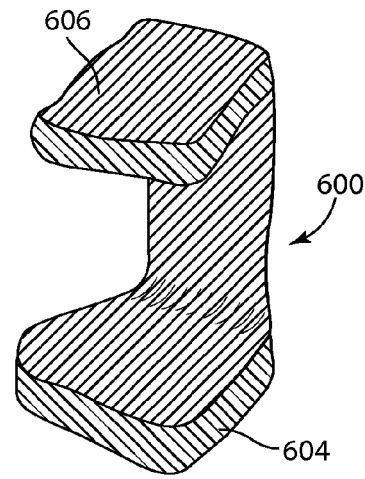
Figure 39B:
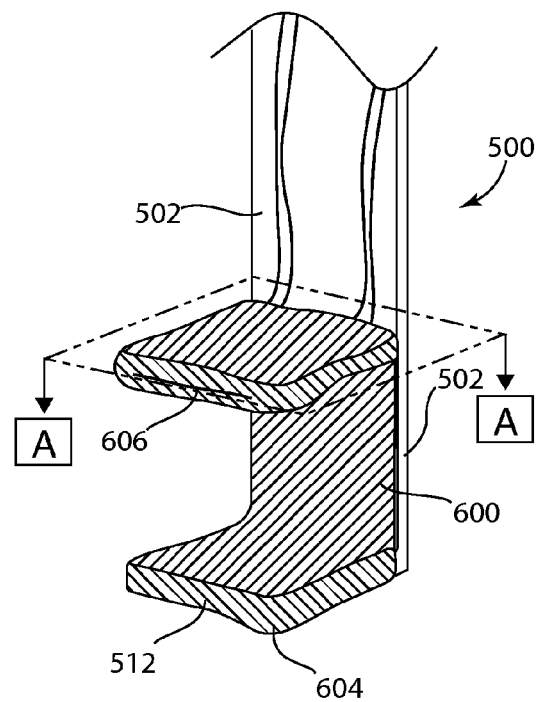
Figure 39C:
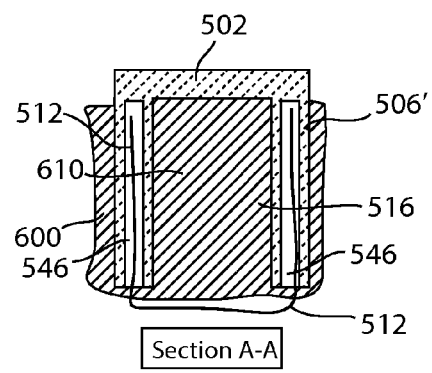

As illustrated in FIGS. 39A to 39E, a patch insertion tool 500 may include a patch 600 secured over a distal retaining arm 504 and a proximal retaining arm 506. The illustrated patch 600 includes at least two patch cavities 610 that are configured to be received over one or more of the distal patch retaining arms 504 and the proximal patch retaining arms 506. The patch 600 is shown with a distal patch cavity 610 receiving at least a portion of the distal patch retaining arm 504 and a proximal patch cavity 610 receiving at least a portion of the proximal patch retaining arm 506. In addition, a patch retention line 512 is provided to facilitate the securement of patch 600 over the distal patch retaining arm 504 and the proximal patch retaining arm 506. The distal patch retaining arm 504 defines at least one distal patch retaining grooves 544 (not shown) and the proximal patch retaining arm 506 defines at least one proximal patch retaining line groove 546 extending from the elongated body 502. The distal patch retaining line grooves 544 and the proximal patch retaining line passages 546 are generally configured to receive one or more patch retaining lines 512 that have been threaded through a patch 600 one or more times. The proximal patch retaining arm 506 is shown defining two proximal patch retaining line grooves 546 including one on each side of the proximal patch retaining arm gap 516. As shown in FIG. 39C, a first patch retaining line 512 may extend along a first proximal patch retaining line groove 546, then pass through a proximal portion 606 of the patch 600, then extend over a portion of an outer surface of the patch 600, and then be threaded through the patch 600, and then extend along a second proximal patch retaining line groove 546. Similarly, a second patch retaining line 512 may pass along a first distal patch retaining line groove 544, then pass through a distal portion 604 of the patch 600, then extend over a portion of an outer surface of the patch 600, and then be threaded through the patch 600, and then extend along a second distal patch retaining line groove 544. Both the first and the second retaining lines may be secured at the distal portion of the insertion tool 500 and/or, as illustrated for exemplary purposes, may extend proximally along the elongated body 502 to permit a surgeon to manipulate the lines before, during or after use of delivery tool 500. To release the lines, one or more knots in the patch retaining line 512 may be untied, the patch retaining lines 512 may be cut, and/or one end of the patch retaining line 512 may be pulled to slide the patch retaining lines 512 out of patch 600 and/or the insertion tool 500. Once removed, cut or otherwise released, the patch 600 may be slid off of the distal retaining arm 504 and a proximal retaining arm 506 either simultaneously or sequentially.

As illustrated in FIGS. 40A to 40E, a patch insertion tool 500 may include a mesh 600 retained by a apparatus 500 with only a single distal retaining arm 504. The illustrated patch 600 includes a single patch cavity 610 that is configured to be received over the distal patch retaining arm 504. The patch 600 is shown with the distal patch cavity 610 receiving the entire length of the distal patch retaining arm 504 and extending proximally along a length of the elongated body 502, although it is also possible that only portions of tool 500 and arms 504 are covered by patch 600. In addition, a patch retention line 512 may be provided to retain the patch 600 over elongated body 502 and the distal patch retaining arm 504. One or more patch retaining lines 512 may be threaded through patch 600 one or more times at a proximal location of the patch and may be configured to retain a proximal portion of patch 600 at a desired location along the elongated body. As illustrated, the patch retaining line 512 may be threaded through a proximal portion 606 of the patch 600, then extend over a portion of an outer surface of the patch 600, and then again threaded through the patch 600, after which the patch retaining line 512 is secured relative to the elongated body. It is possible to thread alternative portions of patch 600, as well as it is possible that multiple retention lines 512 may be used. The patch retaining line 512 may be releasably secured at the distal portion of the insertion tool 500 or, as illustrated for exemplary purposes, may extend proximally along the elongated body 502. To release the lines, one or more knots in the patch retaining line 512 may be untied, the patch retaining lines 512 may be cut, and/or one end of the patch retaining line 512 may be pulled to slide the patch retaining line 512 out of the patch 600 and/or distal end of the insertion tool 500. Once removed, cut or otherwise released, the patch 600 may be slid off of the distal retaining arm 504 within the patient.

Alternatively, as illustrated in FIGS. 41A to 41D, a patch insertion tool 500 may include a patch 600 secured between a distal retaining arm 504 and a proximal retaining arm 506 adjacent to the elongated body 502 wherein the patch retention line 512 may be threadedly received along the length of the patch 600. Particularly, the patch retention line 512 may be secured to the proximal retention arm 506, then threaded through a first side of patch 600, then positioned in the distal retention arm 504, then threaded through a second side of the patch 600, and then again placed onto the proximal retention arm 506.

To releasably secure the patch with retaining line 512, the distal patch retaining arm 504 defines at least one distal patch retaining line groove 544 and the proximal patch retaining arm 506 defines at least one proximal patch retaining line groove 546. The distal patch retaining line grooves 544 and the proximal patch retaining line groove 546 are generally configured to retain one or more patch retaining lines 512 that have been threaded through a patch 600 one or more times. The proximal patch retaining arm 506 is shown defining two proximal patch retaining line grooves 546 including one on each side of the retaining arm gap 516. As particularly shown in FIG. 41, a patch retaining line 512 originating from the proximal end of the elongated body 502 may be received along a first proximal patch retaining line groove 546 and then through a second proximal patch retaining line groove 546. The patch retention line 512 continues along a first side of patch 600 distally approximately parallel to the longitudinal axis of patch delivery tool 500. The patch retaining line 512 is received within a first distal patch retaining line groove 544 and then through a second distal patch retaining line groove 544. The patch retention line 512 continues proximally along a second side of patch 600 approximately parallel to the longitudinal axis of tool 500 and the distal end is secured with a knot to itself adjacent to the proximal patch retaining arm 506. Alternatively, the patch retaining line 512 may be otherwise secured at the distal end of the insertion tool 500 or may extend proximally along the elongated body 502. To release the lines, the one or more knots in the patch retaining line 512 may be untied, the patch retaining lines 512 may be cut, and/or one end of the patch retaining line 512 may be pulled to slide the patch retaining line 512 out of the patch 600 and/or distal end of the insertion tool 500. In the embodiment illustrated, patch retaining line 512 may be tightened or otherwise foreshortened by cinching slip knot 108. This process may follow the placement/deployment of fixation apparatus 100 (or 309) by fixation delivery apparatus 400, and, in this illustrative embodiment, a portion of 512 may remain with the patch once delivered. Alternatively, line 512 may be removed, cut or otherwise released, and patch 600 may be removed from the insertion tool 500. Trailing line of line 512 may additionally be cut to length. Those skilled in the art would recognize multiple retention lines 512 could be used so as to secure patch 600 to tool 500.

An alternative embodiment as particularly illustrated in FIGS. 42A to 42D, a patch insertion tool 500 may include a patch 600 secured between a distal retaining arms 504 and a proximal retaining arms 506. The patch delivery tool 500 as shown, may have at least one patch retention line 512 threadedly received through a proximal portion 606 and a distal portion 604 of patch 600. Particularly, the patch retention line 512 may be secured through the proximal retention arm 506 and the patch retention line 512 may be threaded through a proximal portion 606 of patch 600. The patch retention line 512 may then be threaded through a distal portion 604 of patch 600 and secured through the distal retention arms 504. The patch retention line 512 may then be passed through the proximal retention arm 506 and secured or passed proximally. The patch retention line 512 is provided to secure the patch 600 to the distal patch retaining arm 504 and to the proximal patch retaining arm 506. The distal patch retaining arm 504 defines at least one distal patch retaining line passage 534 and the proximal patch retaining arm 506 defines at least one proximal patch retaining line passage 536 extending through arms 504 and 506. The distal patch retaining line passages 534 and the proximal patch retaining line passages 536 are generally configured to receive one or more patch retaining lines 512 that have been threaded through a patch 600 one or more times. As illustrated, the distal patch retaining arm 504 defines four proximal patch retaining line passages 534 including two on each side of the distal patch retaining arm gap 514. The proximal patch retaining arm 506 is shown defining four proximal patch retaining line passages 536 including two on each side of the proximal patch retaining arm gap 516.

As shown in FIGS. 42A to 42D, a patch retaining line 512 may extend through a first proximal patch retaining line passage 536 and may then be threaded through a proximal portion 606 of the patch 600. The line may then be threaded through another location in the proximal portion 606 and passed through a second proximal patch retaining line passage 536. The line may then be threaded through a third proximal patch retaining line passage 536 and then threaded through another location in the proximal portion 606 of patch 600. The line may then be threaded through a another proximal patch retaining line passage 536. The line 512 is then threaded through a location in the distal portion 604 and passed through a first distal patch retaining line passage 534. The line 512 is similarly threaded through the distal retaining arm 504 and associated line passages 534 and distal portion 604 of patch 600 as shown in FIGS. 42B and 42D. The line is then directed proximally along the longitudinal axis of the elongated body 502. The retaining line 512 may be secured at the distal end of the insertion tool 500 or, as illustrated for exemplary purposes, may extend proximally along the elongated body 502. To release the lines, one or more knots in the patch retaining line 512 may be untied, the patch retaining lines 512 may be cut, and/or one end of the patch retaining line 512 may be pulled to slide the patch retaining line 512 out of the patch 600 and/or passages 534, 536 of insertion tool 500. Once removed, cut or otherwise released, the patch 600 may be slid off of the distal retaining arm 504 and a proximal retaining arm 506 either simultaneously or sequentially.

Although the various descriptions and illustrations shown herein exemplify a variety of ways and means to temporarily or releasably secure a patch 600 to a delivery tool 500, those skilled in the art would recognize that these are illustrative and are not intended to be limiting. Moreover, it is possible to use combinations of the securement modalities described herein, or portions thereof, to effect the same outcomes.

Although the various embodiments illustrated herein of retaining arms 504 and 506 of treatment delivery apparatus 500 show arms 504 and 506 in a fixed relationship with 500, one skilled in the art would recognize that arms 504 and/or 506 could be rotatably or otherwise adjustable to change the configuration of tool 500 as needed to accommodate delivery, deployment, affixation of patch 600 and/or removal of delivery tool 500. For example, arm 504 may have a hinged or otherwise articulated relationship with delivery tool 500 (not shown). In one exemplary embodiment of an hinged arm 504, the projection of arm 504 from tool body 502 may be more closely aligned with the elongated axis of tool body 502 in a first configuration, such as delivery of patch to the disc space; whereas, during affixation of the patch, arm 504 could assume a second configuration wherein arm 504 may be more perpendicular to the axis of the body 502 (as is shown generally in the drawings). It is also anticipated that arm 506 (if present) could similarly be adjustable. Those skilled in the art would recognize this is exemplary and is not intended to be exhaustive of the various alternative configurations to provide means for adjusting the emanation of arms 504 and 506 from tool body 502.

The fixation delivery apparatus 400, fixation apparatus 100 (or, for example, 309), treatment insertion tools 500 and patches 600 may be used in a variety of procedures for repair, re-approximation, reinforcement, retention, reconstruction, or fixation of the intervertebral disc 200 or its components, such as the annulus 202. The fixation apparatus and patch-like devices may be used together or as separate reparative apparatuses in the repair of disc aberrations. In one exemplary methodology, a patch 600 may be positioned within a defect in an intervertebral annulus with a patch insertion tool 500. A fixation apparatus 100 may then be secured in at least a portion of the patch 600 and intervertebral disc using a fixation delivery apparatus 400, or other devices for securing fixation apparatus as disclosed herein and as will be recognized by those skilled in the art upon review of the present disclosure to effect a repair, re-approximation, reinforcement, retention, reconstruction, or fixation of the intervertebral disc.

Steps of an exemplary embodiment of a method and devices to effect a repair are particularly illustrated in FIGS. 43A to 43E. As shown, distal portion 604 of the patch 600 may be secured to an inner surface of an annular defect and the proximal portion 606 may be secured to an outer surface of the intervertebral disc on the opposite side of the aperture. The patch 600, once positioned, may span a portion of the aperture. The fixation apparatus 100 may function to draw towards or together the tissues surrounding the defect or aperture, and may perform the reparative treatment cooperatively with the patch 600. The patch 600 may also function to facilitate ingrowth of tissue or to otherwise function as indicated throughout this disclosure and as will be recognized by those skilled in the art upon review of the present disclosure.

Figure 43A:
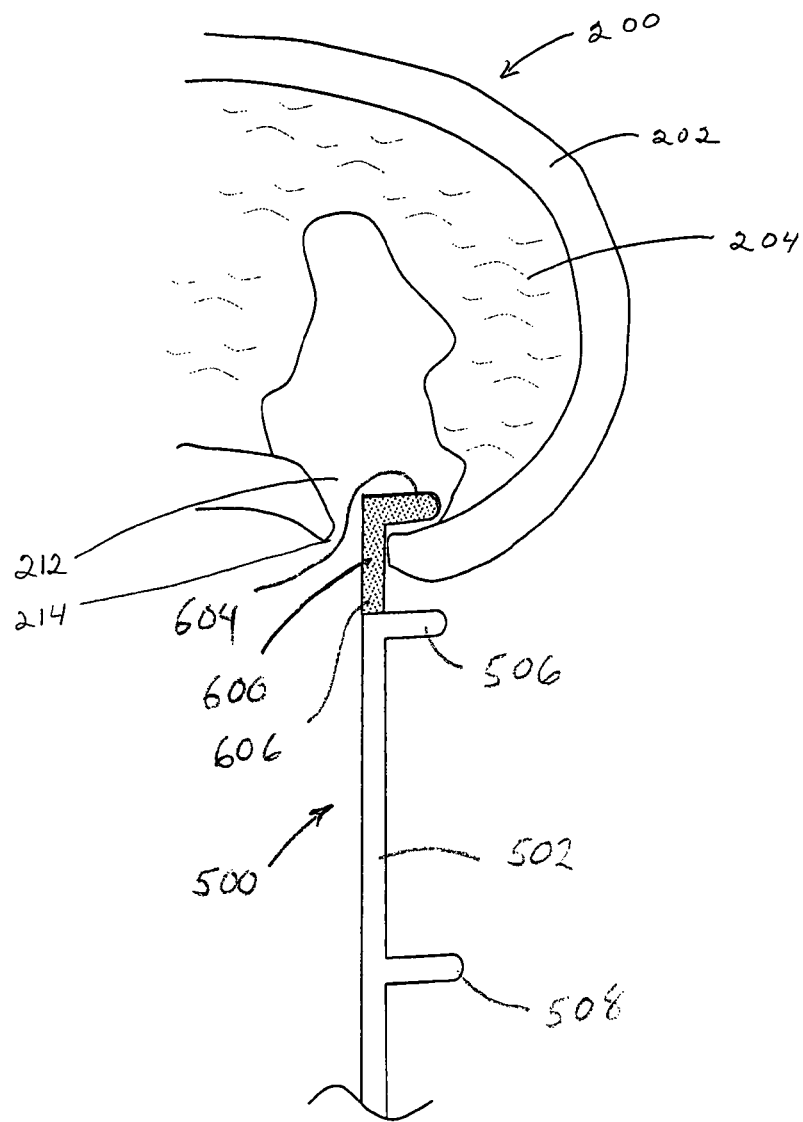
FIGS. 43A-43E illustrate an exemplary method for treatment of an annulus using embodiments of a treatment device and delivery tool, a fixation apparatus, and a fixation delivery apparatus in accordance with aspects of the present inventions.
Figure 43B:
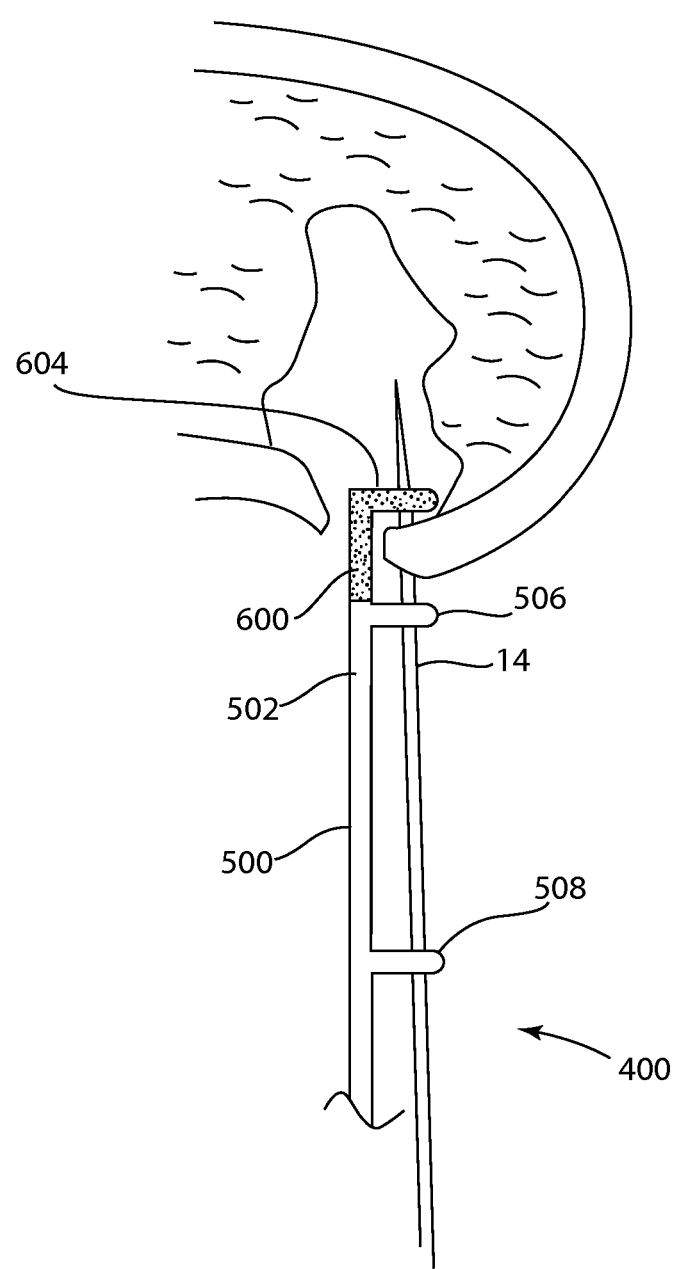

As depicted in FIG. 43A, a patch 600 may be releasably secured over a distal portion of the patch insertion tool 500 such that the distal patch retention arm 504 and a distal portion of the elongated body 502 may be received within the patch mounting cavity 610 of the patch 600. The distal patch retention arm 504 is shown extending into the distal portion 604 of the patch 600 through patch mounting cavity 610. The distal portion of the insertion tool 500 with patch 600 may be inserted into a cavity 212 within an intervertebral disc through an aperture 214 in the intervertebral disc 200 of a patient. The treatment delivery apparatus 500 is manipulated by a surgeon to position the distal portion 604 of the patch 600 at a position in proximity or adjacent to an inner surface of the annulus 202 and/or cavity 212 of an intervertebral disc 200 where it is to be secured.

Figure 43C:
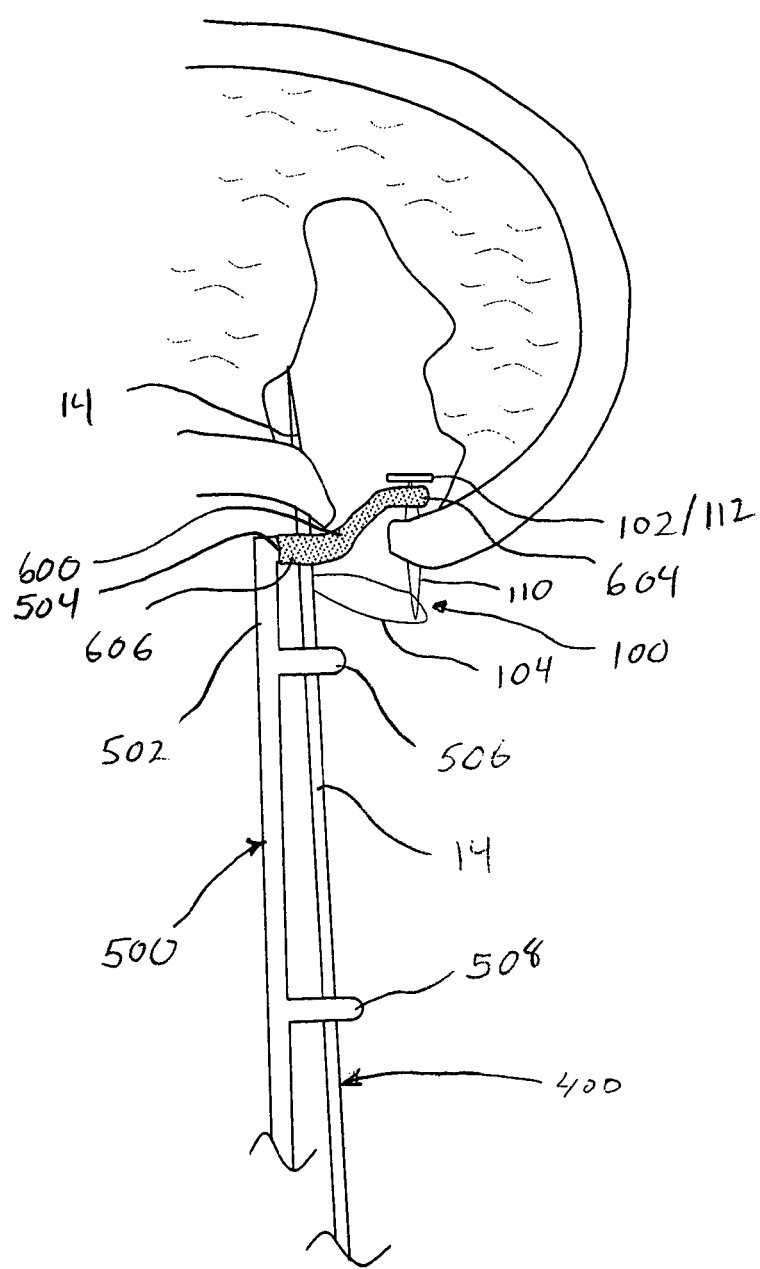

After patch placement as depicted in 43B, fixation delivery apparatus 400 may be inserted longitudinally along the patch delivery tool 500 through the guide 508, through the patch retaining arm gap 516 of arm 506, through disc tissue and, through the patch 600 positioned on the distal portion of the patch delivery tool 500. The shaft 14, or other component of the fixation delivery apparatus 400, may be advanced until the shaft 14 is positioned at a location where the physician desires to dispense an anchor 102 of a fixation apparatus 100 and/or tissue stop 54 restricts further penetration. Once positioned at the desired location, an anchor 102, such as the illustrated first anchor 112, may be dispensed from shaft 14 of apparatus 400. Once the first anchor 112 is dispensed, shaft 14 of apparatus 400 may be withdrawn from the first location leaving the first anchor 112 of fixation apparatus 100 within the tissue and/or cavity of the intervertebral disc. As shown in FIG. 43C, filament loop or eyelet 110 and elongate member 104 of the fixation apparatus 100 may extend from the intervertebral disc.

As depicted in 43C, the distal portion 504 of the insertion tool 500 with patch 600 may then be positioned at an alternative location proximate the annular aperture and at a desired position adjacent to an outer surface of the intervertebral disc, where it may be secured. In doing so, the distal patch retaining arm 504 of the patch insertion tool 500 may be repositioned within the patch mounting cavity 610 of the patch 600 to locate the proximal portion 606 of the patch 600 over the distal patch retaining arm 504. The distal end of shaft 14, or other components of tool 400, may be inserted through the proximal portion 606 of patch 600 through the distal patch retaining arm gap 514 of the distal patch retaining arm 504. The shaft 14 of a fixation delivery apparatus 400 may then be inserted through disc tissue at a second location as desired by the surgeon. The shaft 14 of the fixation delivery apparatus 400 may again be advanced until the shaft 14 is positioned at a location where the physician desires to dispense an anchor 102 of a fixation apparatus 100. Once positioned at the desired location, an anchor 102, such as the illustrated second anchor 122, may be dispensed from shaft 14. Once the second anchor 122 is dispensed, the shaft 14 of the fixation delivery apparatus 400 may be withdrawn from the second location leaving the second anchor 122 of the fixation apparatus 100 within the cavity and/or tissue (such as the annulus or nucleus) of the intervertebral disc. Eyelets 110 and bands 104 of the fixation apparatus 100 may extend from the intervertebral disc and/or the patch 600.

Figure 43D:
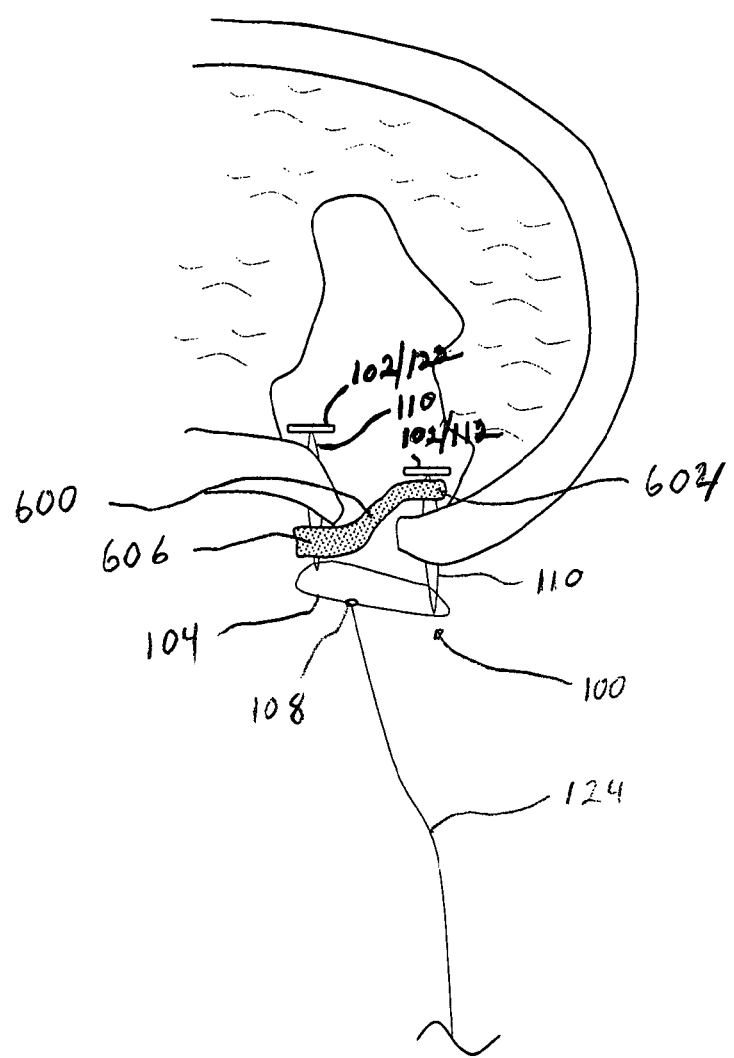
Figure 43E:
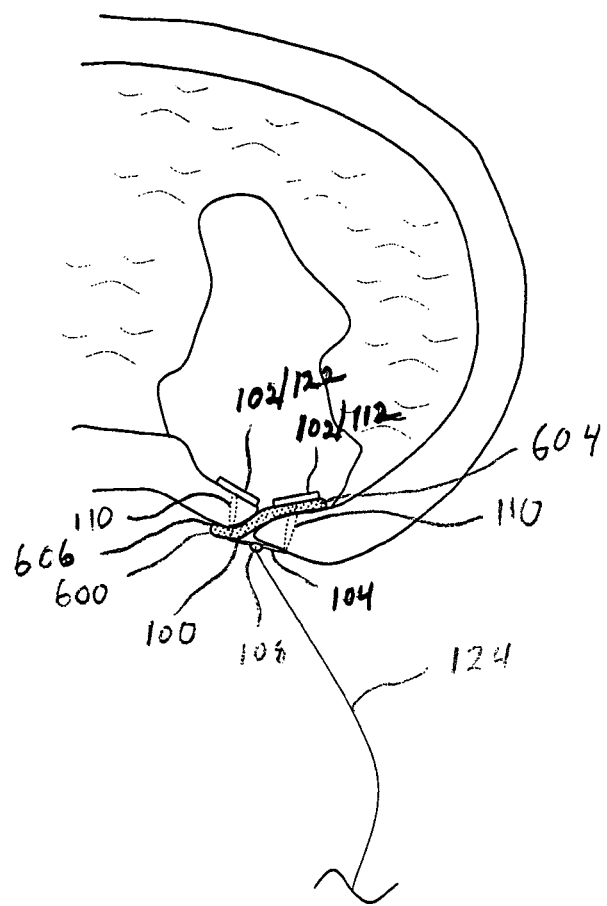

As depicted in FIG. 43D, fixation delivery apparatus 400 is withdrawn from the intervertebral disc and patch 600, leaving the fixation apparatus 100 in a loose, unclenched, or untightened configuration secured through the patch 600 and disc tissue. The distal patch retaining arm 504 is also removed from the patch mounting cavity 610 of the patch 600. A cinch line 124 of the fixation apparatus 100 may extend from the intervertebral disc to a location where it may be accessed by the surgeon. As illustrated, the elongated member 104 is secured in a cinchable loop by a retention device 108 in the form of a slip knot, although other band retention or locking devices as previously described may be used. The loop formed by the elongated member 104 extends through loops 110 which are affixed to the anchors 102. Although FIG. 43 shows a fixation device comprising eyelets and looped bands, those skilled in the art would realize that alternative elongate member configurations could be used to effect the same purpose. As shown in FIG. 43E, the loop may be cinched or tightened by sliding the retention device 108 along the elongated member 104. This cinching or tightening draws the band portions (110 and 104) between anchors 102 together and may reparatively retain, stabilize, re-approximate or otherwise repair tissues surrounding a defect and/or aperture by drawing tissues towards one another and/or against the patch 600. Patch 600 may act as a filler to fill a defect in the intervertebral disc.

Steps of another exemplary method are particularly illustrated in FIGS. 44A to 44E. As illustrated, a patch 600 may be positioned through an aperture in an intervertebral disc in a C-type configuration and may have patch delivery devices as previously described, for example in FIGS. 34 and 42. In the illustrated method of FIGS. 44A to 44E, the distal portion 604 of patch 600 may be secured to an inner portion of an intervertebral disc (such as an inner portion of the annulus) and the proximal portion 606 may be secured to an outer surface of the intervertebral disc. As illustratively shown, ends of patch 600 may be generally placed on the same medial-lateral side of aperture 214, although this is illustrative and not intended to be limiting A fixation apparatus 100 (or 309) may be used to secure the patch to the intervertebral disc. The fixation apparatus 100 may also draw together or otherwise enable closure of the annular aperture or defect of the intervertebral disc. The patch 600, once positioned, may extend from the aperture and may function to permit closure of the aperture, to facilitate the ingrowth of tissue, and/or to otherwise function as indicated throughout this disclosure and as will be recognized by those skilled in the art upon review of the present disclosure.

Figure 44A:
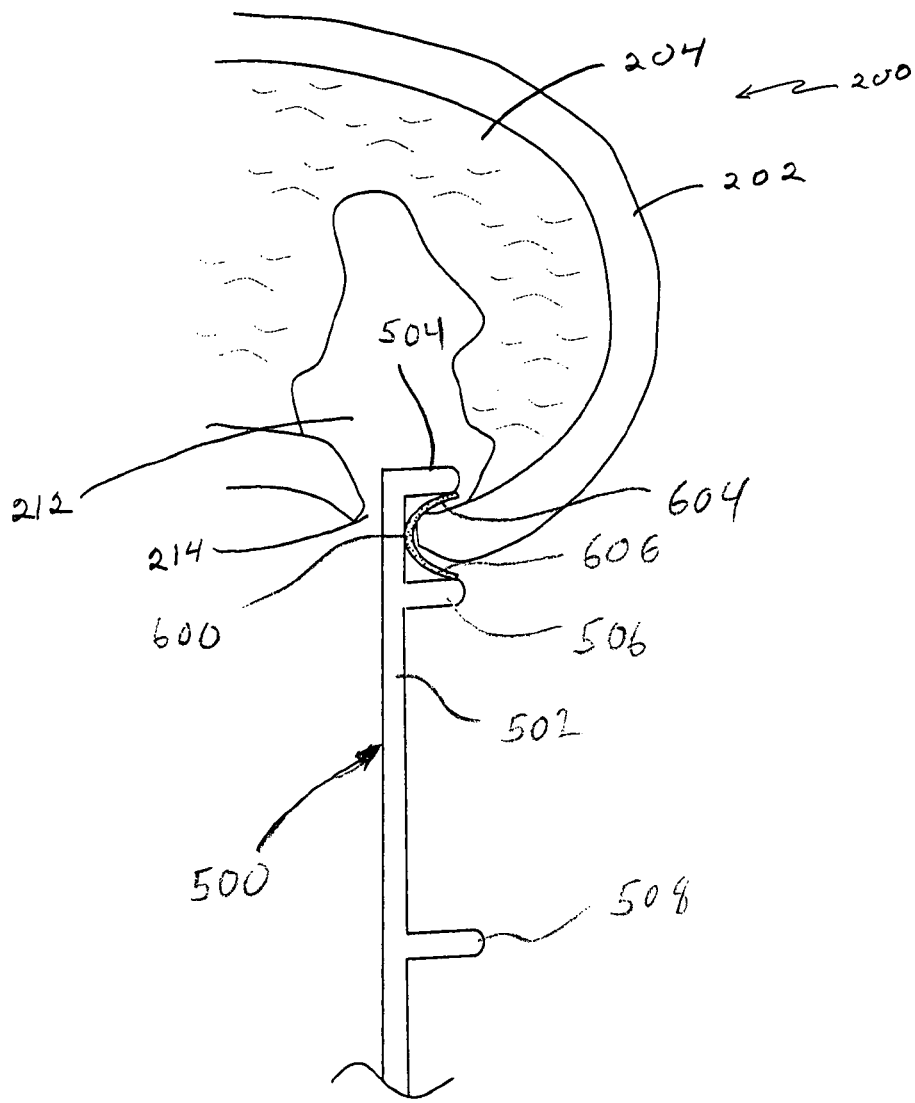
FIGS. 44A-44E illustrate an exemplary method for treatment of an annulus using embodiments of a patch-like device and a delivery tool, a fixation apparatus, and a fixation delivery apparatus in accordance with aspects of the present inventions.
Figure 44B:
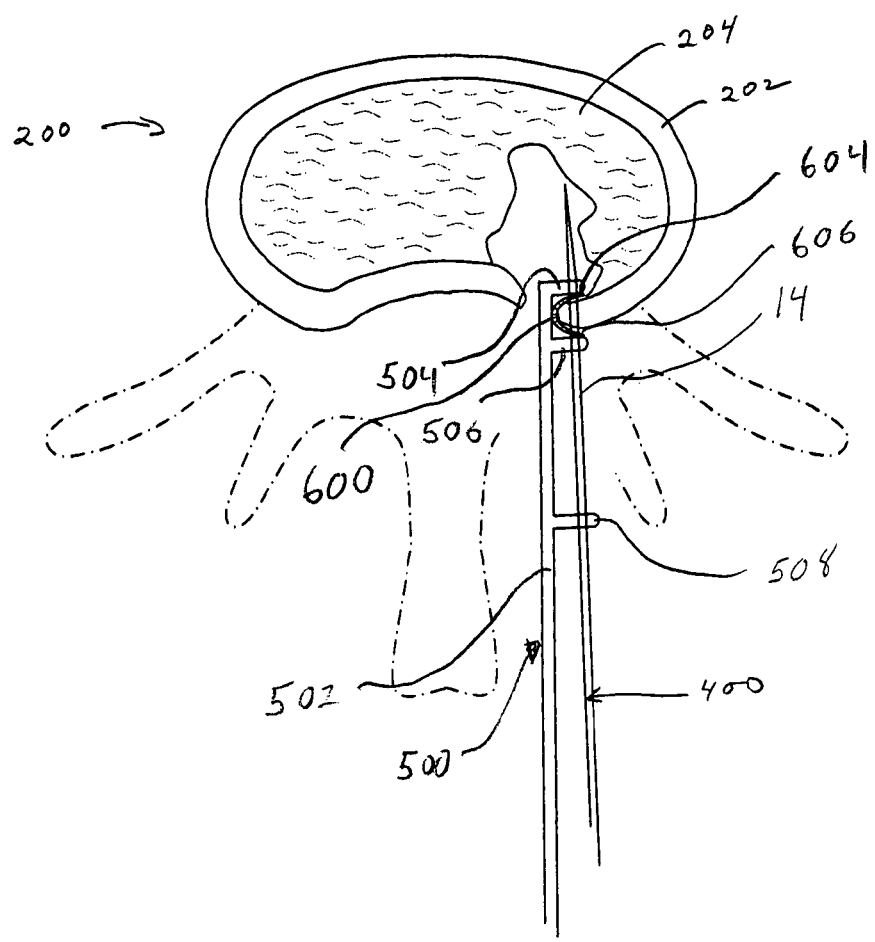
Figure 44C:
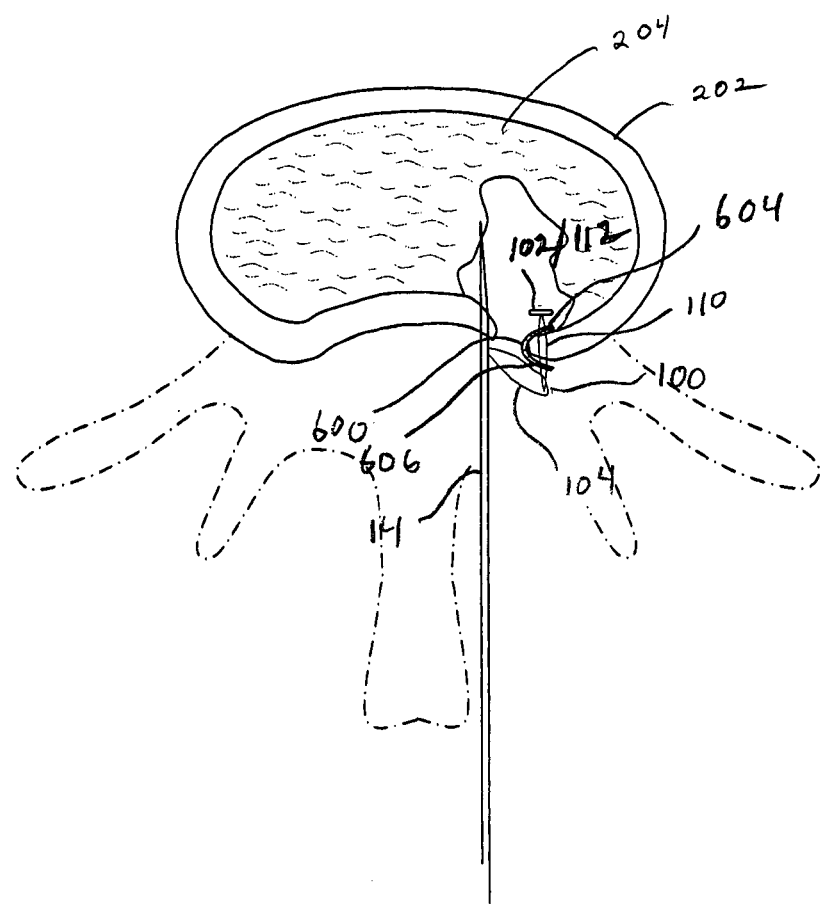

As depicted in FIG. 44A, a patch 600 is releasably secured to a distal portion of the mesh delivery apparatus 500. Device 600 is secured between the distal retention arm 504 and the proximal patch arm 506. The distal retention arm 504 is shown releasably securing the distal portion 604 of device 600. The proximal retention arm 506 is shown releasably securing the proximal portion 606 of device 600. The overall configuration of the device resembles a "C" in cross-section, opening away from the elongated body 502 of the patch insertion tool 500. The distal portion of the patch insertion tool 500 with patch 600 may be inserted into a cavity within an intervertebral disc through an aperture in the intervertebral disc of a patient. The patch insertion tool 500 may be manipulated by a surgeon to position the distal portion 604 of the patch 600 at a position adjacent to an inner surface of disc tissue within a cavity of an intervertebral disc where the patch may be secured and the proximal portion 606 of the patch 600 at a position adjacent to an outer surface of an intervertebral disc, where the patch may also be secured. As illustrated, the proximal portion 606 and the distal portion 604 of the device 600 may be configured to be secured on the same medial-lateral side of an annular aperture, although it is possible that it could also be placed cephalad-caudally, or in alternative positional configurations.

As depicted in 44B, a shaft 14, or components of a fixation delivery apparatus 400, may be inserted longitudinally along the patch delivery tool 500 through guides 508 and then through the proximal retaining arm gap 516 of the proximal retaining arm 506 and up to the patch 600, secured on the distal portion of the patch delivery tool 500. The distal end of shaft 14 may be then inserted through the proximal portion 606 of patch 600 and through intervertebral disc tissue at a first location and then may continue to be inserted through the distal portion 604 of device 600 through the distal retaining arm gap 514 of the distal retaining arm 504. Fixation delivery apparatus 400 may be advanced until the shaft 14 is positioned at a location where the physician desires to dispense an anchor 102 of a fixation apparatus 100. Once positioned at the desired location, an anchor 102, such as the illustrated first anchor 112, may be dispensed from shaft 14. Once the first anchor 112 is dispensed, the shaft 14 of the fixation delivery apparatus 400 may be withdrawn from the first location leaving the first anchor 112 of the fixation apparatus 100 within disc tissue, cavity, and/or device 600. Portions of fixation apparatus 100 may extend from the device 600 and/or the intervertebral disc.

As depicted in 44C, insertion tool 500 may be released from patch 600 and may then be removed from the intervertebral disc. The shaft 14 of a fixation delivery apparatus 400 may then be inserted through the intervertebral disc at a second location as desired by the surgeon, which as illustrated, may be located at an opposing side of an aperture from the first location. The shaft 14 of the fixation delivery apparatus 400 may again be advanced until the shaft 14 is positioned at a location where the physician desires to dispense an anchor 102 of a fixation apparatus 100. Once positioned at the desired location, an anchor 102, such as the illustrated second anchor 122, may be dispensed from the lumen 24 and/or slit 34 of shaft 14. Once the second anchor 122 is dispensed, the shaft 14, or other components of the fixation delivery apparatus 400, may be withdrawn from the second location, leaving the second anchor 122 of the fixation apparatus 100 within disc tissue, and/or the cavity of the intervertebral disc and leaving portions of fixation apparatus 100, such as band 104 and 110 extending from and/or through the intervertebral disc.

Figure 44D:
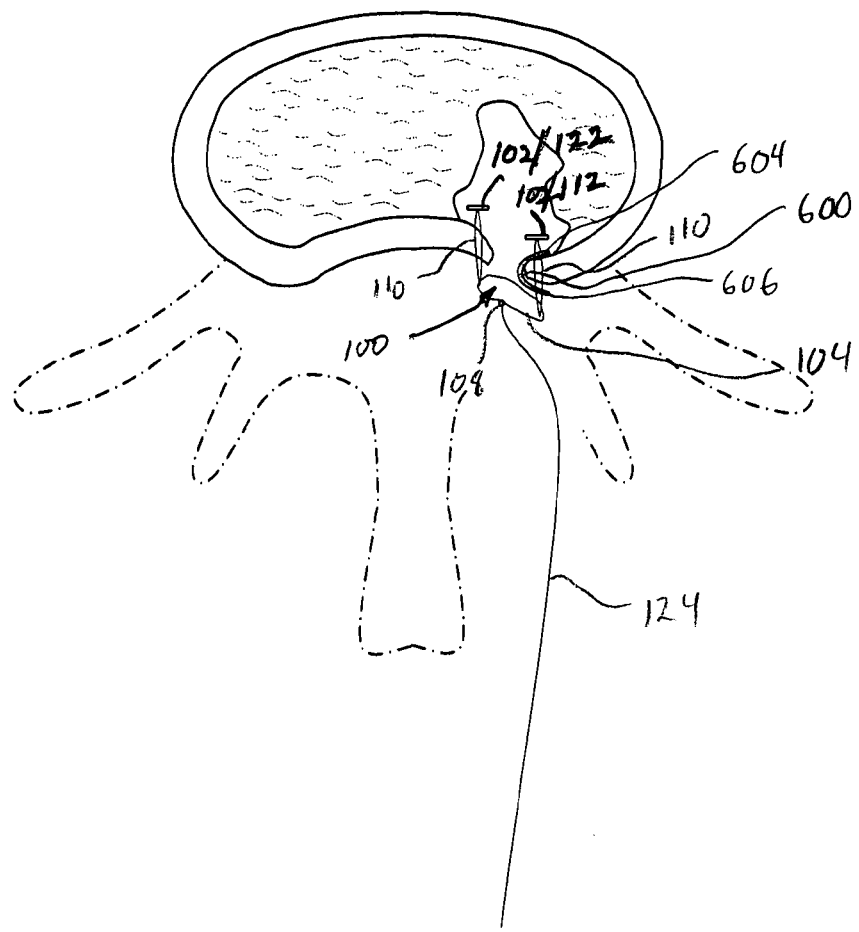
Figure 44E:
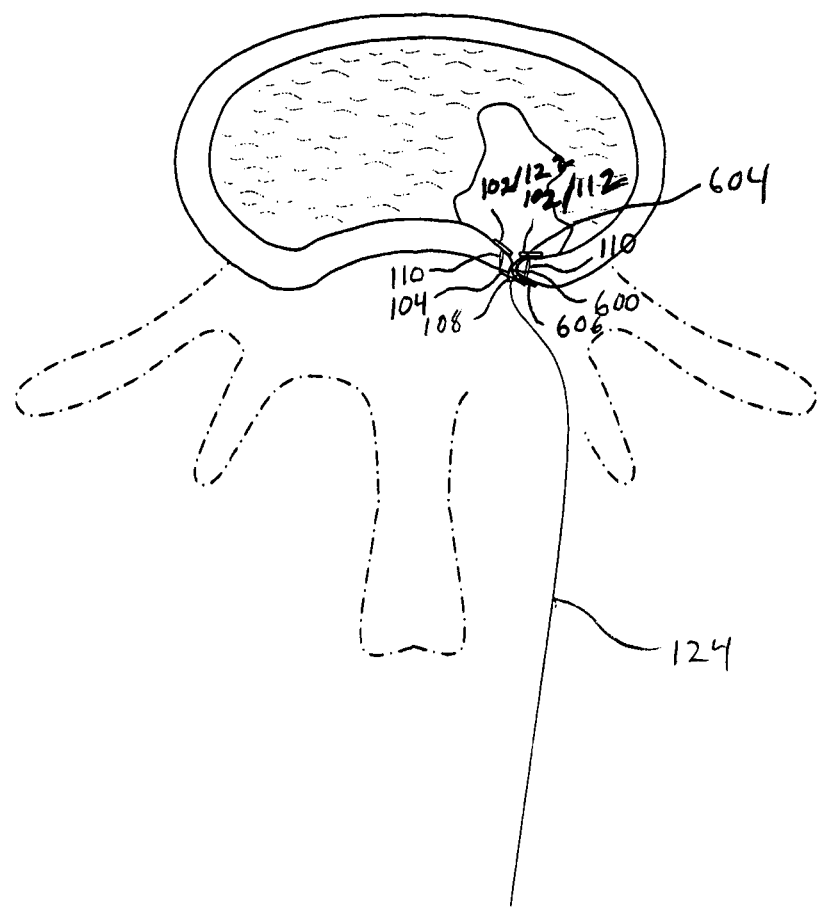

As depicted in FIG. 44D, the shaft 14 of the fixation delivery apparatus 400 may then be withdrawn from the intervertebral disc, leaving the fixation apparatus 100 in a loose or uncinched configuration while secured into and/or through the patch 600 and wholly or partially across the annular aperture in the intervertebral disc. A cinch line 124 of the fixation apparatus 100 may extend from the intervertebral disc to a location where it may be accessed by the surgeon. As illustrated, the elongated member 104 may be, for exemplary purposes, secured in a cinchable loop by a retention device 108 in the form of a slip knot. The loop formed by the elongated member 104 may extend through eyelets 110 which are secured to the anchors 102. As shown in FIG. 44E, the loop may be cinched or tightened by sliding the retention device along the elongated member 104. The cinching or tightening of band 104 may draw together the tissue and the devices surrounding an annular defect and may also effect approximation. Moreover, cinching may further draw anchors into annular tissues. As illustrated, band 104 may be cinched or tightened until the tissues surrounding the aperture and/or defect are drawn towards one another and/or the patch 600, reducing the size of the aperture and/or closing the defect in the intervertebral disc.

Although patch 600 has been illustrated in FIGS. 38 to 46 as having a single configuration/construction, there may be a multitude of configurations/constructions of patches, including patches that may comprise additional elongate elements, such as sutures, to accommodate delivery and deployment of devices to affect annular repair. FIG. 45A shows various alternative configurations of patches 600 that may also include patch tethers 612 to attach the patch to delivery tools 500, as well as to facilitate affixation of the patch to disc tissue. Tethers 612 may be fixed in shape or may be advantageously cinchable with member retention devices 108, such as slip knots. Patch tethers as illustrated may be present on the distal, proximal or both portions of the patch. Tethers in proximity of the exterior of the annulus may advantageously cause less of an inflammatory tissue response than that of larger patch-like devices.

Steps of another exemplary method are particularly illustrated in FIGS. 45A to 45F, wherein more than one patch may utilized in a repair. As illustrated, two patches 600 may be positioned in an intervertebral disc in a Double C-type configuration. In the illustrated method of FIGS. 45A to 45F, the distal portions 604 of the first patch 600 and the second patch 600 may be secured to an inner aspect of an intervertebral disc and the proximal portions 606 of the first patch 600 and the second patch 600 may be secured to an outer aspect of an intervertebral disc. The fixation apparatus 100 may secure one or more of the first and second patches 600 to tissues surrounding an annular aperture in the intervertebral disc. The fixation apparatus 100 may also enable drawing towards one another these tissues and/or patches so as to accommodate closure the aperture and/or defect. The first and second patches 600, once secured, may extend through the aperture, may function to permit closure of the aperture, may facilitate ingrowth of tissue or may otherwise function as indicated throughout this disclosure and as will be recognized by those skilled in the art upon review of the present disclosure.

Figure 45A:
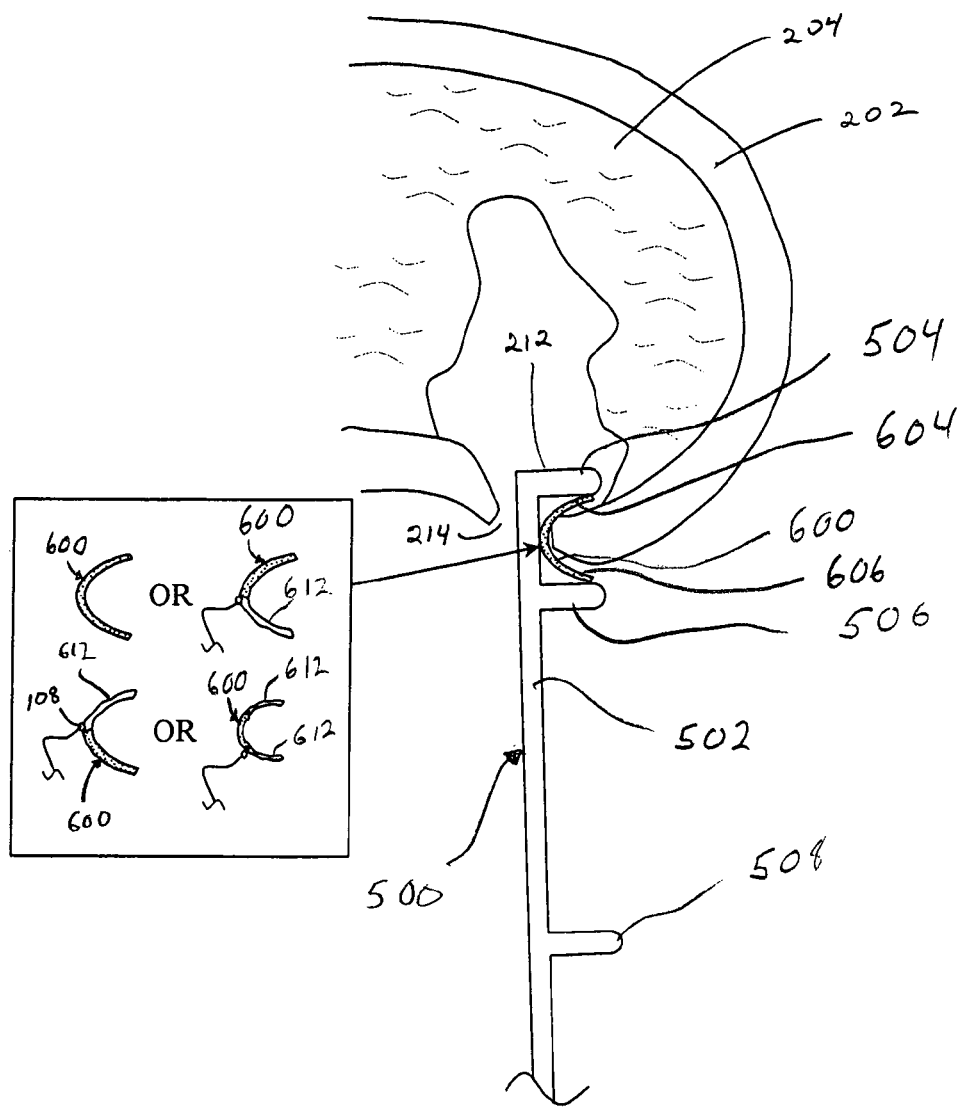
FIGS. 45A-45F illustrate an exemplary method for treatment of an annulus using embodiments of a treatment device and delivery tool, a fixation apparatus, and a fixation delivery apparatus in accordance with aspects of the present inventions.
Figure 45B:
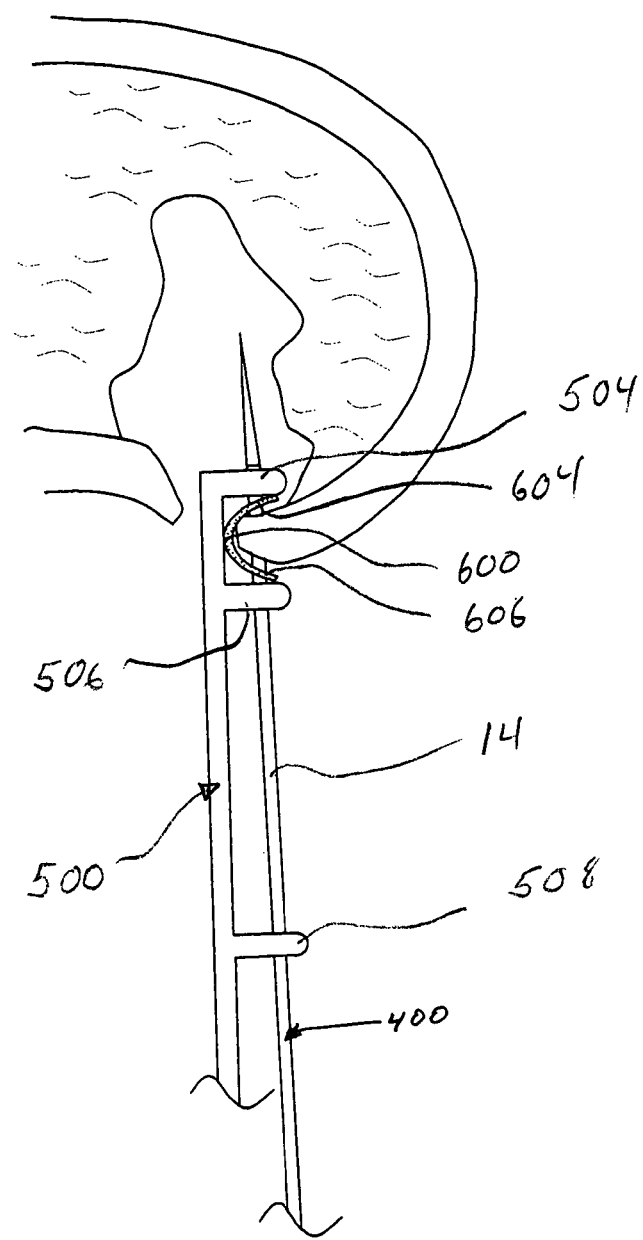

As depicted in FIG. 45A, a first patch 600 may be releasably secured to a distal portion of the patch insertion tool 500. The first patch 600 is secured between the distal patch retention arm 504 and the proximal patch retention arm 506. The distal patch retention arm 504 is shown secured to the distal portion 604 of the first patch 600. The proximal patch retention arm 506 is shown secured to the proximal portion 606 of first patch 600. The overall configuration of the patch resembles a "C" in transverse cross-section opening away from the elongated body 502 of the patch insertion tool 500. The patch insertion tool 500 may be manipulated by a surgeon to position the distal portion 604 of the first patch 600 at a position adjacent to an inner surface of a cavity of an intervertebral disc and the proximal portion 606 of the first patch 600 at a position adjacent to an outer surface of an intervertebral disc where the first patch 600 is to be secured.

As depicted in 45B, a shaft 14, or components of a fixation delivery apparatus 400, may be inserted longitudinally along the patch delivery tool 500 through guide 508 and then through the proximal patch retaining arm gap 516 of the proximal patch retaining arm 506 up to the first patch 600 secured on the distal portion of the patch delivery tool 500. The distal end of the shaft 14 may be inserted through the proximal portion 606 of first patch 600 and then inserted into the intervertebral disc tissue at a first location, as desired by the surgeon. The distal end of the shaft 14 may be then inserted through the distal portion 604 of first patch 600 through the distal patch retaining arm gap 514 of the distal patch retaining arm 504. The shaft 14, or components of the fixation delivery apparatus 400, may be advanced until the shaft 14 is positioned at a location where the physician desires to dispense an anchor 102 of a fixation apparatus 100 (or 308, not shown). Once positioned at the desired location, an anchor 102, such as the illustrated first anchor 112, may be dispensed from the lumen 24 and/or slot 34 of the shaft 14. Once the first anchor 112 is dispensed, the shaft 14 of the fixation delivery apparatus 400 may be withdrawn from the first location leaving the first anchor 112 of the fixation apparatus 100 within the intervertebral disc and portions of the fixation apparatus 100 extending through the first patch 600 and the intervertebral disc.

Figure 45C:
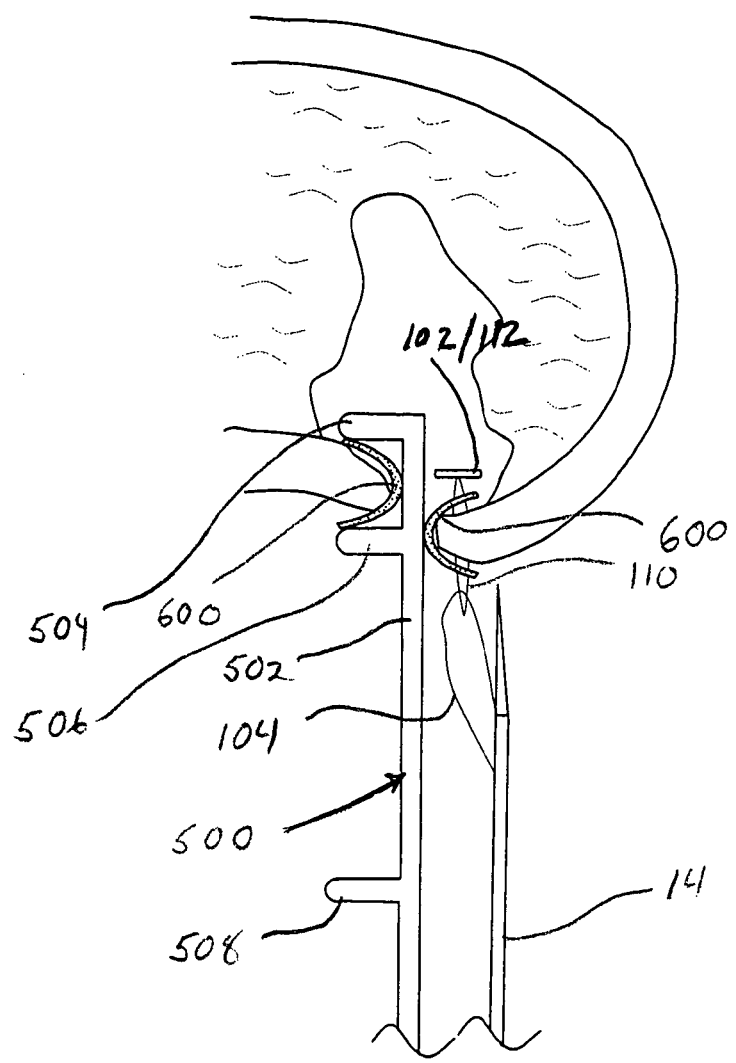
Figure 45D:
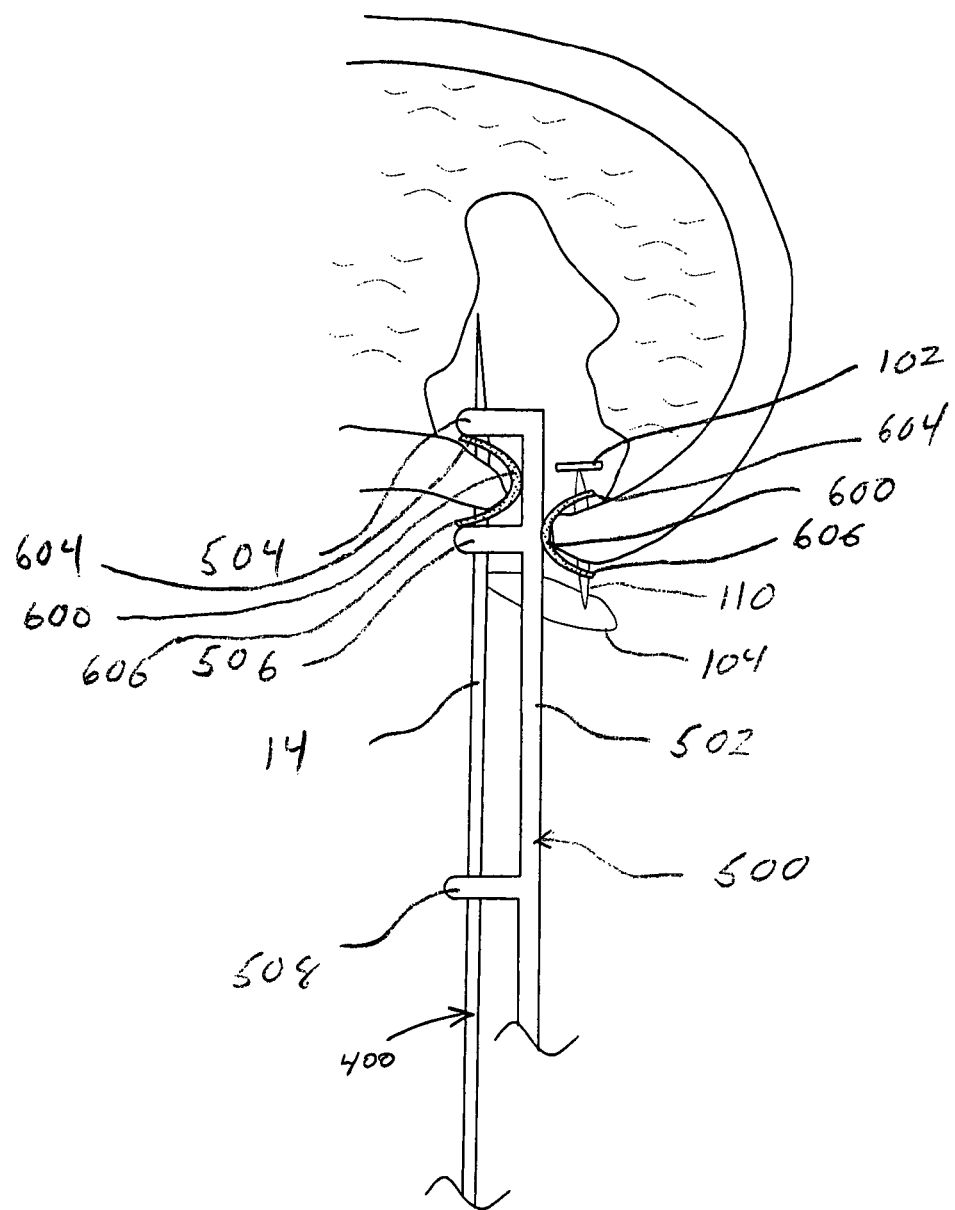

As depicted in FIG. 45C, a second patch 600 may then be provided releasably secured to a distal portion of patch insertion tool 500. The second patch 600 may also be secured between the distal patch retention arm 504 and the proximal patch retention arm 506 and placed at least partially within the intervertebral disc. The patch insertion tool 500 may be manipulated by a surgeon so as to guide where the second patch 600 is to be secured. As illustrated, both the proximal portion 606 and the distal portion 604 of the second patch 600 may be configured to be secured on a second side of an aperture extending into the intervertebral disc.

As depicted in 45D, a shaft 14 of a fixation delivery apparatus 400 may again be inserted longitudinally along the patch delivery tool 500 through the guide 508, through the proximal portion 606 of patch 600, through the intervertebral disc tissue, and through the distal portion 604 of second patch 600. The shaft 14 of the fixation delivery apparatus 400 is advanced until the shaft 14 is positioned at a location where the physician desires to dispense an anchor 102 of a fixation apparatus 100 (or, for example, 308). Once positioned at the desired location, an anchor 102, such as the illustrated second anchor 122, is dispensed from the lumen 24 and/or slot 34 of shaft 14. Once the second anchor 122 is dispensed, the shaft 14 of the fixation delivery apparatus 400 may be withdrawn from the second location.

Figure 45E:
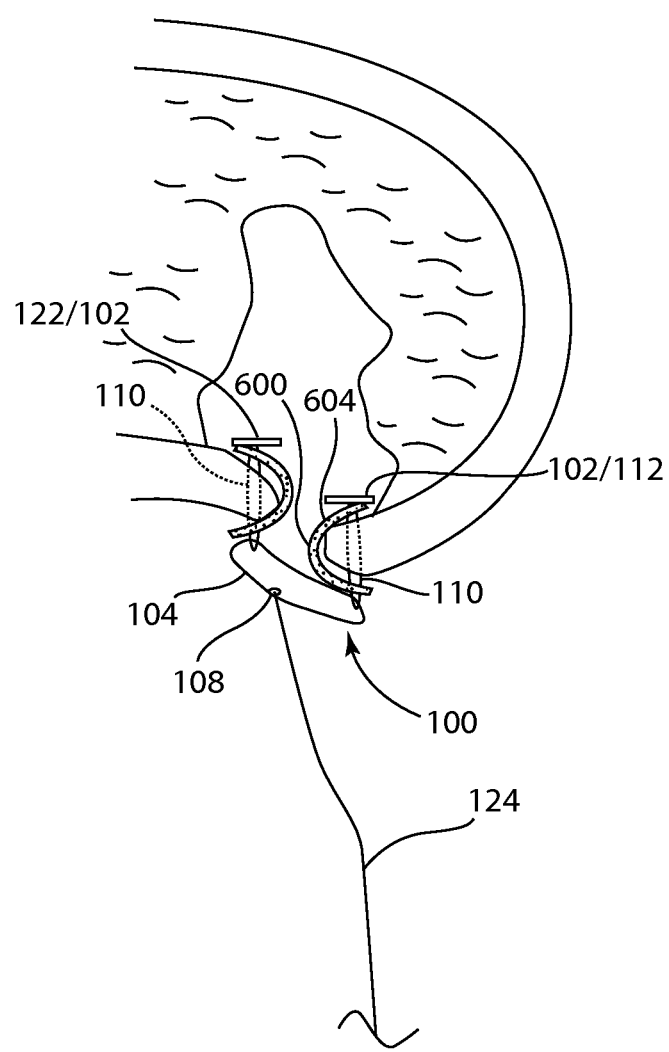

As depicted in FIG. 45E, the shaft 14 of the fixation delivery apparatus 400 may then be withdrawn from the intervertebral disc leaving the fixation apparatus 100 in a loose or uncinched configuration secured through the first patch 600, across the aperture in the intervertebral disc, and through the second patch 600. It should be noted that placement of fixation devices, such as 308, with device delivery apparatuses 400 may result in separate anchor bands being placed and cinched into each patch 600 and an additional elongate member 104 connecting the two anchor bands 308 and/or patches 600 may be utilized to draw towards one another the patches and the surrounding disc tissue. In an alternative embodiment using fixation apparatuses 100, an additional cinchable elongate member 104 may be secured to each patch and drawing on cinch line 124 may further draw together the two patches. It is also conceivable to place and secure more than two patches in a similar fashion.

Figure 45F:
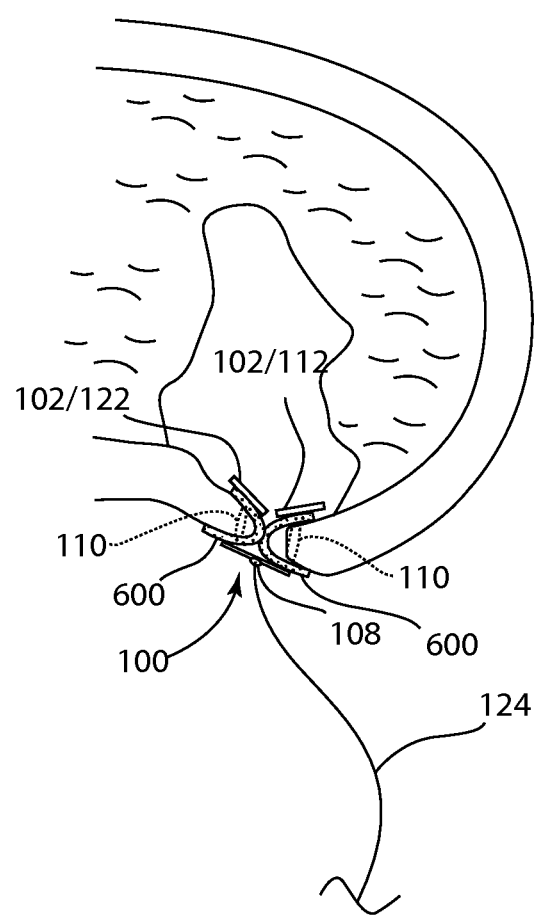

Continuing with illustrated apparatus 100 of FIG. 45E, a cinch line 124 may extend from the intervertebral disc to a location where it may be accessed by the surgeon. As illustrated, the elongated member 104 may again be, for exemplary purposes, secured in a cinchable loop by a retention device 108 in the form of a slip knot. The loop formed by the elongated member 104 may pass through loops 110 attached to anchors 102. As shown in FIG. 45F, the loop may be cinched or tightened by sliding the retention device along the elongated member 104. As previously described, cinching or tightening may draw the edges of the aperture toward one another and/or against the first and second patches 600, reducing the size of the aperture and/or closing the defect in the intervertebral disc.

Steps of yet another exemplary method are particularly illustrated in FIGS. 46A to 46F. As illustrated, a patch 600 may be secured across an aperture in a linear-type configuration. In the illustrated method of FIGS. 46A to 46F, the distal portion 604 of the patch 600 may be secured to an inner surface of an intervertebral disc and the proximal portion 606 may be secured to an inner surface of the intervertebral disc on the opposite side of an aperture and/or defect. The patch 600, once positioned may span the defect or aperture. The fixation apparatus 100 may additionally facilitate drawing together and/or closing the defect. The patch 600 may cooperate with the fixation apparatus in closing the aperture. In addition or alternatively, the patch 600 may function to facilitate in growth of tissue and/or to otherwise function as indicated throughout this disclosure and as will be recognized by those skilled in the art upon review of the present disclosure.

Figure 46A:
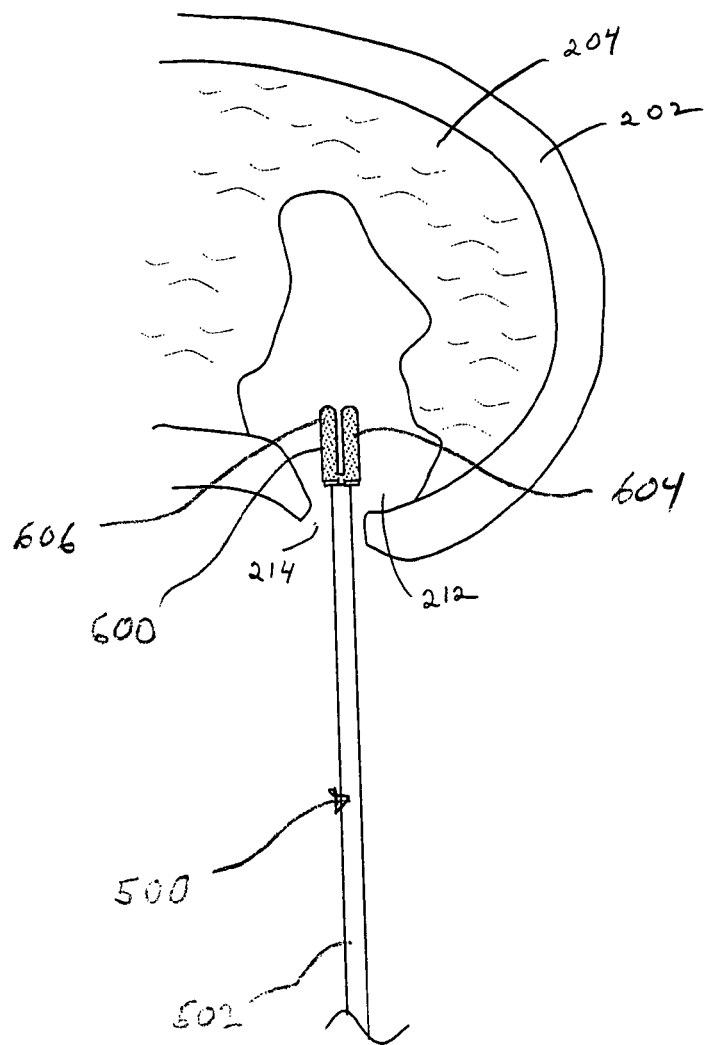
FIGS. 46A-46F illustrate an exemplary method for treatment of an annulus using embodiments of a patch, a patch delivery tool, a fixation apparatus, and a fixation delivery apparatus in accordance with aspects of the present inventions.
Figure 46B:
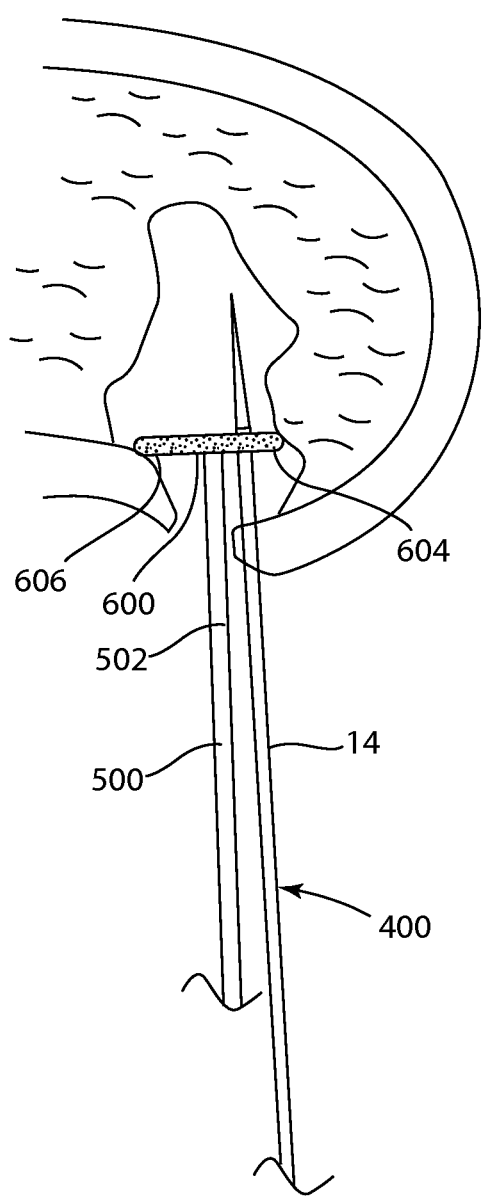
Figure 46C:
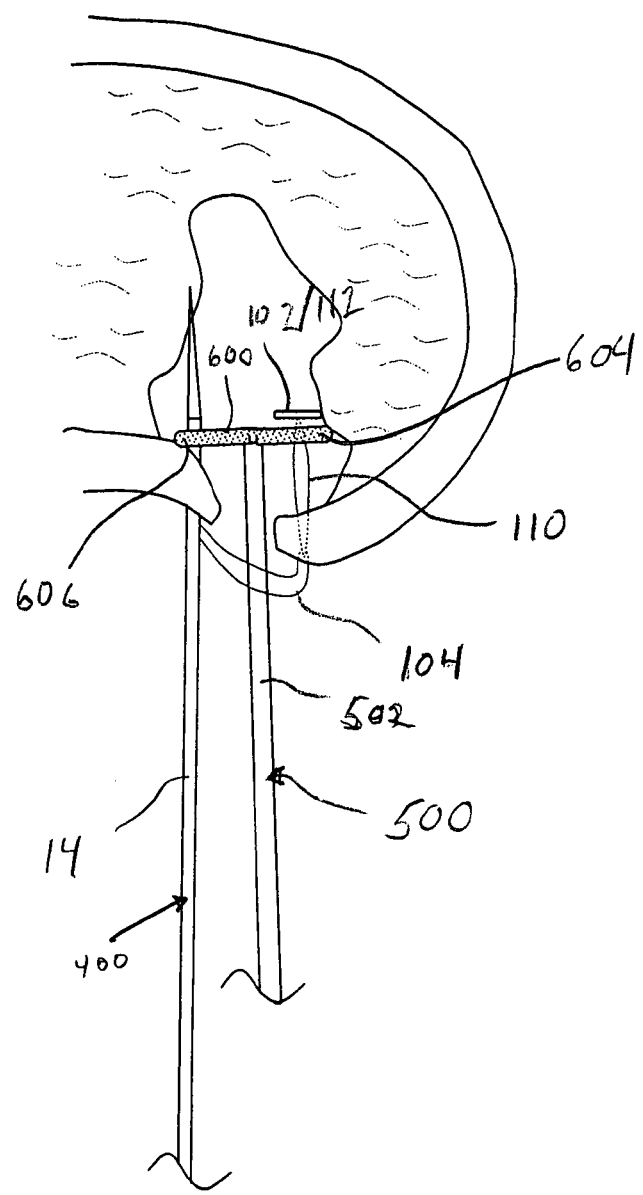

As depicted in FIG. 46A, a patch 600 may be releasably secured over a distal portion of patch insertion tool 500 such that the distal patch retention arm 504 and a distal portion of the elongated body 502 are received within the patch mounting cavity 610 of the patch 600. The distal patch retention arm 504 is shown having a collapsible configuration where the distal patch retention arm 504 is foldable between a perpendicular and a longitudinal orientation. The perpendicular orientation, for example, may permit the simplified introduction of a fixation apparatus 100 and/or portions fixation delivery apparatus 400, thereof, through the patch 600. The longitudinal orientation, for example, may permit the simplified introduction of apparatus 500 with patch 600 through an aperture in an intervertebral disc. As illustrated, each opposing lateral portion of the distal patch retention arm may extend into a patch mounting cavity 610 of the patch 600. The distal portion of the insertion tool 500 with patch 600 is inserted into a cavity within an intervertebral disc through an aperture in the intervertebral disc of a patient with both opposing lateral portions folded distally (as shown) or proximally (not shown) in an orientation substantially along a longitudinal axis of the elongated body 502. The patch insertion tool 500 is manipulated by a surgeon to position in an intervertebral disc tissue where it is to be secured.

As depicted in 46B lateral portions may extend outwardly from insertion tool 500 once patch 600 is positioned within and/or on surrounding disc tissue, and a shaft 14, or components of a fixation delivery apparatus 400, may be inserted longitudinally along patch delivery tool 500. The distal end of the shaft 14 is passed into or through intervertebral disc tissue at a first location as desired by the surgeon. The distal end of the shaft 14 may then be inserted through the distal portion 604 of patch 600. The shaft 14 of fixation delivery apparatus 400 may be advanced until the shaft 14 is positioned at a location where the physician desires to dispense an anchor 102 of a fixation apparatus 100 (or, for example 308). Once positioned at the desired location, an anchor 102, such as the illustrated first anchor 112, is dispensed from shaft 14. Once the first anchor 112 is dispensed, the shaft 14 of the fixation delivery apparatus 400 is withdrawn from the first location leaving the first anchor 112 of the fixation apparatus 100 within the intervertebral disc.

As depicted in 46C, the distal portion of the insertion tool 500 with patch 600 may then be positioned within the disc to position the proximal portion 606 of the patch 600 at a desired location where it is to be secured. In doing so, the proximal patch retaining arm 506 of the patch insertion tool 500 may be repositioned within the cavity of the intervertebral disc to locate the proximal portion 606 of the patch 600 at a second location proximate an aperture or defect. The shaft 14 of a fixation delivery apparatus 400 may then be inserted through the intervertebral disc at a second location, as desired by the surgeon, and passed through a proximal portion 606 of patch 600 on the proximal patch retaining arm 506. The shaft 14 of the fixation apparatus fixation delivery apparatus 400 may again be advanced until the shaft 14 is positioned at a location where the physician desires to dispense a second anchor 122 of a fixation apparatus 100. Once positioned at the desired location, an anchor 102, such as the illustrated second anchor 122, is dispensed from shaft 14. Once the second anchor 122 is dispensed, the shaft 14 of the fixation delivery apparatus 400 may be withdrawn from the second location, leaving the second anchor 122 of the fixation apparatus 100 within the intervertebral disc.

Figure 46D:
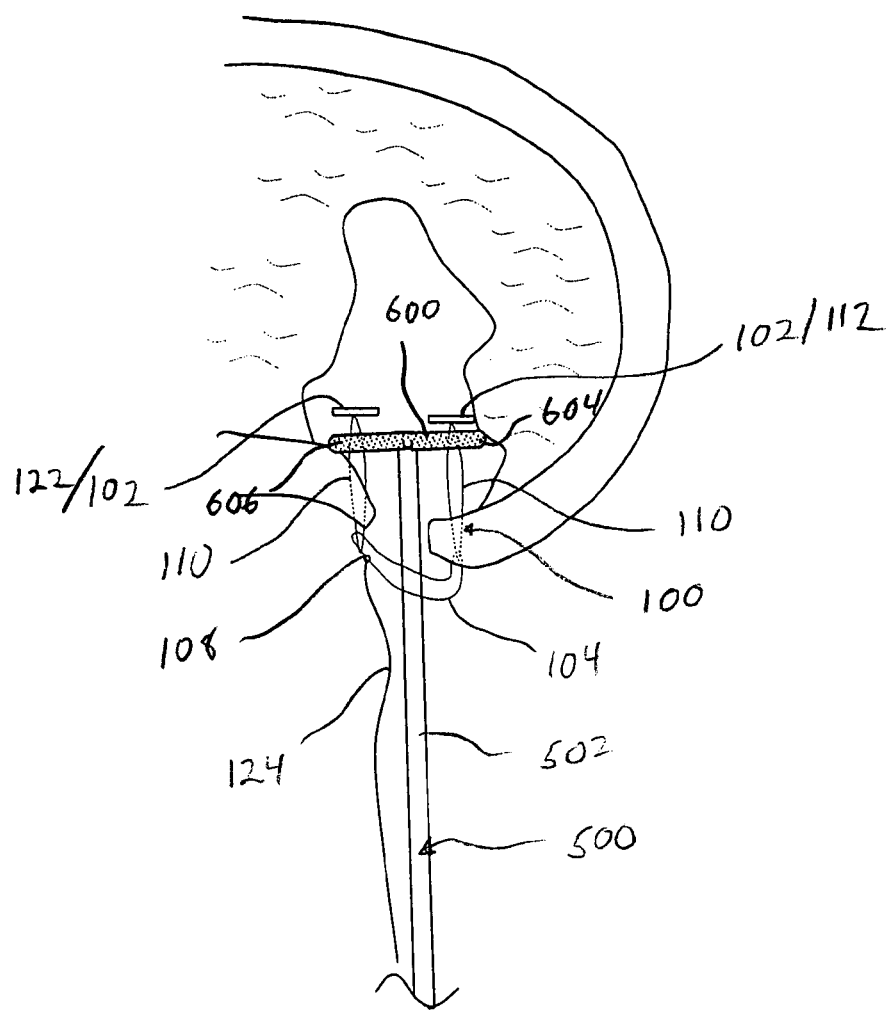
Figure 46E:
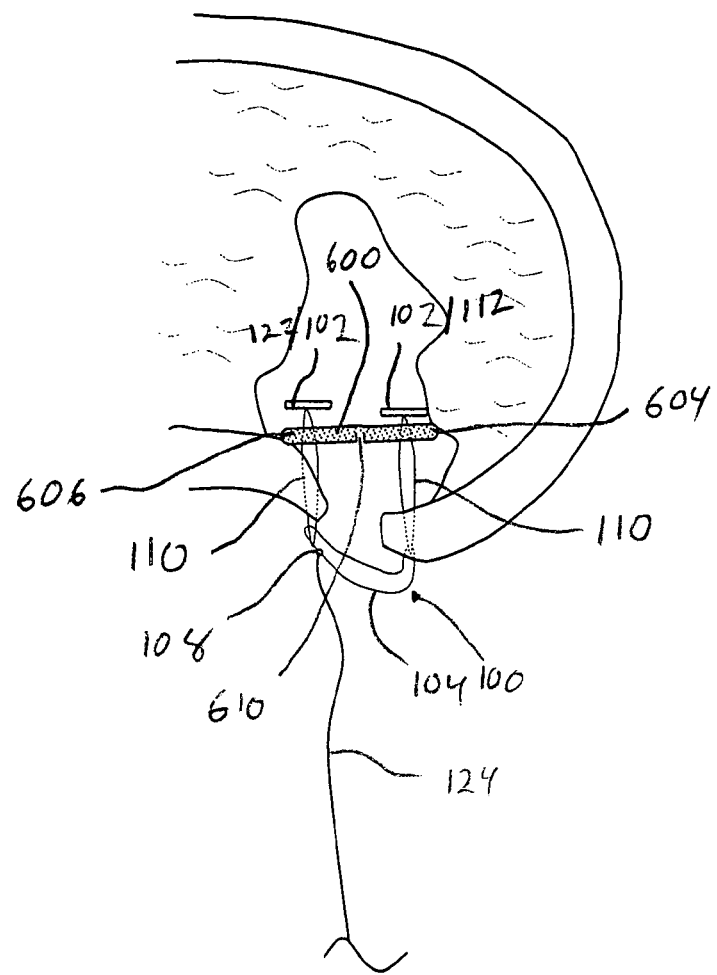
Figure 46F:
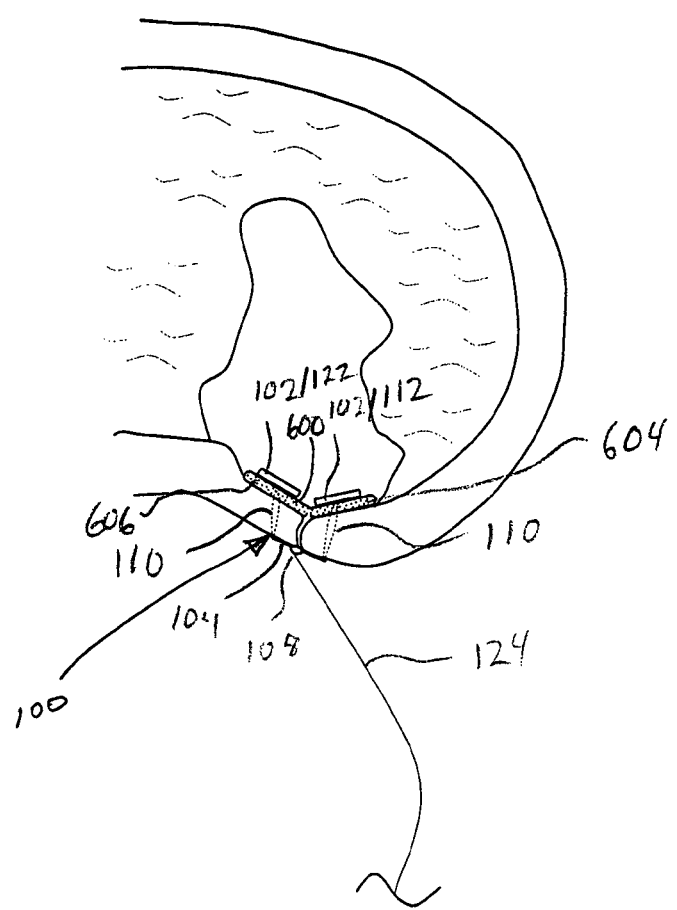

As depicted in FIGS. 46D, 46E, and 46F, patch delivery apparatus 500 may then be withdrawn from the intervertebral disc. To withdraw the patch insertion tool 500, the lateral aspects of the distal patch retention arm 504 may be collapsed into a longitudinal orientation for withdrawal from the patch mounting cavity 610 of patch 600 and/or withdrawal through the aperture in the intervertebral disc. Once withdrawn, the patch 600 may be left secured to the inner surface of an intervertebral disc with fixation apparatus 100 in a loose or uncinched configuration. A cinch line 124 of the fixation apparatus 100 may extend from the intervertebral disc to a location where it may be accessed by the surgeon. As illustrated, the elongated member 104 is secured in a cinchable loop by a retention device 108 in the form of a knot. The loop formed by the elongated member 104 may extend through the eyelets 110 which are secured to anchors 102. As shown in FIG. 46F, the loop may be cinched or tightened by sliding the retention device along the elongated member 104. As previously described, cinching or tightening eyelets 110 together tends to draw the first anchor 112 and the second anchor 122 toward the inner surface of the intervertebral disc. As illustrated, the loop may draw together toward one another the tissue surrounding the aperture and patch material, and may reduce the size of and/or close the annular defect.

It should also be noted that those skilled in the art, upon review of the present disclosure, will recognize that the described apparatus, delivery tools and patches or portions thereof may be rendered visible or more visible via fluoroscopy, if desired, through the incorporation of radio-opaque materials or markers. In one aspect, the implantable devices are constructed with magnetic resonance imaging (MRI) compatible materials. In particular, devices and/or their components could be wholly or partially radiopaque, as result of, for example: compounding various radiopaque materials (e.g., barium sulphate) into device materials; affixing radiopaque materials to device structures (e.g., bands of platinum, gold, or their derivative alloys); deposition of radiopaque materials onto device structures (e.g., deposition of platinum, gold of their derivative alloys); processing radiopaque materials into device structures (e.g., braiding/weaving platinum or gold wires or its alloy derivatives).

Other embodiments of the invention will be apparent to those skilled in the art after consideration of this disclosure and practice of the inventions disclosed herein. It is intended that this specification and examples be considered as exemplary only, with a true scope and spirit of the invention being indicated by the following claims.

The following is claimed:

1. A medical apparatus comprising:
   a delivery apparatus releasably carrying a fixation apparatus,
   the delivery apparatus including a body, a tubular shaft extending from the body and having a distal end, a displacement rod longitudinally displaceable within the body and the tubular shaft and including a proximal end and a distal end, and an actuator coupled to the body and attached to the proximal end of the displacement rod,
   the fixation apparatus including first and second anchors, a flexible band connecting the first and second anchors and including a cinch line releasably coupled to the delivery apparatus, and a tether having a proximal end and a distal end;
   wherein the actuator is operable by a user to sequentially eject the first anchor and the second anchor from the distal end of the tubular shaft, and
   wherein the proximal end of the tether is secured to the delivery apparatus and the distal end of the tether is attached to the second anchor such that the tether is operable to prevent ejection of the second anchor from the tubular shaft during ejection of the first anchor from the tubular shaft.

2. The medical apparatus of claim 1, wherein the fixation apparatus includes a first suture connected to the first anchor, a separate, second suture connected to the second anchor, and wherein the band includes a separate, third suture coupled to the first and second sutures, the third suture forming a suture loop having an adjustable length, and the cinch line is configured such that applying tension to the cinch line foreshortens the adjustable length of the suture loop.

3. The medical apparatus of claim 2, wherein the first and second sutures are each in the form of a suture loop, and wherein the third suture extends through the loops formed by the first and second sutures such that the first and second anchors are slidably coupled to the third suture.

4. The medical apparatus of claim 1, wherein the delivery apparatus further includes a system for regulating movement of the actuator and the displacement rod.

5. The medical apparatus of claim 4, wherein the system for regulating movement of the actuator is configured to allow the actuator and the displacement rod to be advanced a first distance so as to eject the first anchor from the distal end of the tubular shaft, and wherein the tether is operable to resist expulsion of the second anchor from the tubular shaft during deployment of the first anchor.

6. The medical apparatus of claim 5, wherein the system for regulating movement of the actuator is configured to allow the actuator and the displacement rod to be advanced a second distance so as to eject the second anchor from the distal end of the tubular shaft.

7. The medical apparatus of claim 6, wherein the delivery apparatus is further configured to sever the tether during ejection of the second anchor from the distal end of the tubular shaft so that the tether does not resist ejection of the second anchor from the distal end of the tubular shaft.

8. The medical apparatus of claim 1, wherein the tether extends through the tubular shaft, and wherein the proximal end of the tether is attached to the delivery apparatus within the body of the delivery apparatus.

9. The medical apparatus of claim 8, wherein the delivery apparatus includes a tether severing element in the body including a cutting edge for severing the tether.

10. The medical apparatus of claim 1, wherein the delivery apparatus includes a guide extending into the body, a guide spring biasing the guide toward the actuator, and displacement spring in the body biasing the displacement rod in a proximal direction and away from the distal end of the tubular shaft, and wherein the actuator includes a groove, and wherein the guide extends into and is slidably received by the groove so as to regulate movement of the actuator and the displacement rod.

11. The medical apparatus of claim 1, wherein the groove includes a first longitudinally extending portion having a first length, and a second longitudinally extending portion having a second length, and wherein the actuator is configured to be advanceable a first distance corresponding to the first length so as to eject the first anchor from the distal end of the tubular shaft, and is further configured to be advanceable a second distance corresponding to the second length so as to eject the second anchor from the distal end of the tubular shaft.

12. The medical apparatus of claim 11, wherein the groove further includes a radially extending portion between the first and second longitudinally extending portions, and wherein the actuator is rotatable relative to the body after it has been advanced the first distance.

13. The medical apparatus of claim 12, wherein the actuator is configured to be advanceable the second distance after it has been rotated relative to the body.

14. The medical apparatus of claim 13, wherein the delivery apparatus is configured such that advancing the actuator the second distance causes the tether line to be severed within the body.

15. The medical apparatus of claim 1, wherein the fixation apparatus is configured to secure an implant to soft tissue of a patient.

16. The medical apparatus of claim 15, wherein the implant is a therapeutic device.

17. The medical apparatus of claim 16 wherein the implant is an orthopedic device.

18. The medical apparatus of claim 17 wherein the orthopedic device is a mesh configured to repair a defect in an annulus of an intervertebral disc.

19. The medical apparatus of claim 1, wherein the fixation apparatus is configured to re-approximate a defect in soft tissue of a patient.

20. The medical apparatus of claim 19, wherein the soft tissue is an intervertebral disc annulus.

* * * * *